United States Patent
Hatakeyama et al.

(10) Patent No.: US 11,720,019 B2
(45) Date of Patent: Aug. 8, 2023

(54) RESIST COMPOSITION AND PATTERN FORMING PROCESS

(71) Applicant: Shin-Etsu Chemical Co., Ltd., Tokyo (JP)

(72) Inventors: Jun Hatakeyama, Joetsu (JP); Tomomi Watanabe, Joetsu (JP)

(73) Assignee: SHIN-ETSU CHEMICAL CO., LTD., Tokyo (JP)

(*) Notice: Subject to any disclaimer, the term of this patent is extended or adjusted under 35 U.S.C. 154(b) by 168 days.

(21) Appl. No.: 17/157,011

(22) Filed: Jan. 25, 2021

(65) Prior Publication Data

US 2021/0278763 A1 Sep. 9, 2021

(30) Foreign Application Priority Data

Feb. 27, 2020 (JP) .................. 2020-031900

(51) Int. Cl.

| | |
|---|---|
| G03F 7/004 | (2006.01) |
| C07C 381/12 | (2006.01) |
| G03F 7/038 | (2006.01) |
| C07C 65/10 | (2006.01) |
| C07C 61/135 | (2006.01) |
| C07C 59/115 | (2006.01) |
| C07C 205/58 | (2006.01) |
| C07C 63/70 | (2006.01) |
| C07C 311/03 | (2006.01) |
| C07D 275/06 | (2006.01) |
| C07C 309/19 | (2006.01) |
| C08F 220/18 | (2006.01) |
| C08F 212/14 | (2006.01) |
| G03F 7/039 | (2006.01) |

(52) U.S. Cl.
CPC .......... *G03F 7/0045* (2013.01); *C07C 59/115* (2013.01); *C07C 61/135* (2013.01); *C07C 63/70* (2013.01); *C07C 65/10* (2013.01); *C07C 205/58* (2013.01); *C07C 309/19* (2013.01); *C07C 311/03* (2013.01); *C07C 381/12* (2013.01); *C07D 275/06* (2013.01); *C08F 212/24* (2020.02); *C08F 220/1806* (2020.02); *G03F 7/0382* (2013.01); *G03F 7/0392* (2013.01); *C07C 2603/62* (2017.05); *C07C 2603/74* (2017.05)

(58) Field of Classification Search
CPC .................................................. C07C 381/12
See application file for complete search history.

(56) References Cited

U.S. PATENT DOCUMENTS

| | | | |
|---|---|---|---|
| 8,785,105 B2 | 7/2014 | Ohsawa et al. | |
| 9,052,592 B2* | 6/2015 | Nakamura | G03F 7/0045 |
| 9,233,919 B2 | 1/2016 | Ohsawa et al. | |
| 9,766,541 B2 | 9/2017 | Yamazaki et al. | |
| 10,295,904 B2* | 5/2019 | Hatakeyama | G03F 7/2006 |
| 10,437,147 B2* | 10/2019 | Nagamine | G03F 7/0045 |
| 10,968,175 B2* | 4/2021 | Hatakeyama | C08F 220/18 |
| 11,175,580 B2* | 11/2021 | Hatakeyama | G03F 7/0397 |
| 11,181,823 B2 | 11/2021 | Hatakeyama et al. | |
| 2010/0075256 A1* | 3/2010 | Joo | C07C 309/12 |
| | | | 430/286.1 |
| 2014/0080062 A1* | 3/2014 | Thackeray | G03F 7/0392 |
| | | | 430/296 |
| 2016/0349612 A1 | 12/2016 | Fujiwara et al. | |
| 2017/0205709 A1 | 7/2017 | Hatakeyama et al. | |
| 2017/0369616 A1 | 12/2017 | Hatakeyama et al. | |
| 2018/0095364 A1 | 4/2018 | LaBeaume et al. | |
| 2018/0364574 A1* | 12/2018 | Hatakeyama | G03F 7/0045 |
| 2020/0089111 A1* | 3/2020 | Hatakeyama | G03F 7/0397 |
| 2021/0055652 A1* | 2/2021 | Hatakeyama | G03F 7/168 |
| 2021/0149300 A1* | 5/2021 | Hatakeyama | G03F 7/0048 |

FOREIGN PATENT DOCUMENTS

| | | |
|---|---|---|
| JP | 2001-194776 A | 7/2001 |
| JP | 2002-226470 A | 8/2002 |
| JP | 2002-363148 A | 12/2002 |
| JP | 2012-107151 A | 6/2012 |
| JP | 2013-166748 A | 8/2013 |
| JP | 2017-15777 A | 1/2017 |
| JP | 2018-118962 A | 8/2018 |
| KR | 10-2018-0002022 A | 1/2018 |
| WO | 2008/066011 A1 | 6/2008 |

OTHER PUBLICATIONS

Office Action dated Feb. 5, 2022, issued in KR application No. 10-2020-0105244, with English Translation. (Counterpart to U.S. Appl. No. 16/877,742)(13 pages).
Non-Final Action dated Mar. 31, 2022, issued in U.S. Appl. No. 16/877,742.
Non-Final Action dated Sep. 28, 2022, issued in U.S. Appl. No. 16/877,742.
Non-Final Action dated Apr. 28, 2021, issued in U.S. Appl. No. 16/565,776.
Notice of Allowance dated Jul. 13, 2021, issued in U.S. Appl. No. 16/565,776.

* cited by examiner

Primary Examiner — Amanda C. Walke
(74) Attorney, Agent, or Firm — WHDA, LLP

(57) ABSTRACT

A resist composition comprising a quencher containing a sulfonium salt having the formula (A).

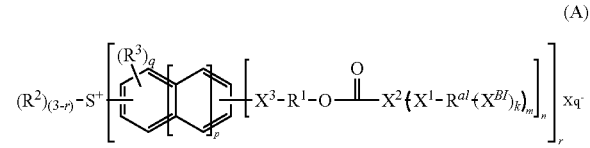

(A)

15 Claims, No Drawings

RESIST COMPOSITION AND PATTERN FORMING PROCESS

CROSS-REFERENCE TO RELATED APPLICATION

This non-provisional application claims priority under 35 U.S.C. § 119(a) on Patent Application No. 2020-031900 filed in Japan on Feb. 27, 2020, the entire contents of which are hereby incorporated by reference.

TECHNICAL FIELD

This invention relates to a resist composition and a pattern forming process.

BACKGROUND ART

As integration density and operating speed of LSIs become higher, the effort to make the pattern rule finer is in rapid progress. In particular, the enlargement of the logic memory market to comply with the wide-spread use of smartphones drives forward the miniaturization technology. As the advanced miniaturization technology, manufacturing of microelectronic devices at the 10-nm node by double patterning of the ArF immersion lithography has been implemented in a mass scale. Manufacturing of 7-nm node devices as the next generation by the double patterning technology is approaching to the verge of high-volume application. The candidate for 5-nm node devices as the next generation but one is extreme ultraviolet (EUV) lithography.

As the pattern feature size is reduced, approaching to the diffraction limit of light, light contrast lowers. In the case of positive resist film, a lowering of light contrast leads to reductions of resolution and focus margin of hole and trench patterns.

Chemically amplified resist compositions comprising an acid generator capable of generating an acid upon exposure to light or electron beam (EB) include chemically amplified positive resist compositions wherein deprotection reaction takes place under the action of acid and chemically amplified negative resist compositions wherein polarity switch or crosslinking reaction takes place under the action of acid. Quenchers are often added to these resist compositions for the purpose of controlling the diffusion of the acid to unexposed region to improve the contrast. The addition of quenchers is fully effective to this purpose. A number of amine quenchers were proposed as disclosed in Patent Documents 1 to 3.

With respect to the acid labile group used in (meth) acrylate polymers for the ArF lithography resist composition, deprotection reaction takes place when a photoacid generator capable of generating a sulfonic acid having fluorine substituted at α-position (referred to as "α-fluorinated sulfonic acid") is used, but not when an acid generator capable of generating a sulfonic acid not having fluorine substituted at α-position (referred to as "α-non-fluorinated sulfonic acid") or carboxylic acid is used. If a sulfonium or iodonium salt capable of generating an α-fluorinated sulfonic acid is combined with a sulfonium or iodonium salt capable of generating an α-non-fluorinated sulfonic acid, the sulfonium or iodonium salt capable of generating an α-non-fluorinated sulfonic acid undergoes ion exchange with the α-fluorinated sulfonic acid. Through the ion exchange, the α-fluorinated sulfonic acid thus generated by light exposure is converted back to the sulfonium or iodonium salt while the sulfonium or iodonium salt of an α-non-fluorinated sulfonic acid or carboxylic acid functions as a quencher. Patent Document 4 discloses a resist composition comprising a sulfonium or iodonium salt capable of generating a carboxylic acid as a quencher.

Sulfonium and iodonium salt type quenchers are photodecomposable like photoacid generators. That is, the amount of quencher in the exposed region is reduced. Since acid is generated in the exposed region, the reduced amount of quencher leads to a relatively increased concentration of acid and hence, an improved contrast. However, the acid diffusion in the exposed region is not suppressed, indicating the difficulty of acid diffusion control.

CITATION LIST

Patent Document 1: JP-A 2001-194776
Patent Document 2: JP-A 2002-226470
Patent Document 3: JP-A 2002-363148
Patent Document 4: WO 2008/066011

SUMMARY OF THE INVENTION

For chemically amplified resist compositions in which an acid catalyst is used, it is desired to develop a quencher capable of achieving a high sensitivity and reducing the edge roughness (LWR) of line patterns or improving the critical dimension uniformity (CDU) of hole patterns.

The invention has been made in view of the above-described problems, and an object of the invention is to provide a resist composition that achieves a high sensitivity, minimal LWR, and improved CDU independent of whether it is of positive or negative tone, and a pattern forming process using the resist composition.

The inventors have found that a resist composition having a high sensitivity, minimal LWR, improved CDU, high contrast, high resolution, and wide process margin is obtained using, as a quencher, a sulfonium salt having a structure in which an iodized or brominated hydrocarbyl group (excluding an iodized or brominated aromatic ring) is bonded to an aromatic ring via an ester bond-containing group.

That is, the invention provides a resist composition and a pattern forming process described below.

1. A resist composition comprising a quencher containing a sulfonium salt having the formula (A):

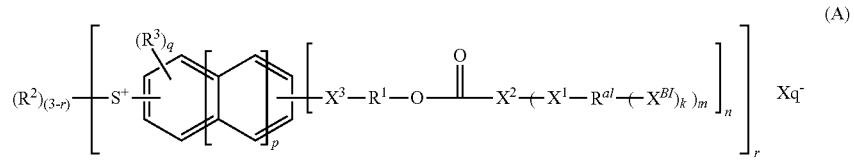

wherein k, m, and n are each independently an integer of 1 to 3, p is 0 or 1, q is an integer of 0 to 4, r is an integer of 1 to 3, X$^{BI}$ is iodine or bromine, R$^{a1}$ is a C$_1$-C$_{20}$ (k+1)-valent aliphatic hydrocarbon group which may contain at least one selected from an ether bond, a carbonyl group, an ester bond, an amide bond, a sultone ring, a lactam ring, a carbonate group, a halogen other than iodine, a C$_6$-C$_{12}$ aryl group, a hydroxyl group, or a carboxyl group, X$^1$ is a single bond, an ether bond, an ester bond, an amide bond, a carbonyl group, or a carbonate group, X$^2$ is a single bond or a C$_1$-C$_{20}$ (m+1)-valent hydrocarbon group which may contain at least one selected from an ether bond, a carbonyl group, an ester bond, an amide bond, a sultone ring, a lactam ring, a carbonate group, a halogen other than iodine, a hydroxyl group, or a carboxyl group, X$^3$ is a single bond, an ether bond, or an ester bond, R$^1$ is a single bond or a C$_1$-C$_{20}$ saturated hydrocarbylene group which may contain an ether bond, an ester bond, or a hydroxyl group, R$^2$ is a C$_1$-C$_{20}$ hydrocarbyl group which may contain a heteroatom, two R$^2$s may be the same or different, and may bond together to form a ring with a sulfur atom to which the two R$^2$s are attached when r=1, R$^3$ is a hydroxyl group, a carboxyl group, a nitro group, a cyano group, fluorine, chlorine, bromine, iodine, an amino group, or a C$_1$-C$_{20}$ saturated hydrocarbyl group, C$_1$-C$_{20}$ saturated hydrocarbyloxy group, C$_2$-C$_{20}$ saturated hydrocarbylcarbonyloxy group, C$_2$-C$_{20}$ saturated hydrocarbyloxycarbonyl group, or C$_1$-C$_4$ saturated hydrocarbylsulfonyloxy group which may contain fluorine, chlorine, bromine, iodine, a hydroxyl group, an amino group, or an ether bond, and Xq$^-$ is a halide ion, a sulfonic acid anion not having fluorine at an α-position, a carboxylic acid anion, or a sulfonamide anion.

2. The resist composition of the item 1, further comprising an organic solvent.

3. The resist composition of the item 1 or 2, further comprising an acid generator capable of generating fluorosulfonic acid, fluoroimidic acid, or fluoromethide acid.

4. The resist composition of any one of the items 1 to 3, further comprising a base polymer.

5. The resist composition of the item 4, wherein the base polymer comprises recurring units having the formula (a1) or recurring units having the formula (a2):

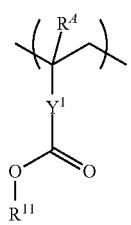

(a1)

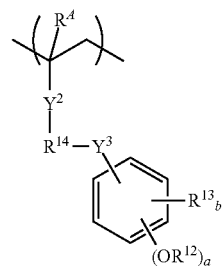

(a2)

wherein R$^A$ is each independently hydrogen or a methyl group,

Y$^1$ is a single bond, a phenylene group, a naphthylene group, or a C$_1$-C$_{12}$ linking group containing at least one selected from an ester bond or a lactone ring, Y$^2$ is a single bond or an ester bond, Y$^3$ is a single bond, an ether bond, or an ester bond, R$^{11}$ and R$^{12}$ are each independently an acid labile group, R$^{13}$ is fluorine, a trifluoromethyl group, a cyano group, a C$_1$-C$_6$ saturated hydrocarbyl group, a C$_1$-C$_6$ saturated hydrocarbyloxy group, a C$_2$-C$_7$ saturated hydrocarbylcarbonyl group, a C$_2$-C$_7$ saturated hydrocarbylcarbonyloxy group, or a C$_2$-C$_7$ saturated hydrocarbyloxycarbonyl group, R$^{14}$ is a single bond or a C$_1$-C$_6$ alkanediyl group in which some carbon may be replaced by an ether bond or an ester bond, a is 1 or 2, b is an integer of 0 to 4, and 1≤a+b≤5.

6. The resist composition of the item 5 which is a chemically amplified positive resist composition.

7. The resist composition of the item 4, wherein the base polymer is free of an acid labile group.

8. The resist composition of the item 7 which is a chemically amplified negative resist composition.

9. The resist composition of any one of the items 1 to 8, wherein the base polymer comprises recurring units having any one of the formulae (f1) to (f3):

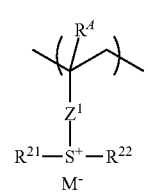

(f1)

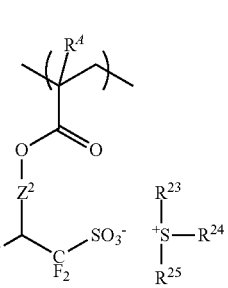

(f2)

-continued

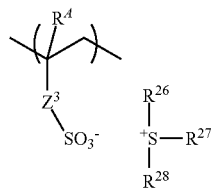

(f3)

wherein $R^A$ is each independently hydrogen or a methyl group, $Z^1$ is a single bond, a $C_1$-$C_6$ aliphatic hydrocarbylene group, a phenylene group, a naphthylene group, a $C_7$-$C_{18}$ combination thereof, —O—$Z^{11}$—, —C(=O)—O—$Z^{11}$—, or —C(=O)—NH—$Z^{11}$—, $Z^{11}$ is a $C_1$-$C_6$ aliphatic hydrocarbylene group, a phenylene group, a naphthylene group, or a $C_7$-$C_{18}$ combination thereof, which may contain a carbonyl group, an ester bond, an ether bond, or a hydroxyl group, $Z^2$ is a single bond, —$Z^{21}$—C(=O)—O—, —$Z^{21}$—O—, or —$Z^{21}$—O—C(=O)—, $Z^{21}$ is a $C_1$-$C_{12}$ saturated hydrocarbylene group which may contain a carbonyl group, an ester bond, or an ether bond, $Z^3$ is a single bond, a methylene group, an ethylene group, a phenylene group, a fluorinated phenylene group, —O—$Z^{31}$—, —C(=O)—O—$Z^{31}$—, or —C(=O)—NH—$Z^{31}$—, $Z^{31}$ is a $C_1$-$C_6$ aliphatic hydrocarbylene group, a phenylene group, a fluorinated phenylene group, or a trifluoromethyl-substituted phenylene group which may contain a carbonyl group, an ester bond, an ether bond, or a hydroxyl group, $R^{21}$ to $R^{28}$ are each independently a halogen or a $C_1$-$C_{20}$ hydrocarbyl group which may contain a heteroatom, a pair of $R^{23}$ and $R^{24}$, or $R^{26}$ and $R^{27}$ may bond together to form a ring with the sulfur atom to which they are attached, $R^{HF}$ is hydrogen or a trifluoromethyl group, and $M^-$ is a non-nucleophilic counter ion.

10. The resist composition of any one of the items 1 to 9, further comprising a surfactant.

11. A pattern forming process comprising the steps of applying the resist composition of any one of the items 1 to 10 to form a resist film on a substrate, exposing the resist film to high-energy radiation, and developing the exposed resist film in a developer.

12. The pattern forming process of the item 11, wherein the high-energy radiation is ArF excimer laser radiation of wavelength 193 nm or KrF excimer laser radiation of wavelength 248 nm.

13. The pattern forming process of the item 11, wherein the high-energy radiation is electron beam (EB) or extreme ultraviolet (EUV) of wavelength 3 to 15 nm.

Advantageous Effects of the Invention

In the quencher containing a sulfonium salt having the formula (A), iodine atoms or bromine atoms are so absorptive to EUV of wavelength 13.5 nm that they generate secondary electrons and radicals during exposure to promote the decomposition, contributing to a high sensitivity. Because of the large atomic weight, iodine and bromine have a high acid diffusion suppressing effect, resulting in reduced image blurring, minimal LWR, and improved CDU. These actions make it possible to design a resist having a high sensitivity, minimal LWR, and improved CDU.

DESCRIPTION OF THE PREFERRED EMBODIMENTS

As used herein, the singular forms "a," "an" and "the" include plural referents unless the context clearly dictates otherwise. The notation ($C_n$-$C_m$) means a group containing from n to m carbon atoms per group.

Resist Composition

The resist composition comprises a sulfonium salt having the formula (A), and in some cases, comprises a base polymer. The sulfonium salt is an acid generator capable of generating an acid of an anion due to the decomposition of the cation upon light exposure. The anion is derived from a weak acid, therefore, polarity conversion and crosslinking reaction are not caused by the anion. An acid generator capable of generating a strong acid is added separately, and by ion exchange between the strong acid and the sulfonium salt, the sulfonium salt functions as a quencher capable of neutralizing the strong acid. Such a quencher containing a sulfonium salt traps an acid by the same mechanism as in Patent Document 4, controls the diffusion of the acid, and is photodecomposed to improve the contrast.

Unlike in Patent Document 4, the cation in the quencher containing a sulfonium salt used in the present invention has an iodized or brominated hydrocarbyl group (excluding an iodized or brominated aromatic ring). As a result, the quencher is so absorptive to EUV as to generate secondary electrons and radicals and characterized by high decomposition efficiency due to the generated secondary electrons and the radicals. Since the sulfonium salt is a mechanism for the decomposition of the cation, increase in the absorption of EUV by the cation is effective for increasing the decomposition efficiency.

In the case of the acid generator, increase in the decomposition efficiency leads to high sensitivity. At the same time, improved CDU and minimal LWR can be achieved by controlling the acid diffusion of the generated acid by making the anion bulky. However, in the case of the quencher, high decomposition efficiency leads to reduction in the concentration of the quencher for controlling the acid diffusion, and a problem is caused that although the sensitivity is high, the CDU and the LWR are significantly deteriorated.

Even if the concentration of the quencher is reduced, the sulfonium salt having the formula (A) can suppress the acid diffusion because an iodine atom or a bromine atom with a large atomic weight is introduced in the cation. Furthermore, the salt is highly compatible with and thus well dispersible in a polymer. There are achieved improvements in LWR and CDU.

The quencher containing a sulfonium salt having the formula (A) exerts an LWR or CDU improving effect, which may stand good either in positive and negative tone pattern formation by aqueous alkaline development or in negative tone pattern formation by organic solvent development.

If only the sulfonium salt having the formula (A) is dissolved in a solvent without blending with a base polymer and a film is formed, the exposed region dissolves in alkali. That is, the sulfonium salt can be used as a positive resist composition.

Sulfonium Salt

The sulfonium salt in the resist composition is represented by the formula (A).

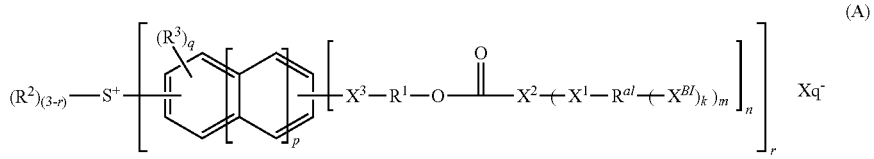

(A)

Herein k, m, and n are each independently an integer of 1 to 3. p is 0 or 1. q is an integer of 0 to 4. r is an integer of 1 to 3.

In the formula (A), $X^{BI}$ is iodine or bromine. When k, m, n and/or r is 2 or 3, a plurality of $X^{BI}$s may be the same or different from each other.

In the formula (A), $R^{a1}$ is a $C_1$-$C_{20}$ (k+1)-valent aliphatic hydrocarbon group which may contain at least one selected from an ether bond, a carbonyl group, an ester bond, an amide bond, a sultone ring, a lactam ring, a carbonate group, a halogen other than iodine, a $C_6$-$C_{12}$ aryl group, a hydroxyl group, or a carboxyl group.

The aliphatic hydrocarbon group may be saturated or unsaturated, and may be straight, branched, or cyclic. Specific examples of the aliphatic hydrocarbon group include alkanediyl groups such as methanediyl, ethane-1,1-diyl, ethane-1,2-diyl, propane-1,1-diyl, propane-1,2-diyl, propane-1,3-diyl, propane-2,2-diyl, butane-1,1-diyl, butane-1,2-diyl, butane-1,3-diyl, butane-2,3-diyl, butane-1,4-diyl, 1,1-dimethylethane-1,2-diyl, pentane-1,5-diyl, 2-methylbutane-1,2-diyl, hexane-1,6-diyl, heptane-1,7-diyl, octane-1,8-diyl, nonane-1,9-diyl, decane-1,10-diyl, undecane-1,11-diyl, and dodecane-1,12-diyl; cycloalkanediyl groups such as cyclopropane-1,1-diyl, cyclopropane-1,2-diyl, cyclobutane-1,1-diyl, cyclobutane-1,2-diyl, cyclobutane-1,3-diyl, cyclopentane-1,1-diyl, cyclopentane-1,2-diyl, cyclopentane-1,3-diyl, cyclohexane-1,1-diyl, cyclohexane-1,2-diyl, cyclohexane-1,3-diyl, and cyclohexane-1,4-diyl; polycyclic saturated hydrocarbylene groups such as norbornane-2,3-diyl and norbornane-2,6-diyl; alkenediyl groups such as 2-propene-1,1-diyl; alkynediyl groups such as 2-propyne-1,1-diyl; cycloalkenediyl groups such as 2-cyclohexene-1,2-diyl, 2-cyclohexene-1,3-diyl, and 3-cyclohexene-1,2-diyl; polycyclic unsaturated hydrocarbylene groups such as 5-norbornene-2,3-diyl; cyclic aliphatic hydrocarbylene-substituted alkanediyl groups such as cyclopentylmethanediyl, cyclohexylmethanediyl, 2-cyclopentenylmethanediyl group, 3-cyclopentenylmethanediyl group, 2-cyclohexenylmethanediyl group, and 3-cyclohexenylmethanediyl group; aliphatic hydrocarbylene groups such as groups obtained from combination of the above-described groups; and trivalent or tetravalent groups obtained by removing one or two hydrogen atoms from the above-described aliphatic hydrocarbylene groups.

Examples of the $C_6$-$C_{12}$ aryl group include phenyl, tolyl, xylyl, 1-naphthyl, and 2-naphthyl.

In the formula (A), $X^1$ is a single bond, an ether bond, an ester bond, an amide bond, a carbonyl group, or a carbonate group. $X^2$ is a single bond or a $C_1$-$C_{20}$ (m+1)-valent hydrocarbon group which may contain at least one selected from an ether bond, a carbonyl group, an ester bond, an amide bond, a sultone ring, a lactam ring, a carbonate group, a halogen other than iodine, a hydroxyl group, or a carboxyl group. $X^3$ is a single bond, an ether bond, or an ester bond.

In the formula (A), $R^1$ is a single bond or a $C_1$-$C_{20}$ saturated hydrocarbylene group which may contain an ether bond, an ester bond, or a hydroxyl group. The saturated hydrocarbylene group may be straight, branched, or cyclic, and specific examples thereof include the above-described alkanediyl groups, cycloalkanediyl groups, and polycyclic saturated hydrocarbylene groups. The saturated hydrocarbylene group is preferably an alkanediyl group.

In the formula (A), $R^2$ is a $C_1$-$C_{20}$ hydrocarbyl group which may contain a heteroatom. The hydrocarbyl group may be straight, branched, or cyclic, and specific examples thereof include $C_1$-$C_{20}$ saturated hydrocarbyl groups, $C_2$-$C_{20}$ unsaturated aliphatic hydrocarbyl groups, $C_6$-$C_{20}$ aryl groups, $C_7$-$C_{20}$ aralkyl groups, and groups obtained from combination thereof.

The saturated hydrocarbyl group may be straight, branched, or cyclic, and specific examples thereof include alkyl groups such as methyl, ethyl, n-propyl, isopropyl, n-butyl, isobutyl, sec-butyl, tert-butyl, n-pentyl, neopentyl, n-hexyl, n-heptyl, n-octyl, 2-ethylhexyl, n-nonyl, n-decyl, n-undecyl, n-dodecyl, n-tridecyl, n-pentadecyl, and n-hexadecyl; and cyclic saturated hydrocarbyl groups such as cyclopentyl and cyclohexyl.

The unsaturated aliphatic hydrocarbyl group may be straight, branched, or cyclic, and specific examples thereof include alkenyl groups such as vinyl, 1-propenyl, 2-propenyl, butenyl, and hexenyl, alkynyl groups such as ethynyl, propynyl, and butynyl, and cyclic unsaturated hydrocarbyl groups such as cyclohexenyl.

Examples of the aryl group include phenyl, methylphenyl, ethylphenyl, n-propylphenyl, isopropylphenyl, n-butylphenyl, isobutylphenyl, sec-butylphenyl, tert-butylphenyl, naphthyl, methylnaphthyl, ethylnaphthyl, n-propylnaphthyl, isopropylnaphthyl, n-butylnaphthyl, isobutylnaphthyl, sec-butylnaphthyl, and tert-butylnaphthyl.

Examples of the aralkyl group include benzyl and phenethyl.

In the foregoing groups, some or all hydrogen atoms may be substituted by a group containing a heteroatom such as oxygen, sulfur, nitrogen, or halogen, and some carbon may be replaced by a group containing a heteroatom such as oxygen, sulfur, or nitrogen, so that the group may contain hydroxyl, carboxyl, a halogen, cyano, amino, nitro, sultone, sulfone, a group containing a sulfonium salt, an ether bond, an ester bond, carbonyl, a sulfide bond, sulfonyl, or an amide bond.

Two $R^2$s may be the same or different, and may bond together to form a ring with a sulfur atom to which the two $R^2$s are attached when r=1. Rings of the following structure are preferred.

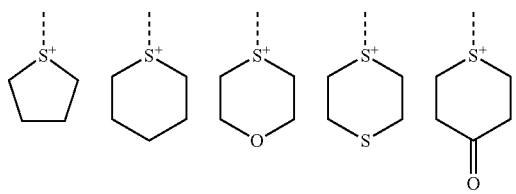

-continued

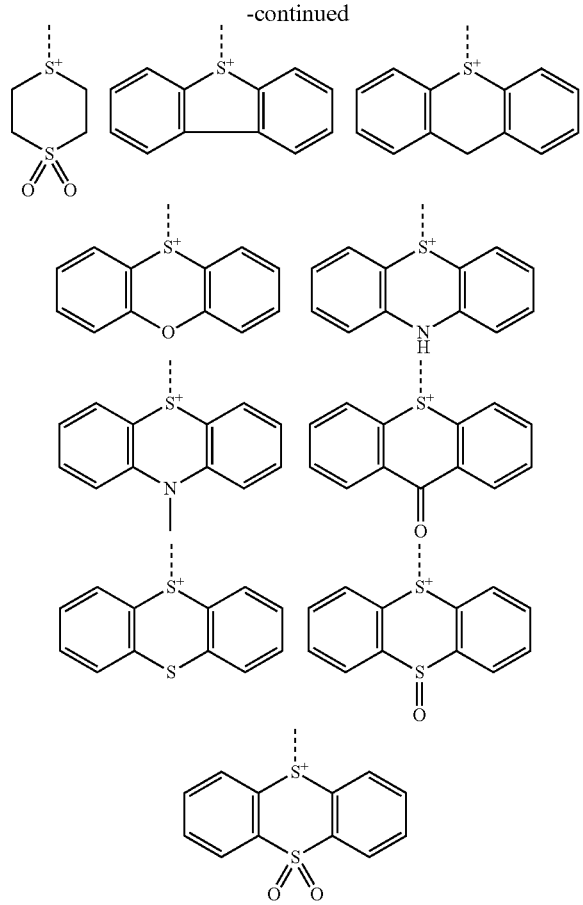

Herein, the broken line designates an attachment to the aromatic ring in the formula (A).

In the formula (A), $R^3$ is a hydroxyl group, a carboxyl group, a nitro group, a cyano group, fluorine, chlorine, bromine, iodine, an amino group, or a $C_1$-$C_{20}$ saturated hydrocarbyl group, $C_1$-$C_{20}$ saturated hydrocarbyloxy group, $C_2$-$C_{20}$ saturated hydrocarbylcarbonyloxy group, $C_2$-$C_{20}$ saturated hydrocarbyloxycarbonyl group, or $C_1$-$C_4$ saturated hydrocarbylsulfonyloxy group which may contain fluorine, chlorine, bromine, iodine, a hydroxyl group, an amino group, or an ether bond.

The saturated hydrocarbyloxy group may be straight, branched, or cyclic, and specific examples thereof include methoxy, ethoxy, n-propyloxy, isopropyloxy, n-butyloxy, isobutyloxy, sec-butyloxy, tert-butyloxy, n-pentyloxy, neopentyloxy, cyclopentyloxy, n-hexyloxy, cyclohexyloxy, n-heptyloxy, n-octyloxy, 2-ethylhexyloxy, n-nonyloxy, n-decyloxy, n-undecyloxy, n-dodecyloxy, n-tridecyloxy, n-pentadecyloxy, and n-hexadecyloxy.

Examples of the saturated hydrocarbylcarbonyloxy group include acetyloxy, propionyloxy, butyryloxy, and isobutyryloxy.

Examples of the saturated hydrocarbyloxycarbonyl group include methoxycarbonyl, ethoxyoxycarbonyl, n-propyloxycarbonyl, isopropyloxycarbonyl, n-butyloxycarbonyl, isobutyloxycarbonyl, sec-butyloxycarbonyl, tert-butyloxycarbonyl, n-pentyloxycarbonyl, neopentyloxycarbonyl, cyclopentyloxycarbonyl, n-hexyloxycarbonyl, cyclohexyloxycarbonyl, n-heptyloxycarbonyl, n-octyloxycarbonyl, 2-ethylhexyloxycarbonyl, n-nonyloxycarbonyl, n-decyloxycarbonyl, n-undecyloxycarbonyl, n-dodecyloxycarbonyl, n-tridecyl oxycarbonyl oxycarbonyl, and n-pentadecyl.

Examples of the cation in the sulfonium salt having the formula (A) are shown below, but not limited thereto.

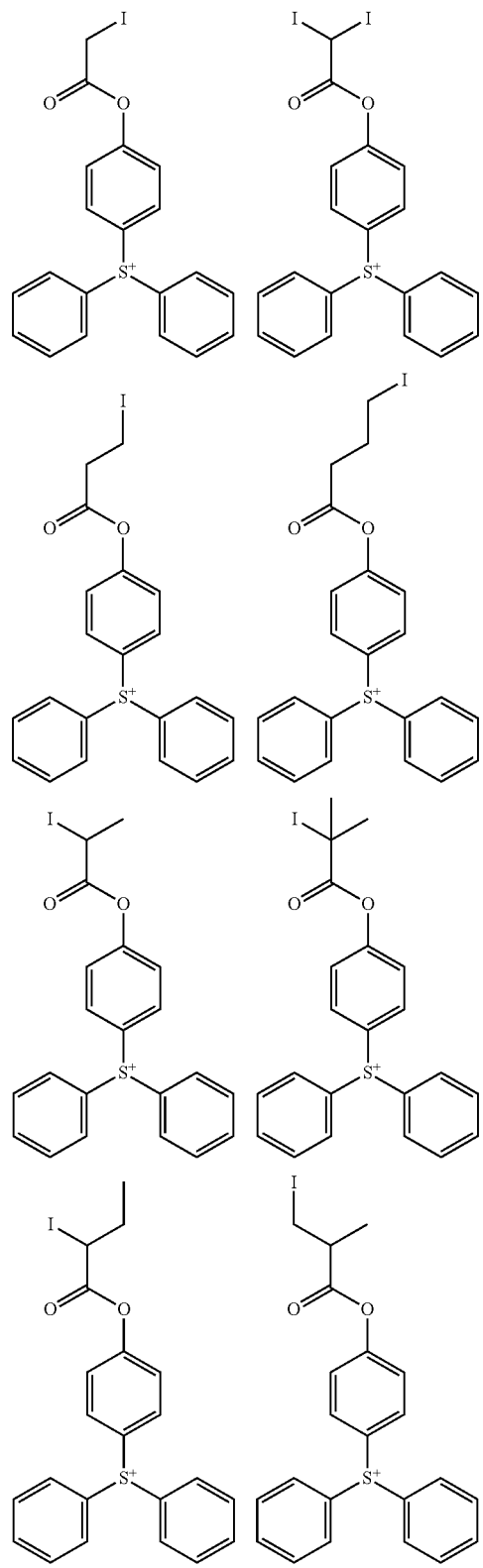

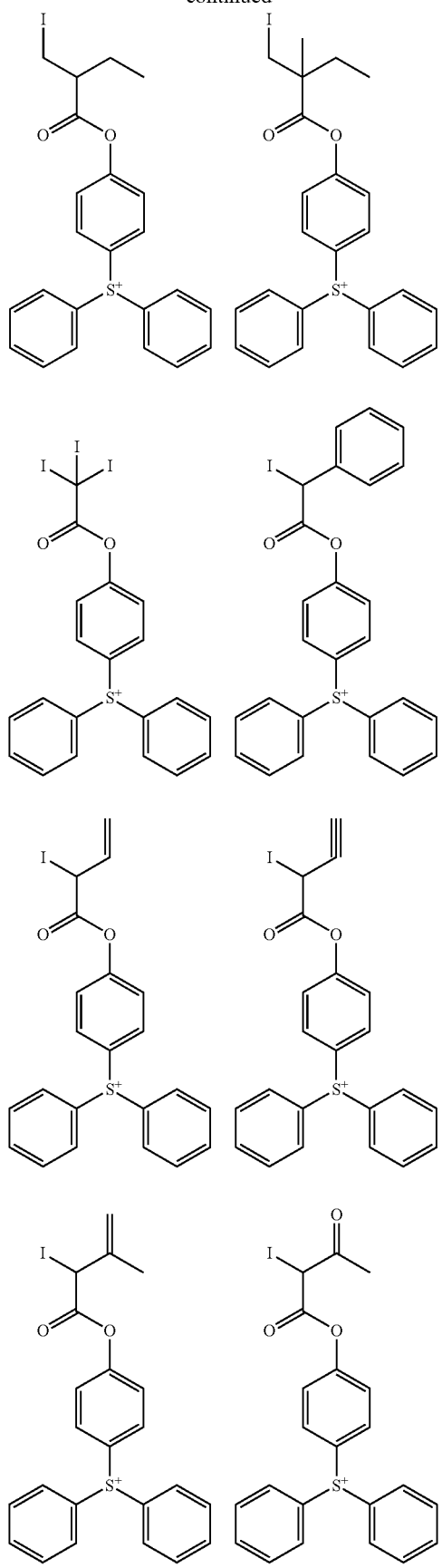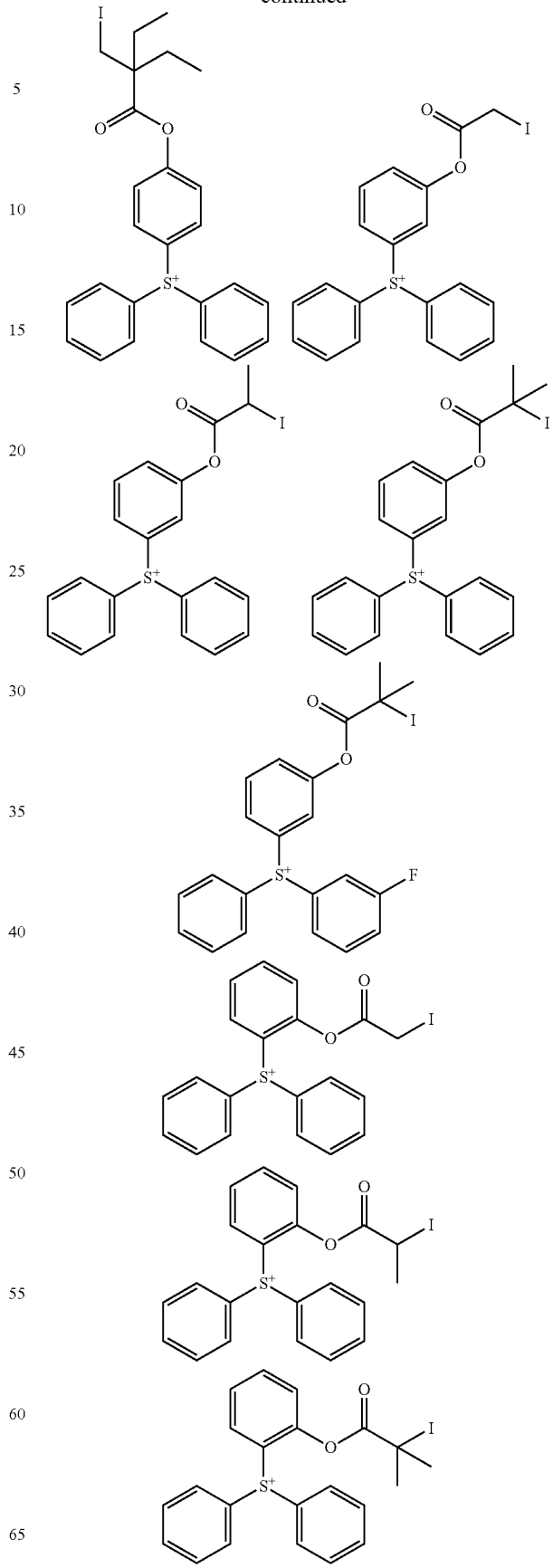

-continued
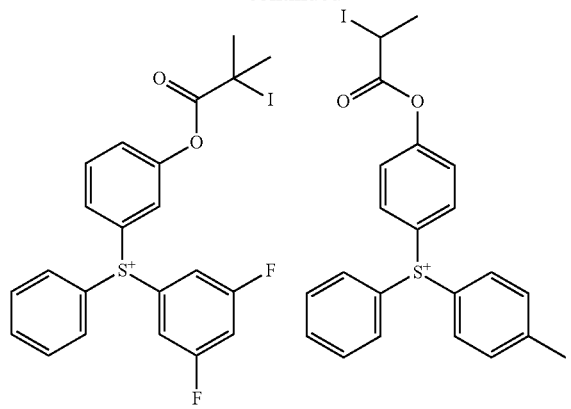
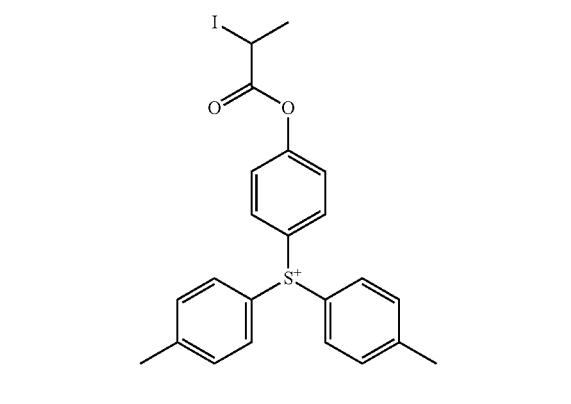
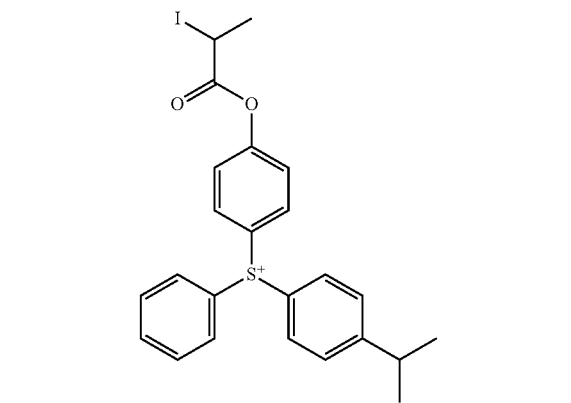
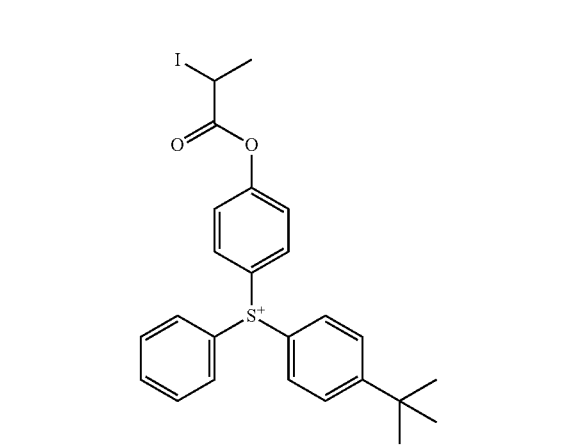
-continued
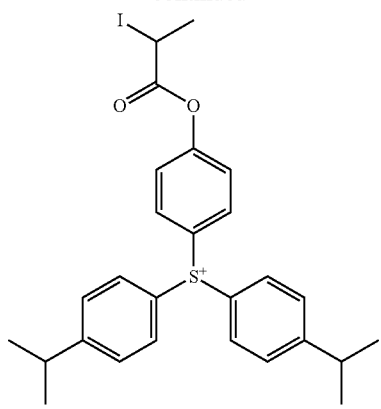
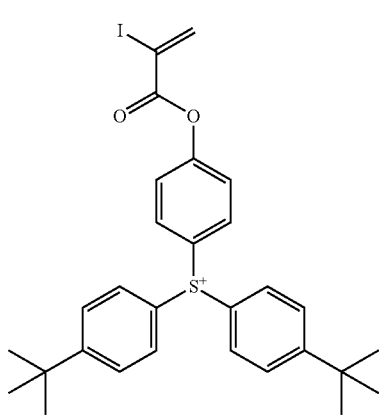
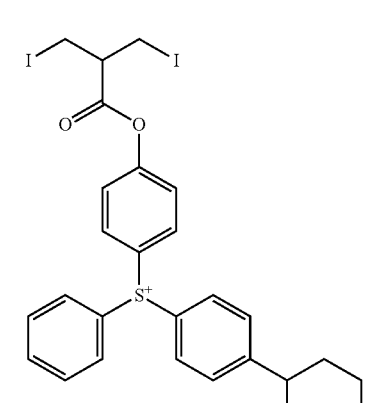
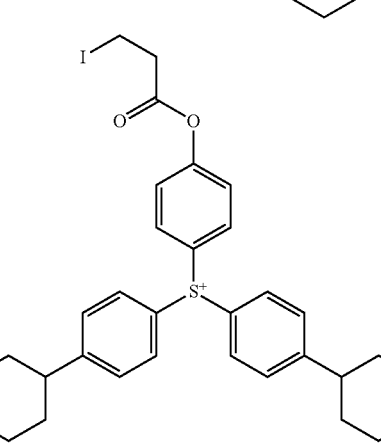

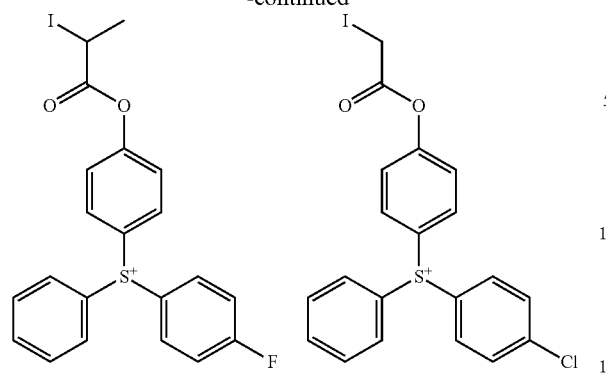
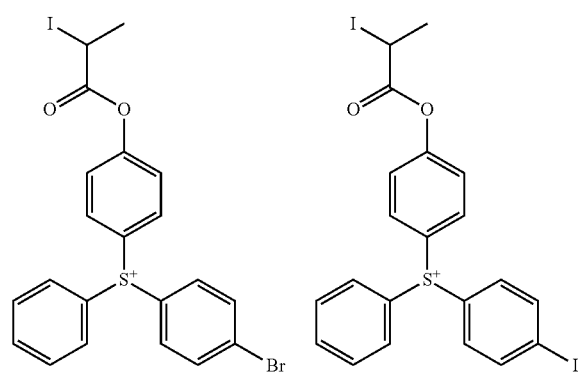
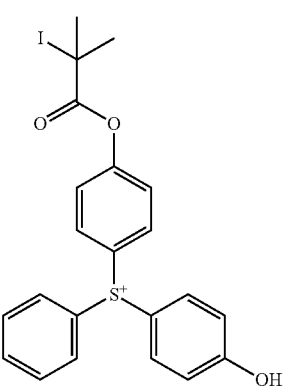
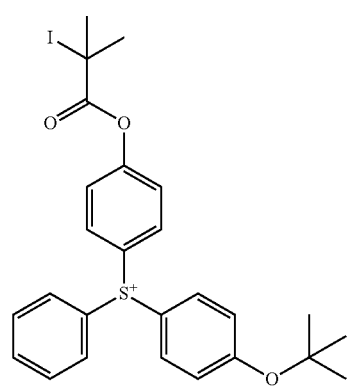
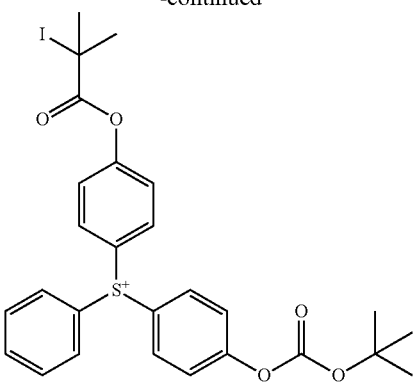
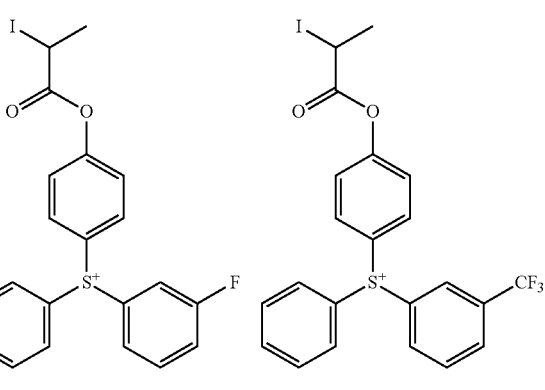
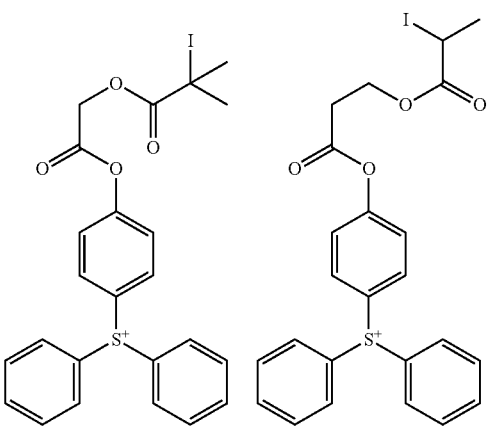

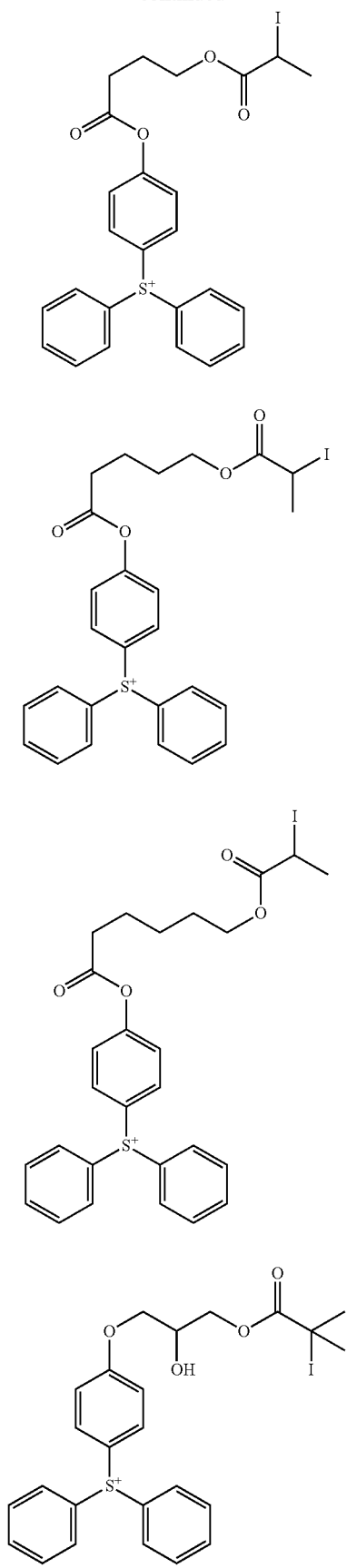

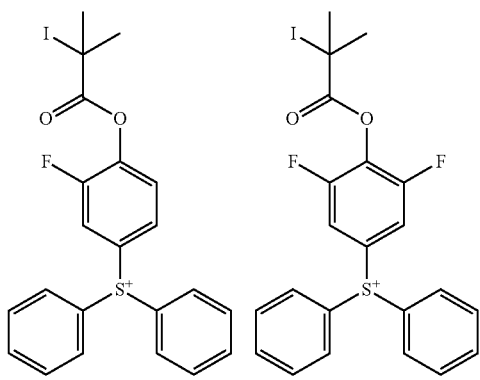
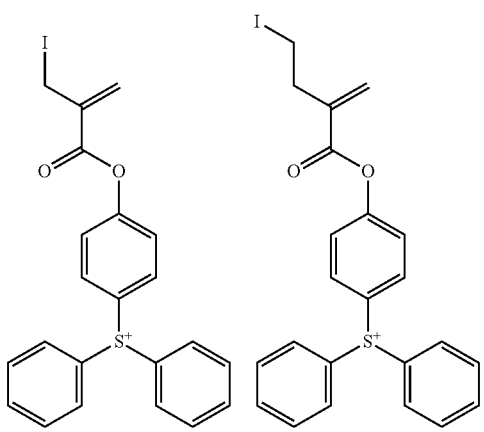
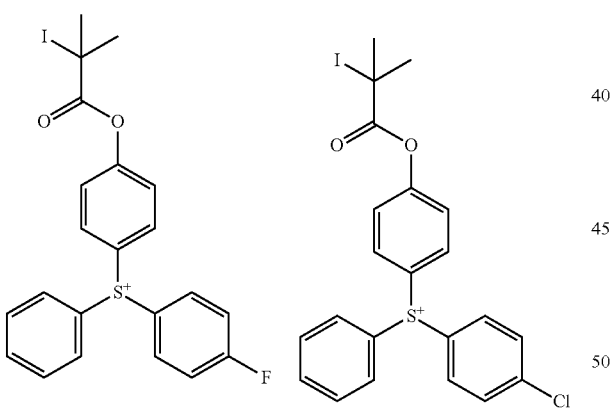
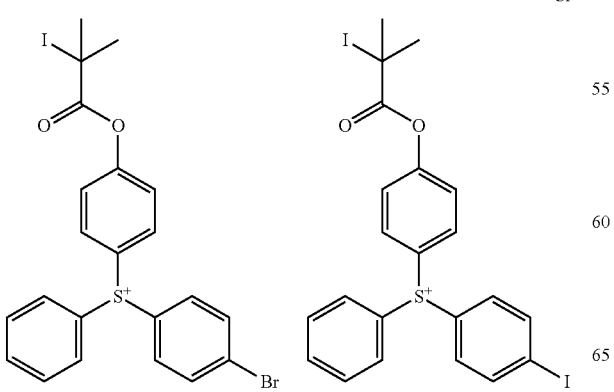
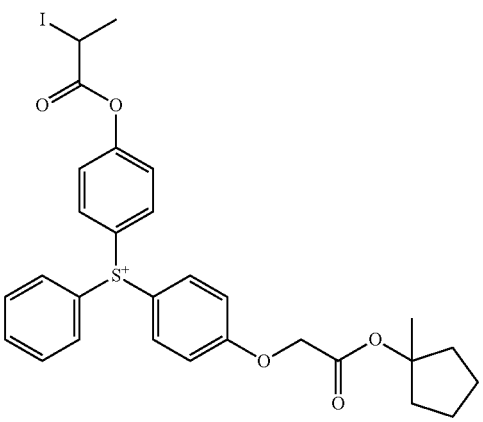
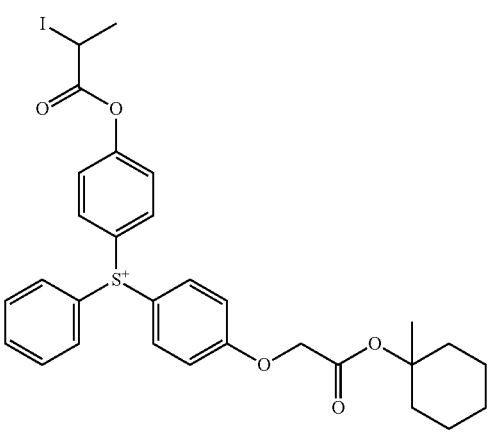
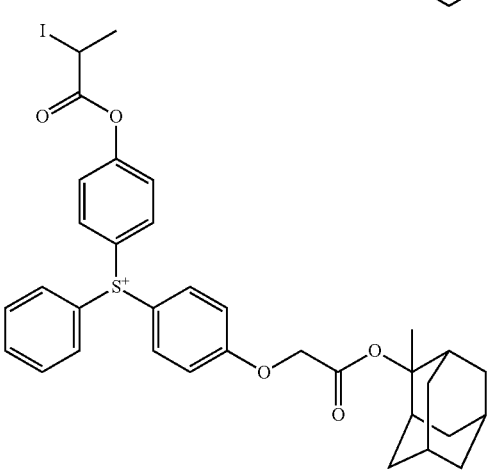
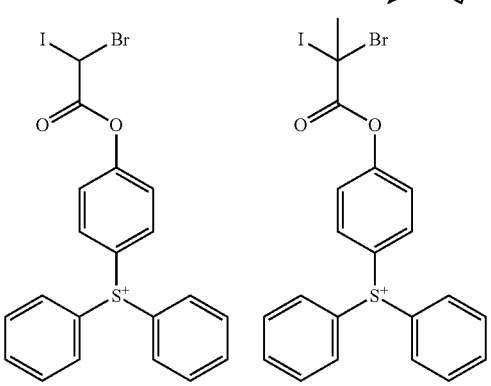

-continued
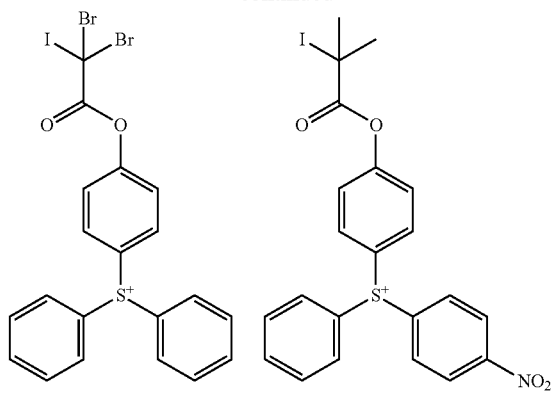
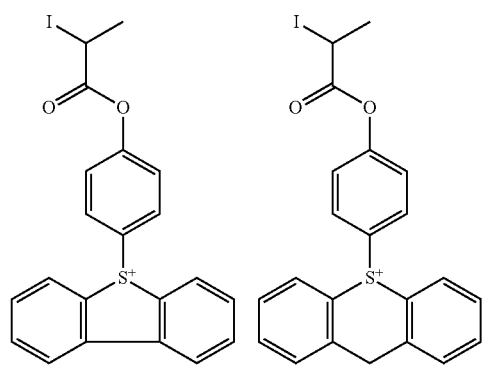
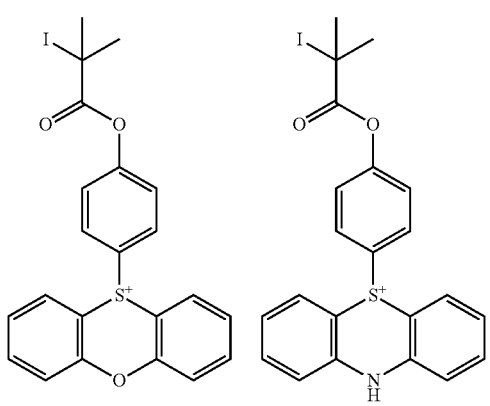
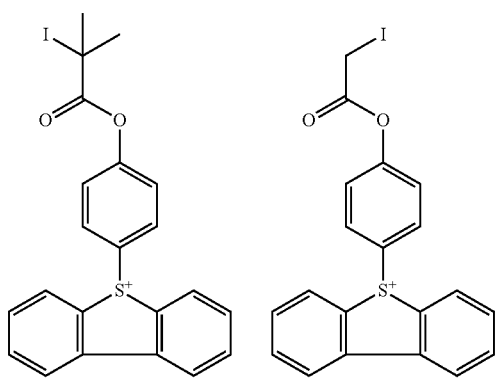
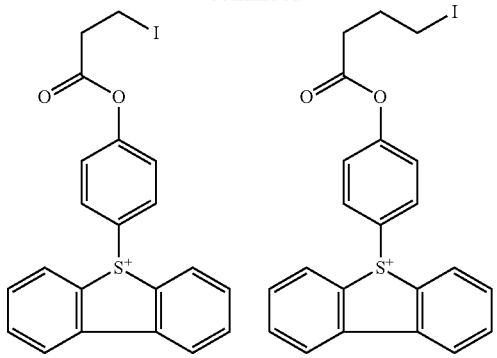
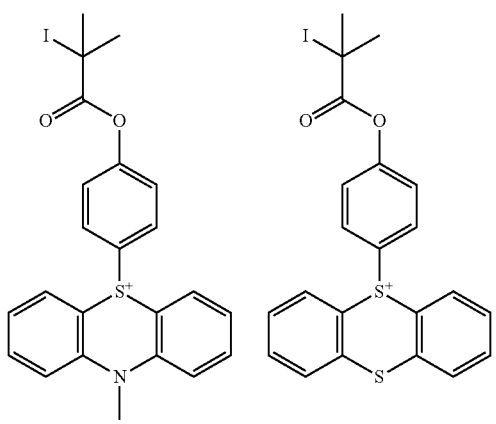
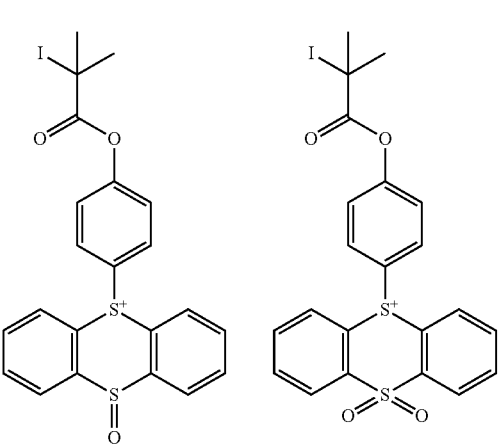
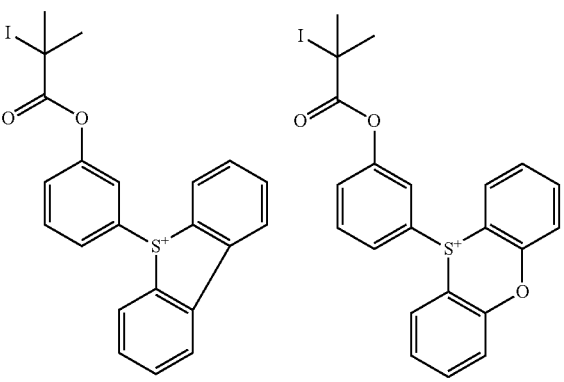

23
-continued
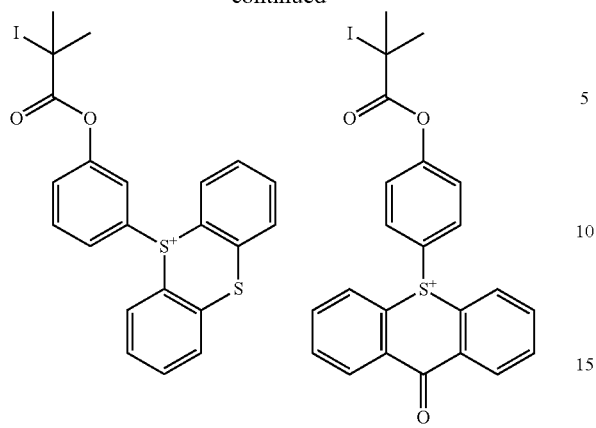
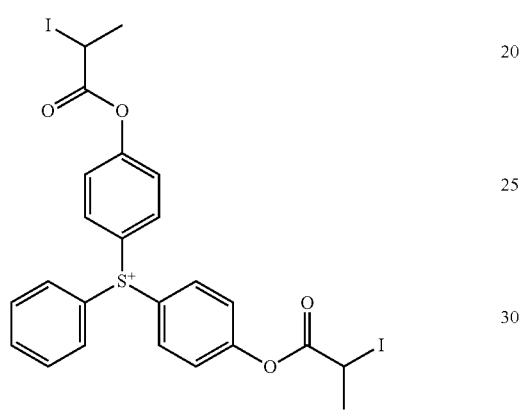
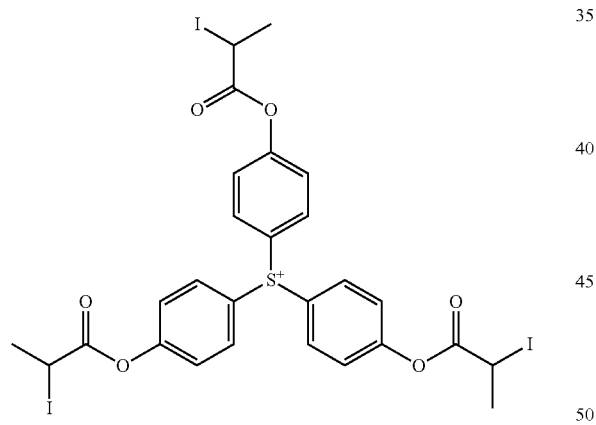
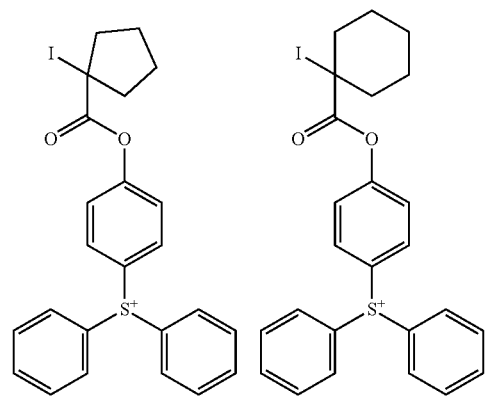
24
-continued
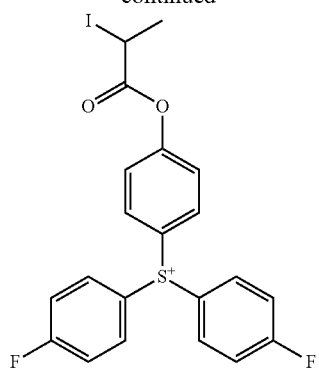
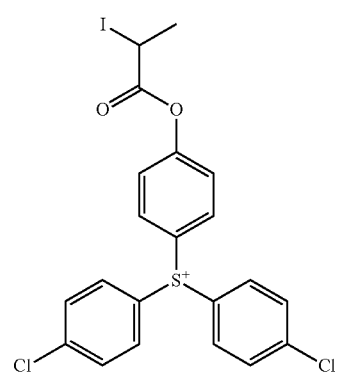
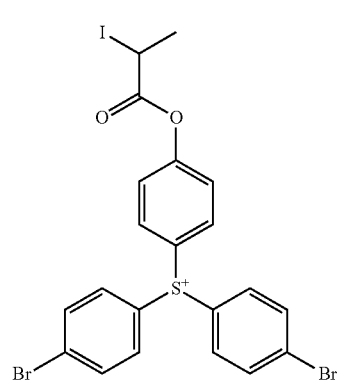
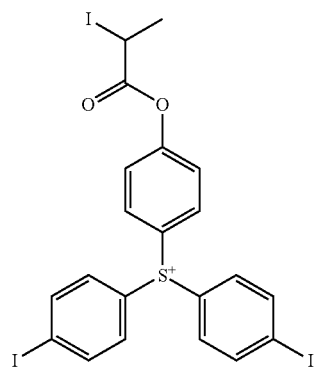

25
-continued
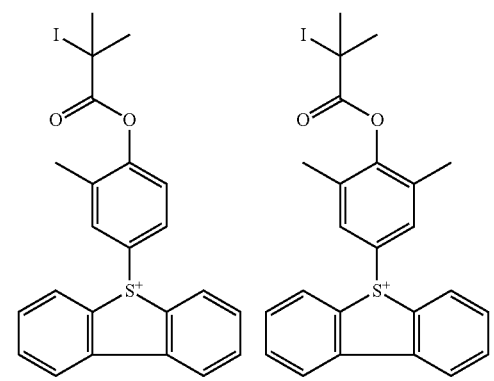
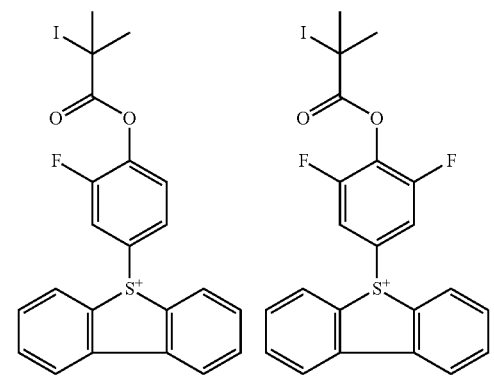
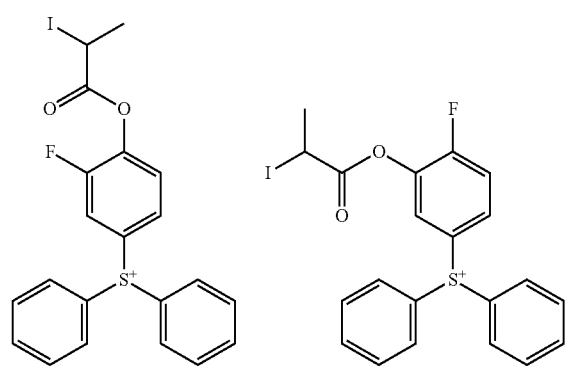
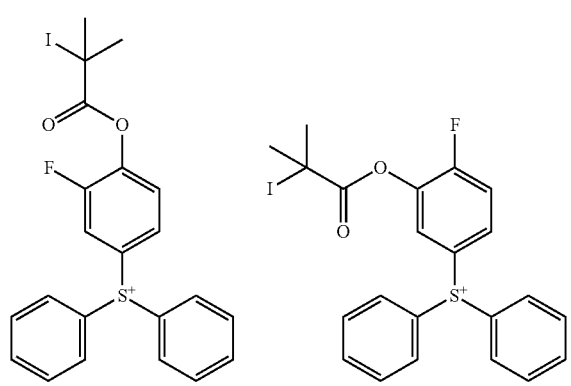
26
-continued
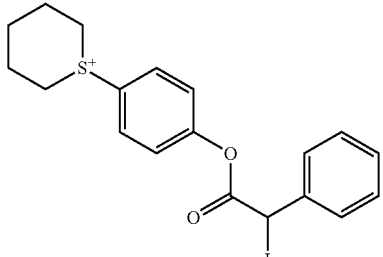
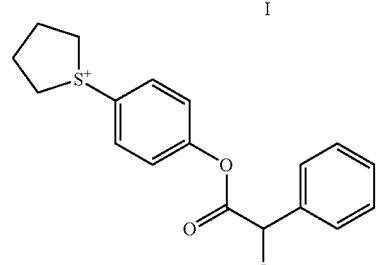
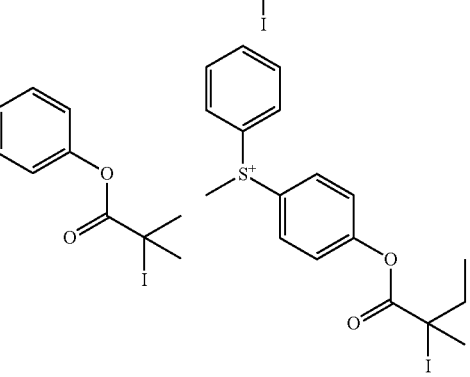
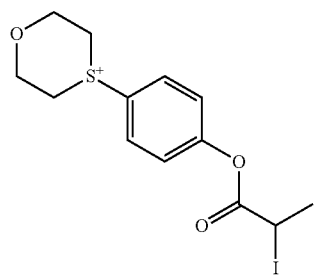
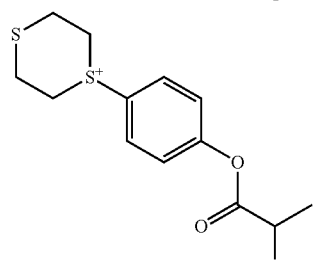
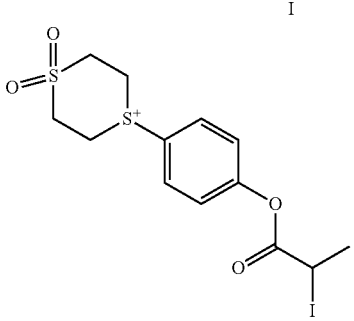

-continued
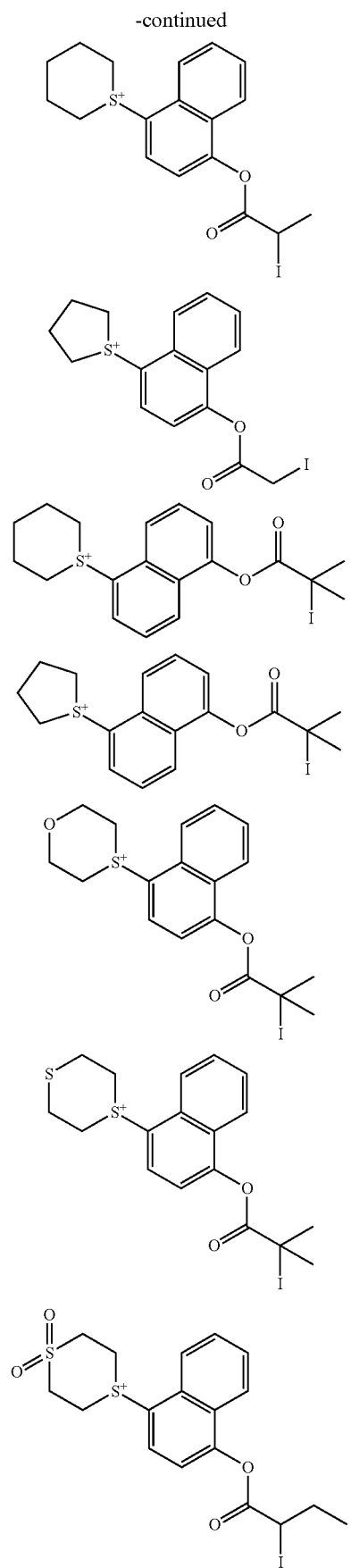
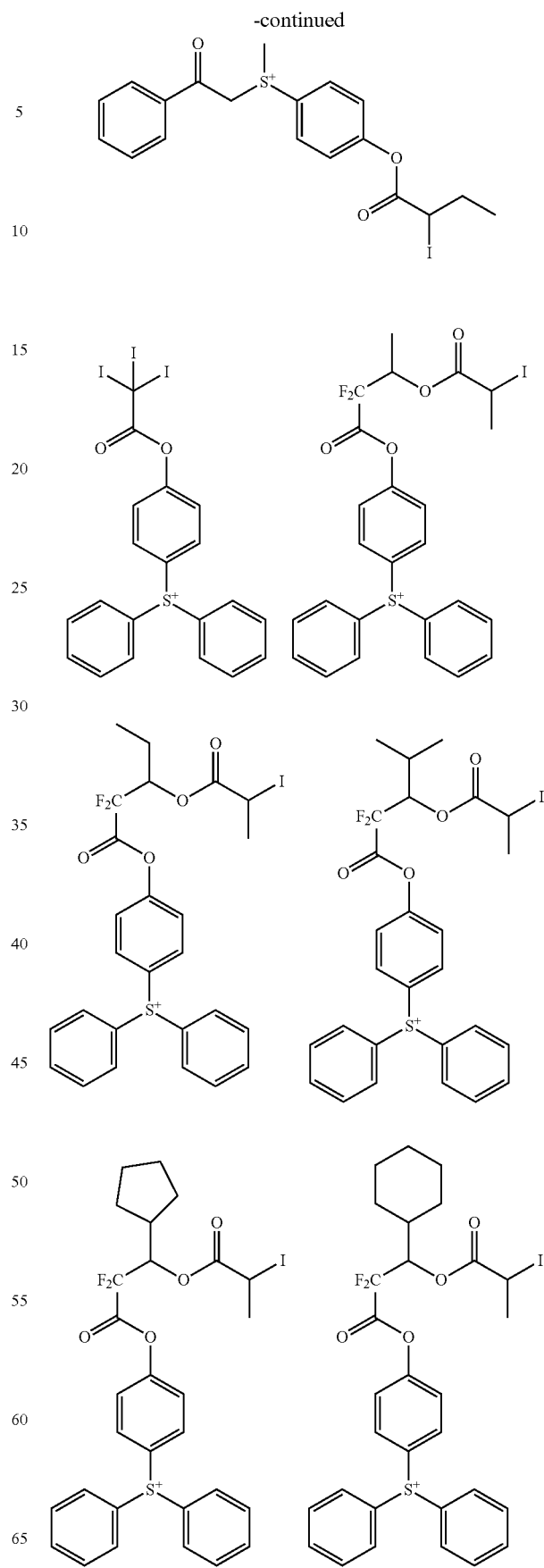

29
-continued
30
-continued
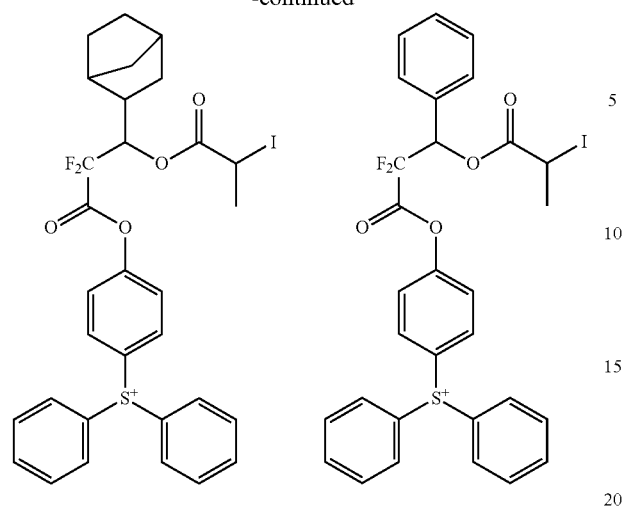
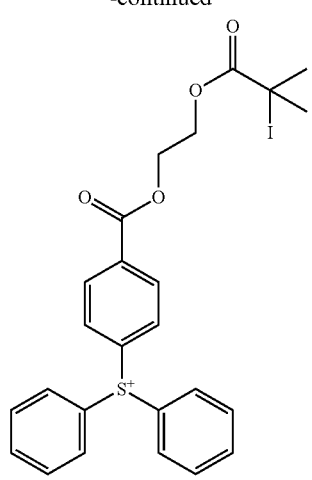
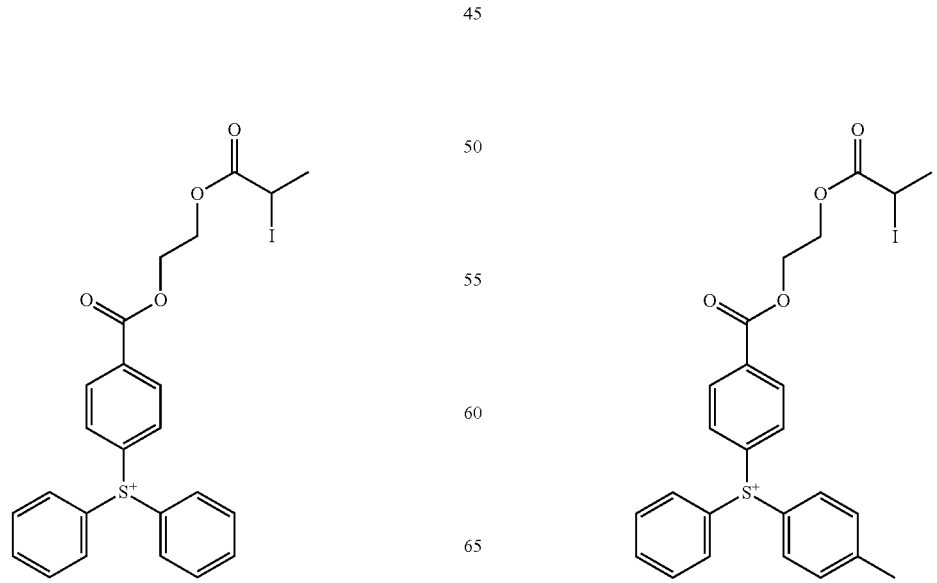

31
-continued
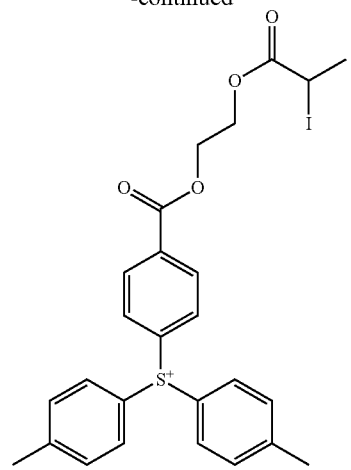
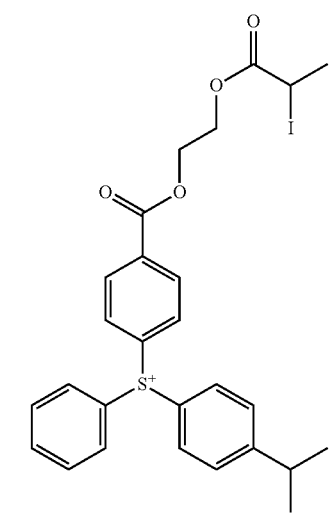
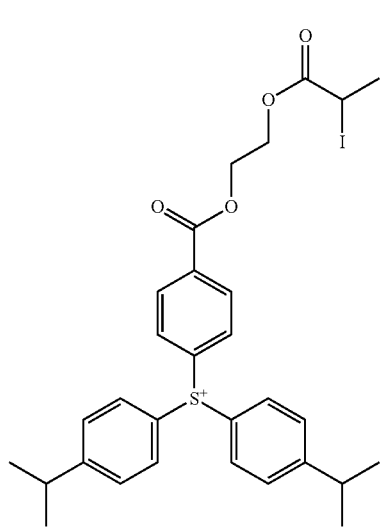
32
-continued
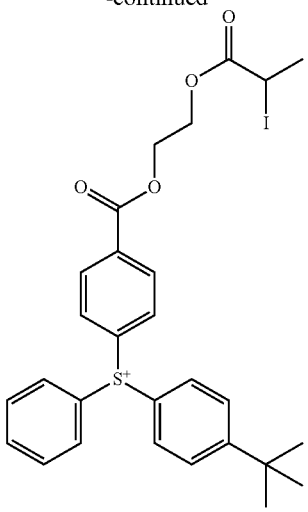
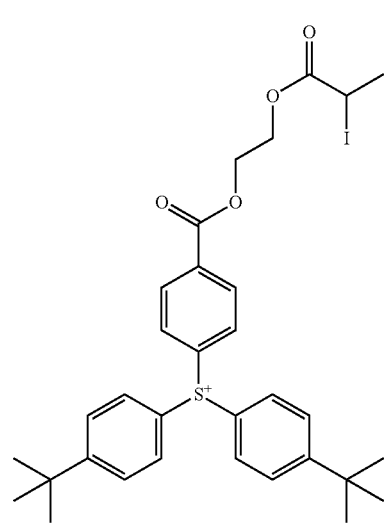
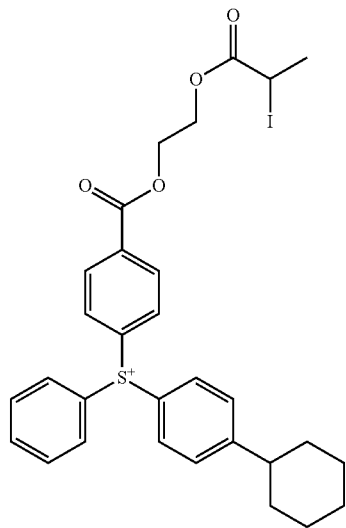

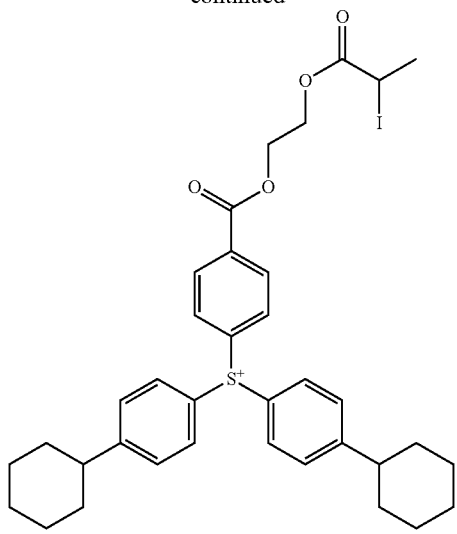
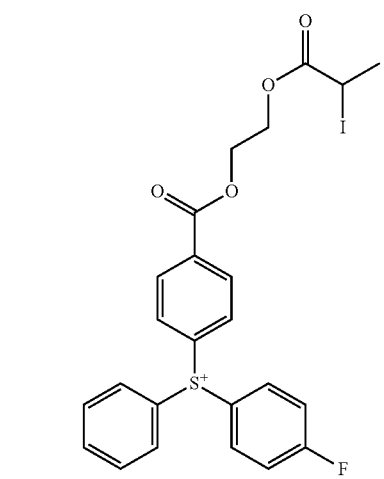
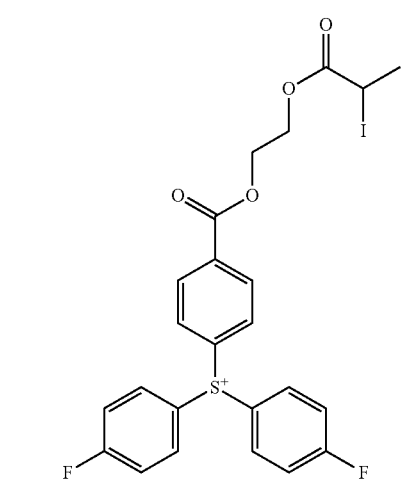
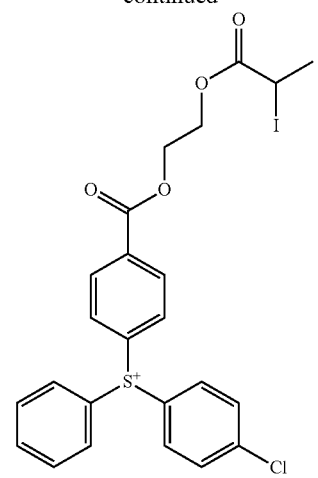
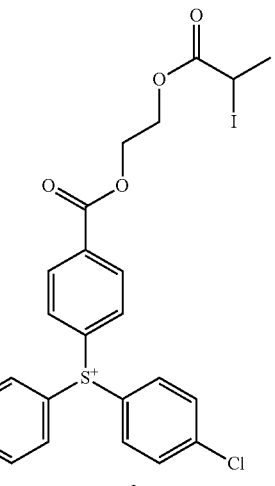
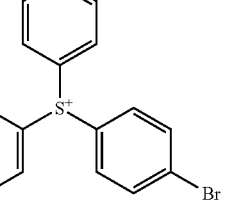
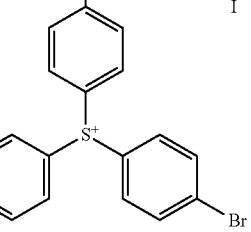

35
-continued

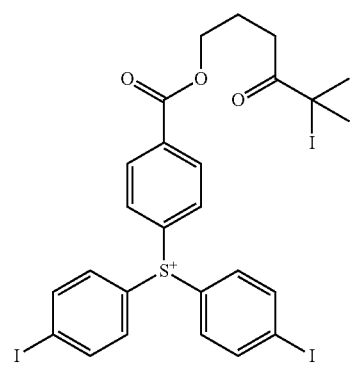
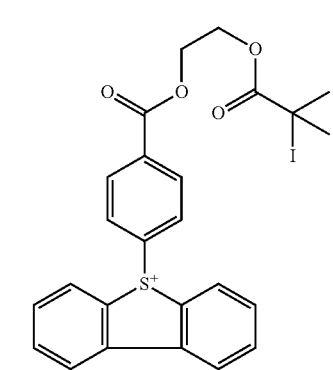
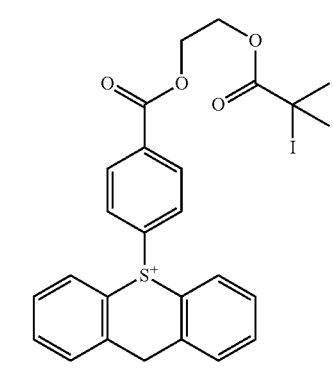
36
-continued
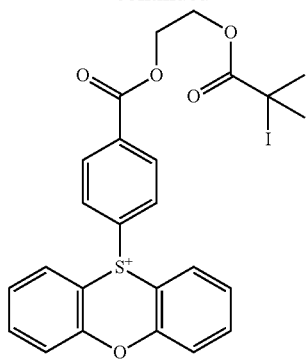
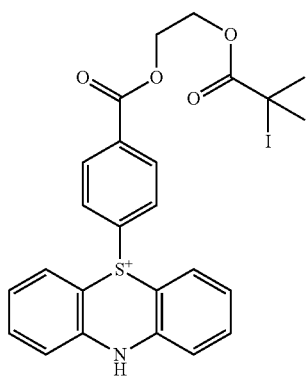
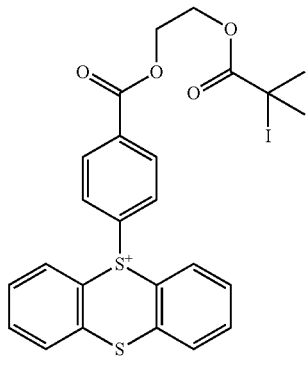
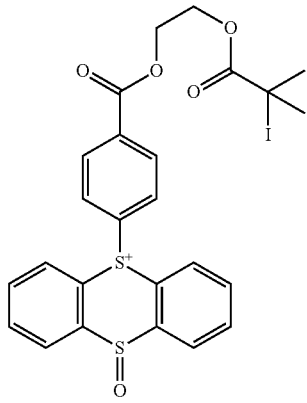

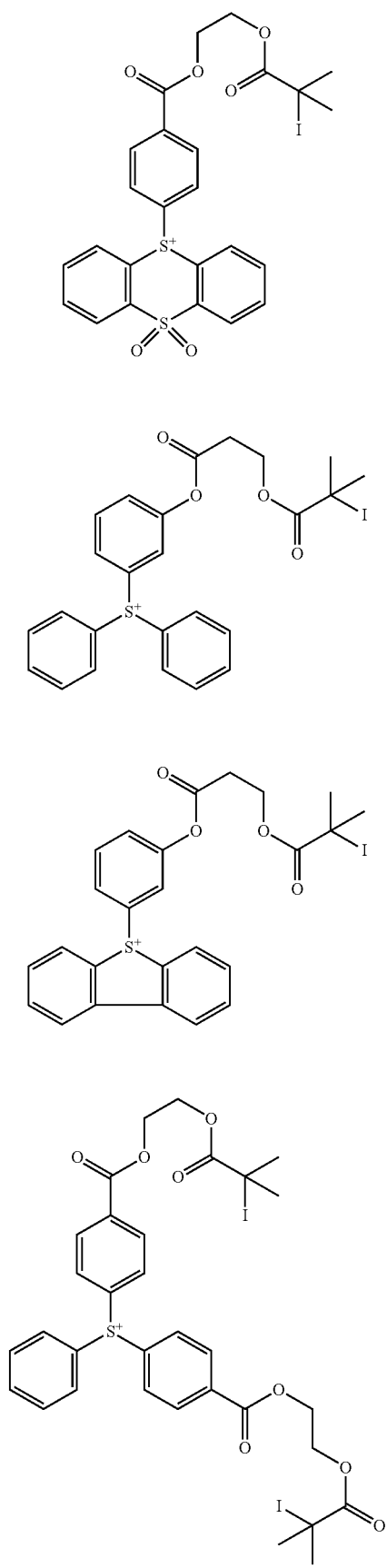
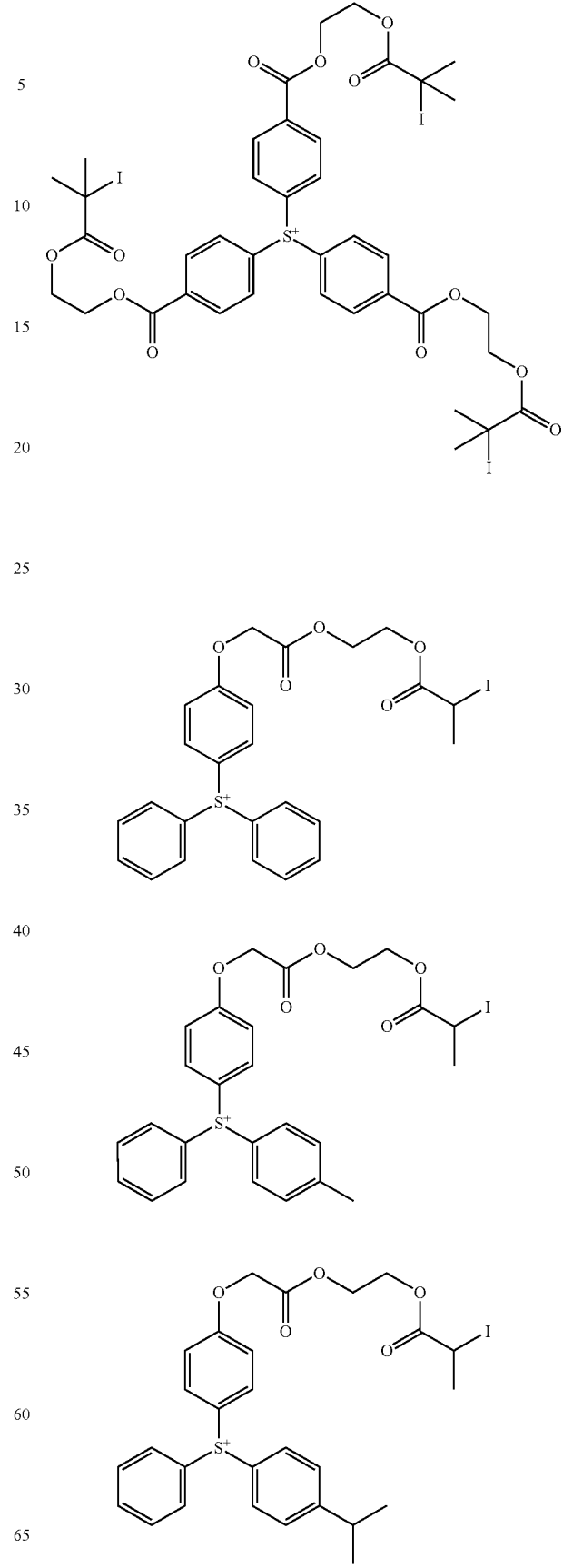

-continued
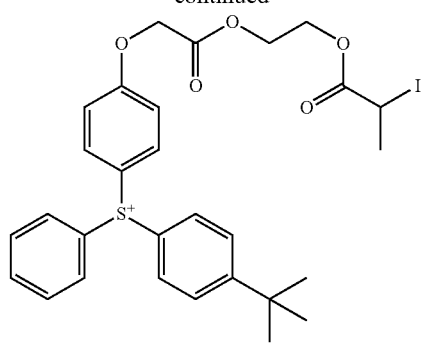
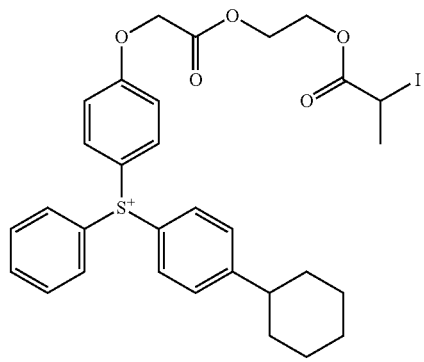
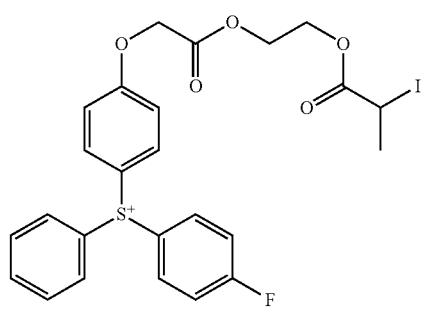
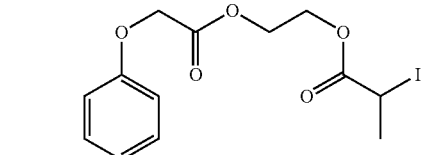
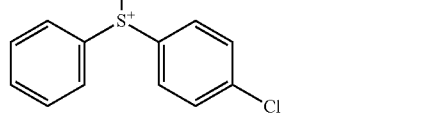
-continued
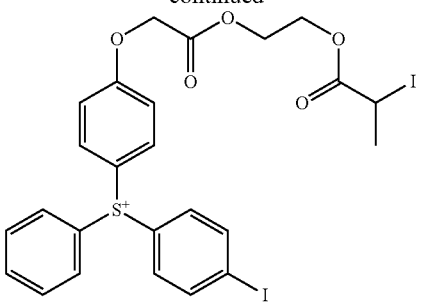
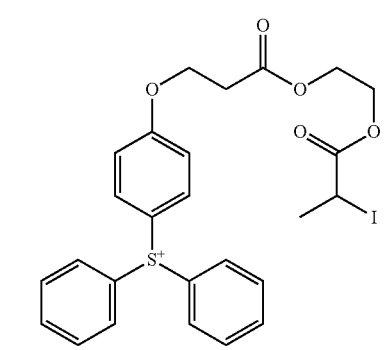
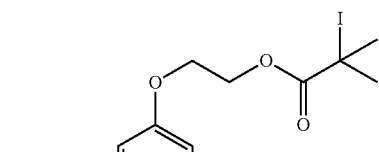
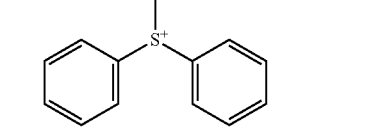
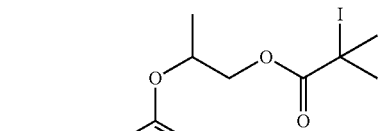
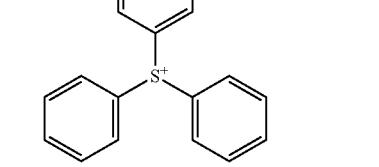
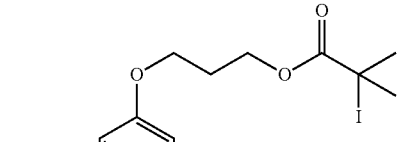
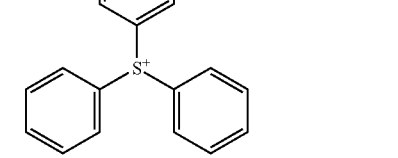

-continued
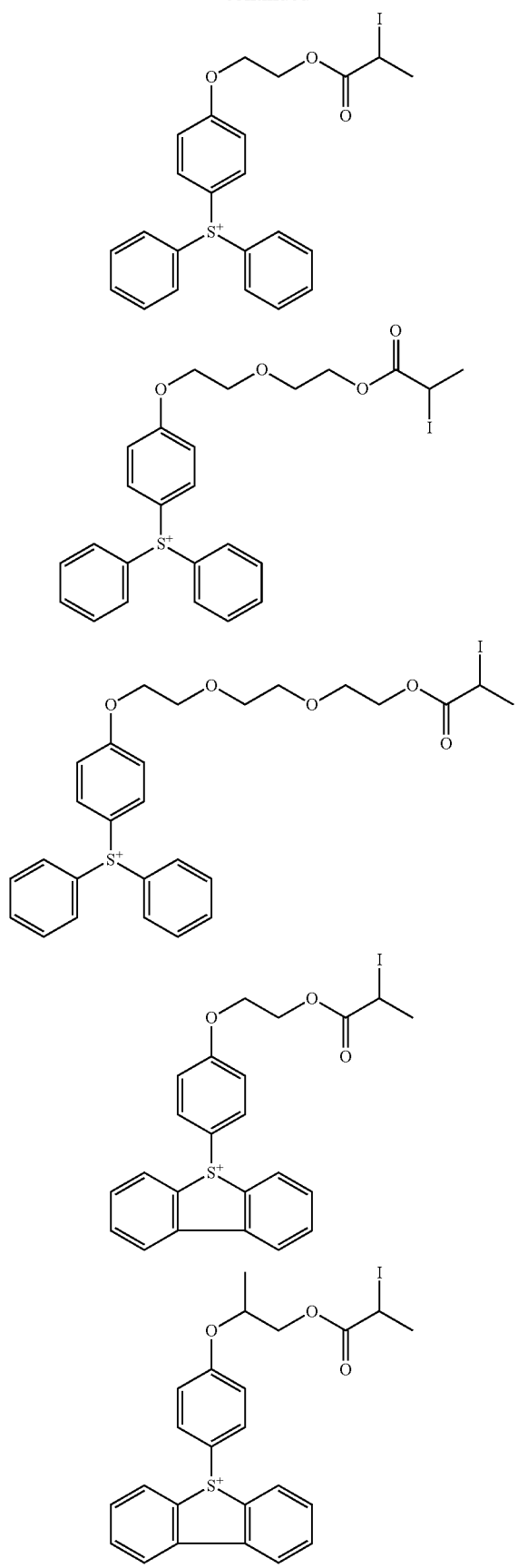
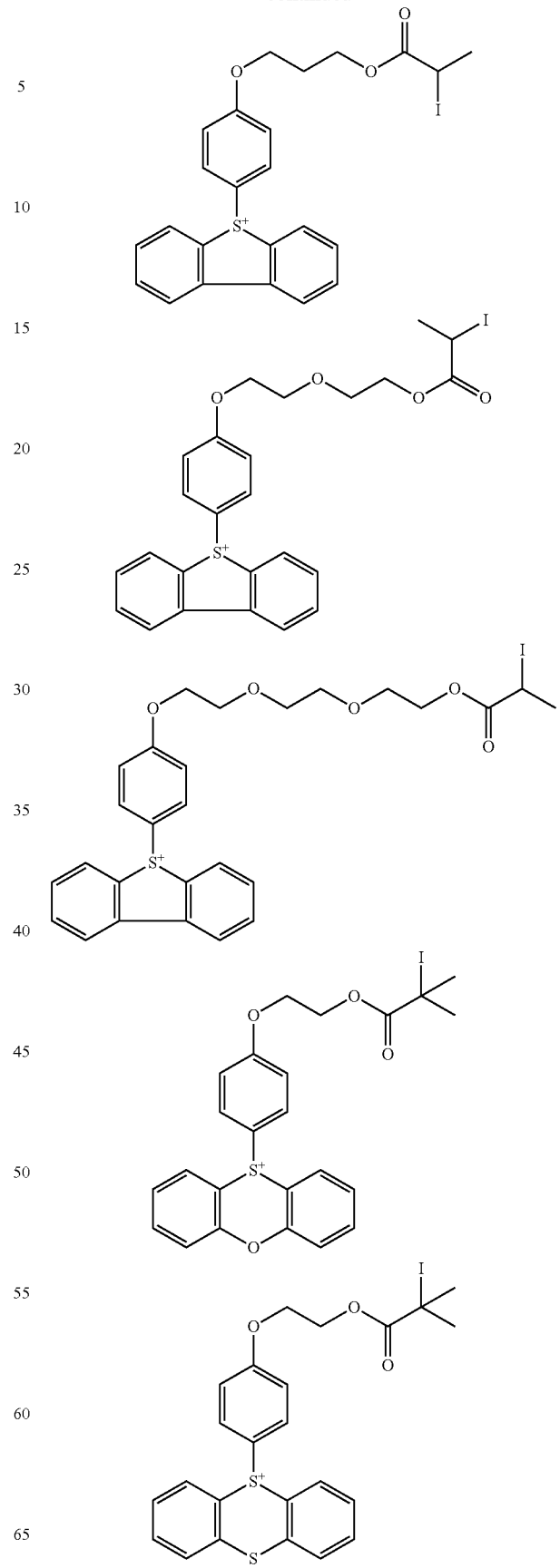

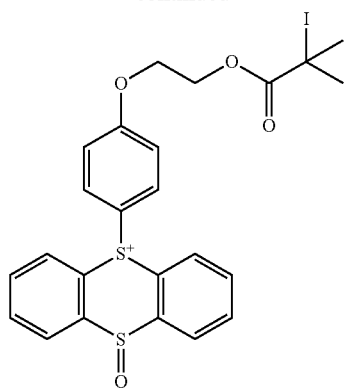
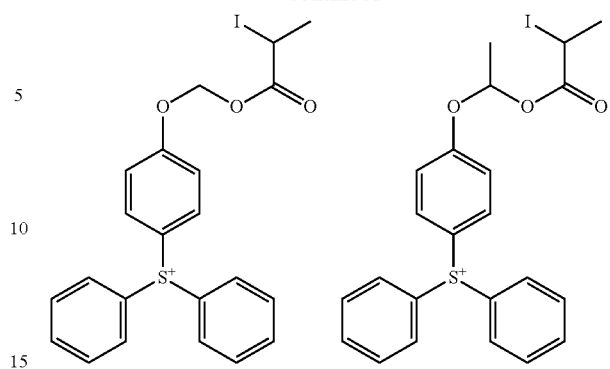
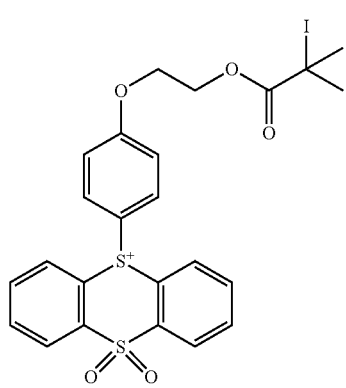
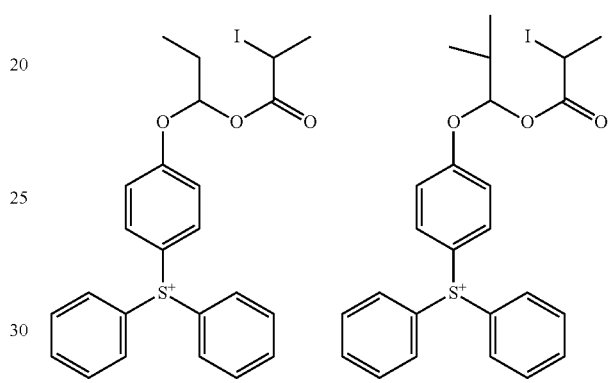
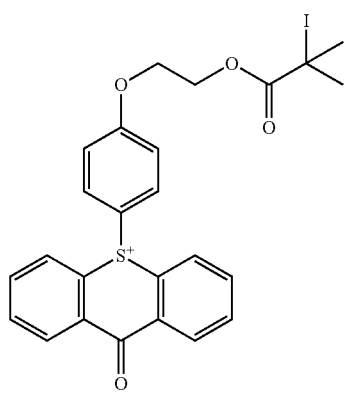
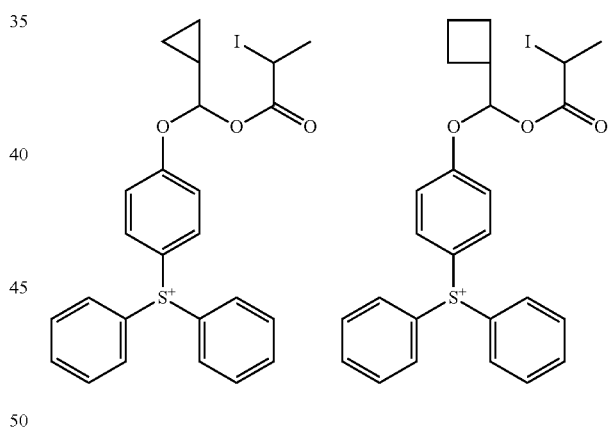
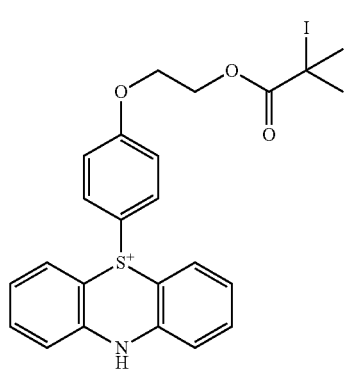
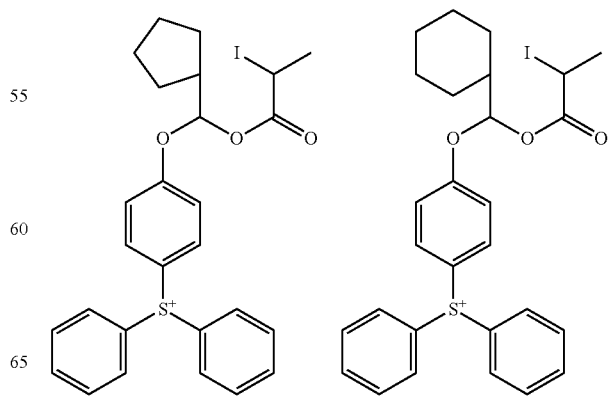

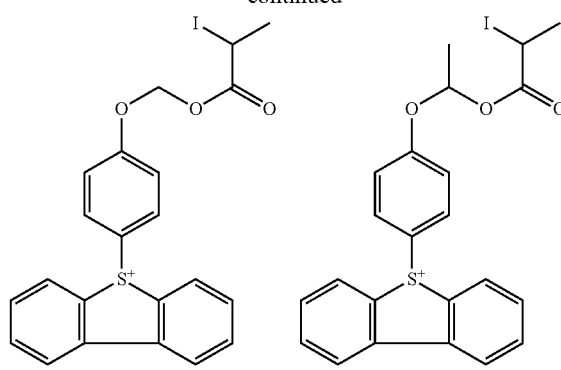
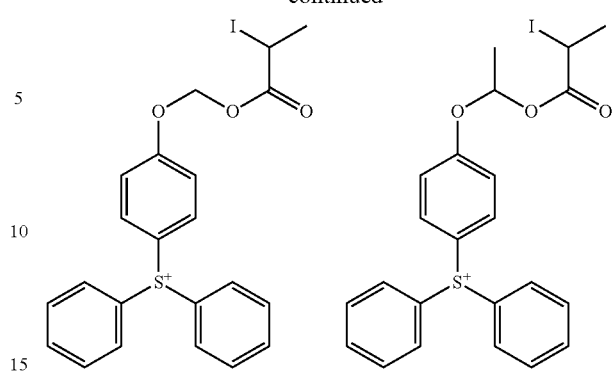
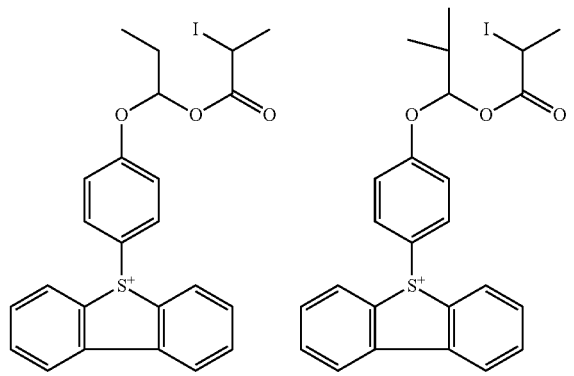
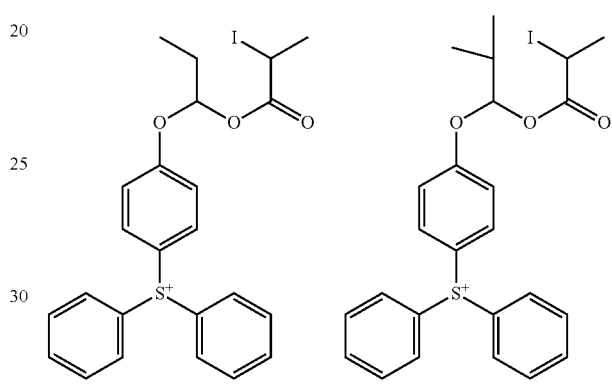
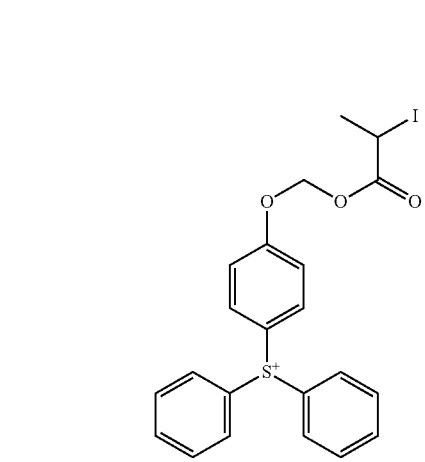
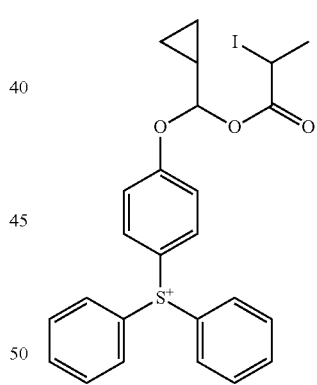
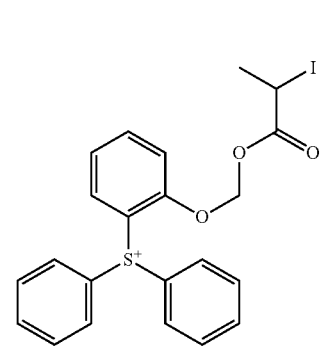
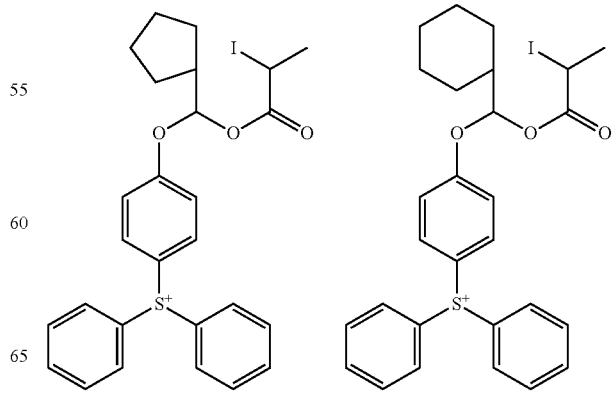

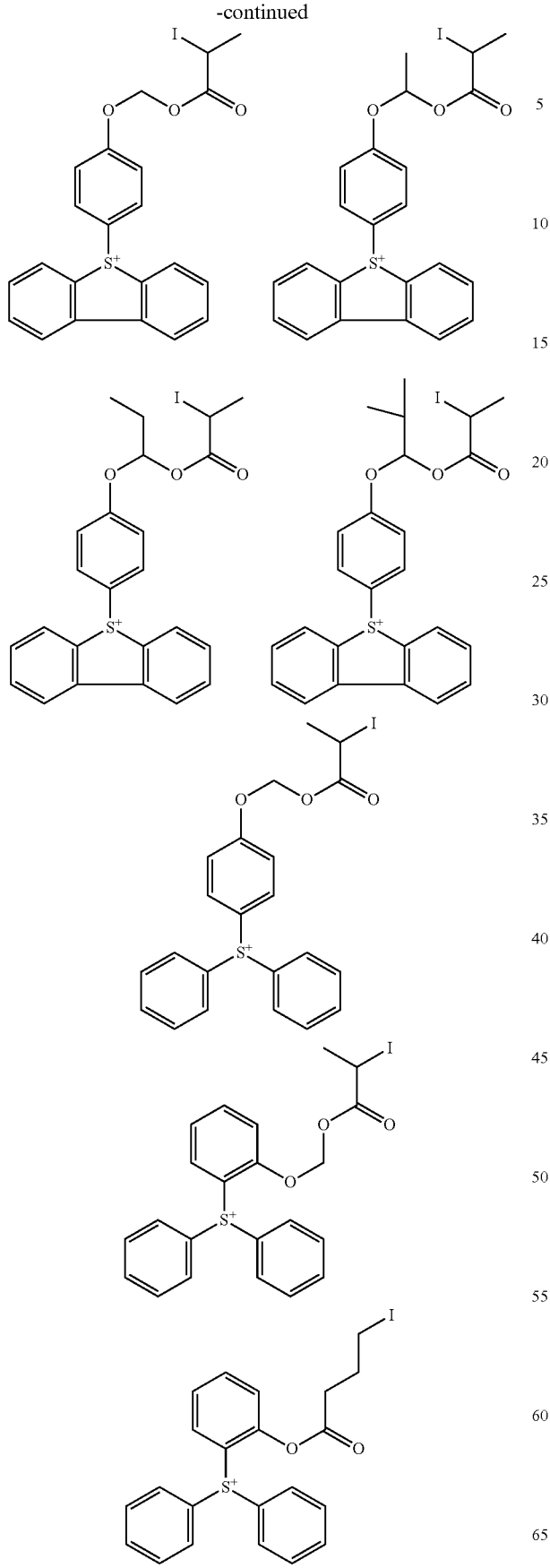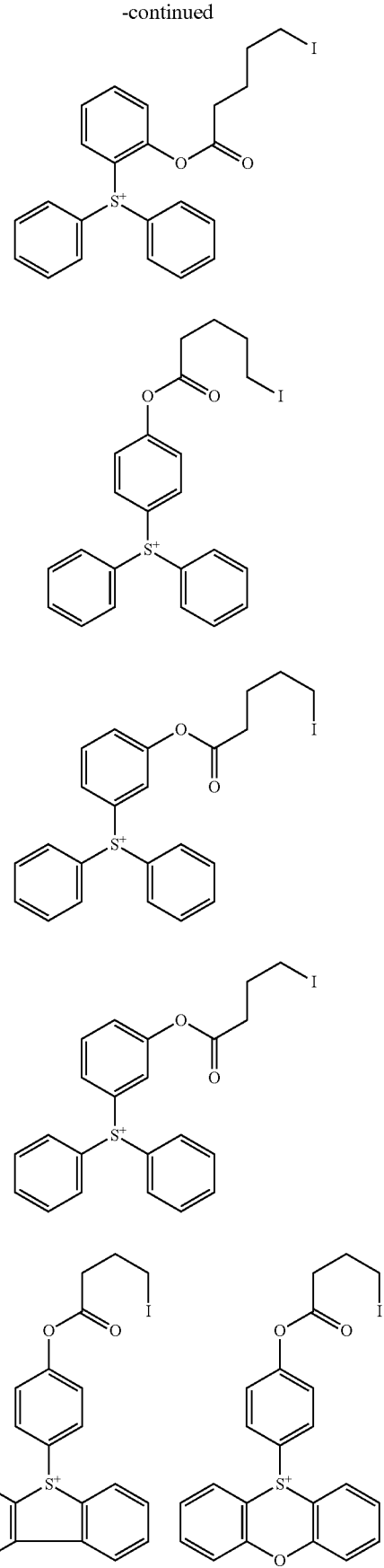

-continued
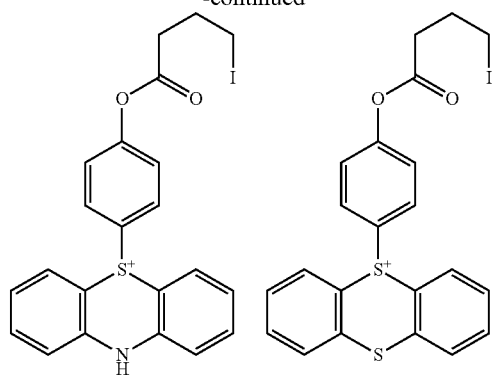
-continued
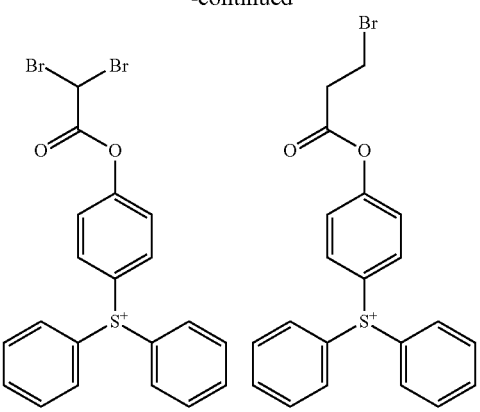

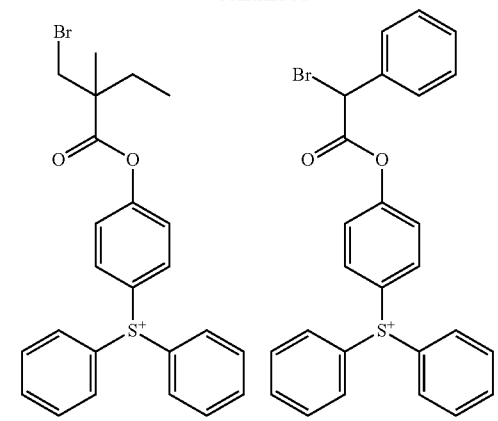
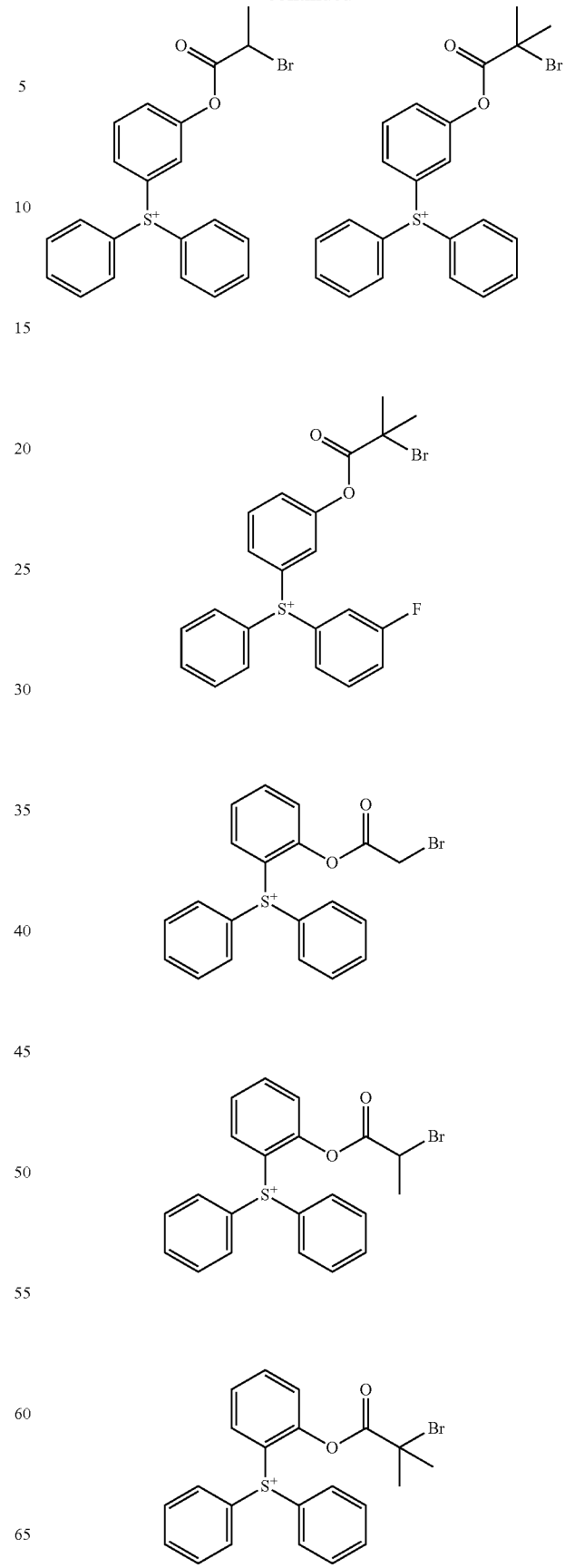

53
-continued
54
-continued
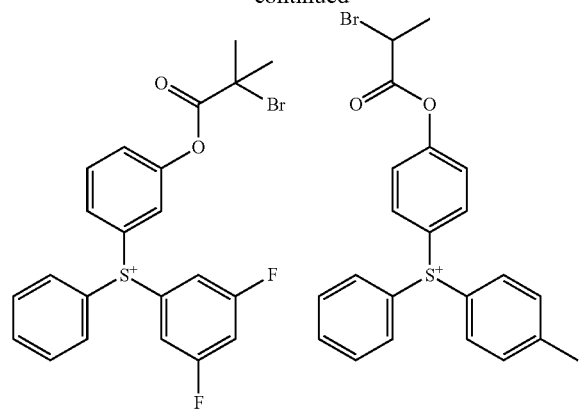
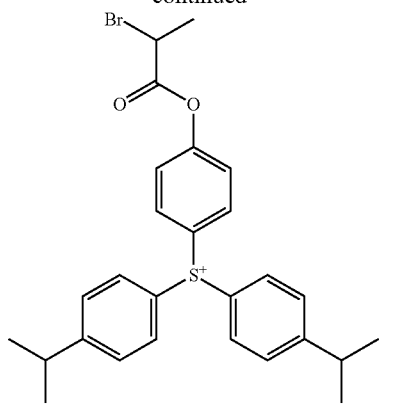
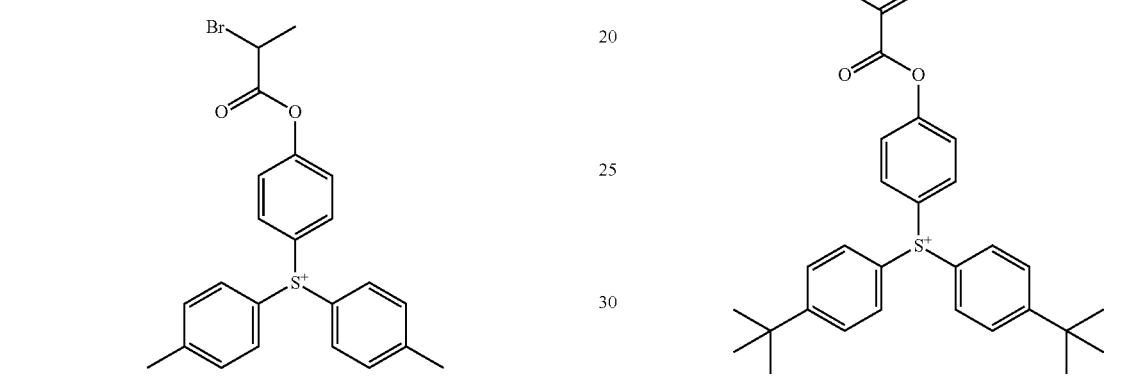
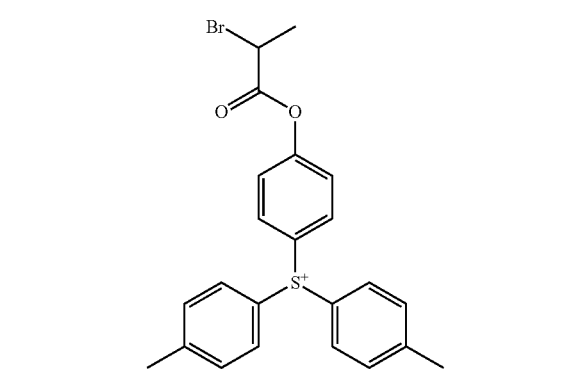
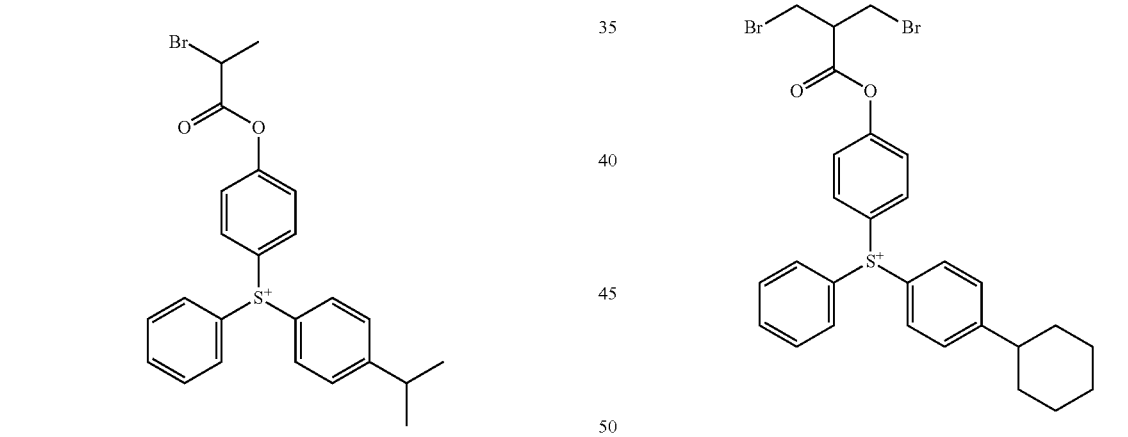
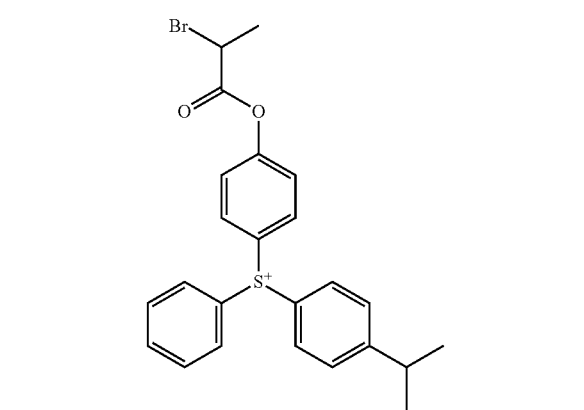
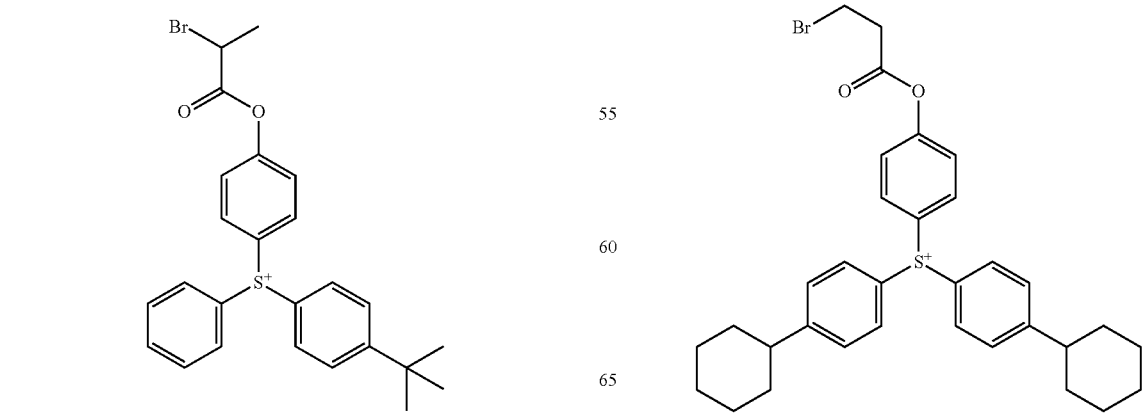
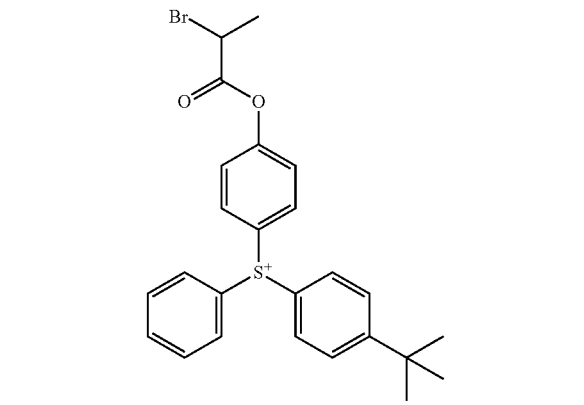

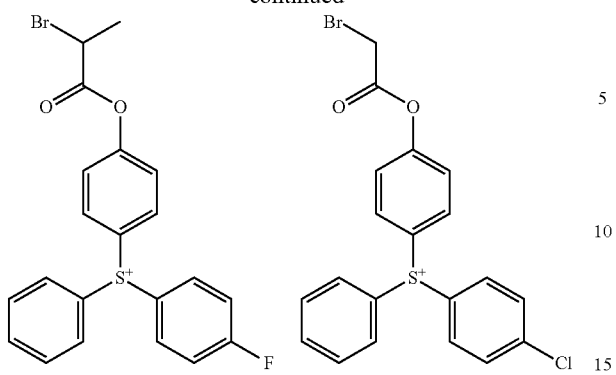
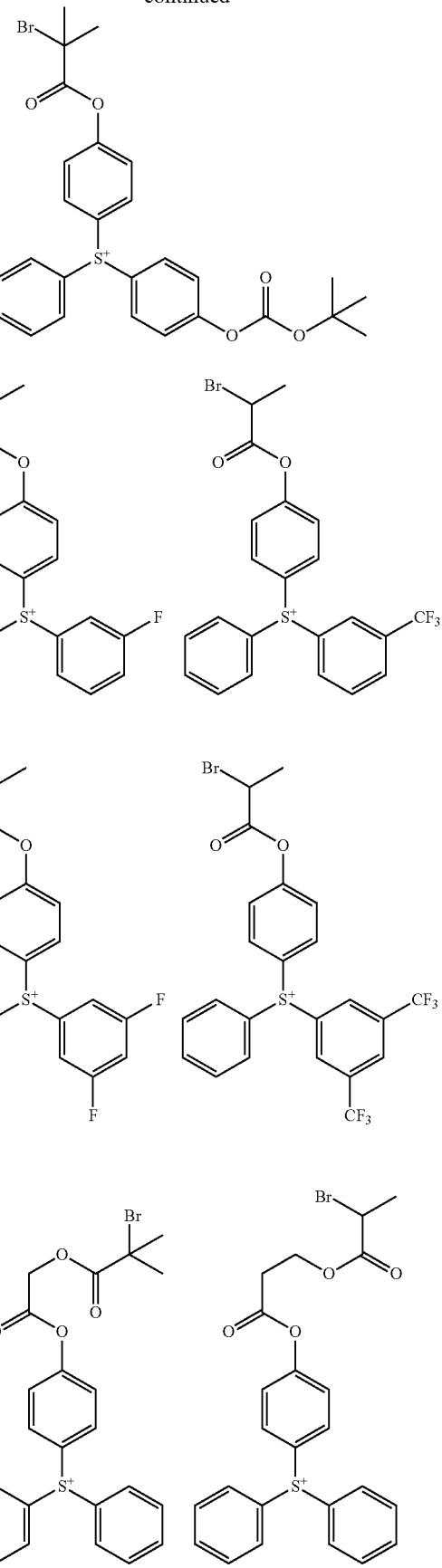

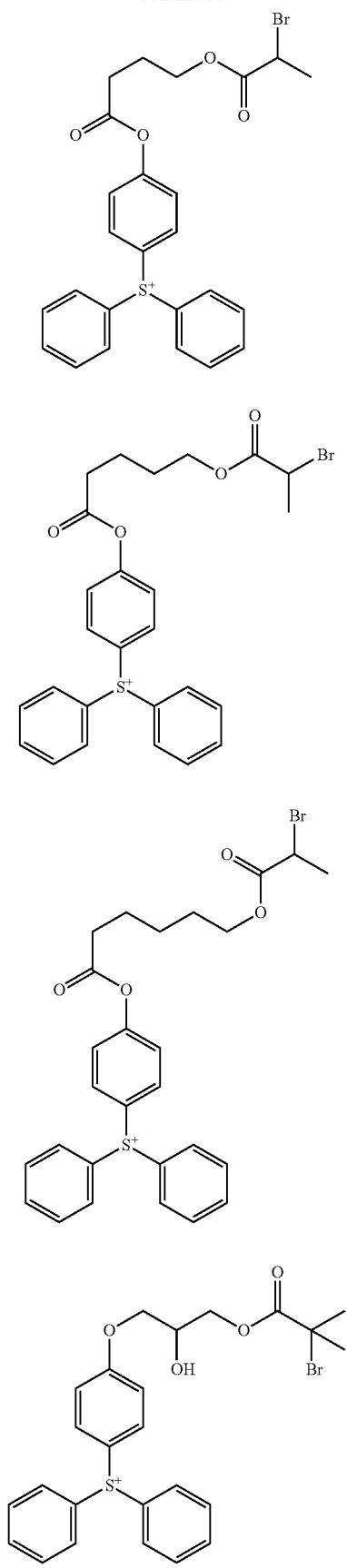
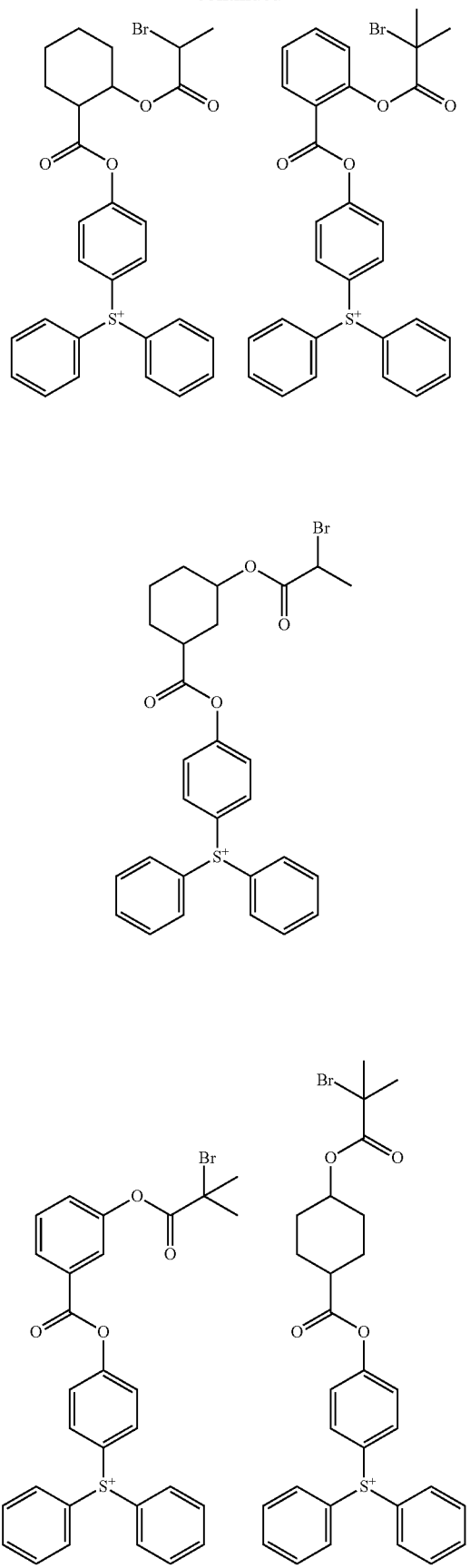

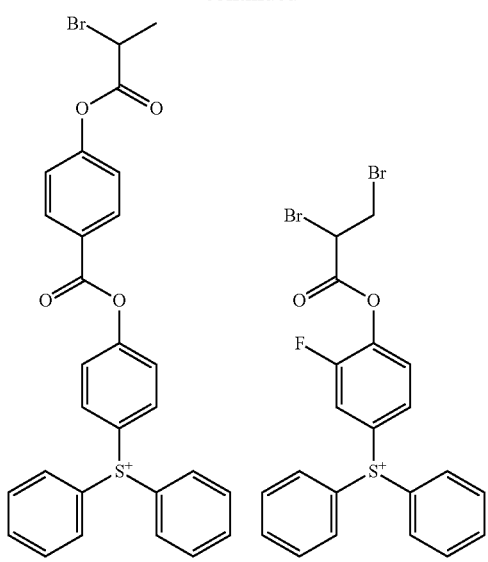 [SMILES: CC(Br)C(=O)Oc1ccc(C(=O)Oc2ccc([S+](c3ccccc3)c3ccccc3)cc2)cc1 ; O=C(Oc1ccc([S+](c2ccccc2)c2ccccc2)cc1F)C(Br)CBr]
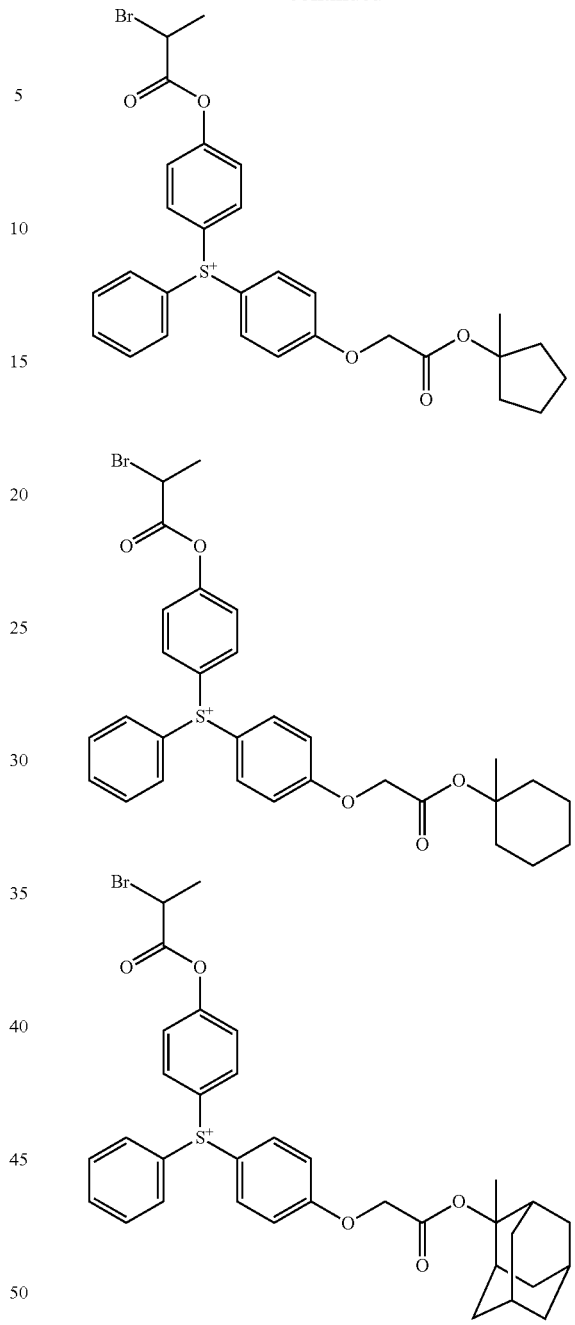
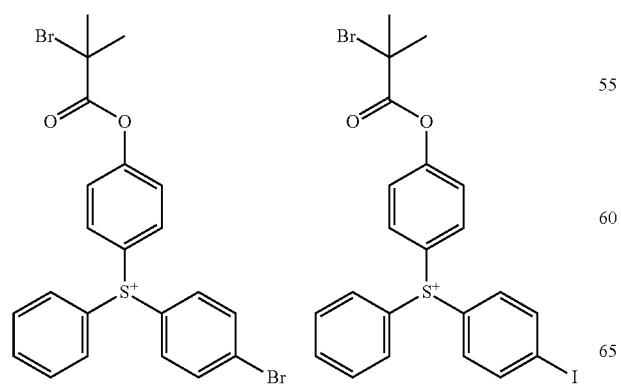

-continued
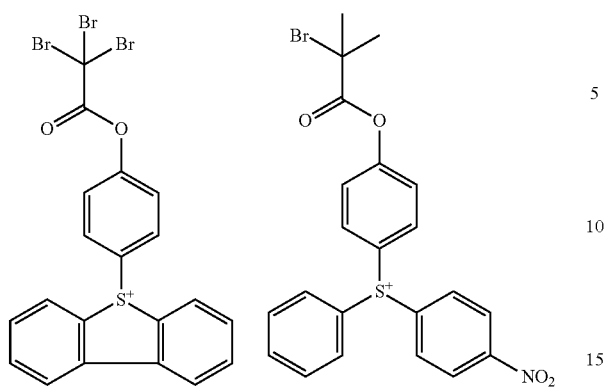
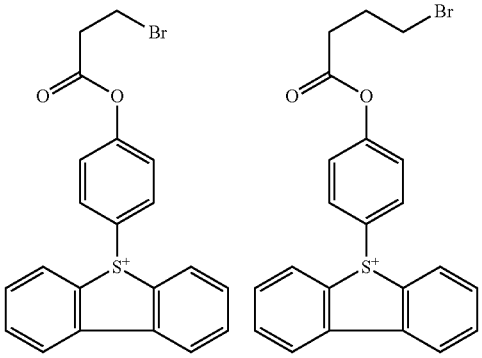
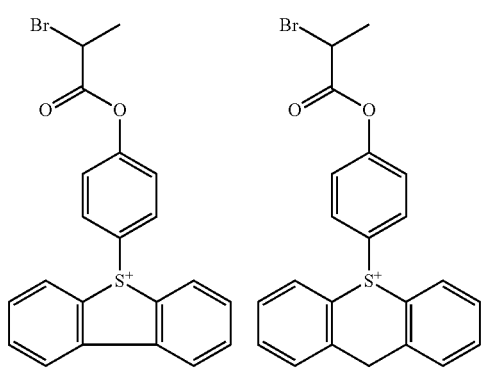
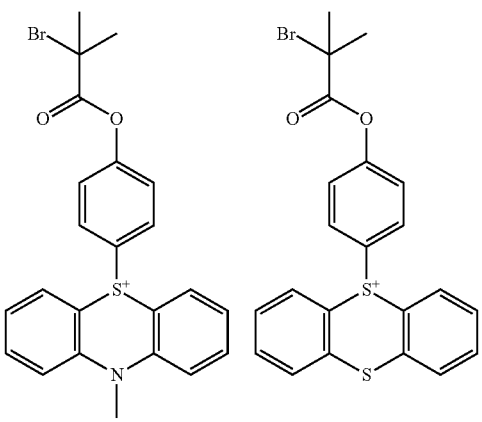
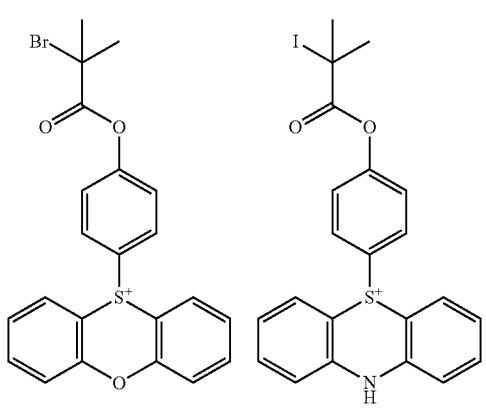
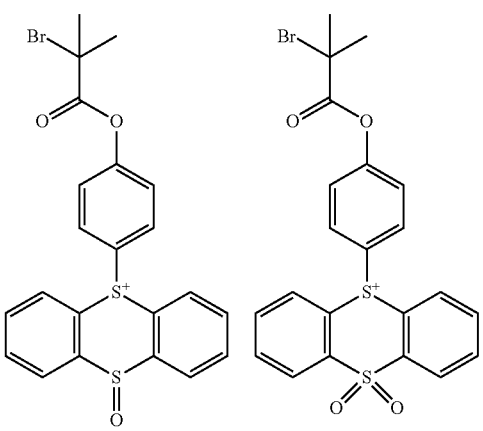
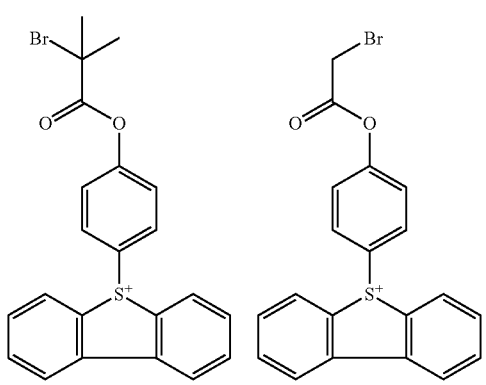
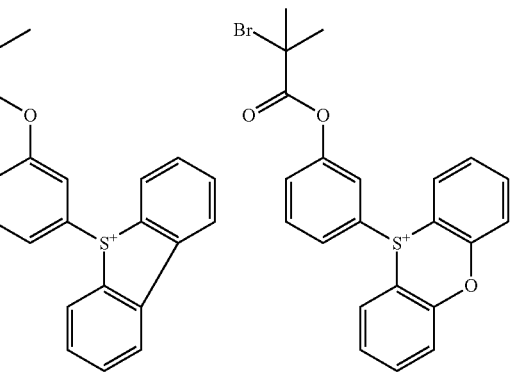

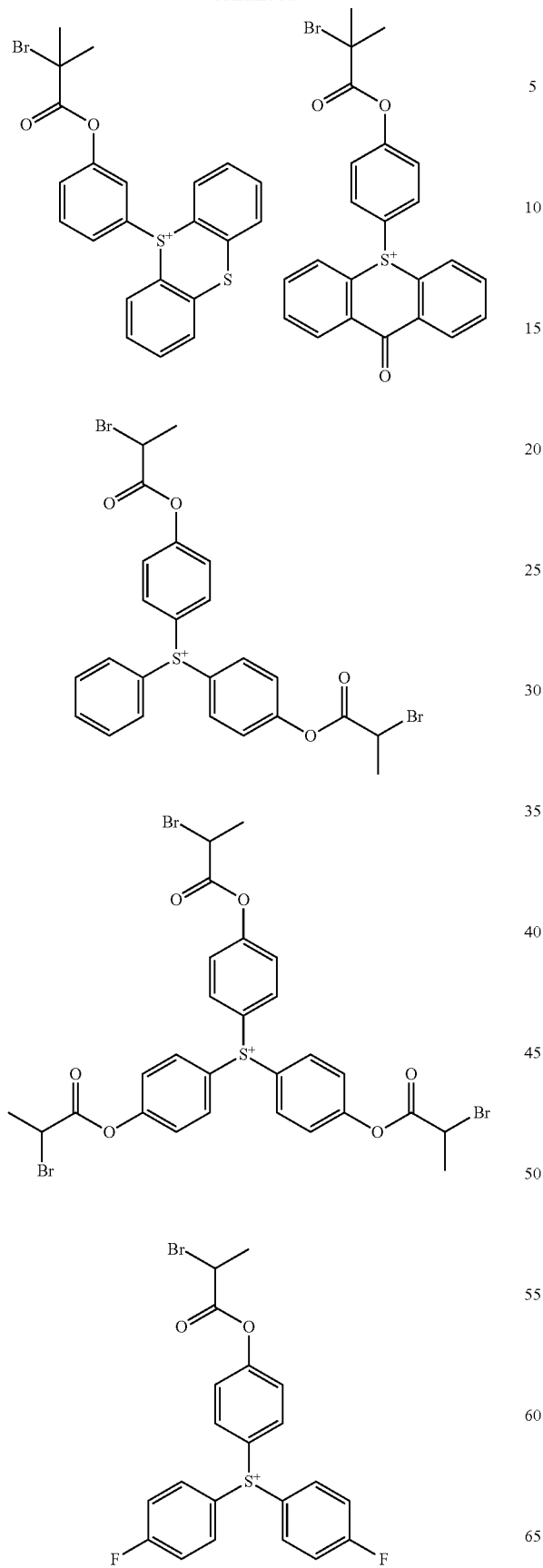
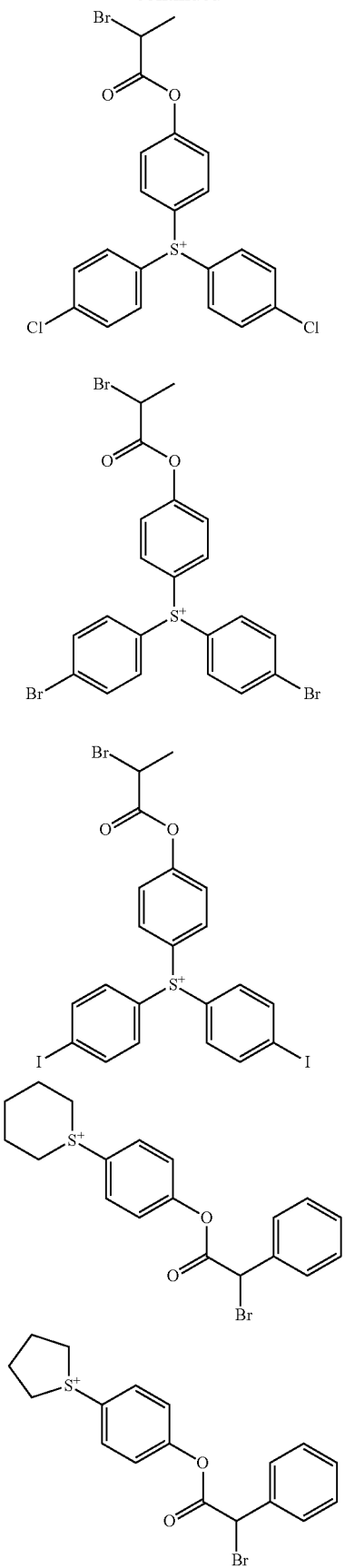

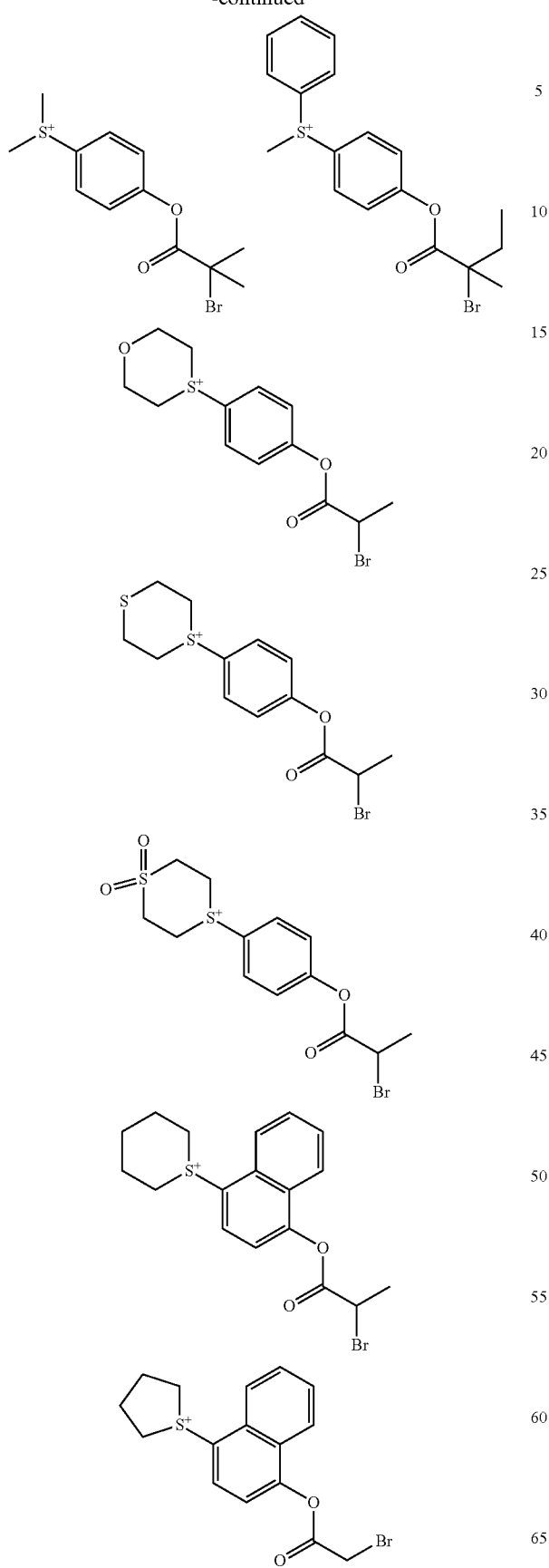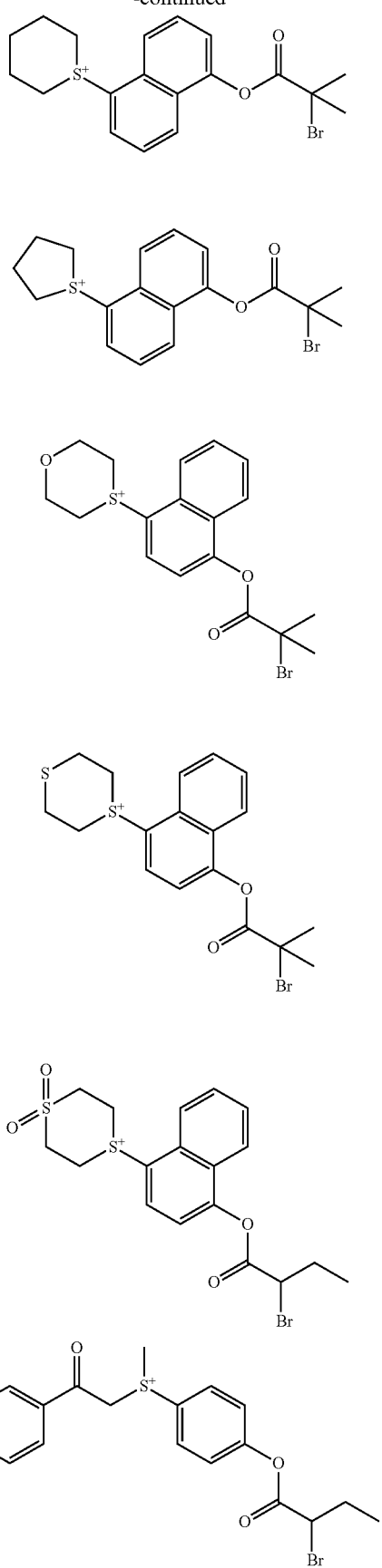

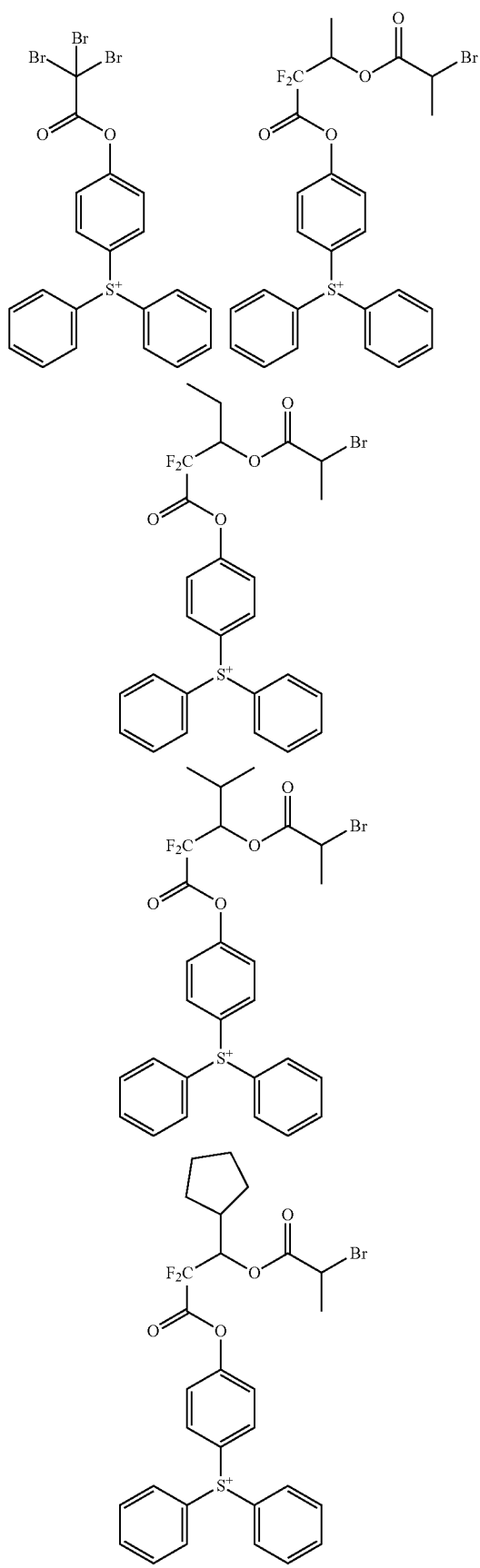
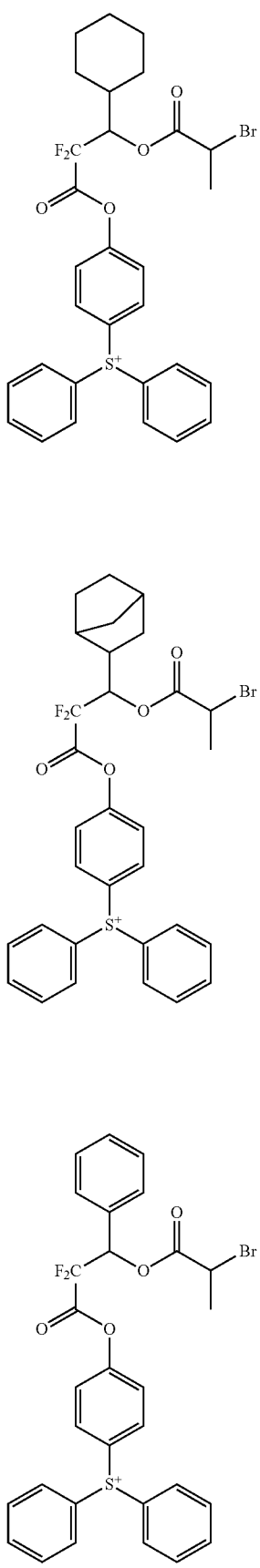

69
-continued
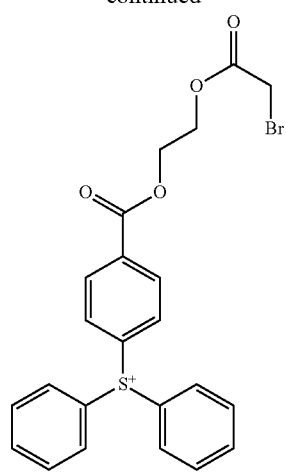
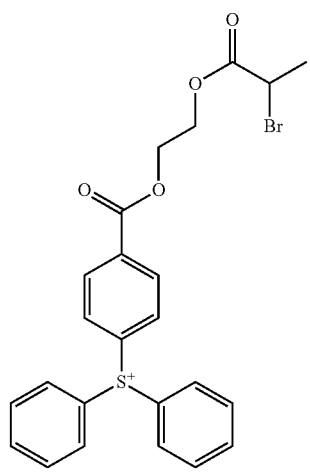
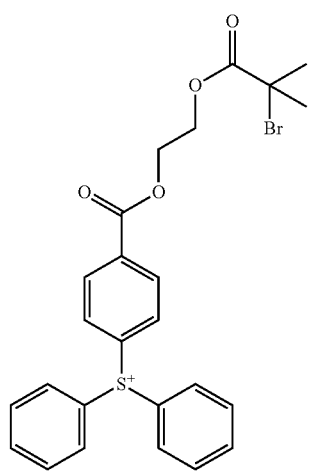
70
-continued
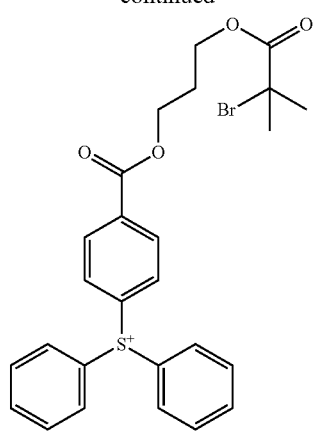
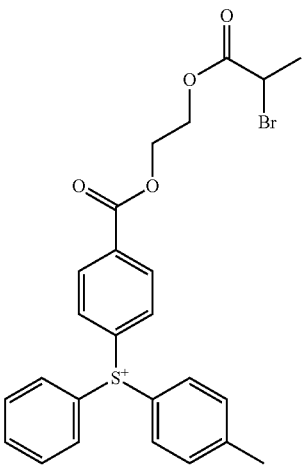
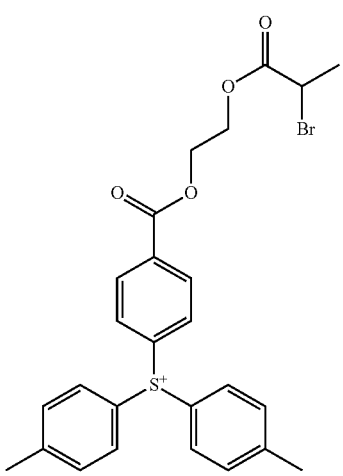

71
-continued
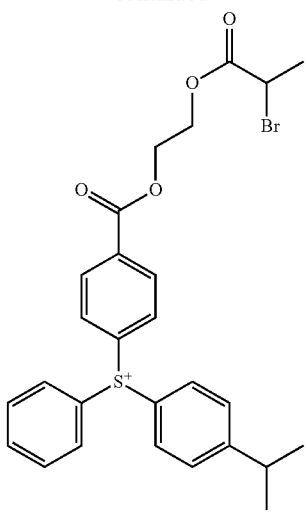 [SMILES: CC(Br)C(=O)OCCOC(=O)c1ccc([S+](c2ccccc2)c2ccc(C(C)C)cc2)cc1]
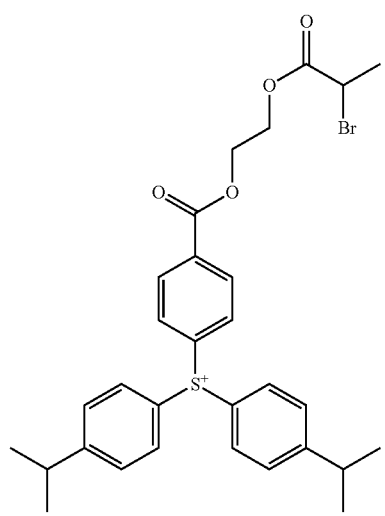
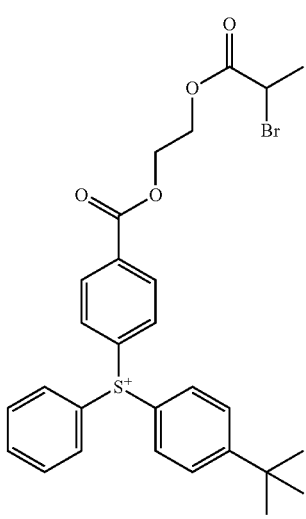
72
-continued
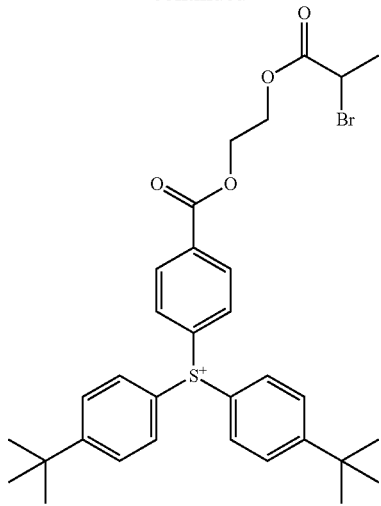
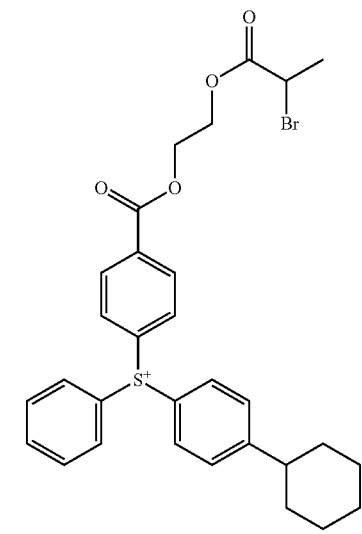
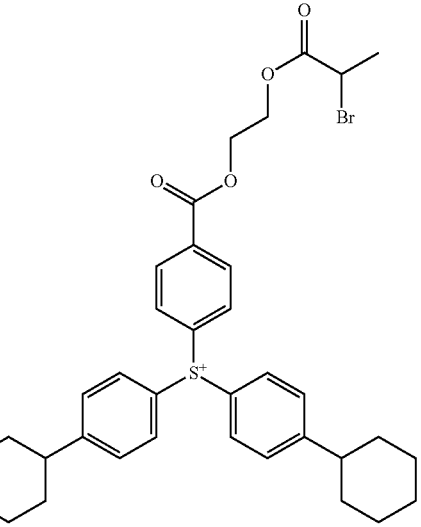

73
-continued
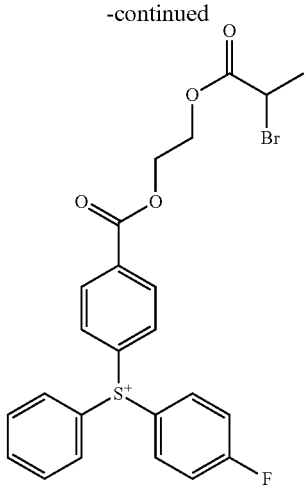
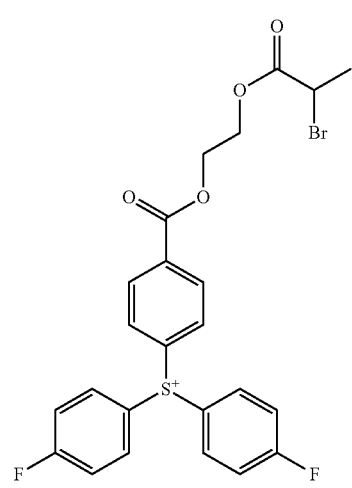
74
-continued
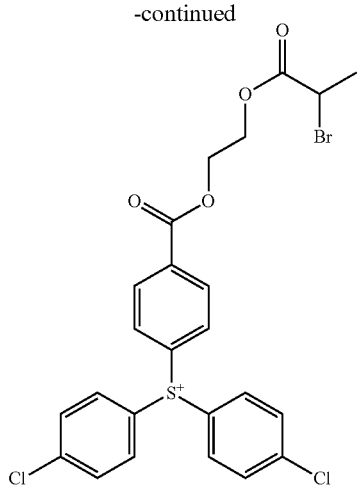
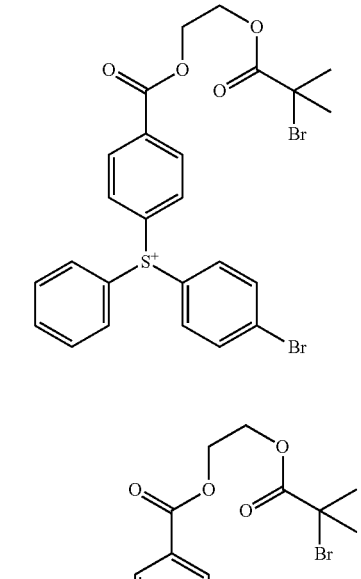
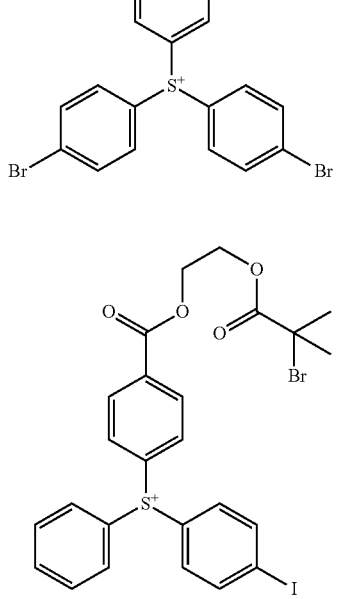

-continued
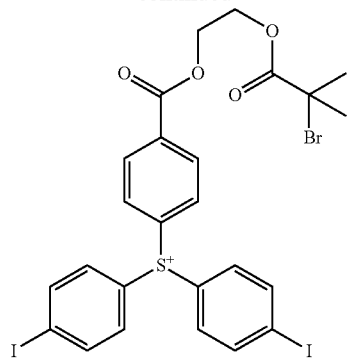
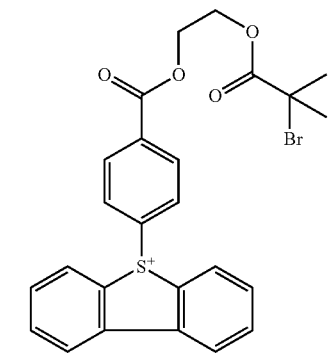
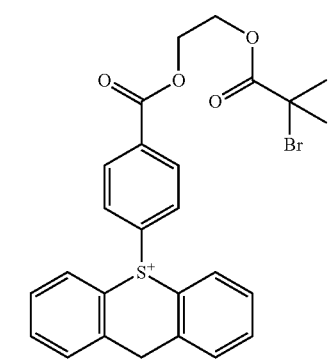
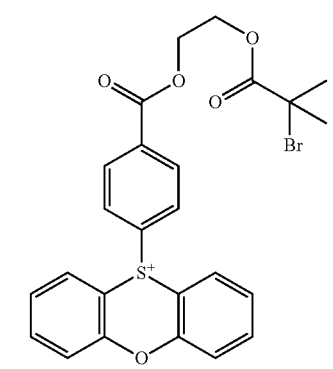
-continued
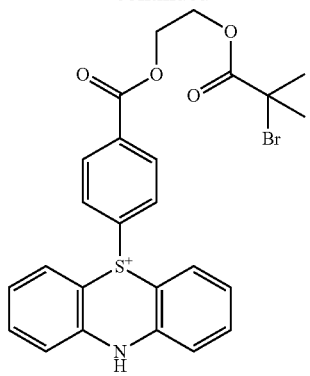
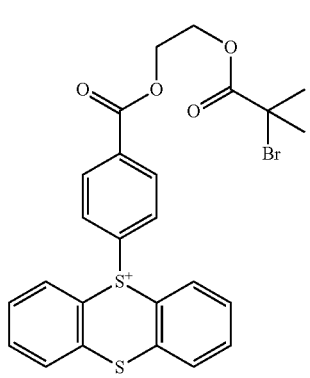
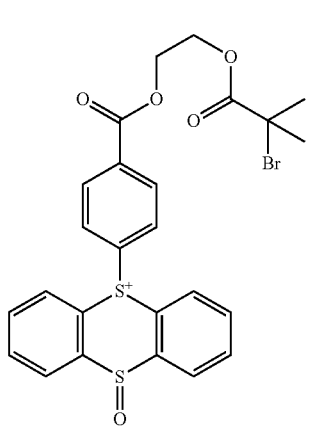
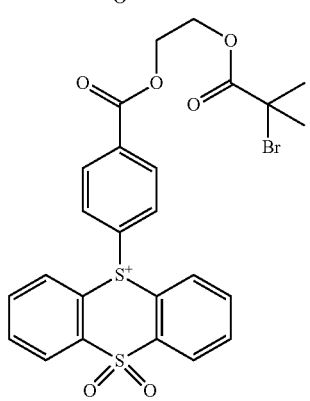

77
-continued
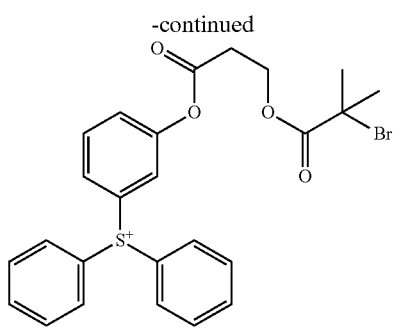
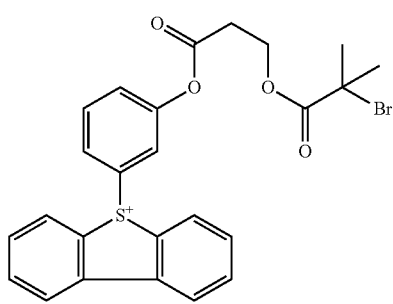
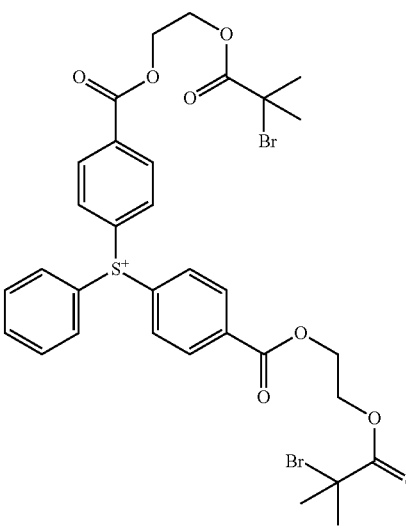
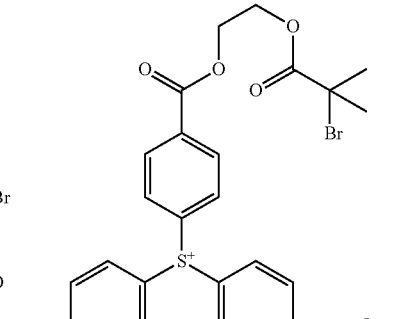
78
-continued
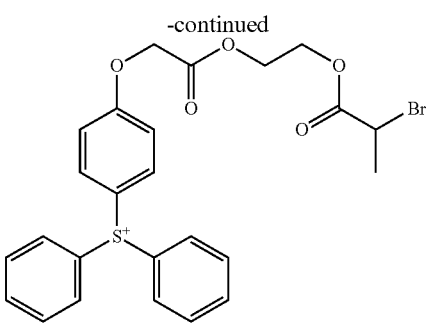
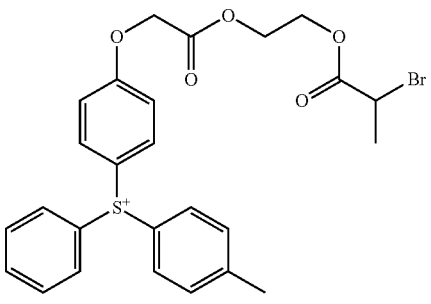
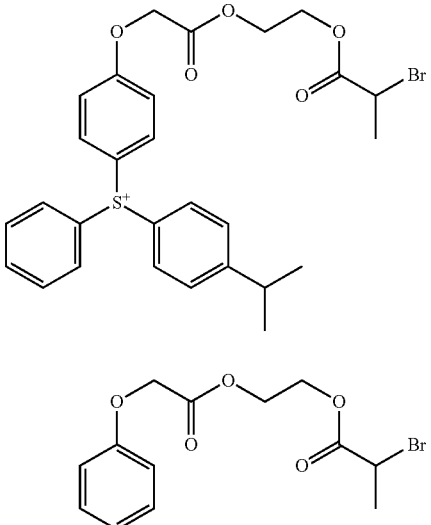
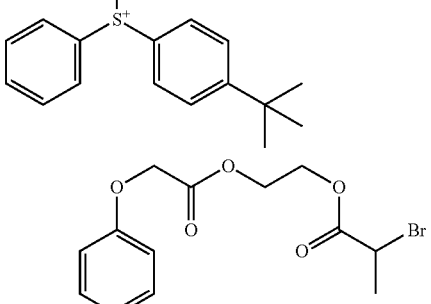
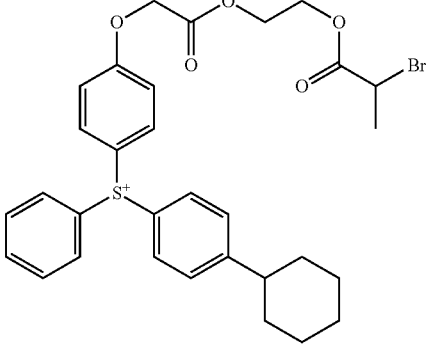

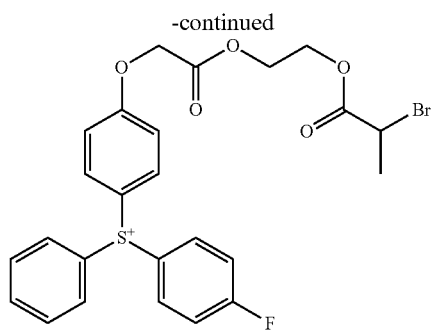
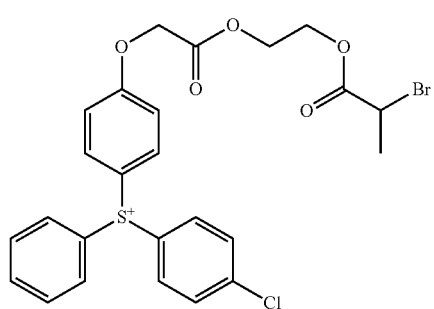
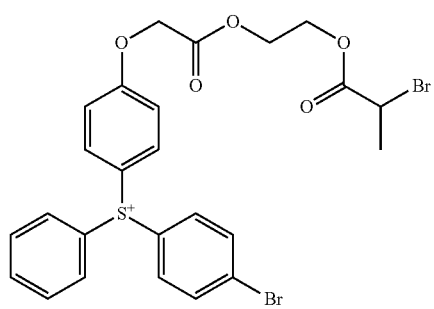
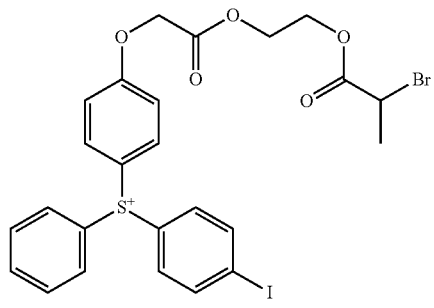
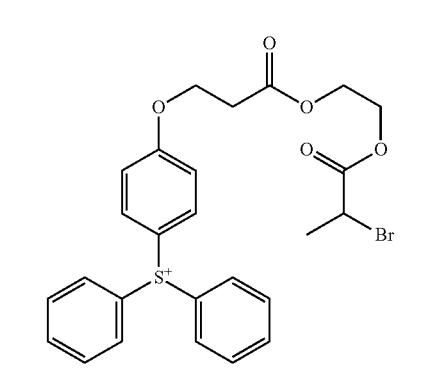
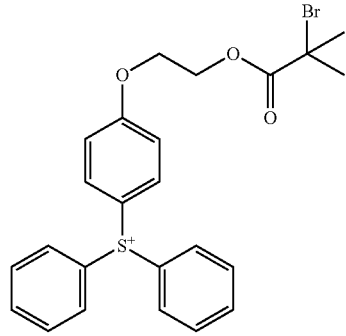
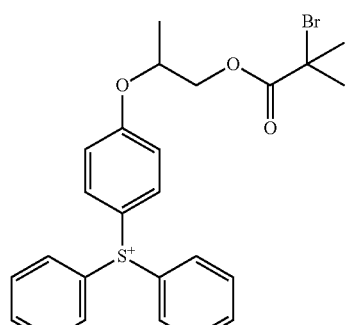
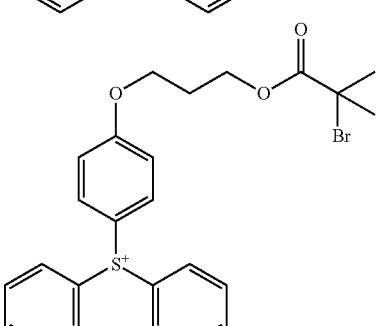
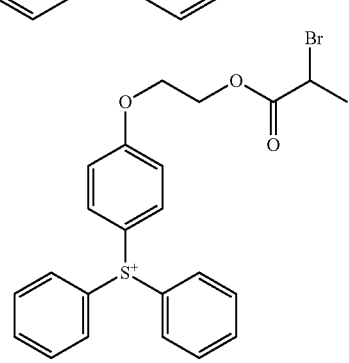
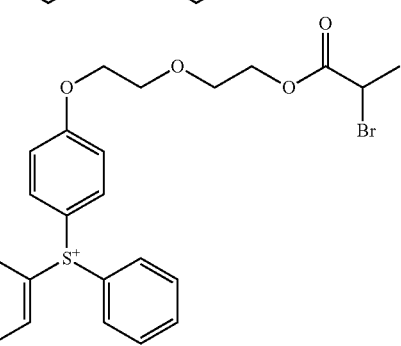

81
-continued
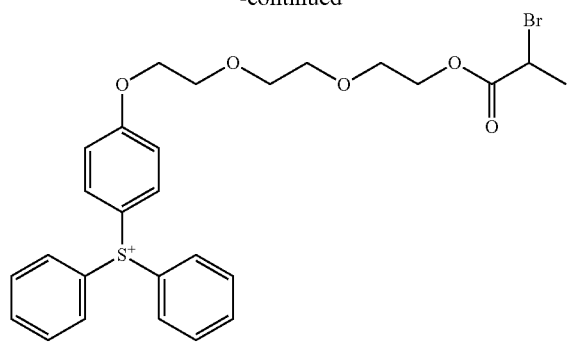
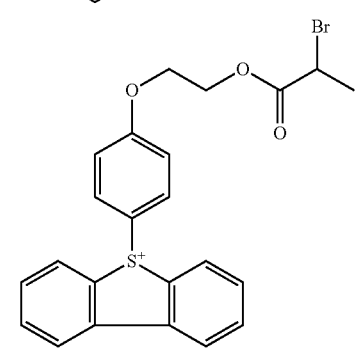
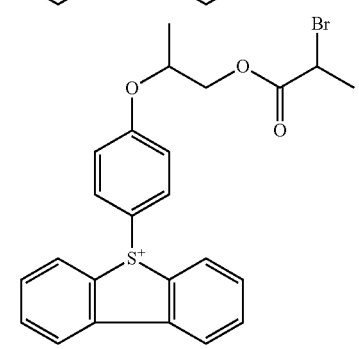
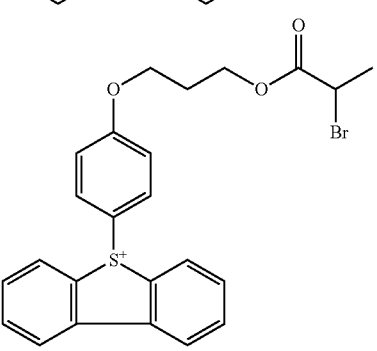
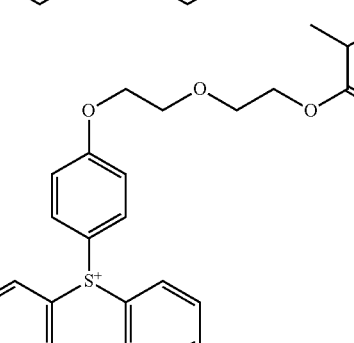
82
-continued
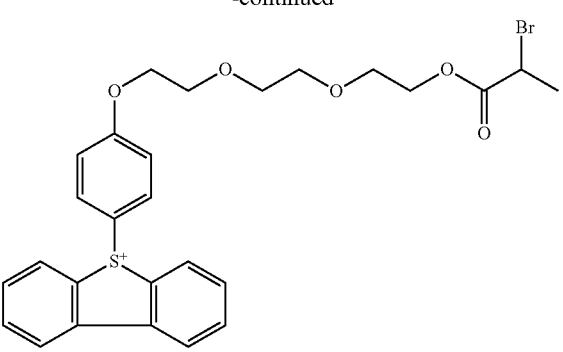
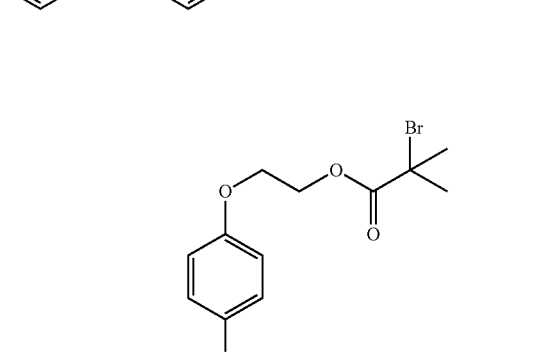
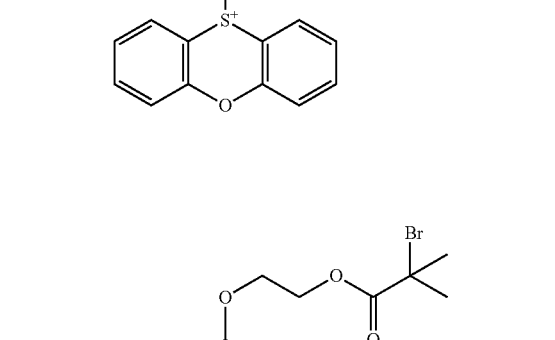
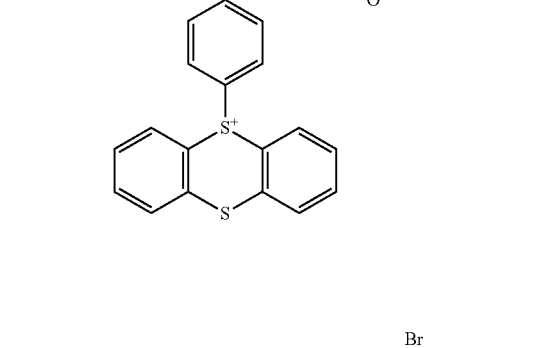
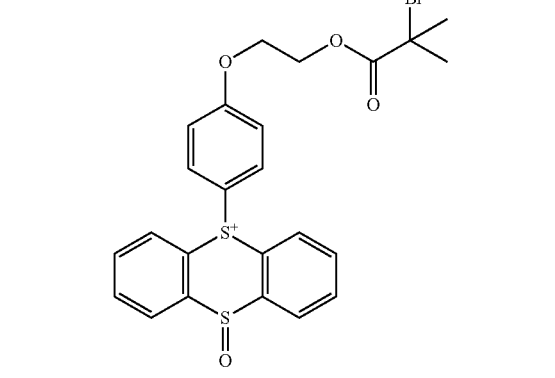

-continued
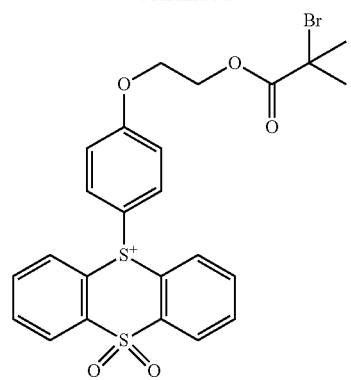
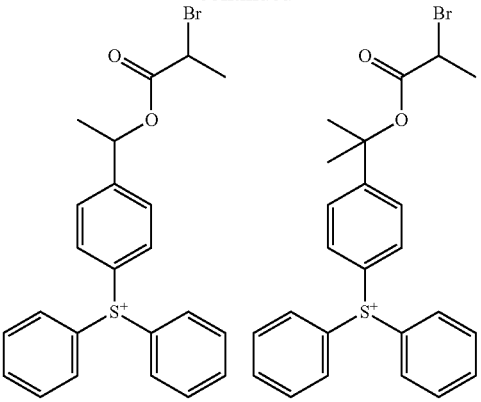
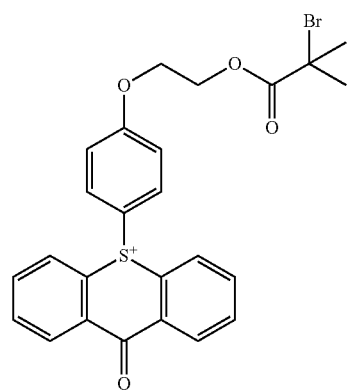
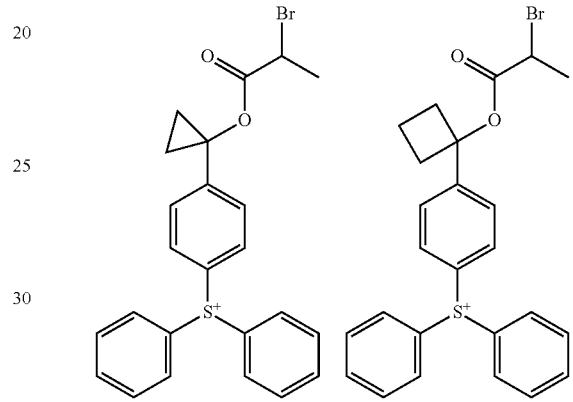
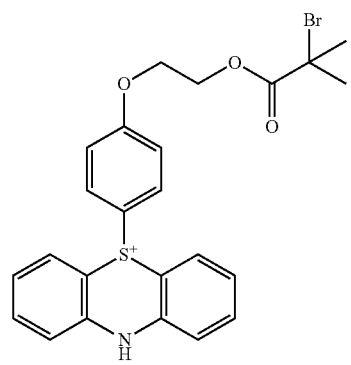
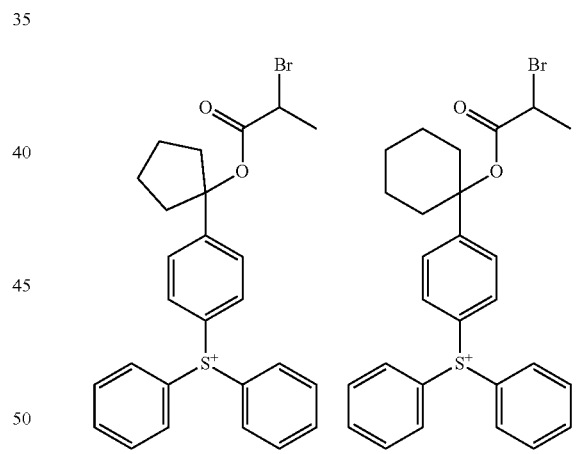
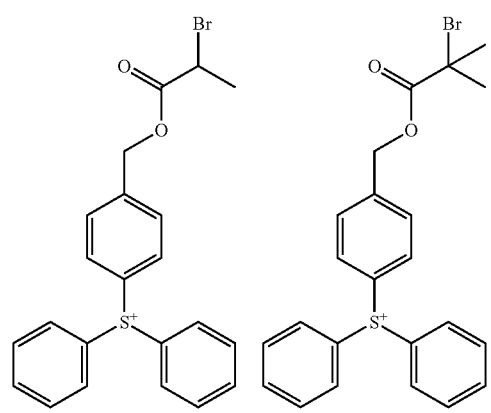
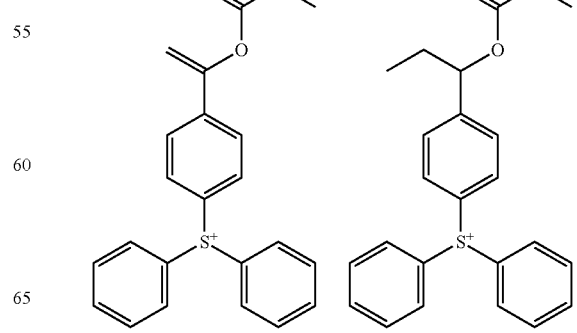

-continued
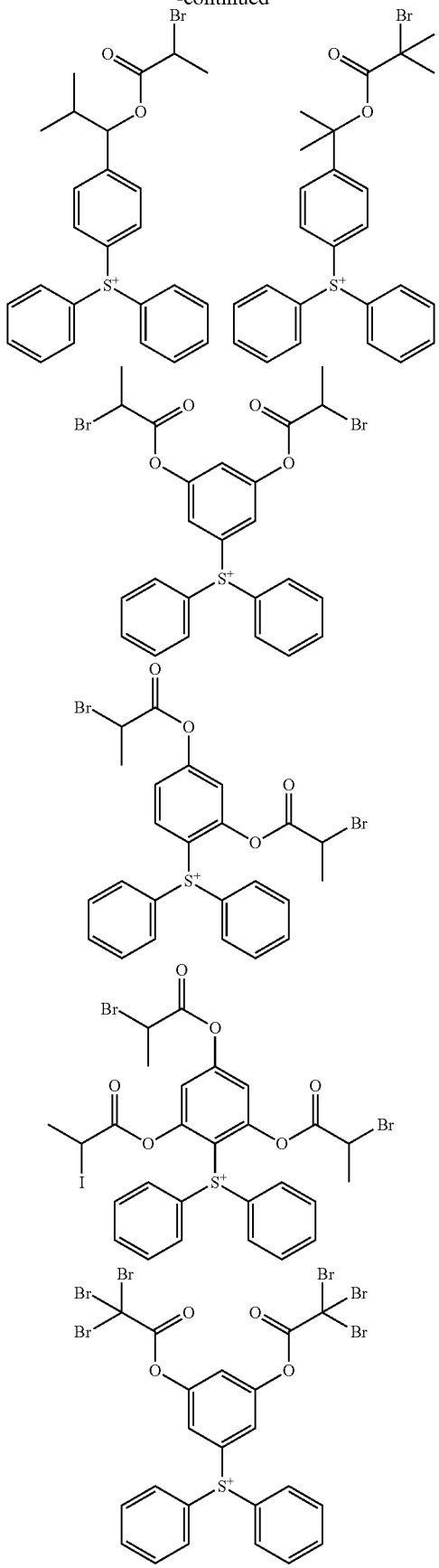
-continued
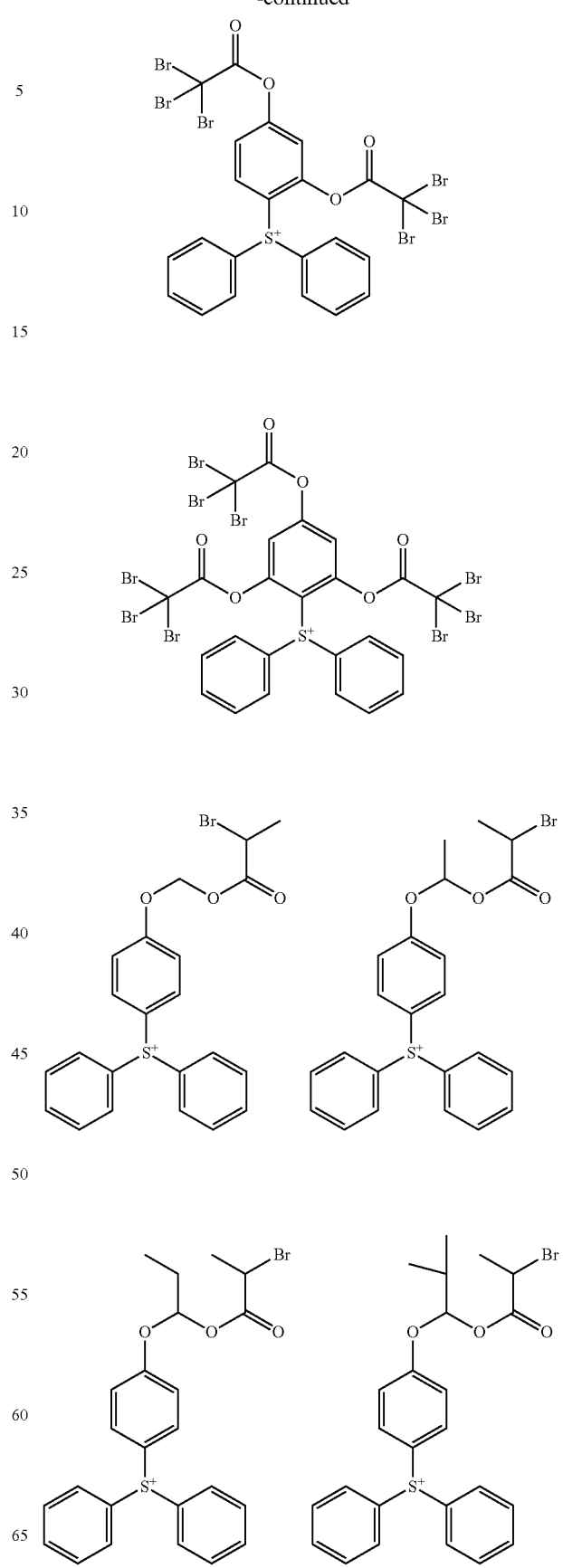

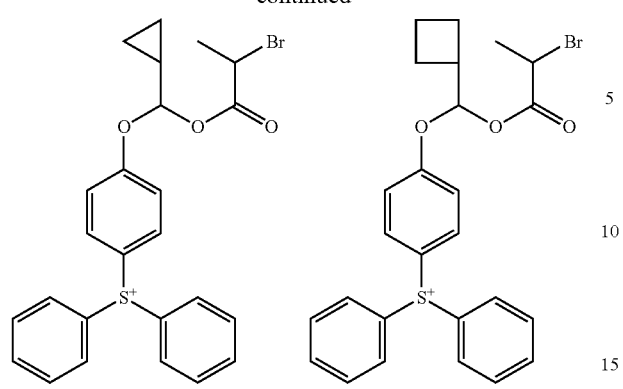
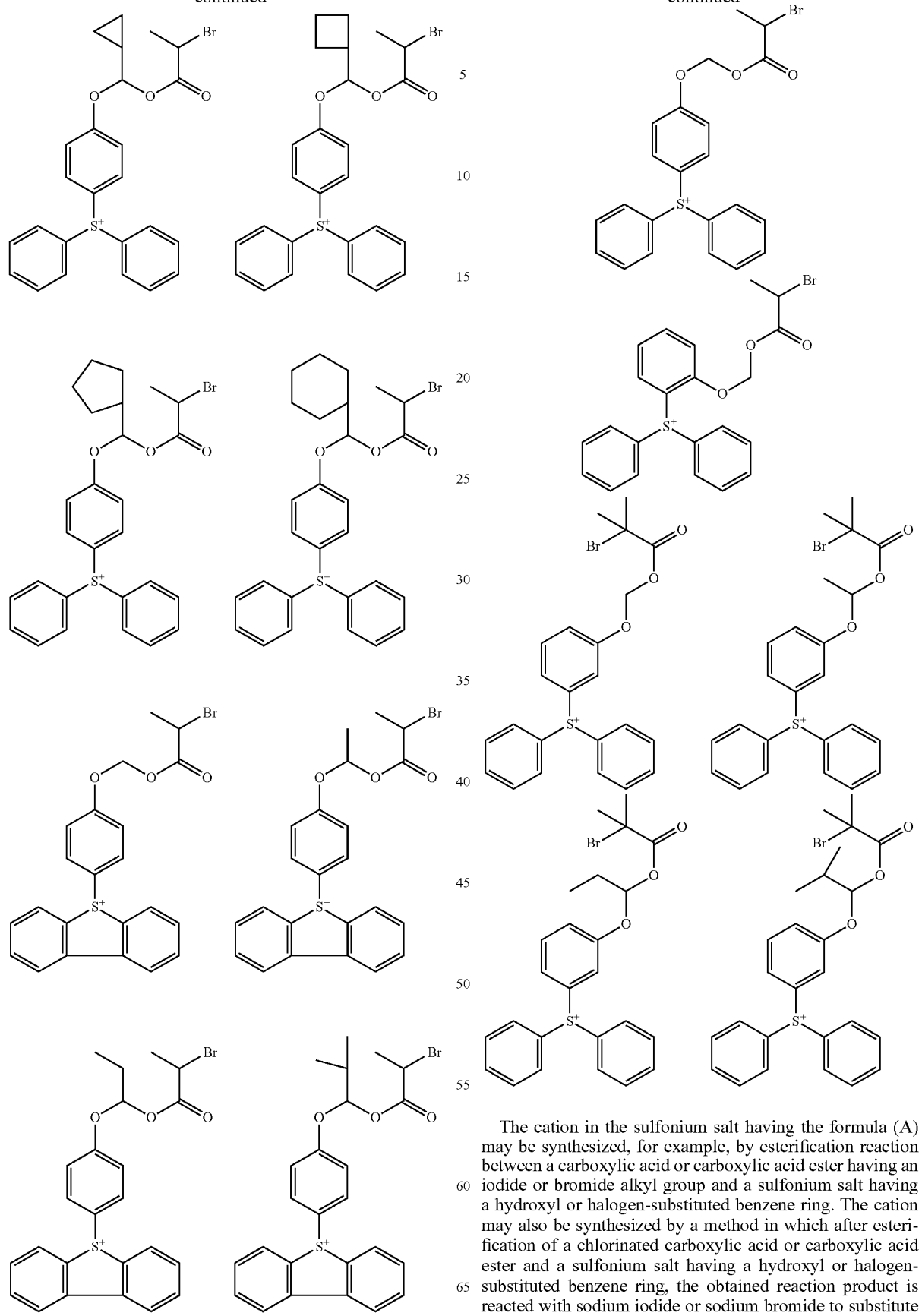

The cation in the sulfonium salt having the formula (A) may be synthesized, for example, by esterification reaction between a carboxylic acid or carboxylic acid ester having an iodide or bromide alkyl group and a sulfonium salt having a hydroxyl or halogen-substituted benzene ring. The cation may also be synthesized by a method in which after esterification of a chlorinated carboxylic acid or carboxylic acid ester and a sulfonium salt having a hydroxyl or halogen-substituted benzene ring, the obtained reaction product is reacted with sodium iodide or sodium bromide to substitute chlorine with iodine or bromine.

In the formula (A), $X_q^-$ is a halide ion, a sulfonic acid anion not having fluorine at the α-position, a carboxylic acid anion, or a sulfonamide anion.

Examples of the halide ion include a chloride ion, a bromide ion, and an iodide ion.

Examples of the sulfonic acid anion not having fluorine at the α-position include the sulfonic acid anions containing nitrogen described in JP-A 2017-78741 and JP-A 2017-76049, and sulfonic acid anions not having fluorine described in JP-A 2003-246774 and JP-A 2010-155824.

Examples of the carboxylic acid anion include the carboxylic acid anions described in JP 3991462 and JP 4226803, the fluorocarboxylic acid anions described in JP-A 2013-92657, JP-A 2015-54833, and JP-A 2015-132679, the iodized benzoic acid anion described in JP-A 2017-219836, and carboxylic acid anions containing nitrogen described in JP-A 2016-88898, JP-A 2016-44135, JP-A 2017-58454, and JP-A 2017-129695.

Examples of the sulfonamide anion include the sulfonamide anion described in JP-A 2013-145256 and the saccharin described in JP-A 2001-330947.

Since these anions do not induce a deprotection reaction of the acid labile group of the positive resist composition, and a crosslinking reaction or polarity conversion reaction of the negative resist composition, the anions functions as a quencher capable of controlling strong acid diffusion under coexistence with the acid generator capable of generating a strong acid.

Specifically, the sulfonic acid anion not having fluorine at the α-position is preferably represented by the formula (B).

$$R^{q1}\text{—}SO_3^- \tag{B}$$

In the formula (B), $R^{q1}$ is hydrogen or a $C_1$-$C_{40}$ hydrocarbyl group which may contain a heteroatom, exclusive of the hydrocarbyl group in which the hydrogen bonded to the carbon atom at α-position of the sulfo group is substituted by fluorine or a fluoroalkyl group.

The hydrocarbyl group of $R^{q1}$ may be saturated or unsaturated, and straight, branched, or cyclic. Examples thereof include alkyl groups such as methyl, ethyl, propyl, isopropyl, n-butyl, sec-butyl, tert-butyl, tert-pentyl, n-pentyl, n-hexyl, n-octyl, 2-ethylhexyl, n-nonyl, and n-decyl; cyclic saturated hydrocarbyl groups such as cyclopentyl, cyclohexyl, cyclopentylmethyl, cyclopentylethyl, cyclopentylbutyl, cyclohexylmethyl, cyclohexylethyl, cyclohexylbutyl, norbornyl, tricyclo[5.2.1.0$^{2,6}$]decanyl, adamantyl, and adamantylmethyl; alkenyl groups such as vinyl, allyl, propenyl, butenyl, and hexenyl; cyclic unsaturated aliphatic hydrocarbyl groups such as cyclohexenyl; aryl groups such as phenyl, naphthyl, alkylphenyl groups (e.g., 2-methylphenyl, 3-methylphenyl, 4-methylphenyl, 4-ethylphenyl, 4-tert-butylphenyl, and 4-n-butylphenyl), dialkylphenyl groups (e.g., 2,4-dimethylphenyl and 2,4,6-triisopropylphenyl), alkylnaphthyl groups (e.g., methylnaphthyl and ethylnaphthyl), dialkylnaphthyl groups (e.g., dimethylnaphthyl and diethylnaphthyl); heteroaryl groups such as thienyl; and aralkyl groups such as benzyl, 1-phenylethyl, and 2-phenylethyl.

In these groups, some of the hydrogen atoms may be substituted by a group containing a heteroatom such as oxygen, sulfur, nitrogen, or a halogen, or some carbon may be replaced by a group containing a heteroatom such as oxygen, sulfur, or nitrogen, so that the group may contain a hydroxyl, cyano, carbonyl, ether bond, ester bond, imino, sulfonic acid ester bond, carbonate bond, lactone ring, sultone ring, carboxylic anhydride, or haloalkyl group.

Examples of the heteroatom-containing hydrocarbyl group include alkoxyphenyl groups such as 4-hydroxyphenyl, 4-methoxyphenyl, 3-methoxyphenyl, 2-methoxyphenyl, 4-ethoxyphenyl, 4-tert-butoxyphenyl, and 3-tert-butoxyphenyl; alkoxynaphthyl groups such as methoxynaphthyl, ethoxynaphthyl, n-propoxynaphthyl, and n-butoxynaphthyl; dialkoxynaphthyl groups such as dimethoxynaphthyl and diethoxynaphthyl; aryloxyalkyl groups, typically 2-aryl-2-oxoethyl groups such as 2-phenyl-2-oxoethyl, 2-(1-naphthyl)-2-oxoethyl, and 2-(2-naphthyl)-2-oxoethyl; cyclic hydrocarbylcarbonyloxyalkyl groups such as cyclohexylcarbonyloxyethyl and adamantylcarbonyloxyethyl; a 2-oxobornyl group; cycloalkylaminoalkyl groups such as cyclohexylaminoethyl and cyclohexylaminopropyl; and arylcarbonyloxyalkyl groups such as phenylcarbonyloxyethyl and naphthylcarbonyloxyethyl.

As the carboxylic acid anion, the anion having the formula (C) is preferred.

$$R^{q2}\text{—}CO_2^- \tag{C}$$

In the formula (C), $R^{q2}$ is a $C_1$-$C_{40}$ hydrocarbyl group which may contain a heteroatom. Examples of the hydrocarbyl group of $R^{q2}$ are as exemplified above for the hydrocarbyl group of $R^{q1}$. Also included are fluorinated alkyl groups such as trifluoromethyl, trifluoroethyl, 2,2,2-trifluoro-1-methyl-1-hydroxyethyl, 2,2,2-trifluoro-1-(trifluoromethyl)-1-hydroxyethyl, and fluorinated aryl groups such as pentafluorophenyl and 4-trifluoromethylphenyl.

As the carboxylic acid anion, the anion having the formula (D) is also preferred.

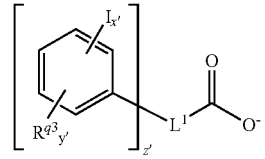

(D)

In the formula (D), $R^{q3}$ is hydroxyl, fluorine, chlorine, bromine, amino, nitro, cyano, or a $C_1$-$C_6$ saturated hydrocarbyl, $C_1$-$C_6$ saturated hydrocarbyloxy, $C_2$-$C_6$ saturated hydrocarbylcarbonyloxy, or $C_1$-$C_4$ saturated hydrocarbylsulfonyloxy group, in which some or all hydrogen may be substituted by a halogen, or —N($R^{q3A}$)—C(=O)—$R^{q3B}$, or —N($R^{q3A}$)—C(=O)—O—$R^{q3B}$. $R^{q3A}$ is hydrogen or a $C_1$-$C_6$ saturated hydrocarbyl group. $R^{q3B}$ is a $C_1$-$C_6$ saturated hydrocarbyl or $C_2$-$C_8$ unsaturated aliphatic hydrocarbyl group.

In the formula (D), x' is an integer of 1 to 5. y' is an integer of 0 to 3, and z' is an integer of 1 to 3. $L^1$ is a single bond, or a $C_1$-$C_{20}$ (z'+1)-valent linking group which may contain at least one group selected from an ether bond, a carbonyl group, an ester bond, an amide bond, a sultone ring, a lactam ring, a carbonate group, a halogen, a hydroxyl group, or a carboxyl group. The saturated hydrocarbyl, saturated hydrocarbyloxy, saturated hydrocarbylcarbonyloxy, and saturated hydrocarbylsulfonyloxy groups may be straight, branched, or cyclic. Groups $R^{q3}$ may be the same or different when y' is 2 or more.

As the sulfonamide anion, the anion having the formula (E) is preferred.

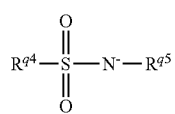
(E)

In the formula (E), $R^{q4}$ is fluorine, a $C_1$-$C_{10}$ hydrocarbyl group, or a $C_1$-$C_{10}$ fluorinated hydrocarbyl group, which may contain a hydroxyl group, an ether bond, or an ester bond. $R^{q5}$ is hydrogen or a $C_1$-$C_{10}$ hydrocarbyl group which may contain a hydroxyl group, an ether bond, or an ester bond. $R^{q4}$ and $R^{q5}$ may bond together to form a ring with the atom to which they are attached. The hydrocarbyl group may be saturated or unsaturated, and may be straight, branched, or cyclic. Examples thereof include $C_1$-$C_{10}$ alkyl, $C_2$-$C_{10}$ alkenyl, $C_2$-$C_{10}$ alkynyl, and $C_6$-$C_{10}$ aryl groups. Examples of the fluorinated hydrocarbyl group include groups obtained by substituting some or all hydrogen atoms in the hydrocarbyl groups with fluorine.

The sulfonium salt having the formula (A) can be synthesized, for example, by esterification reaction of a sulfonium salt having a hydroxyl group with an iodized or brominated carboxylic acid.

The resist composition comprising the sulfonium salt having the formula (A) can be patterned without the base polymer, or with the base polymer blended. In the case of blending with the base polymer, the sulfonium salt having the formula (A) is preferably used in an amount of 0.01 to 1,000 parts by weight, more preferably 0.05 to 500 parts by weight per 100 parts by weight of the base polymer (described below), as viewed from sensitivity and acid diffusion suppressing effect.

Base Polymer

Where the resist composition is of positive tone, the base polymer contained in the resist composition comprises recurring units containing an acid labile group, preferably recurring units having the formula (a1) or recurring units having the formula (a2). These units are simply referred to as recurring units (a1) and (a2).

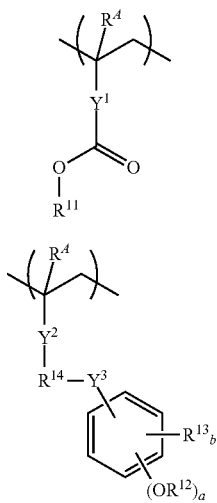
(a1)

(a2)

Herein $R^A$ is each independently hydrogen or a methyl group. $Y^1$ is a single bond, a phenylene group, a naphthylene group, or a $C_1$-$C_{12}$ linking group containing at least one selected from an ester bond or a lactone ring $Y^2$ is a single bond or an ester bond. $Y^3$ is a single bond, an ether bond, or an ester bond. $R^{11}$ and $R^{12}$ are each independently an acid labile group. $R^{13}$ is fluorine, a trifluoromethyl group, a cyano group, a $C_1$-$C_6$ saturated hydrocarbyl group, a $C_1$-$C_6$ saturated hydrocarbyloxy group, a $C_2$-$C_7$ saturated hydrocarbylcarbonyl group, a $C_2$-$C_7$ saturated hydrocarbylcarbonyloxy group, or a $C_2$-$C_7$ saturated hydrocarbyloxycarbonyl group. $R^{14}$ is a single bond or a $C_1$-$C_6$ alkanediyl group in which some carbon may be replaced by an ether bond or an ester bond. a is 1 or 2. b is an integer of 0 to 4. $1 \leq a+b \leq 5$.

Examples of the monomer from which the recurring units (a1) are derived are shown below, but not limited thereto. $R^A$ and $R^{11}$ are as defined above.

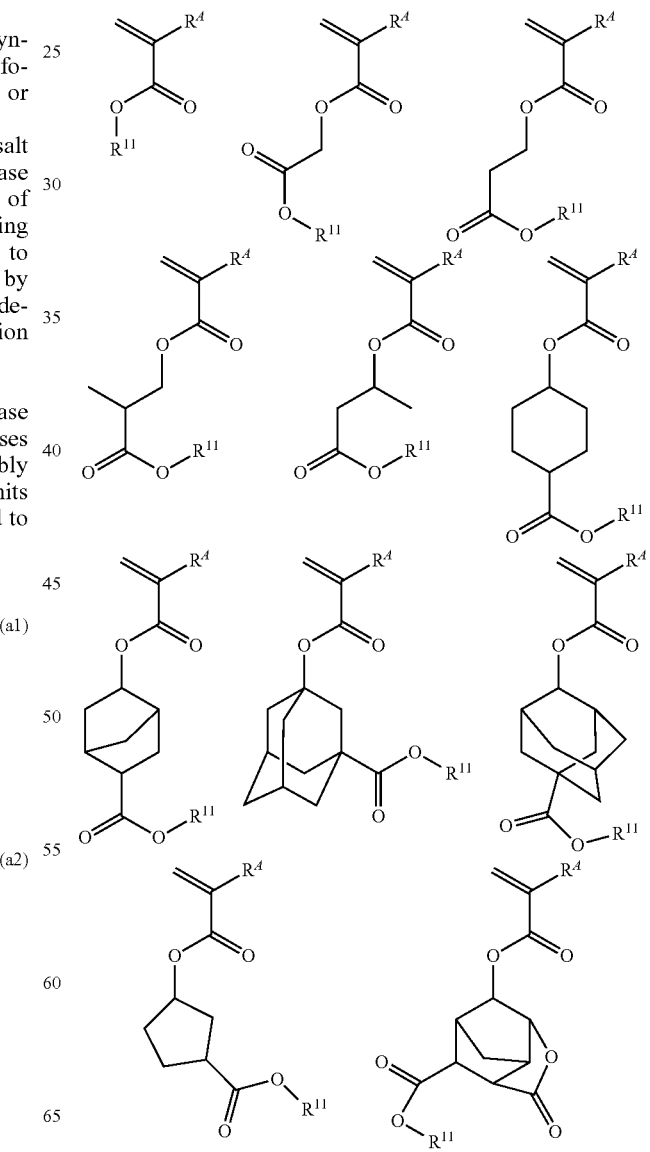

-continued

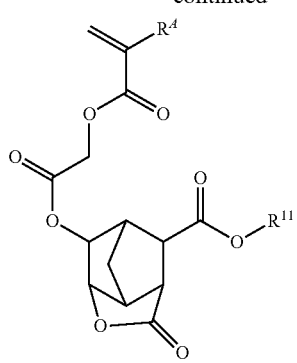
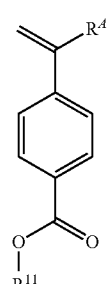
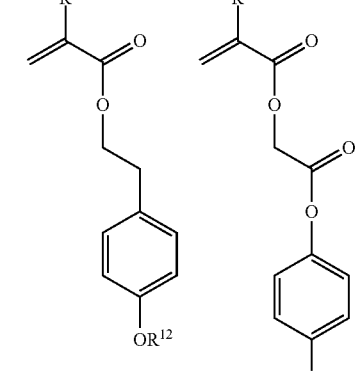

Examples of the monomer from which the recurring units (a2) are derived are shown below, but not limited thereto. $R^A$ and $R^{12}$ are as defined above.

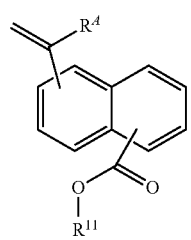
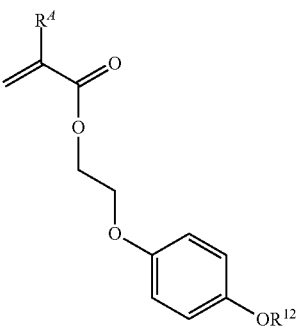

The acid labile groups represented by $R^{11}$ and $R^{12}$ in the formulae (a1) and (a2) may be selected from a variety of such groups, for example, those groups described in JP-A 2013-80033 and JP-A 2013-83821.

Typical of the acid labile group are groups of the following formulae (AL-1) to (AL-3).

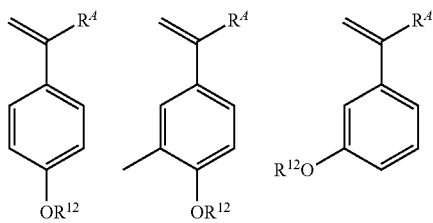

$$\text{-----}(CH_2)_c\text{--}\overset{O}{\underset{\|}{C}}\text{--}O\text{--}R^{L1} \qquad (AL-1)$$

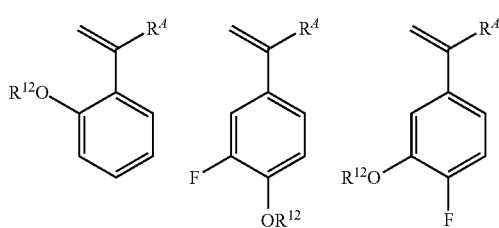

$$\text{----}\overset{R^{L3}}{\underset{R^{L4}}{\overset{|}{\underset{|}{C}}}}\text{--}O\text{--}R^{L2} \qquad (AL-2)$$

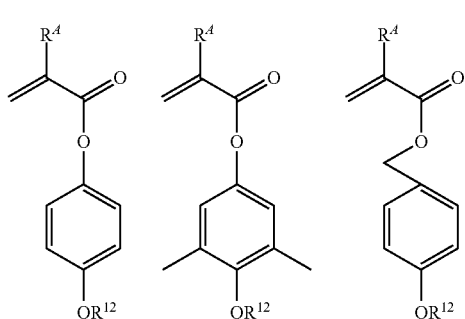

$$\text{----}\overset{R^{L5}}{\underset{R^{L6}}{\overset{|}{\underset{|}{C}}}}\text{--}R^{L7} \qquad (AL-3)$$

Herein the broken line designates a point of attachment.

In the formulae (AL-1) and (AL-2), $R^{L1}$ and $R^{L2}$ are each independently a $C_1$-$C_{40}$ hydrocarbyl group which may contain a heteroatom such as oxygen, sulfur, nitrogen, or fluorine. The hydrocarbyl group may be saturated or unsaturated, and may be straight, branched, or cyclic. Inter alia, $C_1$-$C_{40}$ saturated hydrocarbyl groups are preferred, with $C_1$-$C_{20}$ saturated hydrocarbyl group being more preferred.

In the formula (AL-1), c is an integer of 0 to 10, preferably 1 to 5.

In the formula (AL-2), $R^{L3}$ and $R^{L4}$ are each independently hydrogen or a $C_1$-$C_{20}$ hydrocarbyl group which may contain a heteroatom such as oxygen, sulfur, nitrogen, or fluorine. The hydrocarbyl group may be saturated or unsaturated, and may be straight, branched, or cyclic. Inter alia, $C_1$-$C_{20}$ saturated hydrocarbyl groups are preferred. Any two of $L^{R2}$, $R^{L3}$, and $R^{L4}$ may bond together to form a ring, typically alicyclic, with the carbon atom or carbon and oxygen atoms to which they are attached, the ring containing 3 to 20 carbon atoms, preferably 4 to 16 carbon atoms.

In the formula (AL-3), $R^{L5}$, $R^{L6}$, and $R^{L7}$ are each independently a $C_1$-$C_{20}$ hydrocarbyl group which may contain a heteroatom such as oxygen, sulfur, nitrogen, or fluorine. The hydrocarbyl group may be saturated or unsaturated, and may be straight, branched, or cyclic. Inter alia, $C_1$-$C_{20}$ saturated hydrocarbyl groups are preferred. Any two of $R^{L5}$, $R^{L6}$, and $R^{L7}$ may bond together to form a ring, typically alicyclic, with the carbon atom to which they are attached, the ring containing 3 to 20 carbon atoms, preferably 4 to 16 carbon atoms.

The base polymer may comprise recurring units (b) having a phenolic hydroxyl group as an adhesive group. Examples of the monomer from which the recurring units (b) are derived are shown below, but not limited thereto. Herein $R^A$ is as defined above.

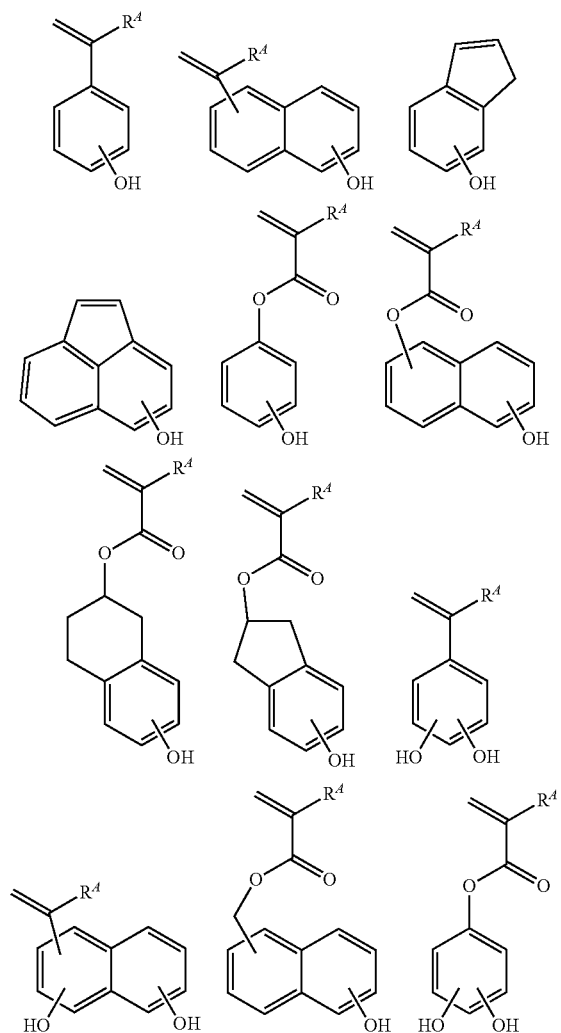

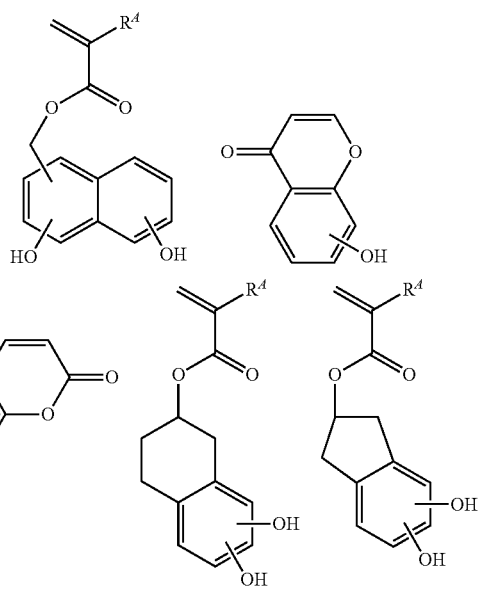

Further, recurring units (c) having another adhesive group selected from a hydroxyl group (other than the foregoing phenolic hydroxyl group), a lactone ring, an ether bond, an ester bond, a carbonyl group, a cyano group, or a carboxyl group may also be incorporated in the base polymer. Examples of the monomer from which the recurring units (c) are derived are shown below, but not limited thereto. Herein $R^A$ is as defined above.

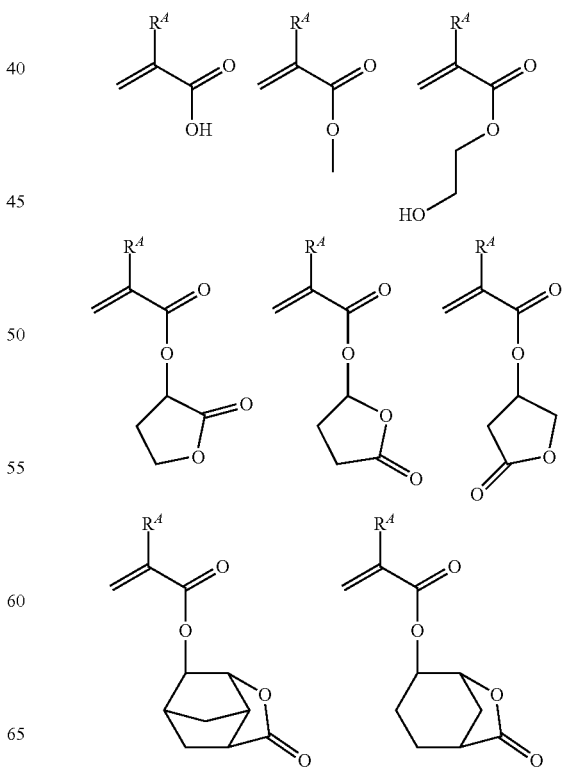

-continued
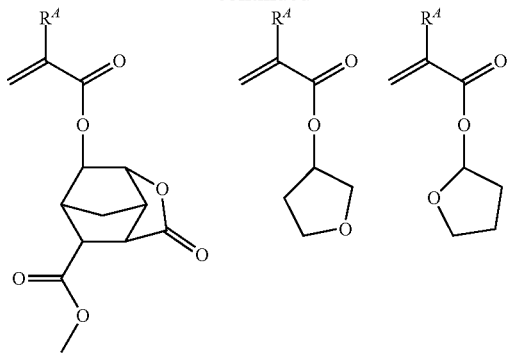
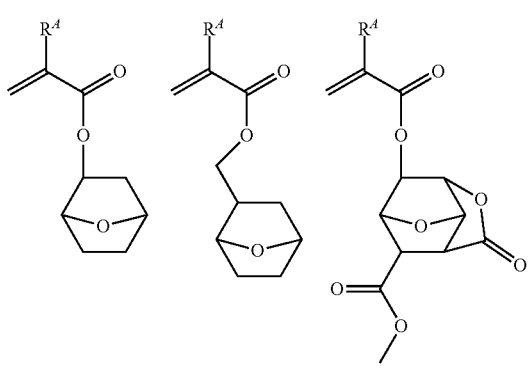
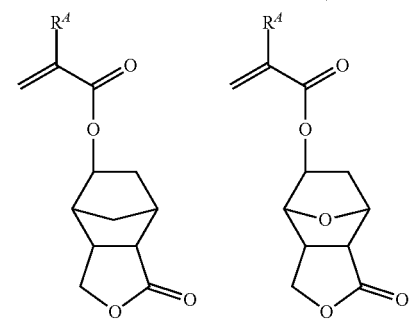
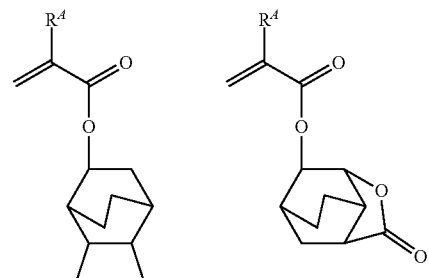
-continued
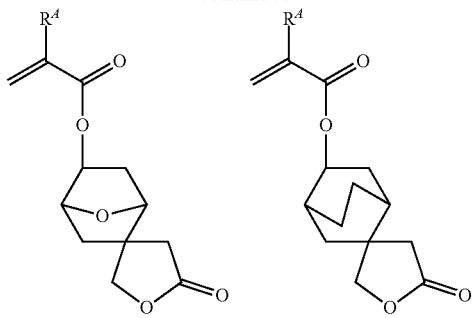
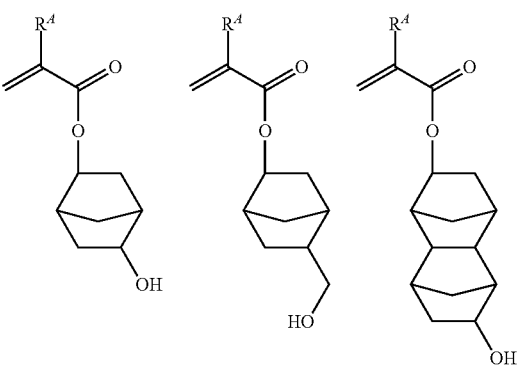
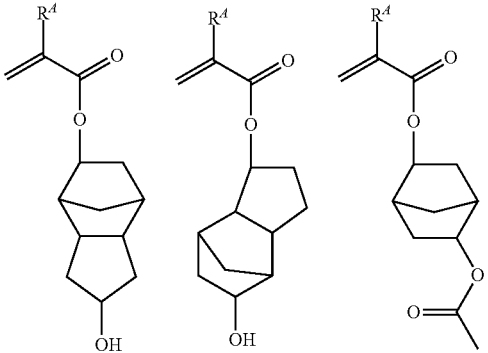
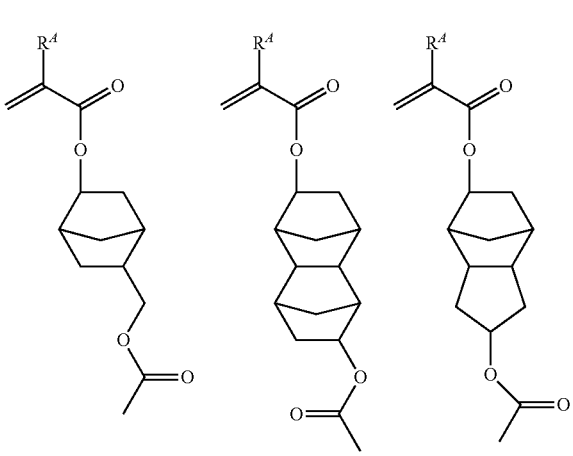

99
-continued
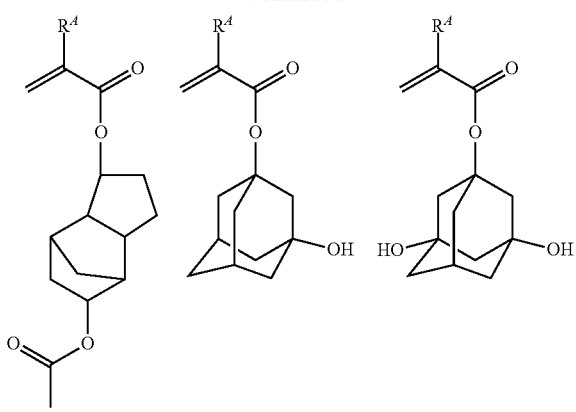
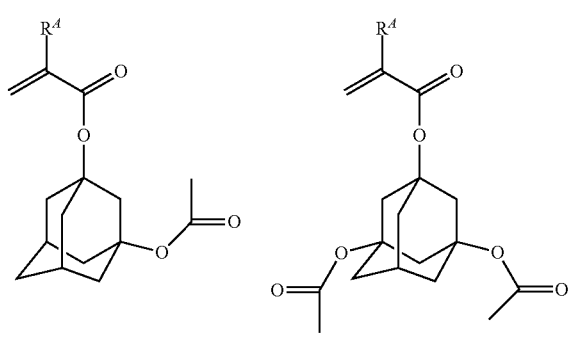
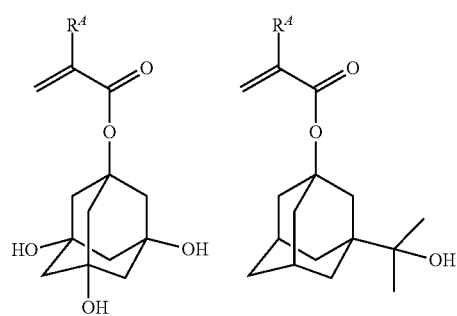
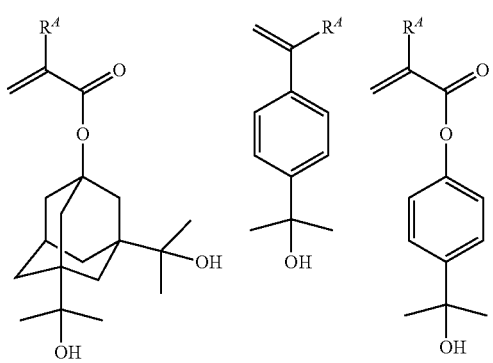
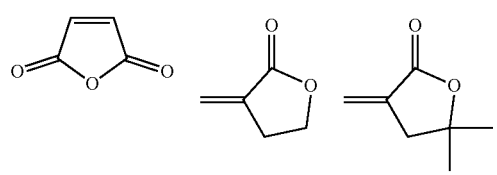
100
-continued
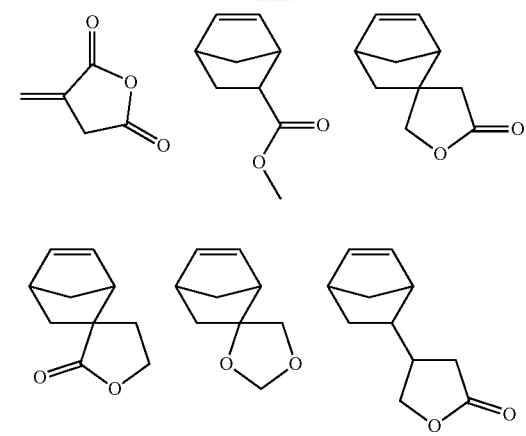
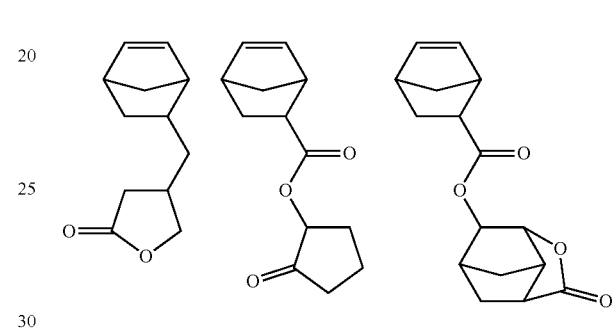
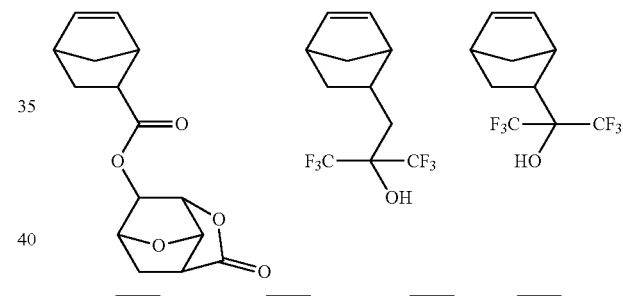
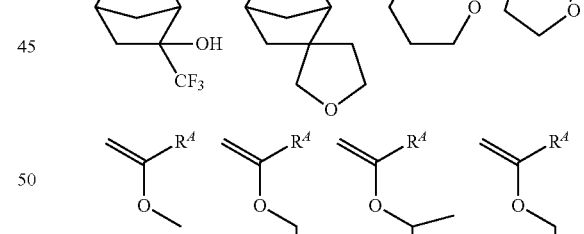
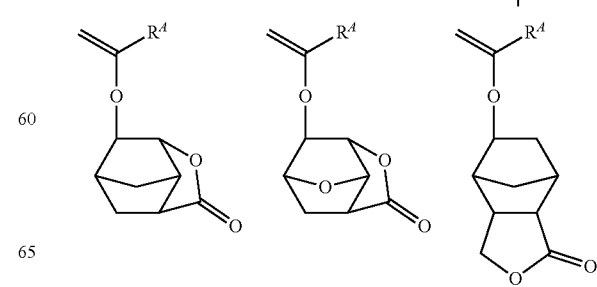

101
-continued
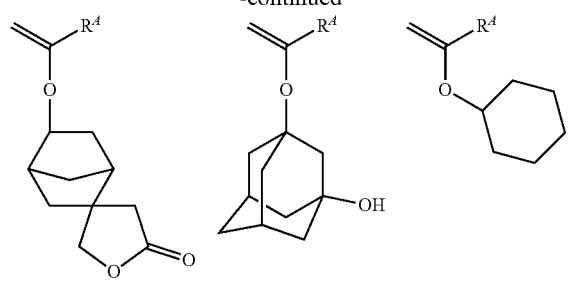
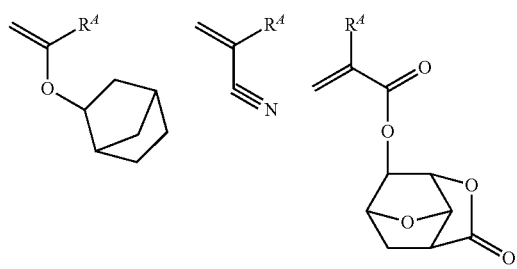
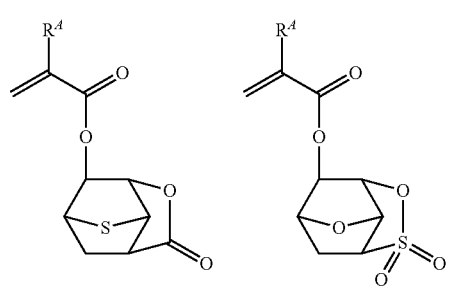
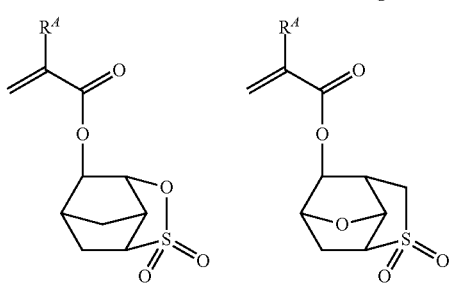
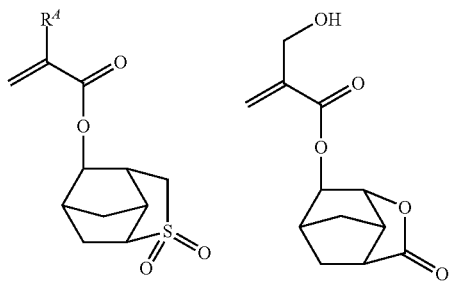
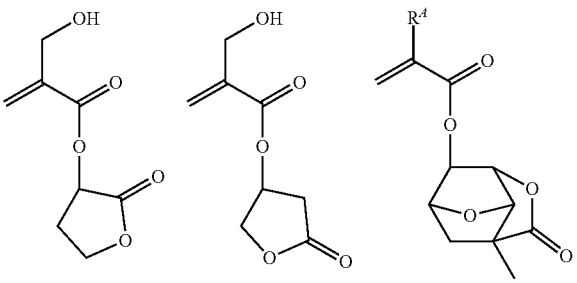
102
-continued
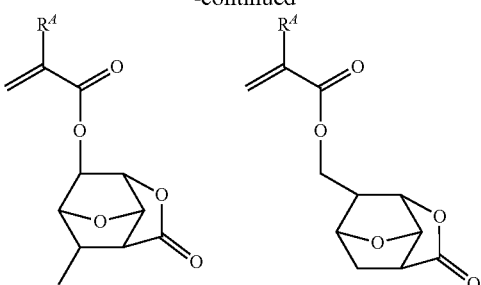
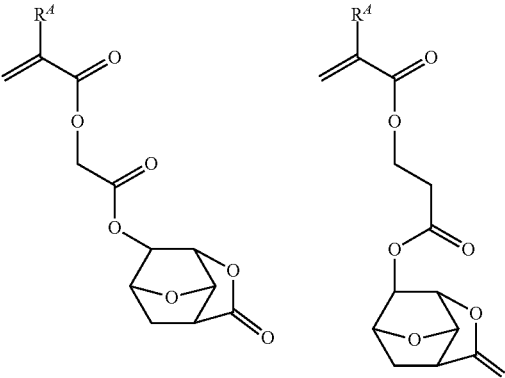
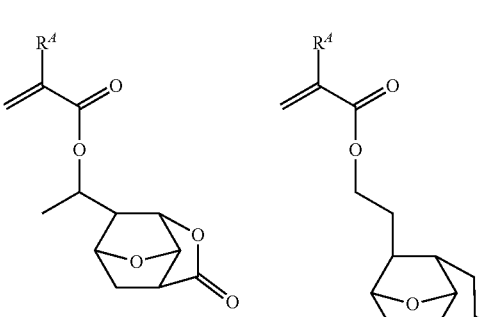
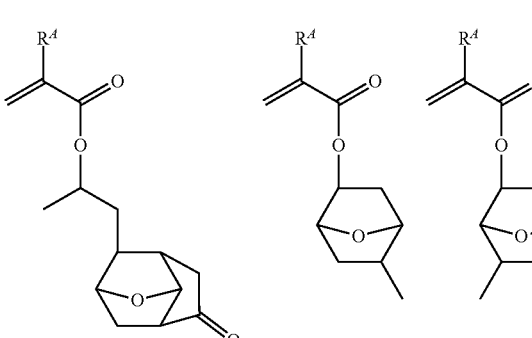
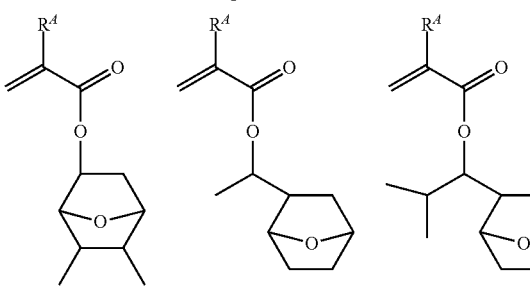

103
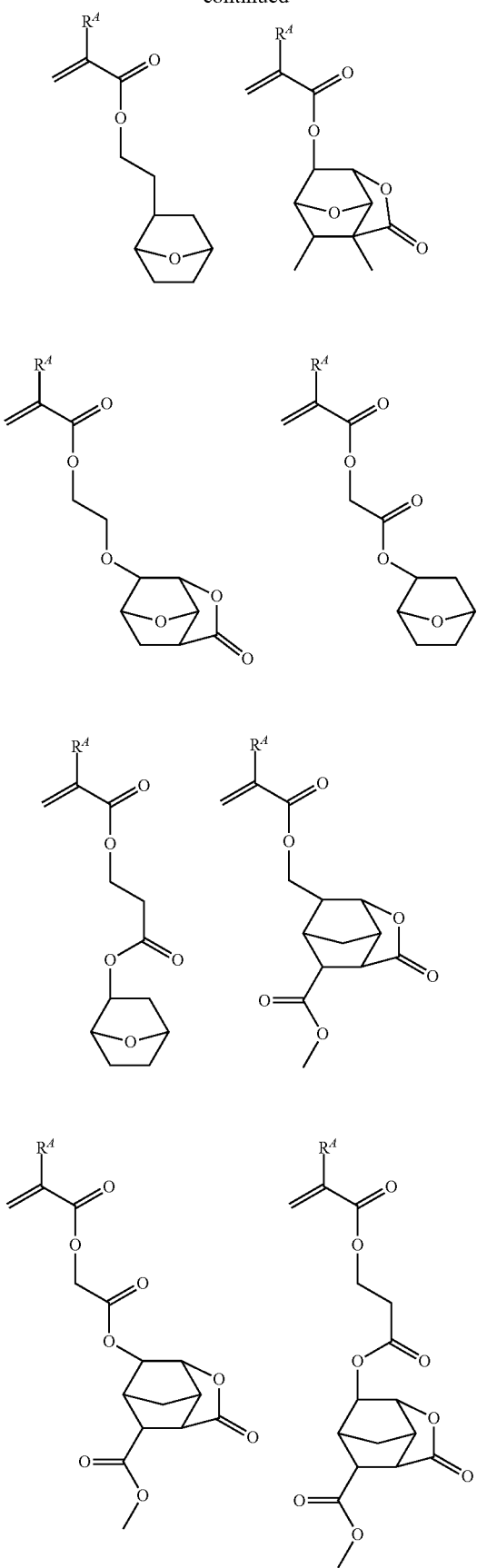
-continued
104
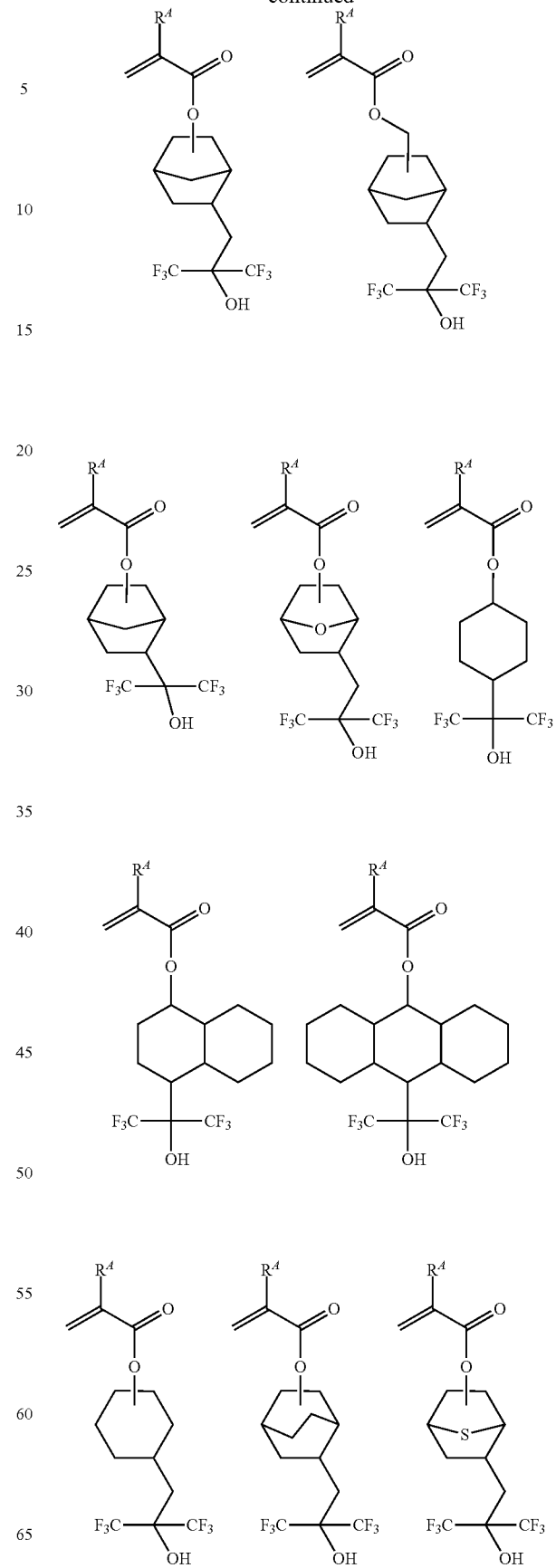
-continued

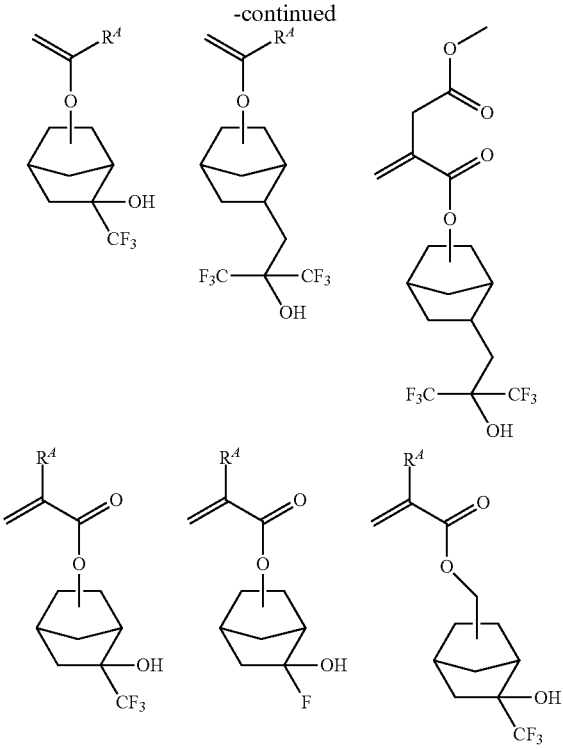
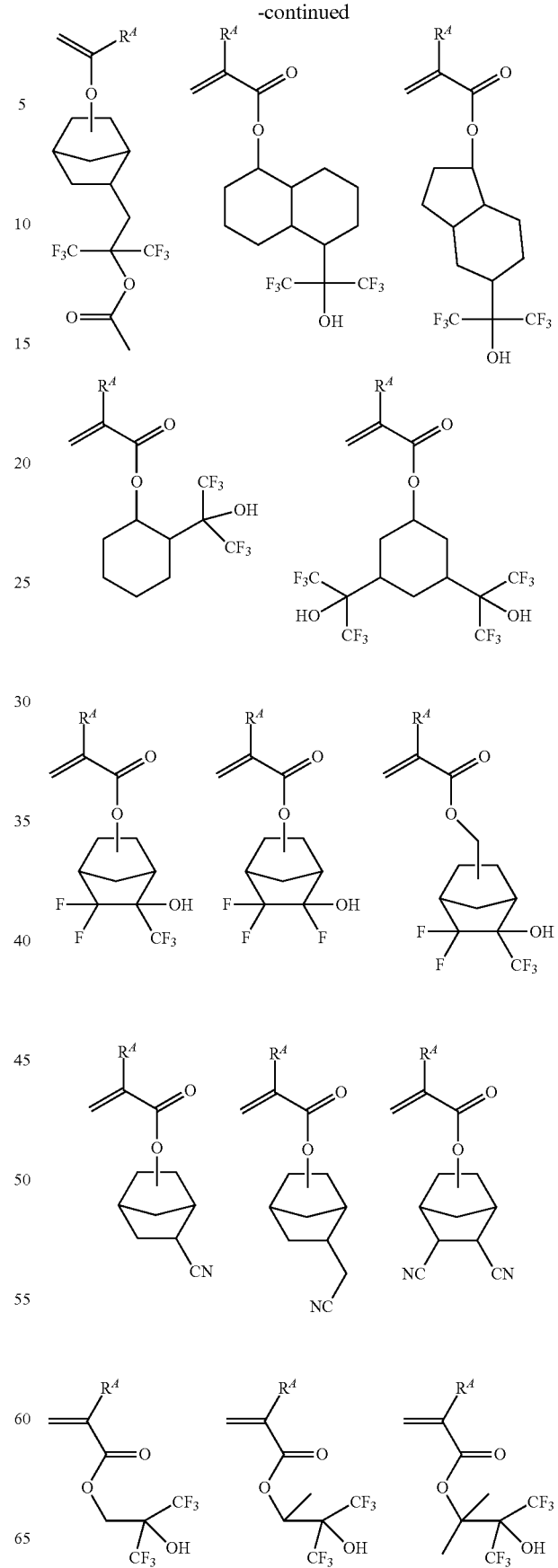

-continued
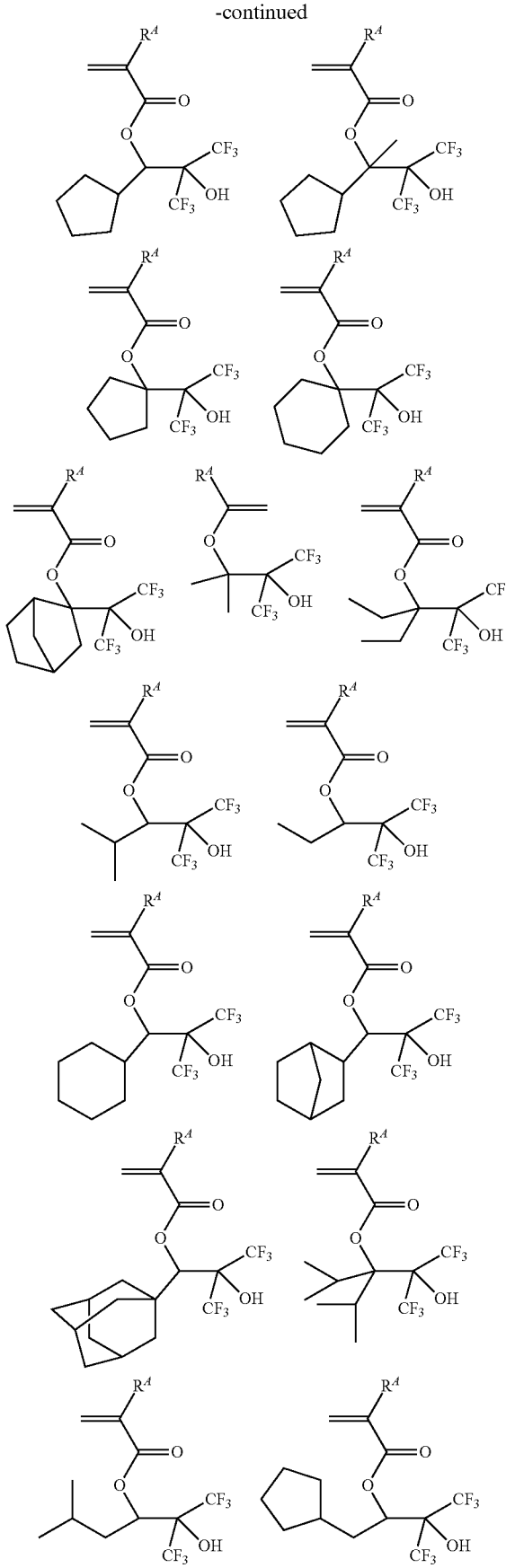
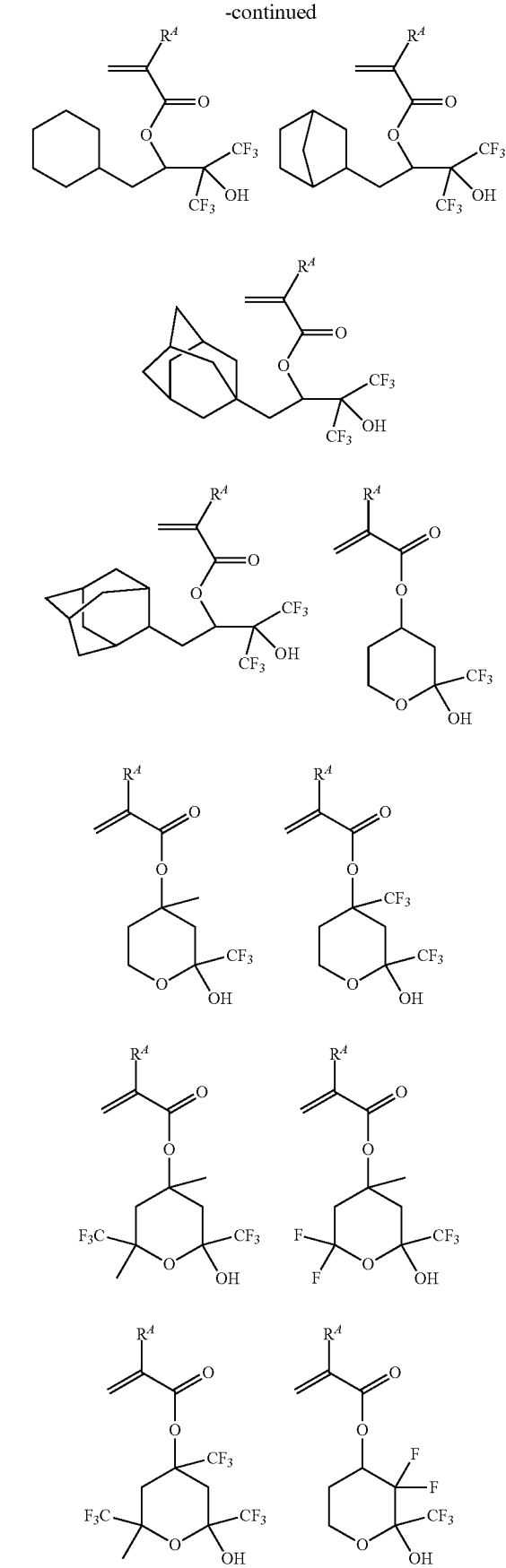

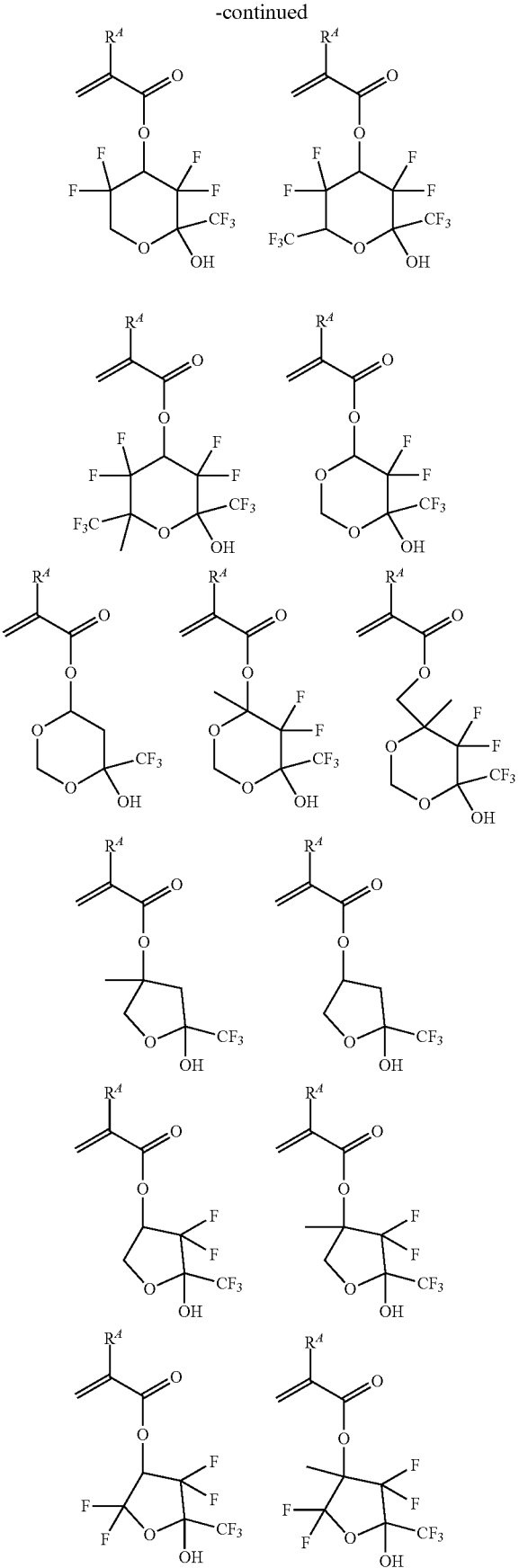
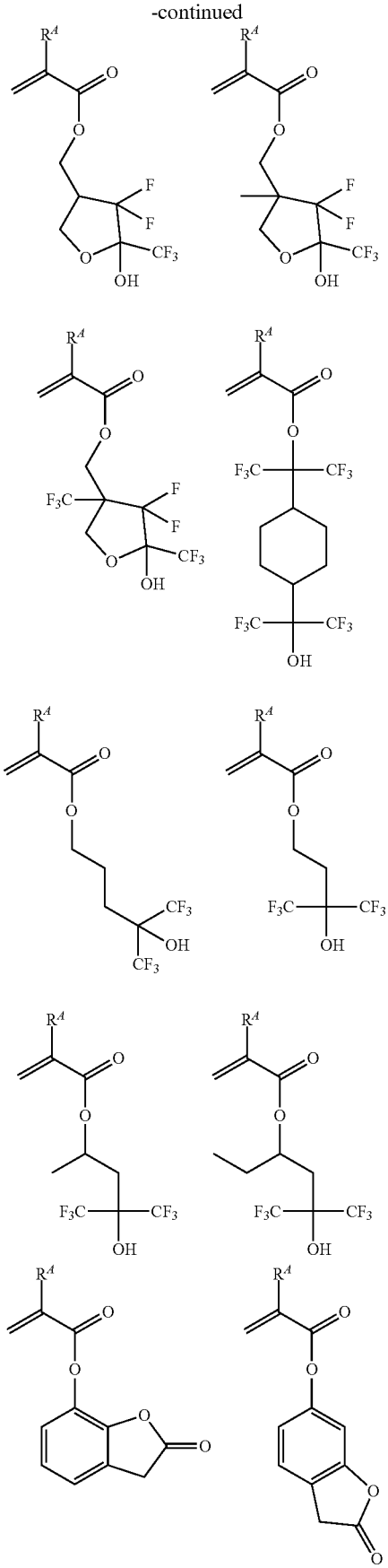

111
-continued
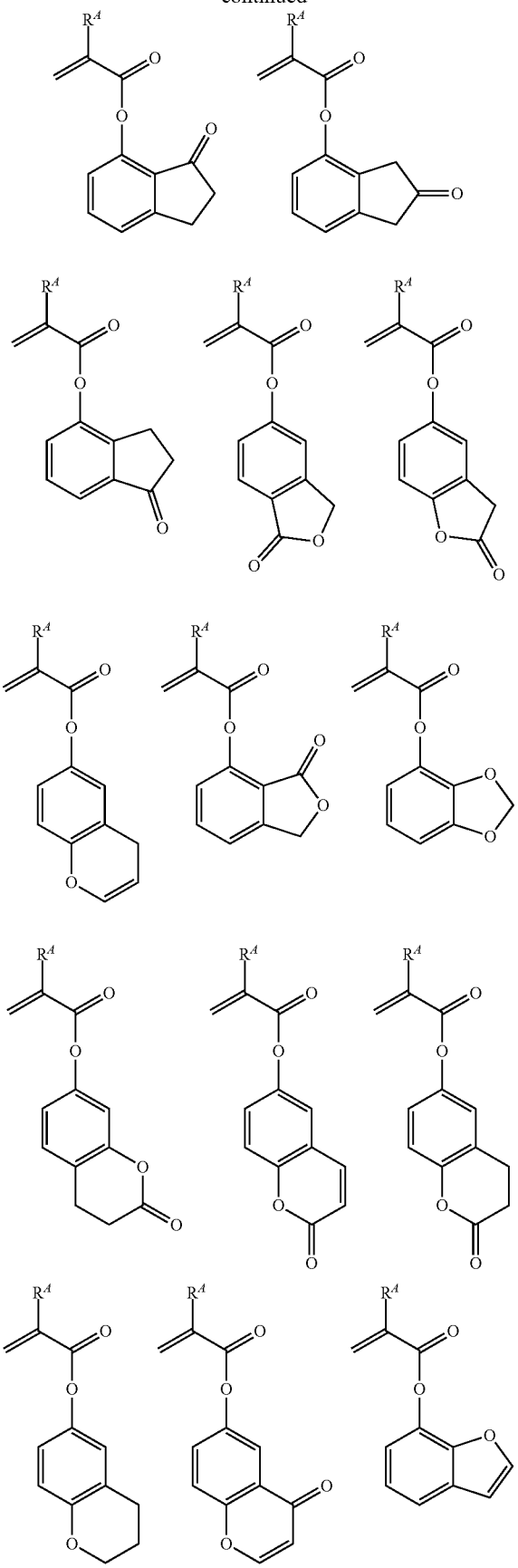
112
-continued
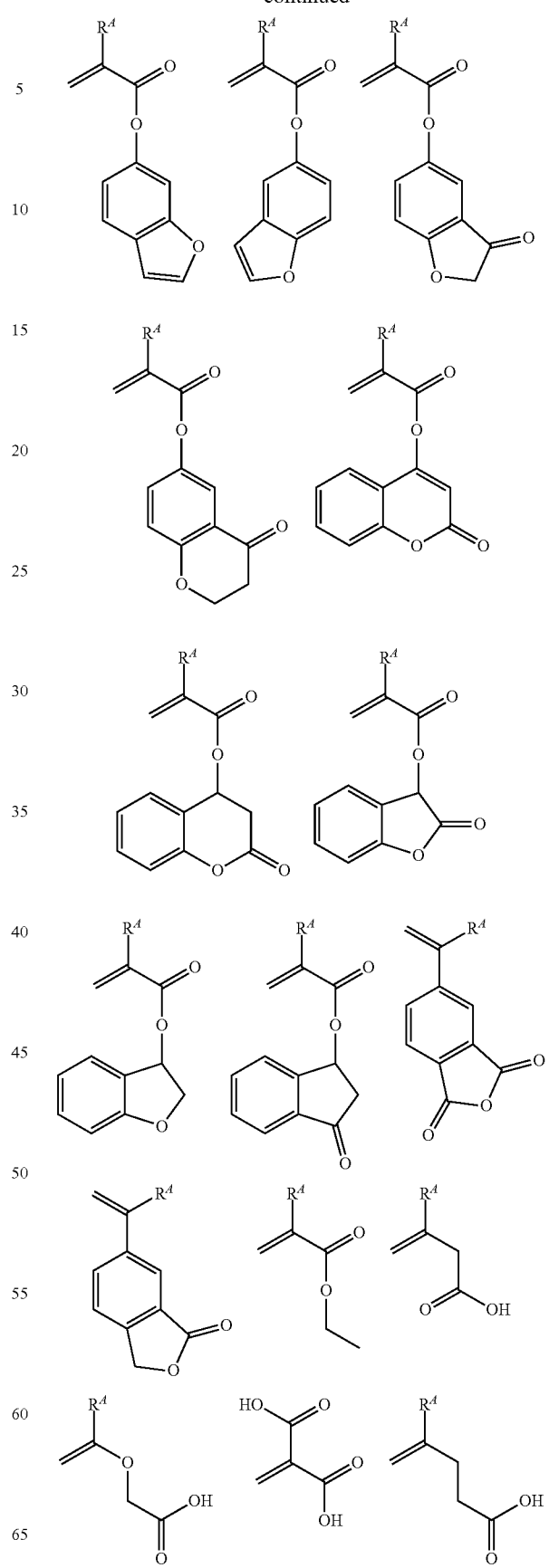

-continued
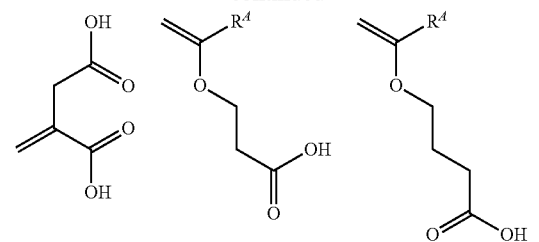
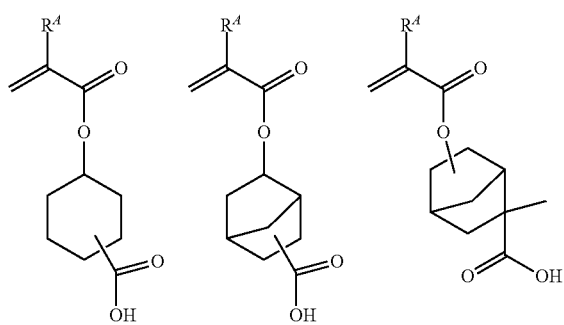
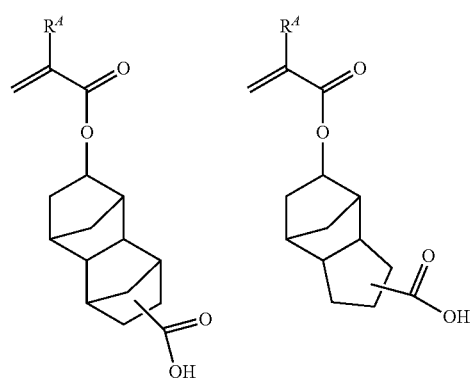
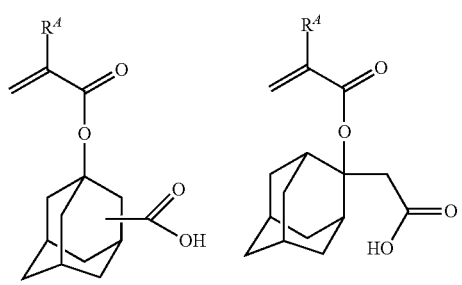
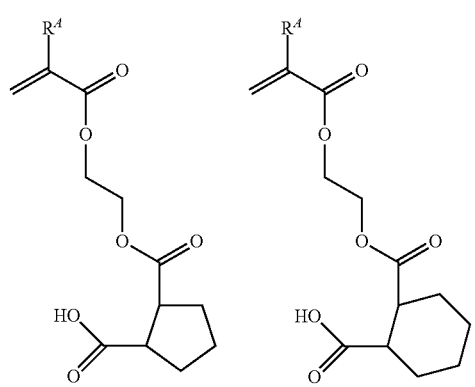
-continued
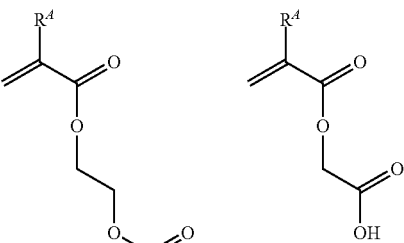
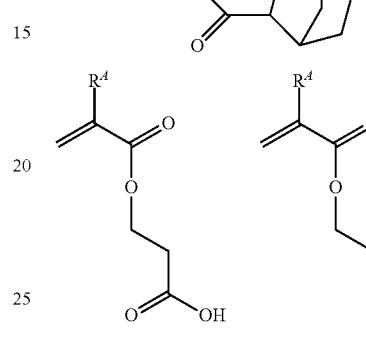
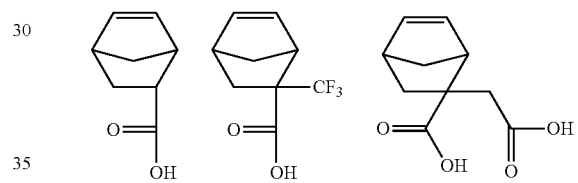
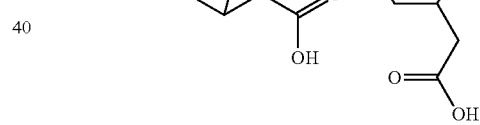
In another preferred embodiment, the base polymer may further comprise recurring units (d) derived from indene, benzofuran, benzothiophene, acenaphthylene, chromone, coumarin, and norbornadiene, or derivatives thereof. Examples of the monomer from which the recurring units (d) are derived are shown below, but not limited thereto.
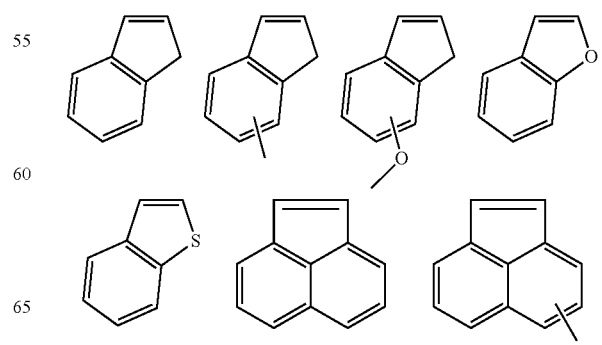

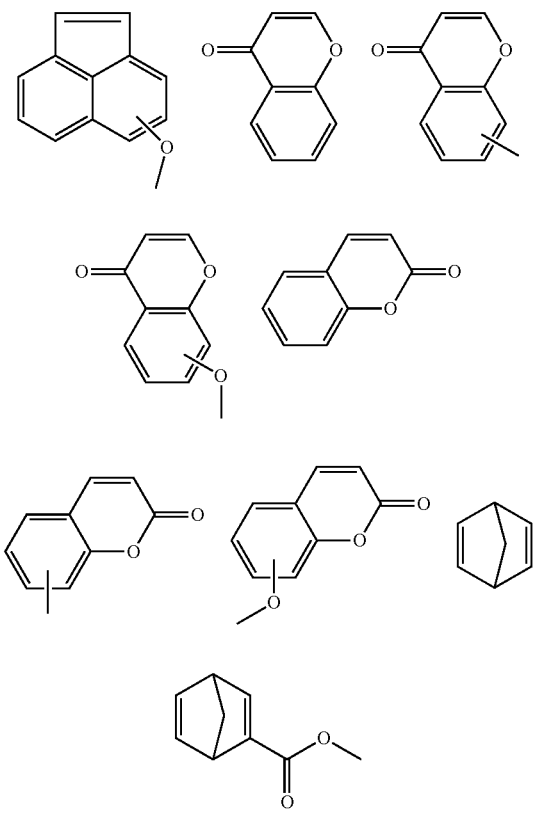

The base polymer may further include recurring units (e) which are derived from styrene, vinylnaphthalene, vinylanthracene, vinylpyrene, methyleneindene, vinylpyridine, or vinylcarbazole.

In a further embodiment, recurring units (f) derived from an onium salt having a polymerizable unsaturated bond may be incorporated in the base polymer. The preferred recurring units (f) are recurring units of at least one type selected from the formulae (f1), (f2), and (f3). These units are simply referred to as recurring units (f1), (f2), and (f3). The recurring units (f1), (f2), and (f3) may be used alone or in combination of two or more types.

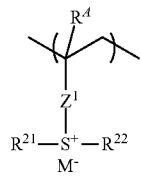 (f1)

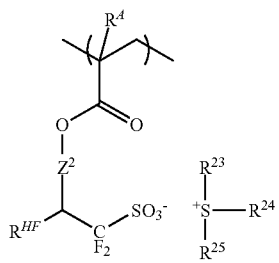 (f2)

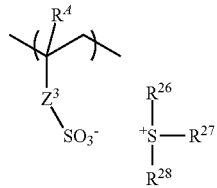 (f3)

In the formulae (f1) to (f3), $R^A$ is each independently hydrogen or a methyl group. $Z^1$ is a single bond, a $C_1$-$C_6$ aliphatic hydrocarbylene group, a phenylene group, a naphthylene group, a $C_7$-$C_{18}$ combination thereof, —O—$Z^{11}$—, —C(=O)—O—$Z^{11}$—, or —C(=O)—NH—$Z^{11}$—. $Z^{11}$ is a $C_1$-$C_6$ aliphatic hydrocarbylene group, a phenylene group, a naphthylene group, or a $C_7$-$C_{18}$ combination thereof, which may contain a carbonyl group, an ester bond, an ether bond, or a hydroxyl group. $Z^2$ is a single bond, —$Z^{21}$—C(=O)—O—, —$Z^{21}$—O—, or —$Z^{21}$—O—C(=O)—. $Z^{21}$ is a $C_1$-$C_{12}$ saturated hydrocarbylene group which may contain a carbonyl group, an ester bond, or an ether bond. $Z^3$ is a single bond, a methylene group, an ethylene group, a phenylene group, a fluorinated phenylene group, —O—$Z^{31}$—, —C(=O)—O—$Z^{31}$—, or —C(=O)—NH—$Z^{31}$—. $Z^{31}$ is a $C_1$-$C_6$ aliphatic hydrocarbylene group, a phenylene group, a fluorinated phenylene group, or a trifluoromethyl-substituted phenylene group which may contain a carbonyl group, an ester bond, an ether bond, or a hydroxyl group. The aliphatic hydrocarbylene groups represented by $Z^{11}$ and $Z^{31}$ may be saturated or unsaturated, and may be straight, branched, or cyclic. The saturated hydrocarbylene group represented by $Z^{21}$ may be straight, branched, or cyclic.

In the formulae (f1) to (f3), $R^{21}$ to $R^{28}$ are each independently a halogen or a $C_1$-$C_{20}$ hydrocarbyl group which may contain a heteroatom. The hydrocarbyl group may be saturated or unsaturated, and may be straight, branched, or cyclic. Illustrative examples are as exemplified below for $R^{101}$ to $R^{105}$ in the formulae (1-1) and (1-2).

A pair of $R^{23}$ and $R^{24}$, or $R^{26}$ and $R^{27}$ may bond together to form a ring with the sulfur atom to which they are attached. Examples of the ring are as exemplified above as the ring that two $R^2$s, taken together, form when r=1 with the sulfur atom to which they are attached in the formula (A).

In the formula (f2), $R^{HF}$ is hydrogen or a trifluoromethyl group.

In the formula (f1), $M^-$ is a non-nucleophilic counter ion. Examples of the non-nucleophilic counter ion include halide ions such as chloride and bromide; fluoroalkylsulfonate ions such as triflate, 1,1,1-trifluoroethanesulfonate, and nonafluorobutanesulfonate; arylsulfonate ions such as tosylate, benzenesulfonate, 4-fluorobenzenesulfonate, and 1,2,3,4,5-pentafluorobenzenesulfonate; alkylsulfonate ions such as mesylate and butanesulfonate; imide ions such as bis(trifluoromethylsulfonyl)imide, bis(perfluoroethylsulfonyl)imide, and bis(perfluorobutylsulfonyl)imide; and methide ions such as tris(trifluoromethylsulfonyl)methide and tris(perfluoroethylsulfonyl)methide.

Also included are sulfonate ions having fluorine substituted at α-position as represented by the formula (f1-1) and sulfonate ions having fluorine substituted at α-position and trifluoromethyl at β-position as represented by the formula (f1-2).

 (f1-1)

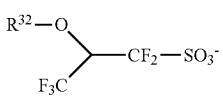

(f1-2)

In the formula (f1-1), $R^{31}$ is hydrogen or a $C_1$-$C_{20}$ hydrocarbyl group which may contain an ether bond, an ester bond, a carbonyl group, a lactone ring, or a fluorine atom. The hydrocarbyl group may be saturated or unsaturated, and may be straight, branched, or cyclic. Examples thereof are as will be exemplified for the hydrocarbyl group of Rill in the formula (1A').

In the formula (f1-2), $R^{32}$ is hydrogen, or a $C_1$-$C_{30}$ hydrocarbyl or $C_2$-$C_{30}$ hydrocarbylcarbonyl group which may contain an ether bond, an ester bond, a carbonyl group, or a lactone ring. The hydrocarbyl group and the hydrocarbyl moiety of the hydrocarbylcarbonyl group may be saturated or unsaturated, and straight, branched, or cyclic. Examples thereof are as will be exemplified for the hydrocarbyl group of $R^{111}$ in the formula (1A').

Examples of the cation in the monomer from which the recurring unit (f1) is derived are shown below, but not limited thereto. Herein $R^A$ is as defined above.

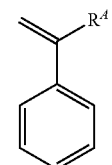

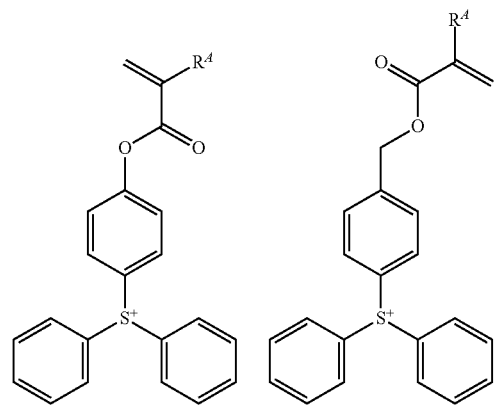

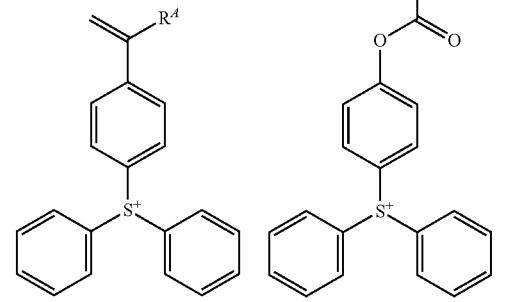

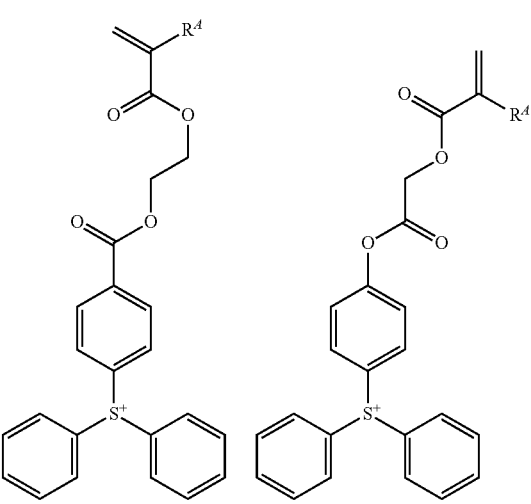

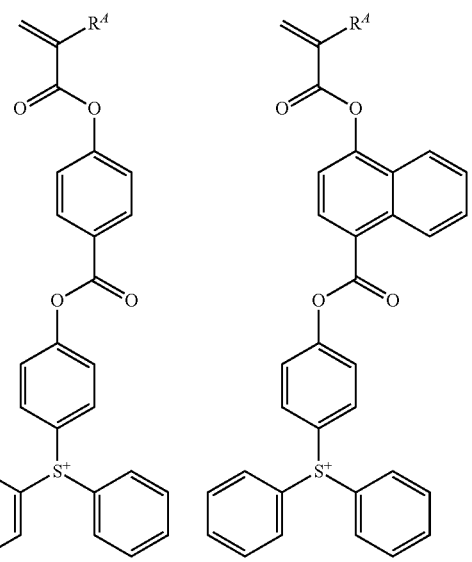

-continued
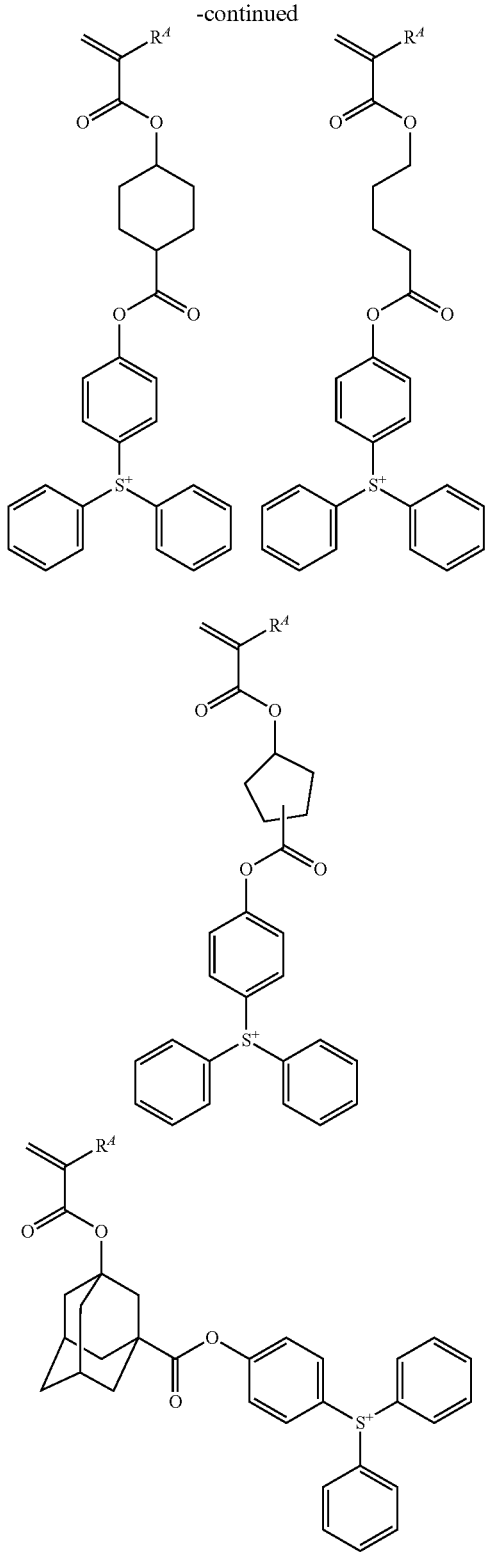
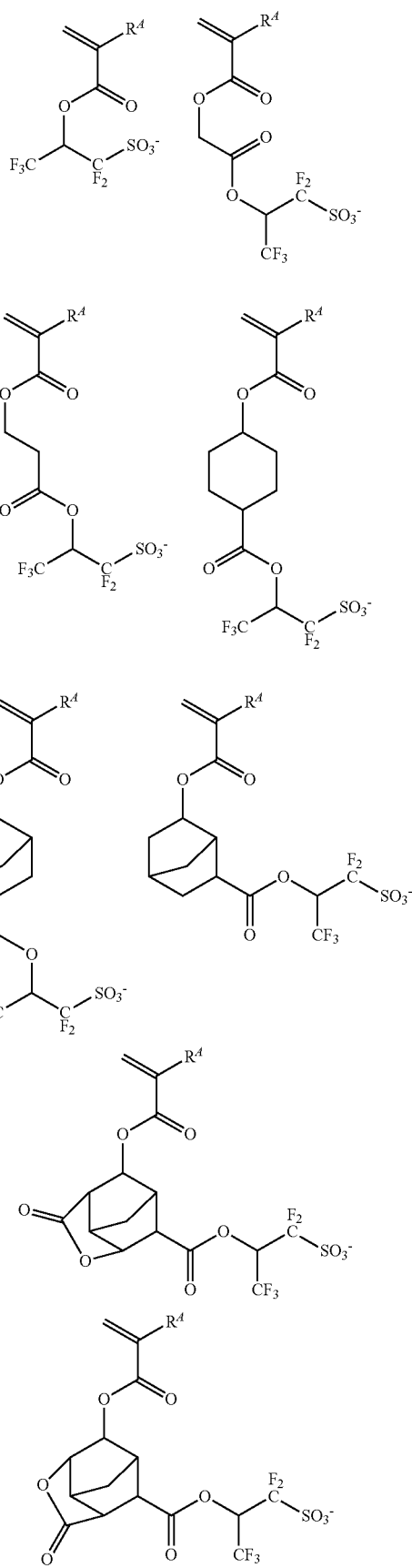
Examples of the cation in the monomer from which the recurring unit (f2) or (f3) is derived are as will be described as the cation in the sulfonium salt having the formula (1-1).
Examples of the anion in the monomer from which the recurring unit (f2) is derived are shown below, but not limited thereto. Herein $R^A$ is as defined above.

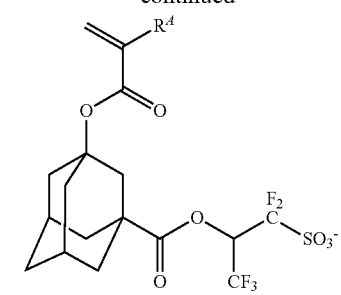
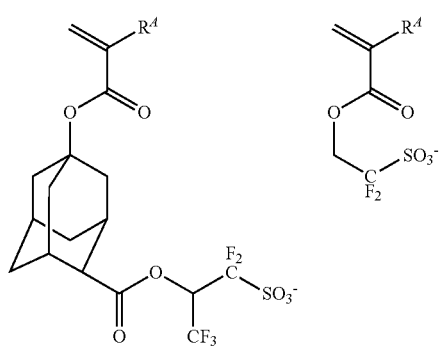
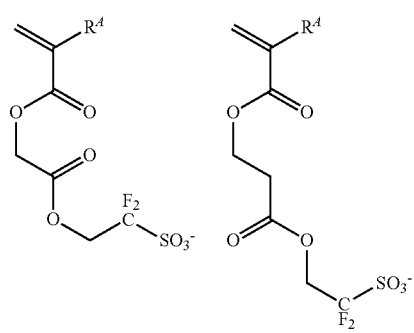
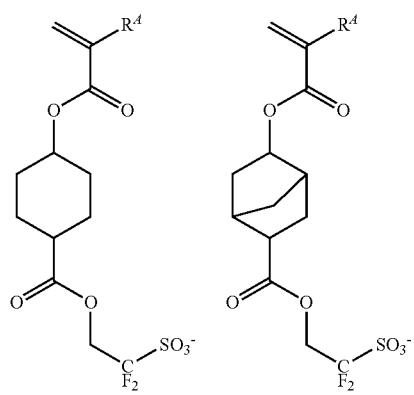
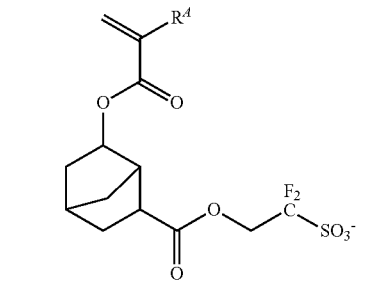
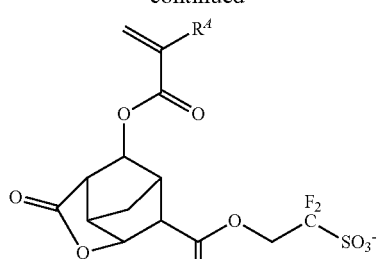
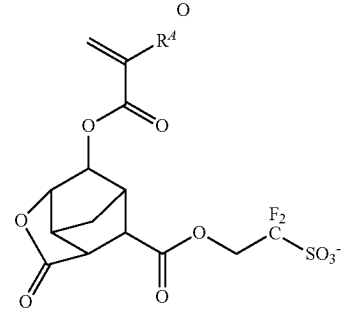
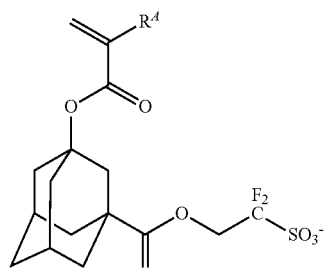
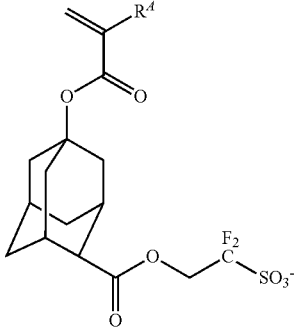
Examples of the anion in the monomer from which the recurring unit (f3) is derived are shown below, but not limited thereto. Herein $R^A$ is as defined above.
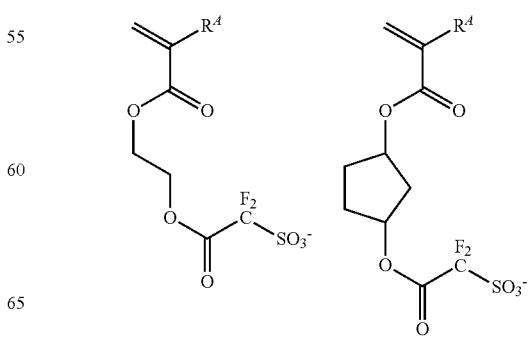

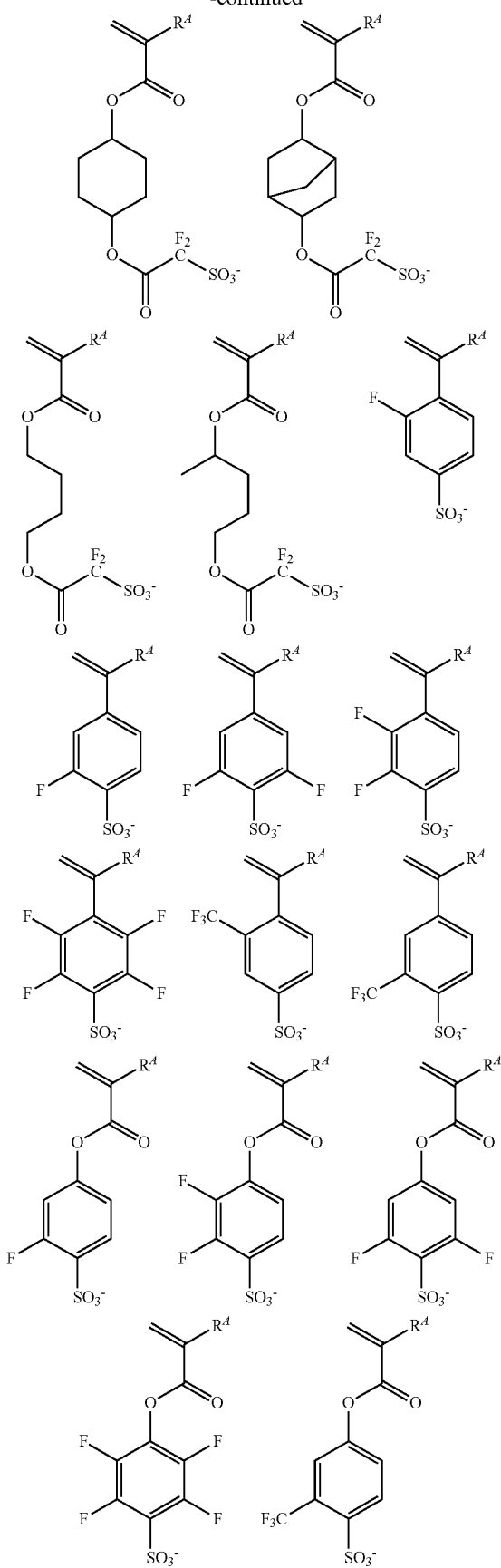

The attachment of an acid generator to the polymer main chain is effective in restraining acid diffusion, thereby preventing a reduction of resolution due to blur by acid diffusion. Also LWR or CDU is improved since the acid generator is uniformly distributed. In the case that the base polymer comprising recurring units (f) (that is, a polymer-bound acid generator) is used, an acid generator capable of generating a strong acid, which will be described later, can be omitted.

The base polymer for formulating the positive resist composition comprises recurring unit (a1) or (a2) having an acid labile group as essential component. A fraction of recurring units (a1), (a2), (b), (c), (d), (e), and (0 is: preferably $0 \leq a1 < 1.0$, $0 \leq a2 < 1.0$, $0 < a1+a2 < 1.0$, $0 \leq b \leq 0.9$, $0 \leq c \leq 0.9$, $0 \leq d \leq 0.8$, $0 \leq e \leq 0.8$, and $0 \leq f \leq 0.5$; more preferably $0 \leq a1 \leq 0.9$, $0 \leq a2 \leq 0.9$, $0.1 \leq a1+a2 \leq 0.9$, $0 \leq b \leq 0.8$, $0 \leq c \leq 0.8$, $0 \leq d \leq 0.7$, $0 \leq e \leq 0.7$, and $0 \leq f \leq 0.4$; and even more preferably $0 \leq a1 \leq 0.8$, $0 \leq a2 \leq 0.8$, $0.1 \leq a1+a2 \leq 0.8$, $0 \leq b \leq 0.75$, $0 \leq c \leq 0.75$, $0 \leq d \leq 0.6$, $0 \leq e \leq 0.6$, and $0 \leq f \leq 0.3$. Notably, $f=f1+f2+f3$, meaning that recurring unit (f) is at least one of recurring units (f1) to (f3). $a1+a2+b+c+d+e+f=1.0$.

For the base polymer for formulating the negative resist composition, an acid labile group is not necessarily essential. The base polymer comprises recurring units (b), and optionally recurring units (c), (d), (e), and/or (0. A fraction of these recurring units is preferably $0 < b \leq 1.0$, $0 \leq c \leq 0.9$, $0 \leq d \leq 0.8$, $0 \leq e \leq 0.8$, and $0 \leq f \leq 0.5$, more preferably $0.2 \leq b \leq 1.0$, $0 \leq c \leq 0.8$, $0 \leq d \leq 0.7$, $0 \leq e \leq 0.7$, and $0 \leq f \leq 0.4$, and even more preferably $0.3 \leq b \leq 1.0$, $0 \leq c \leq 0.75$, $0 \leq d \leq 0.6$, $0 \leq e \leq 0.6$, and $0 \leq f \leq 0.3$. Notably, $f=f1+f2+f3$, meaning that recurring unit (f) is at least one of recurring units (f1) to (f3). $b+c+d+e+f=1.0$.

The base polymer may be synthesized by any desired methods, for example, by dissolving one or more monomers selected from the monomers corresponding to the foregoing recurring units in an organic solvent, adding a radical polymerization initiator thereto, and heating for polymerization.

Examples of the organic solvent which can be used for polymerization include toluene, benzene, tetrahydrofuran (THF), diethyl ether, and dioxane. Examples of the polymerization initiator used herein include 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. The polymerization temperature is preferably 50 to 80° C. The reaction time is preferably 2 to 100 hours, and more preferably 5 to 20 hours.

When a monomer having a hydroxyl group is copolymerized, the hydroxyl group may be replaced by an acetal group susceptible to deprotection with acid, typically ethoxyethoxy, prior to polymerization, and the polymerization may be followed by deprotection with weak acid and water. Alternatively, the hydroxyl group may be replaced by an acetyl, formyl, pivaloyl or similar group prior to polymerization, and the polymerization may be followed by alkaline hydrolysis.

When hydroxystyrene or hydroxyvinylnaphthalene is copolymerized, an alternative method is possible. Specifically, acetoxystyrene or acetoxyvinylnaphthalene is used instead of hydroxystyrene or hydroxyvinylnaphthalene, and after polymerization, the acetoxy group is deprotected by alkaline hydrolysis, for thereby converting the polymer product to hydroxystyrene or hydroxyvinylnaphthalene.

For alkaline hydrolysis, a base such as aqueous ammonia or triethylamine may be used. The reaction temperature is preferably −20° C. to 100° C., and more preferably 0° C. to 60° C. The reaction time is preferably 0.2 to 100 hours, and more preferably 0.5 to 20 hours.

The base polymer should preferably have a weight average molecular weight (Mw) in the range of 1,000 to 500,000, and more preferably 2,000 to 30,000, as measured by gel permeation chromatography (GPC) versus polystyrene standards using THF solvent. With too low a Mw, the resist composition may become less heat resistant. A polymer with too high a Mw may lose alkaline solubility and give rise to a footing phenomenon after pattern formation.

If a base polymer has a wide molecular weight distribution or dispersity (Mw/Mn), which indicates the presence of lower and higher molecular weight polymer fractions, there is a possibility that foreign matter is left on the pattern or the pattern profile is degraded after exposure. The influences of Mw and Mw/Mn become stronger as the pattern rule becomes finer. Therefore, the base polymer should preferably have a narrow dispersity (Mw/Mn) of 1.0 to 2.0, especially 1.0 to 1.5, in order to provide a resist composition suitable for micropatterning to a small feature size.

In the base polymer, it is understood that a blend of two or more polymers which differ in compositional ratio, Mw or Mw/Mn is acceptable.

Acid Generator

The resist composition may comprise an acid generator capable of generating a strong acid that induces a deprotection reaction of a positive resist composition or a polarity switch or crosslinking reaction of a negative resist composition (hereinafter, also referred to as acid generator of addition type). The acid generator of addition type is typically a compound capable of generating an acid upon exposure to actinic ray or radiation (photoacid generator (PAG)). Although the PAG is not particularly limited as long as it is capable of generating an acid upon exposure to high-energy radiation, acid generators capable of generating fluorosulfonic acid, fluoroimidic acid, or fluoromethide acid are preferred. Suitable examples of the PAG include sulfonium salts, iodonium salts, sulfonyldiazomethane, N-sulfonyloxyimide, and oxime-O-sulfonate acid generators.

The acid generator capable of generating fluorosulfonic acid, fluoroimidic acid, or fluoromethide acid is typically capable of generating the α-fluorosulfonic acid anion described in JP-A 2004-531749, JP-A 2007-145797, JP-A 2008-7410, JP-A 2018-101130, JP-A 2018-049177, or WO 2011/093139, the β-fluorosulfonic acid anion described in JP-A 2014-133725, the α-fluorosulfonic acid anion, the fluoroimidic acid anion, or the fluoromethide acid anion described in JP-A 2014-126767, or the fluorosulfonimidate anion described in JP-A 2016-210761.

Specific examples of the PAG include sulfonium salts having the formula (1-1) and iodonium salts having the formula (1-2).

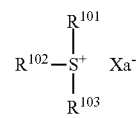

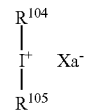

In the formulae (1-1) and (1-2), $R^{101}$ to $R^{105}$ are each independently a halogen or a $C_1$-$C_{20}$ hydrocarbyl group which may contain a heteroatom.

Examples of the halogen include fluorine, chlorine, bromine, and iodine.

The $C_1$-$C_{20}$ hydrocarbyl groups of $R^{101}$ to $R^{105}$ may be saturated or unsaturated, and straight, branched, or cyclic. Specific examples of the hydrocarbyl group include $C_1$-$C_{20}$ alkyl groups such as methyl, ethyl, n-propyl, isopropyl, n-butyl, isobutyl, sec-butyl, tert-butyl, n-pentyl, n-hexyl, n-octyl, n-nonyl, n-decyl, undecyl, dodecyl, tridecyl, tetradecyl, pentadecyl, heptadecyl, octadecyl, nonadecyl, and icosyl; $C_3$-$C_{20}$ cyclic saturated hydrocarbyl groups such as cyclopropyl, cyclopentyl, cyclohexyl, cyclopropylmethyl, 4-methylcyclohexyl, cyclohexylmethyl, norbornyl, and adamantyl; alkenyl groups such as vinyl, propenyl, butenyl, and hexenyl; $C_2$-$C_{20}$ alkynyl groups such as ethynyl, propynyl, and butynyl; $C_3$-$C_{20}$ cyclic unsaturated aliphatic hydrocarbyl groups such as cyclohexenyl and norbornenyl; $C_6$-$C_{20}$ aryl groups such as phenyl, methylphenyl, ethylphenyl, n-propylphenyl, isopropylphenyl, n-butylphenyl, isobutylphenyl, sec-butylphenyl, tert-butylphenyl, naphthyl, methylnaphthyl, ethylnaphthyl, n-propylnaphthyl, isopropylnaphthyl, n-butylnaphthyl, isobutylnaphthyl, sec-butylnaphthyl, and tert-butylnaphthyl; $C_7$-$C_{20}$ aralkyl groups such as benzyl and phenethyl; and groups obtained from combination thereof.

In these groups, some or all of the hydrogen atoms may be substituted by a group containing a heteroatom such as oxygen, sulfur, nitrogen, or a halogen, or some carbon may be replaced by a group containing a heteroatom such as oxygen, sulfur, or nitrogen, so that the group may contain a hydroxyl, cyano, carbonyl, ether bond, ester bond, sulfonic acid ester bond, carbonate, lactone ring, sultone ring, carboxylic anhydride, or haloalkyl group.

Also $R^{101}$ and $R^{102}$ may bond together to form a ring with the sulfur atom to which they are attached. Examples of the ring are as exemplified above as the ring that two $R^2$s, taken together, form when r=1 with the sulfur atom to which they are attached in the formula (A).

Examples of the cation in the sulfonium salt having the formula (1-1) are shown below, but not limited thereto.

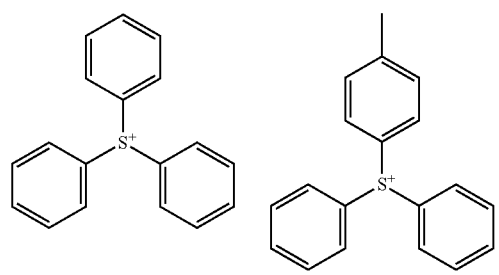

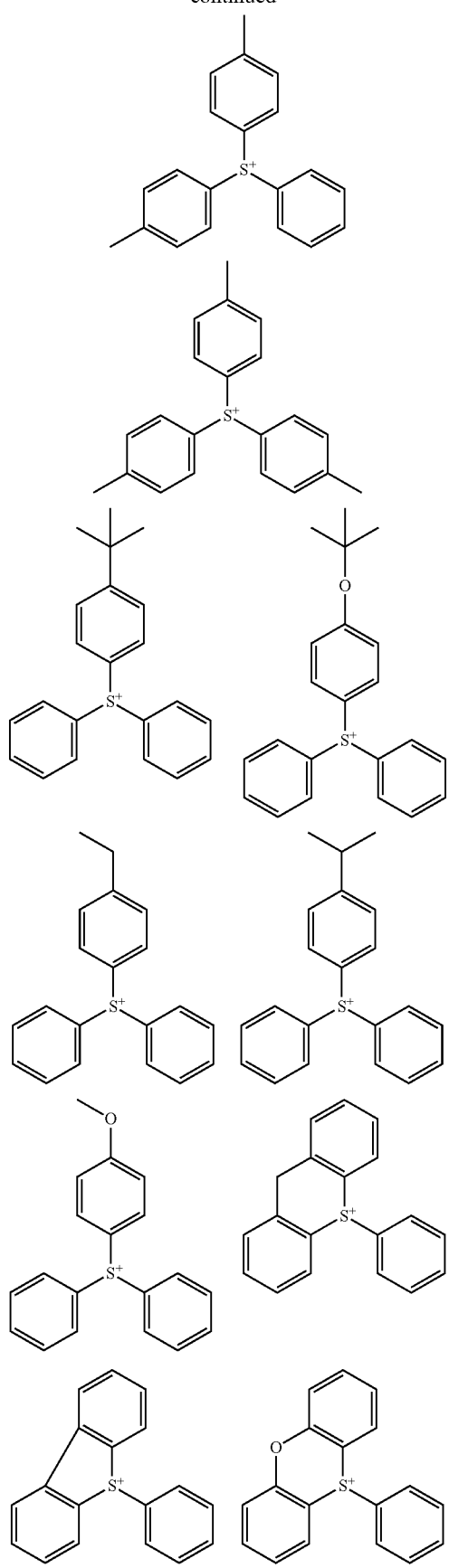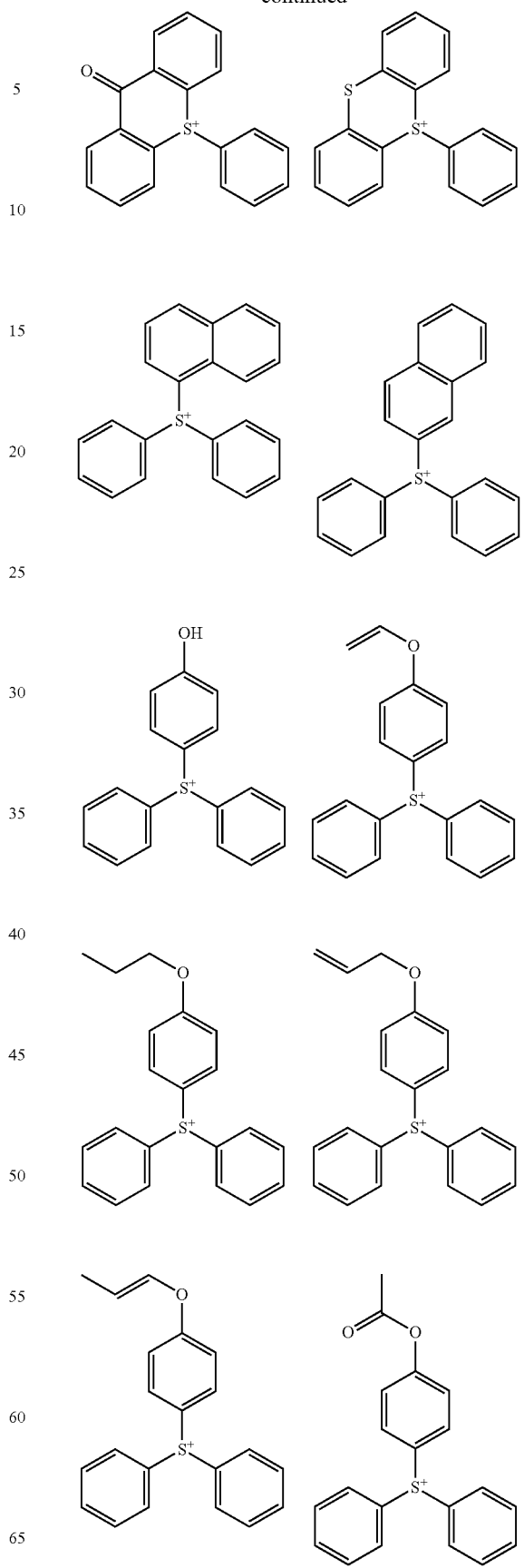

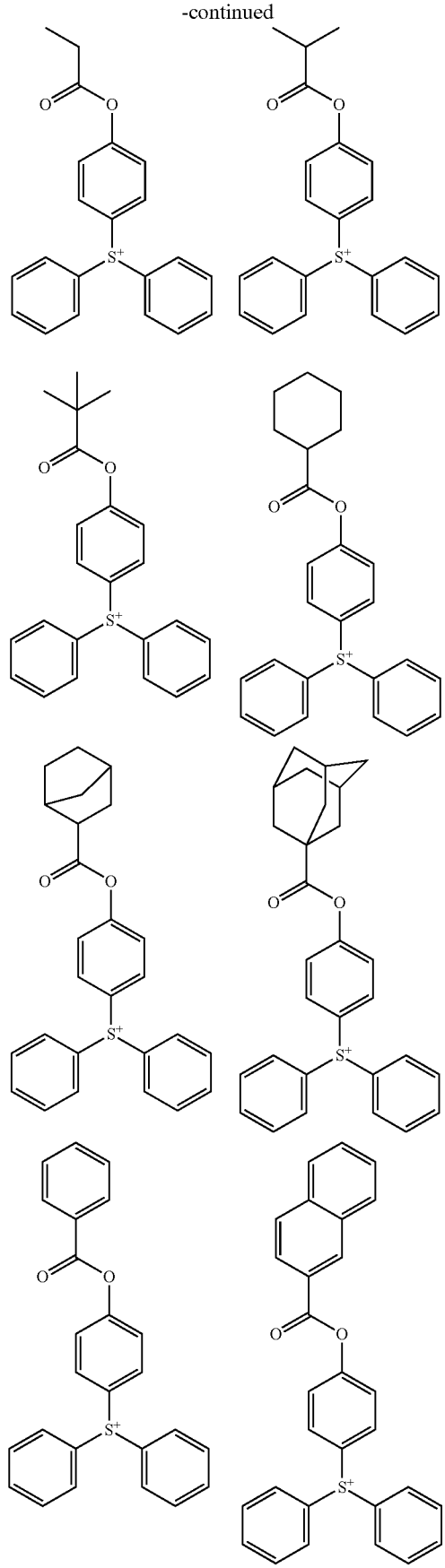
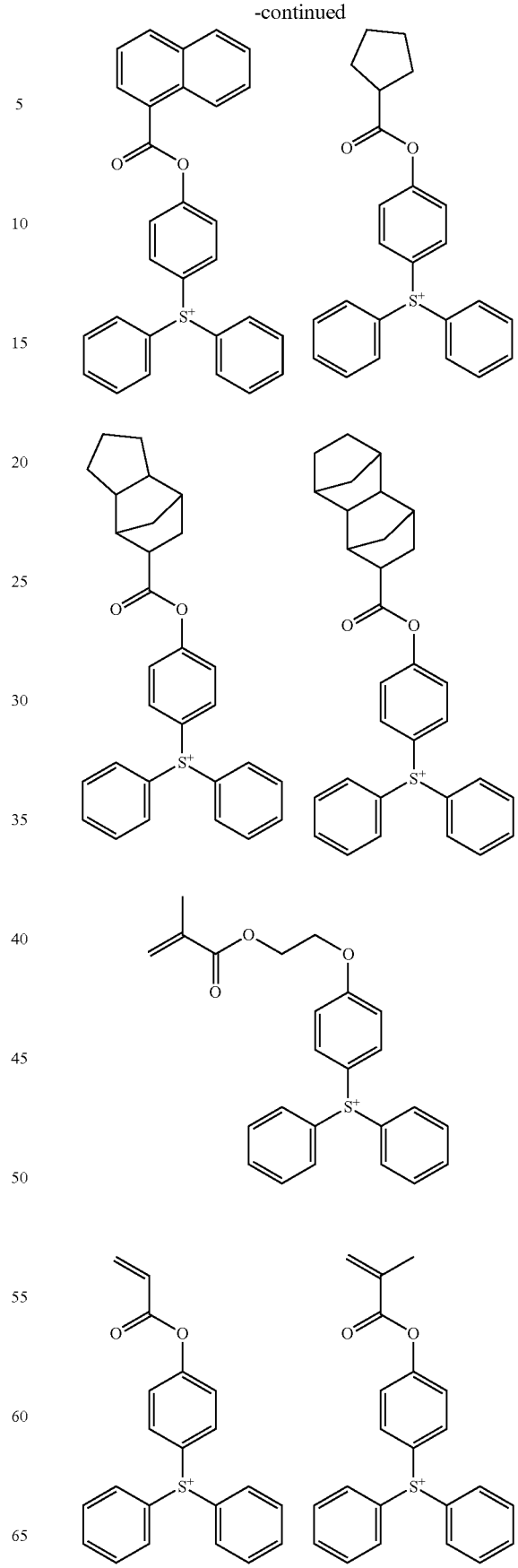

131
-continued
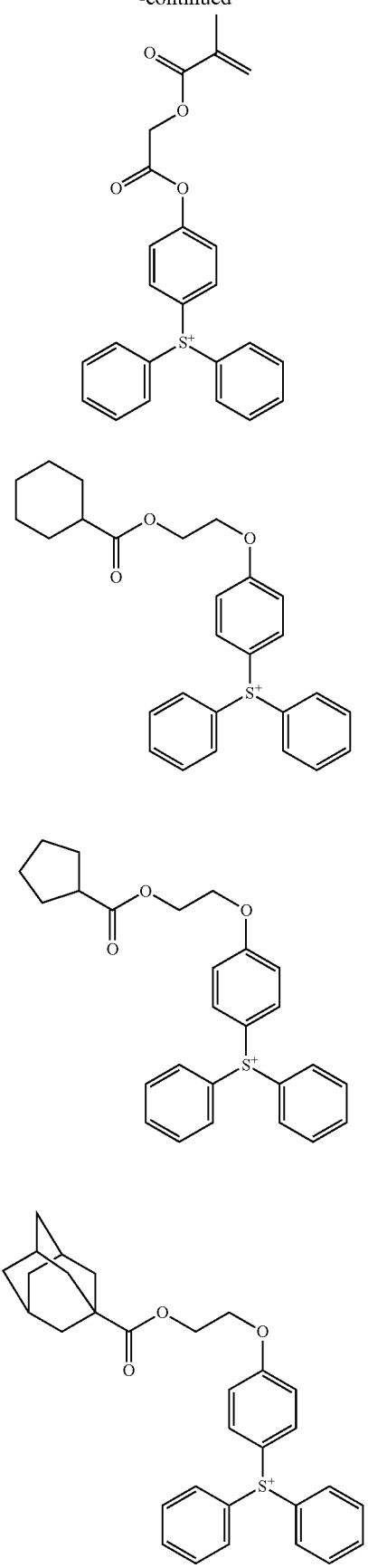 [SMILES: C=C(C)C(=O)OCC(=O)Oc1ccc([S+](c2ccccc2)c2ccccc2)cc1 ; O=C(OCCOc1ccc([S+](c2ccccc2)c2ccccc2)cc1)C1CCCCC1 ; O=C(OCCOc1ccc([S+](c2ccccc2)c2ccccc2)cc1)C1CCCC1 ; O=C(OCCOc1ccc([S+](c2ccccc2)c2ccccc2)cc1)C12CC3CC(CC(C3)C1)C2]
132
-continued
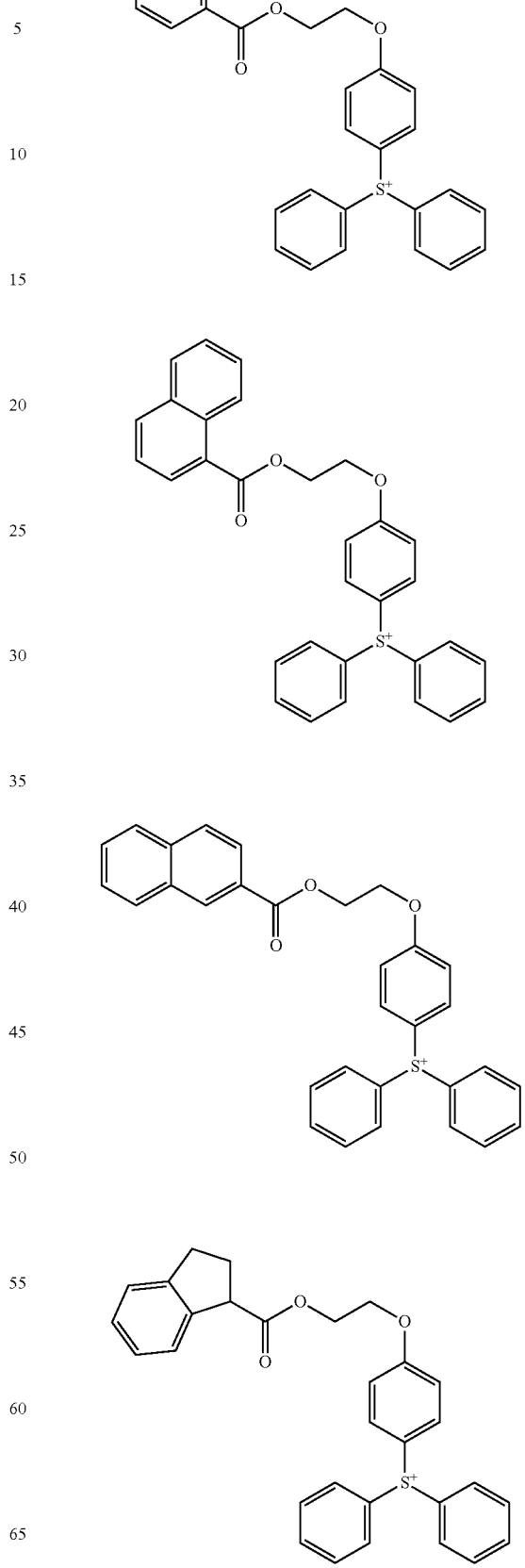

133
-continued
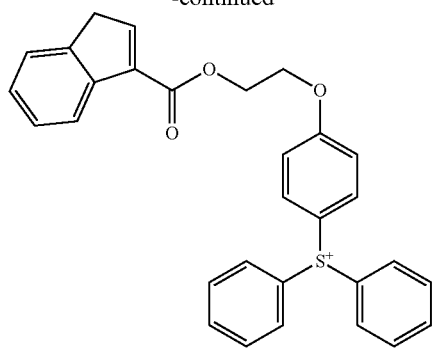
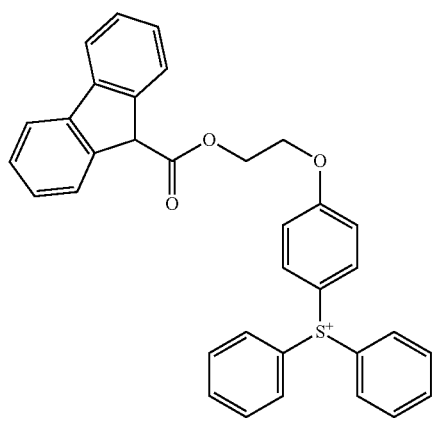
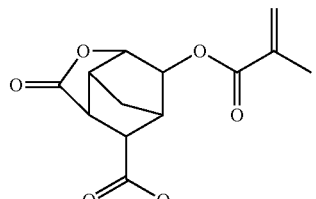
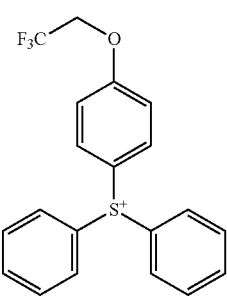
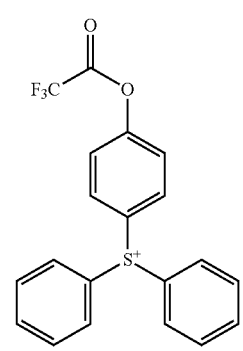
134
-continued
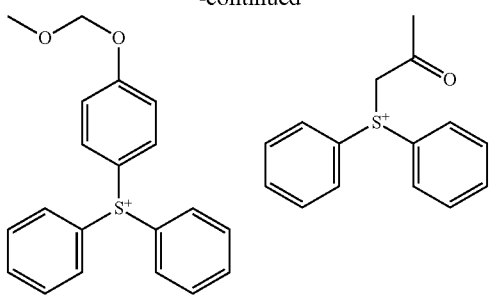
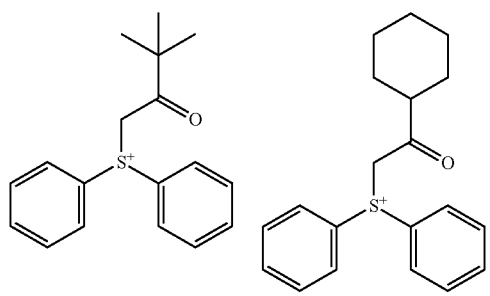
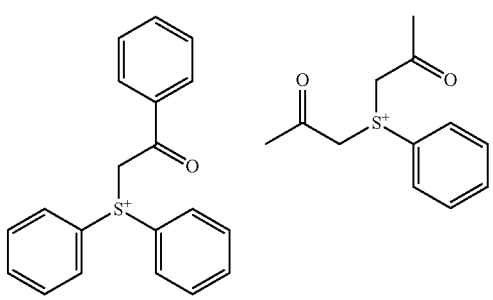
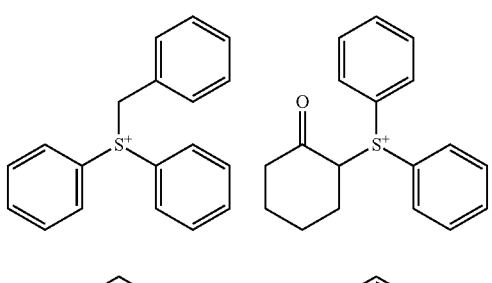
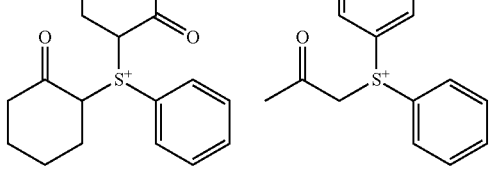
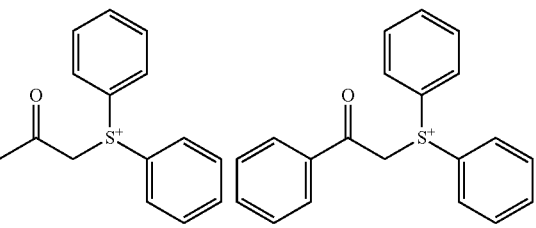

135
-continued
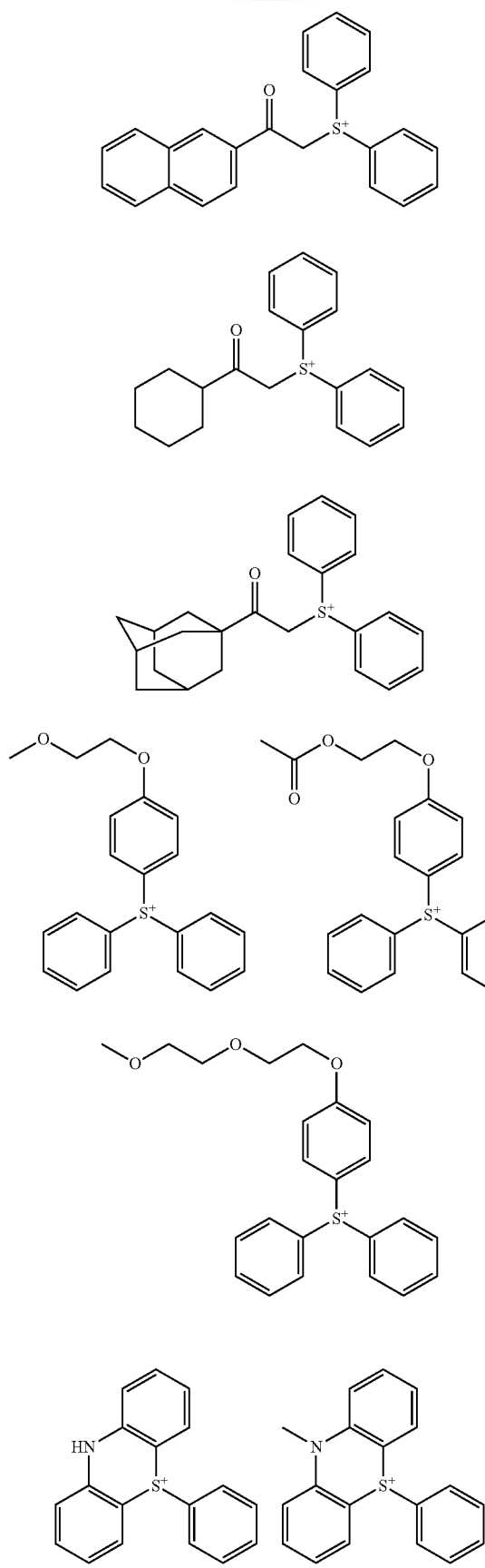
136
-continued
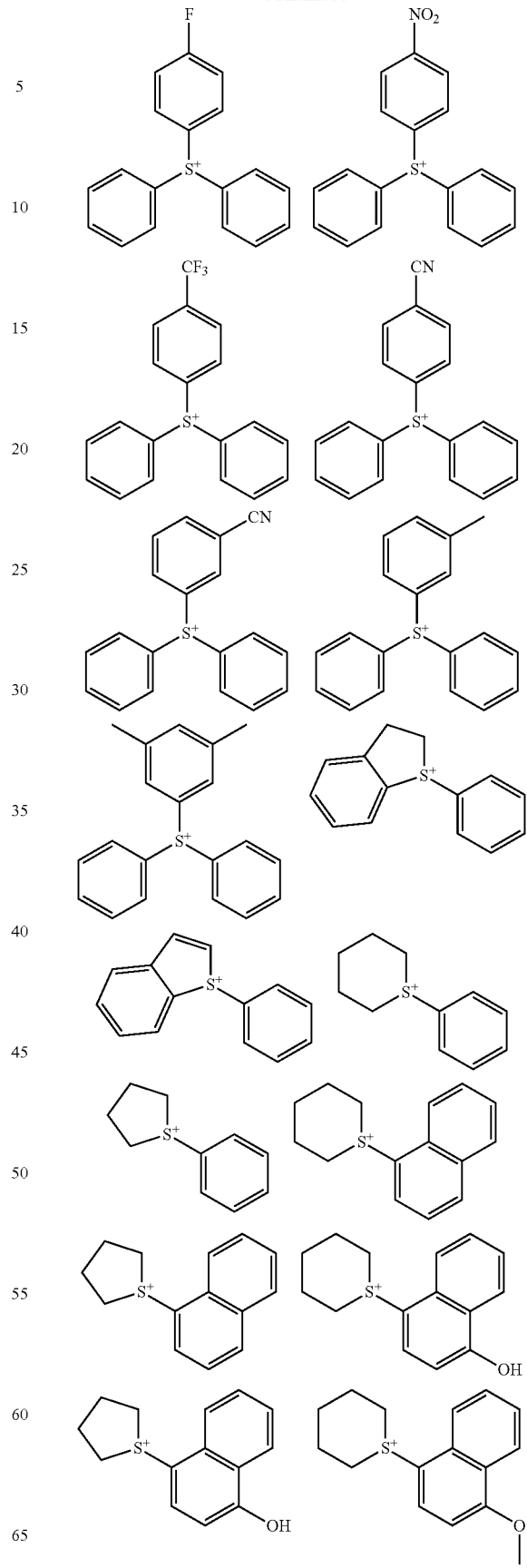

137
-continued
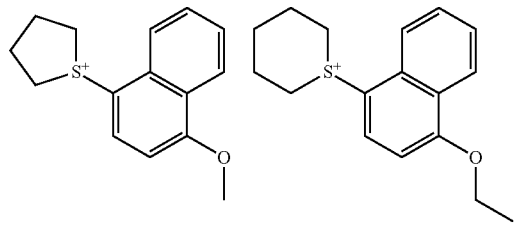
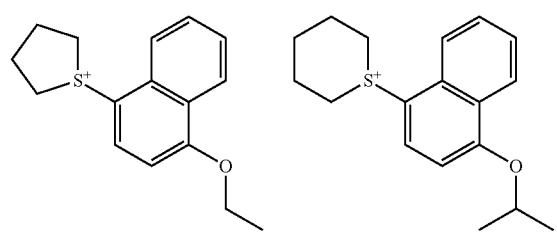
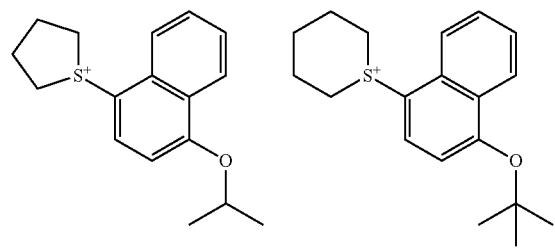
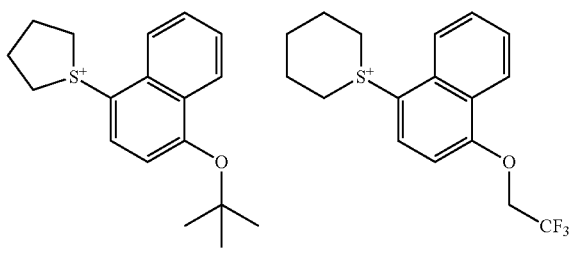
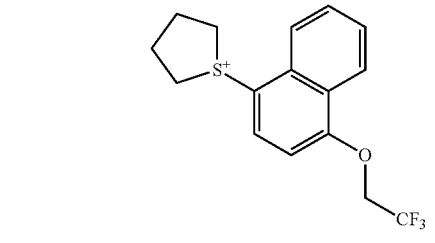
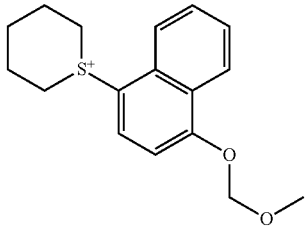
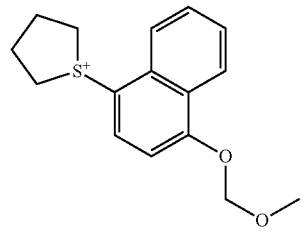
138
-continued
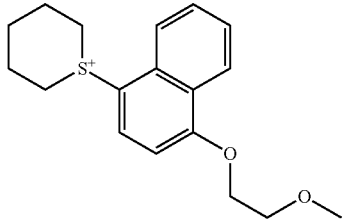
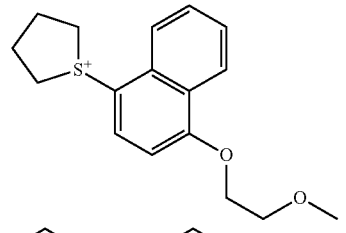
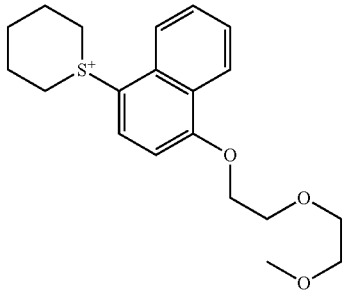
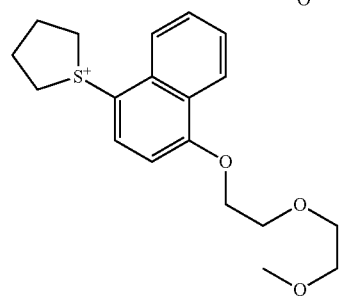
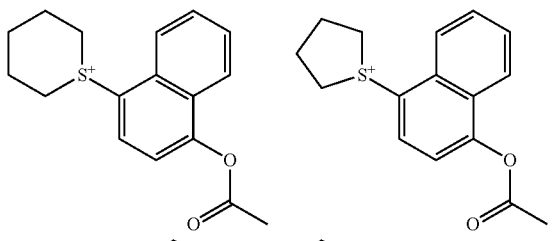
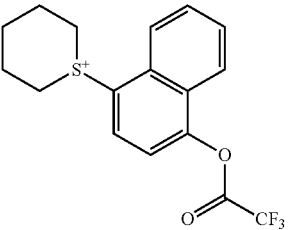
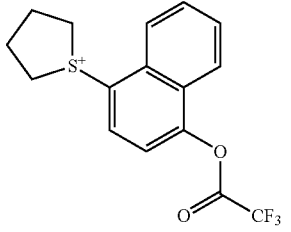

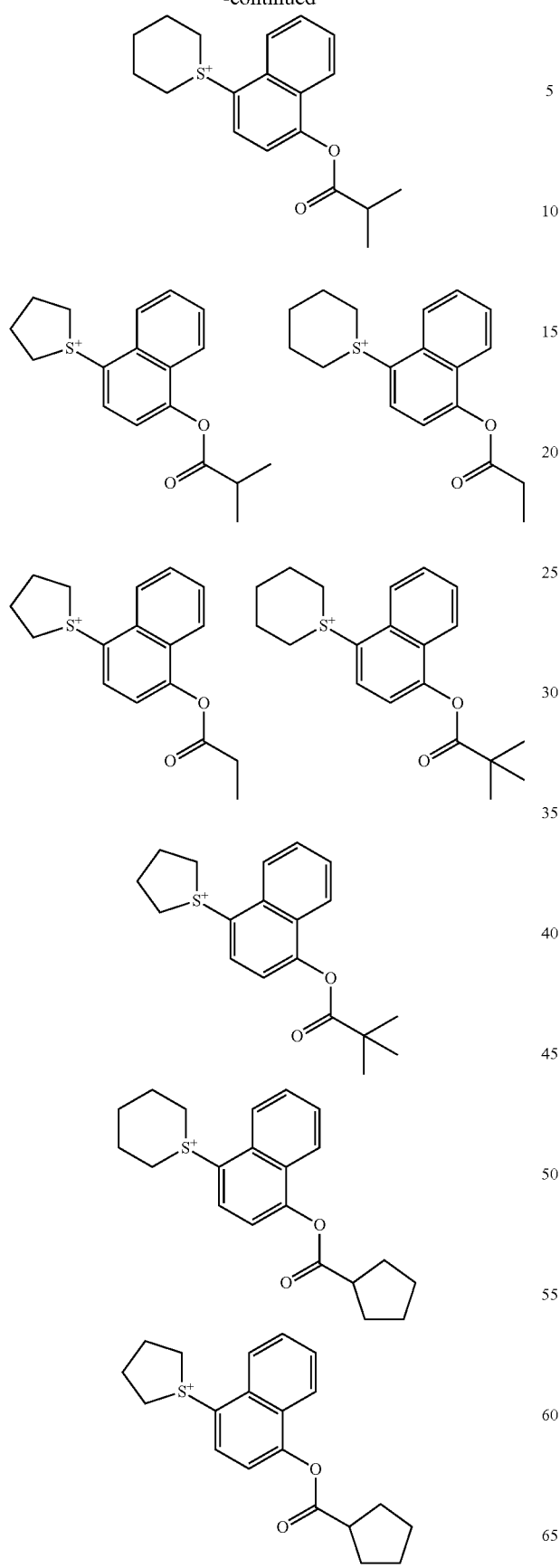

141
-continued
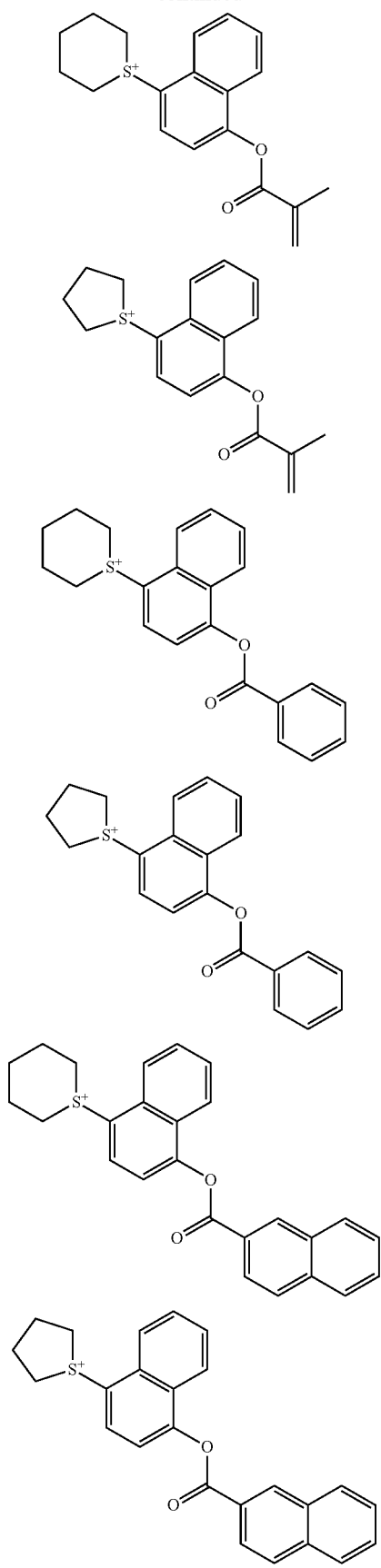
142
-continued
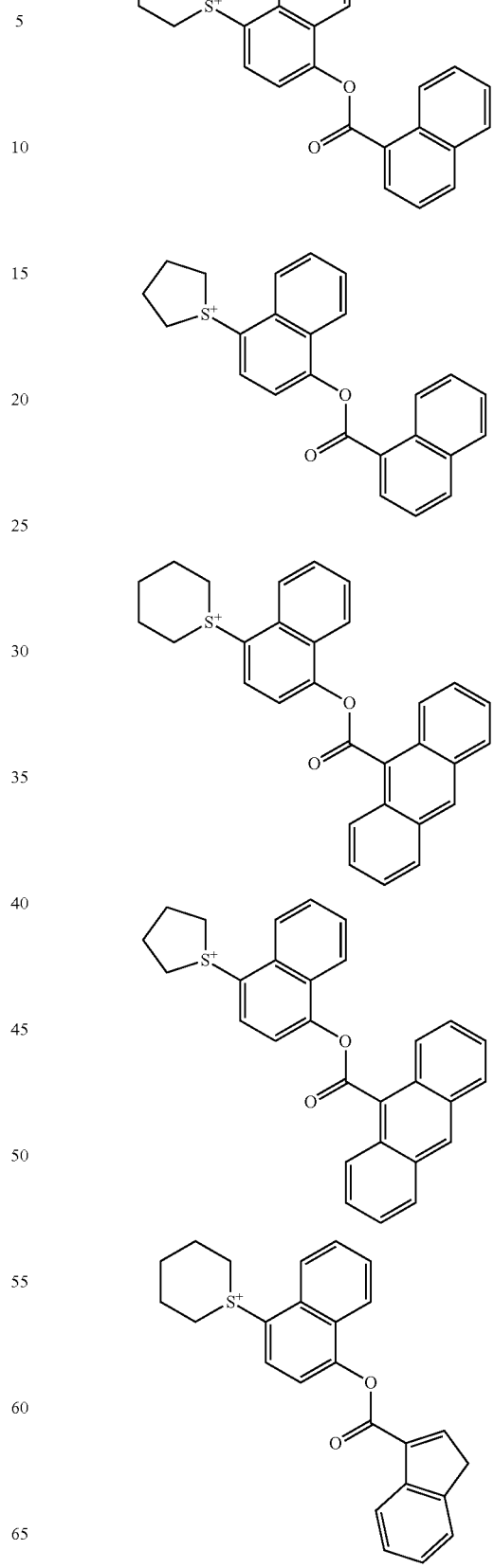

143
-continued
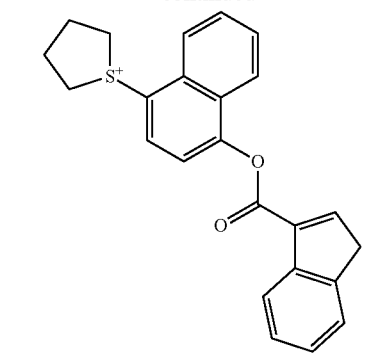
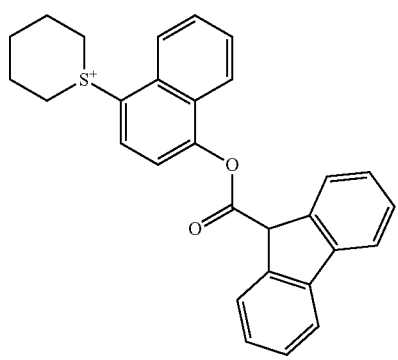
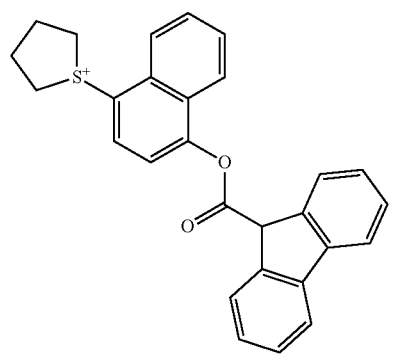
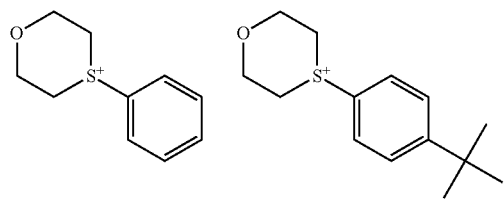
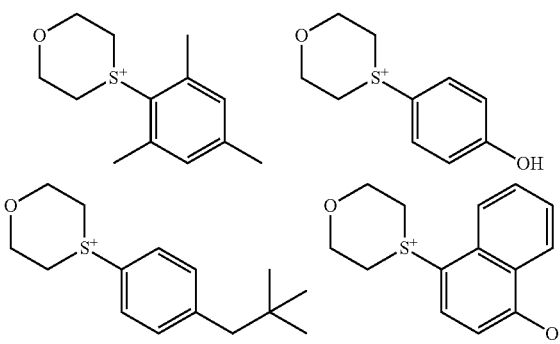
144
-continued
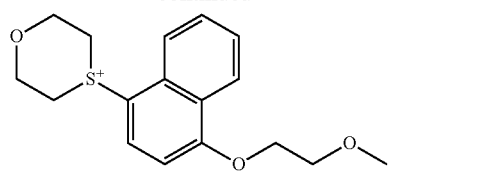
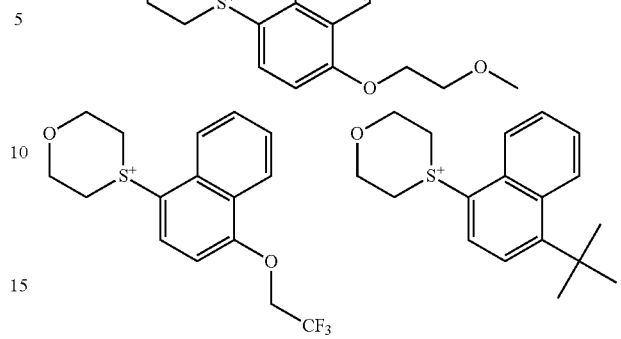
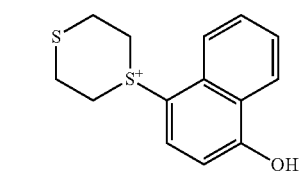
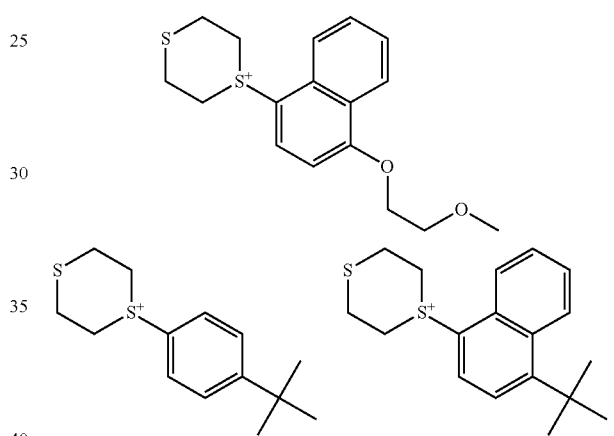
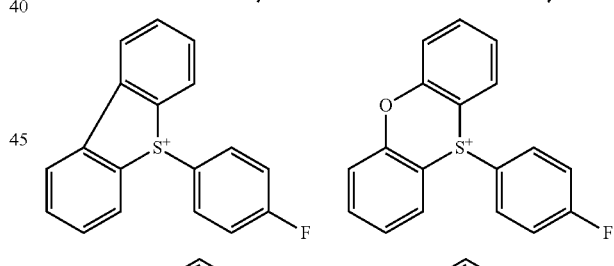
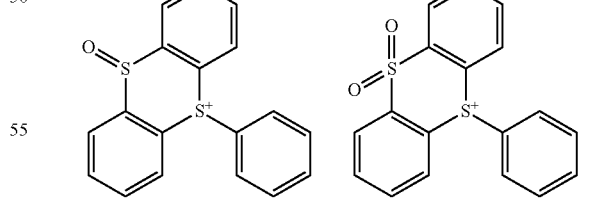
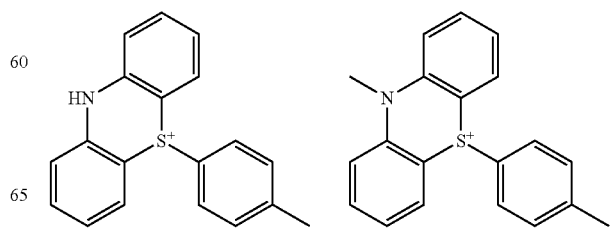

145
-continued
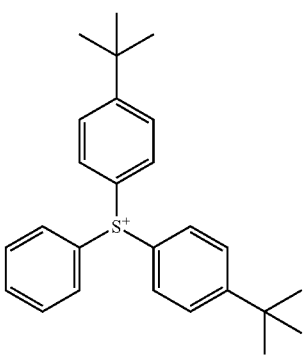
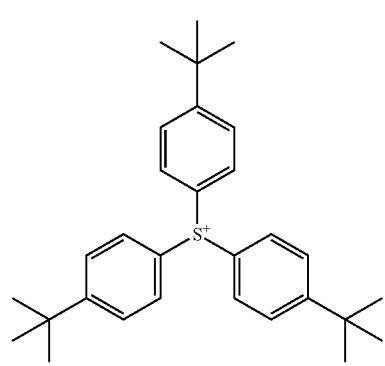
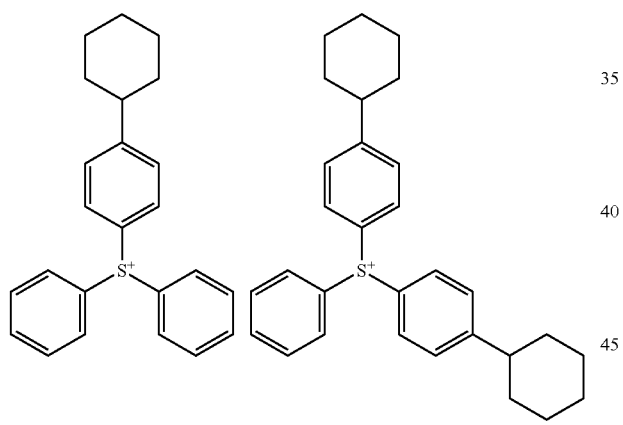
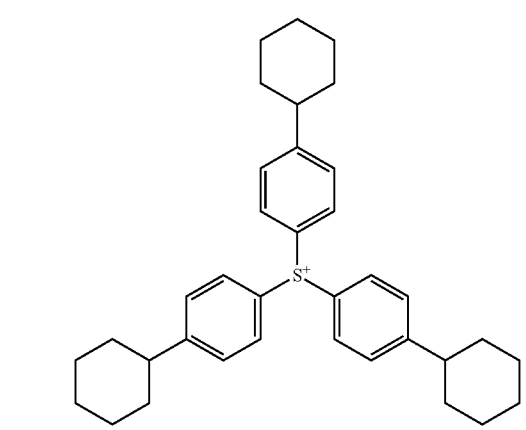
146
-continued
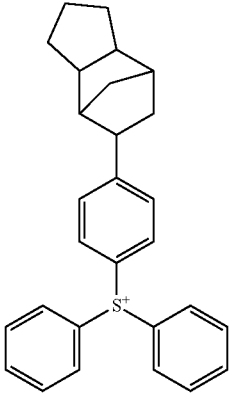
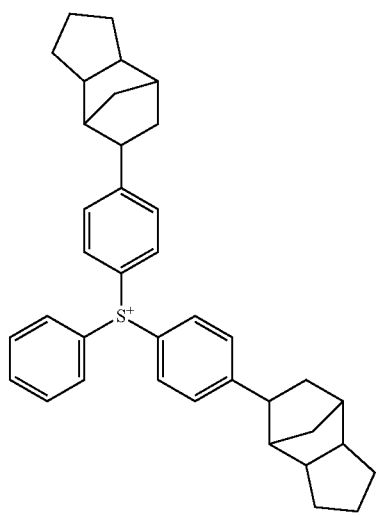
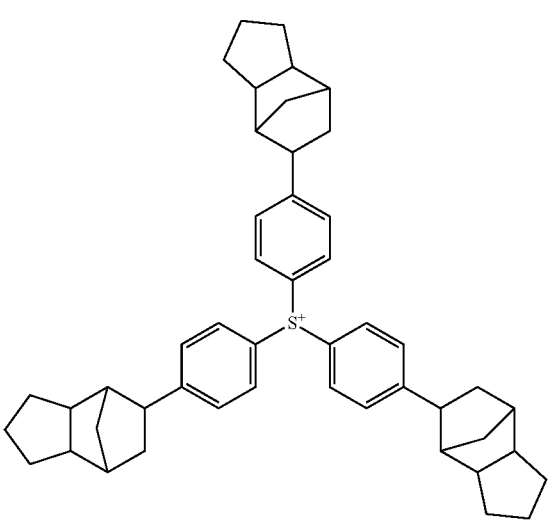

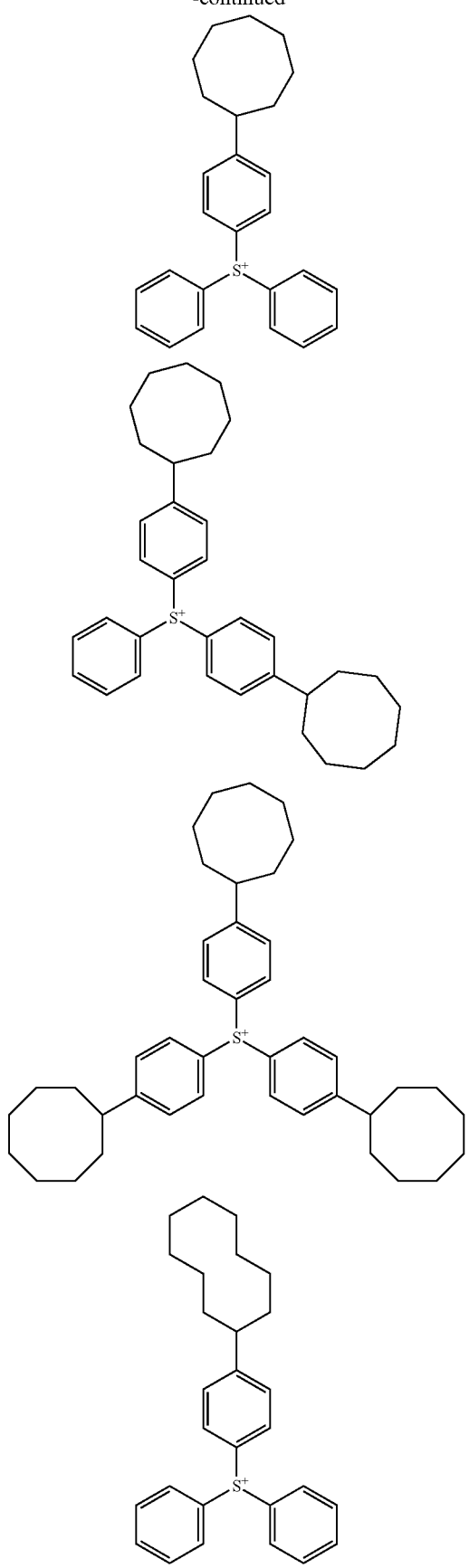
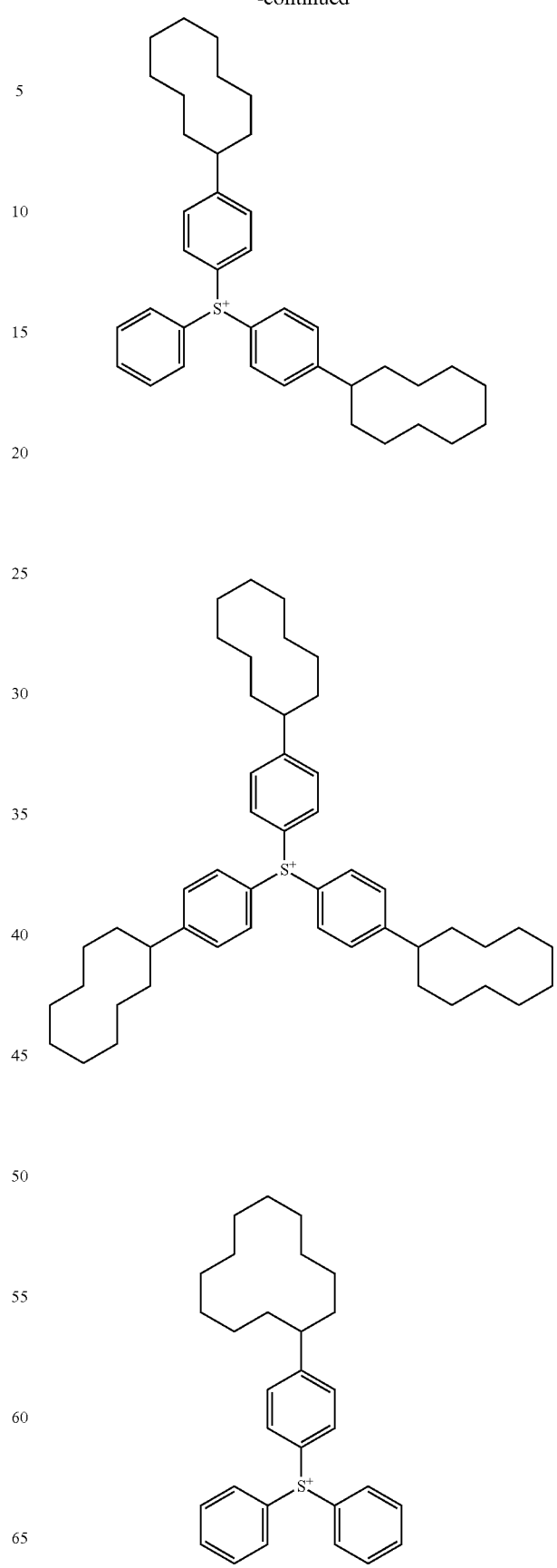

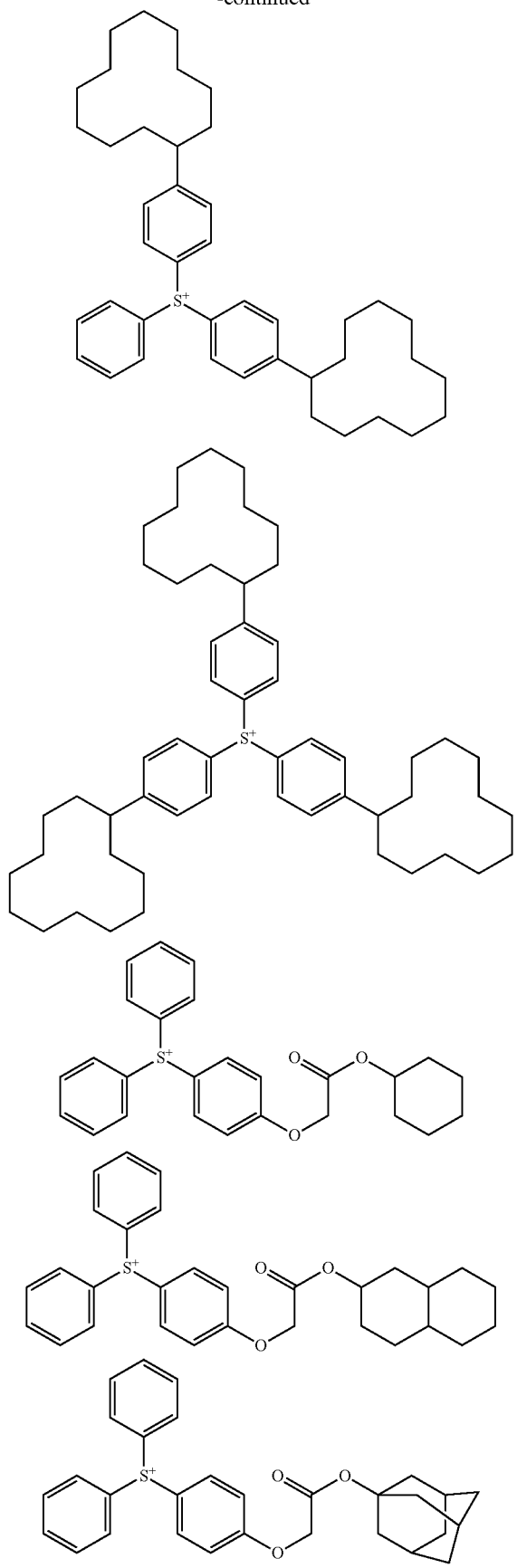
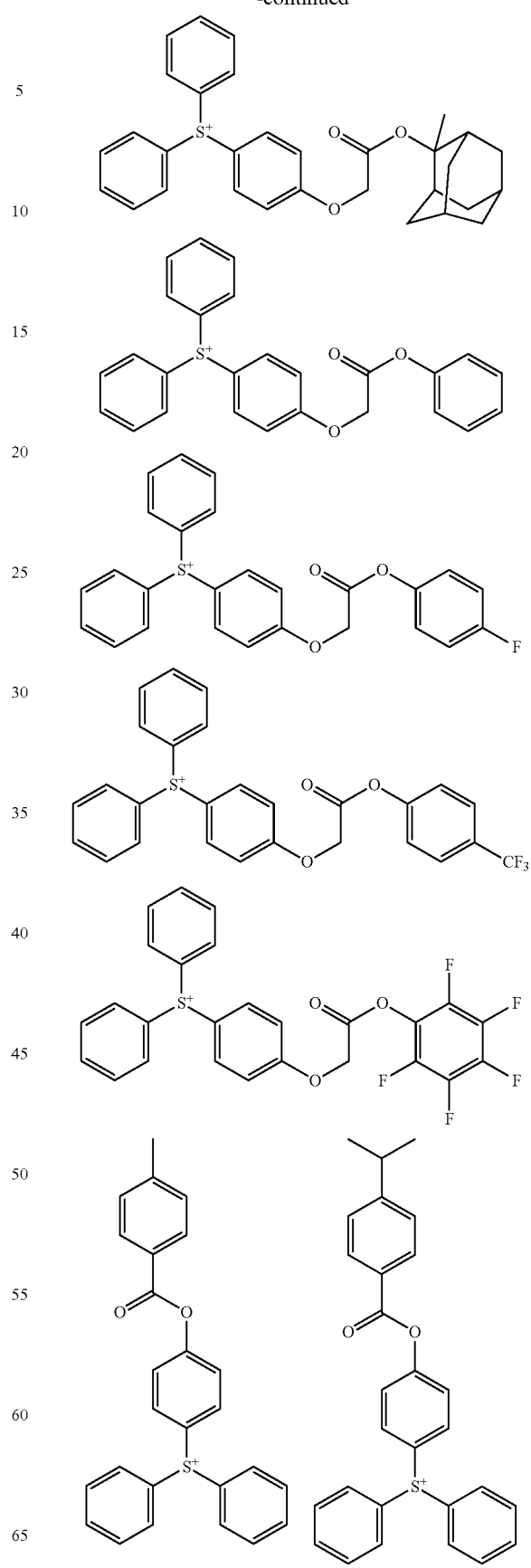

151
-continued
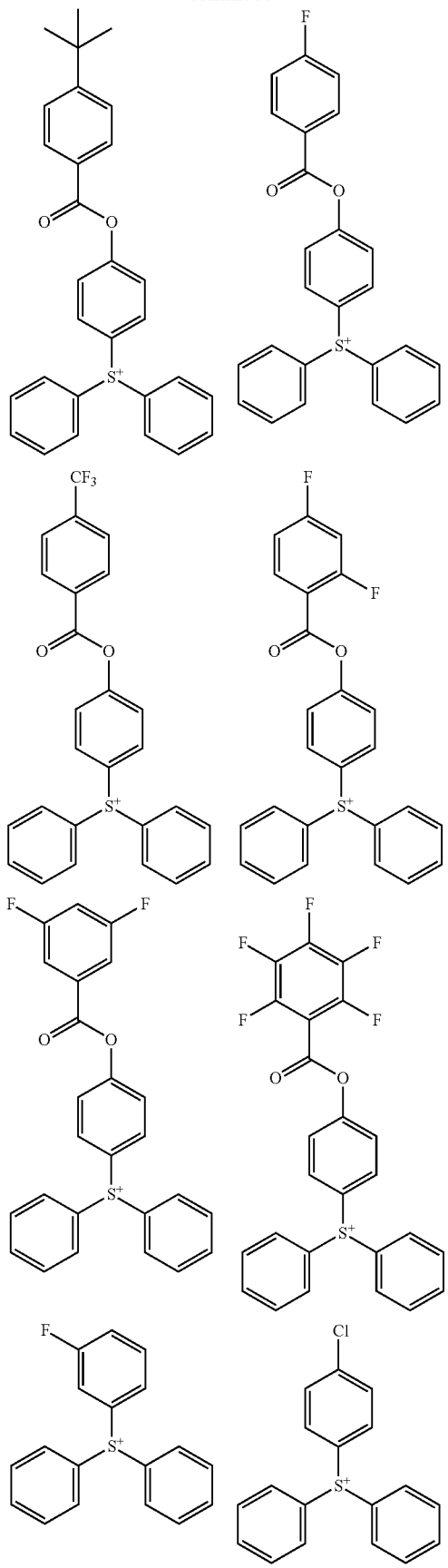
152
-continued
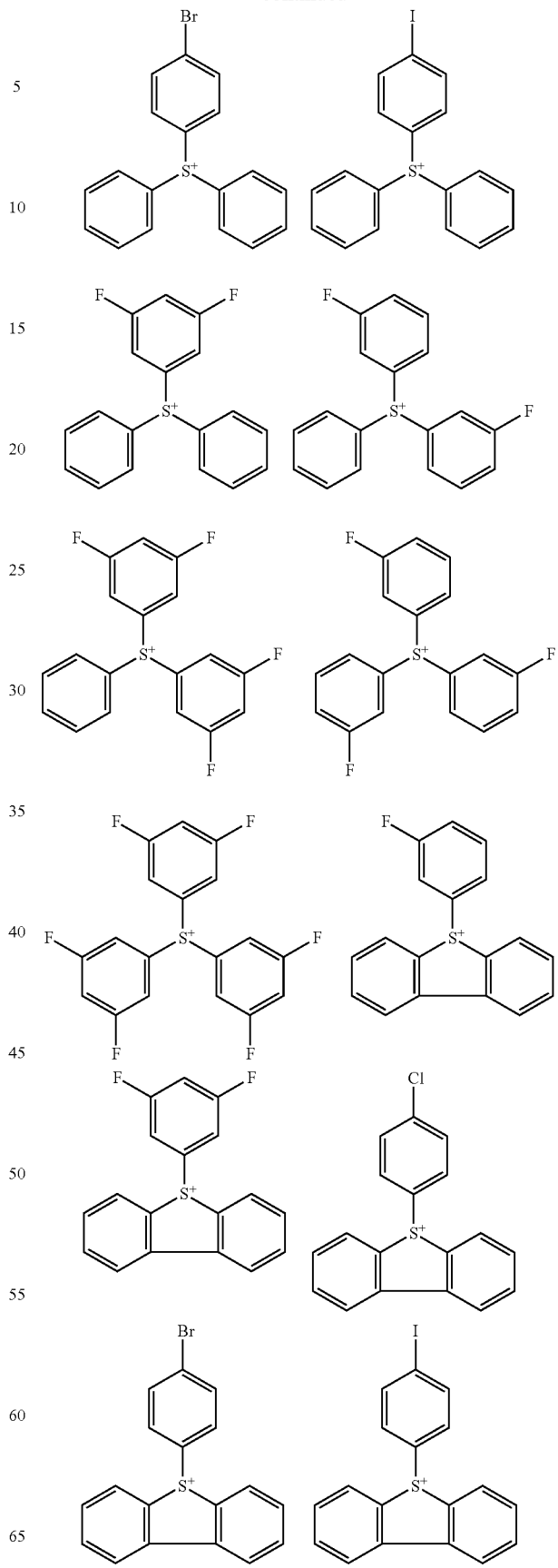

-continued
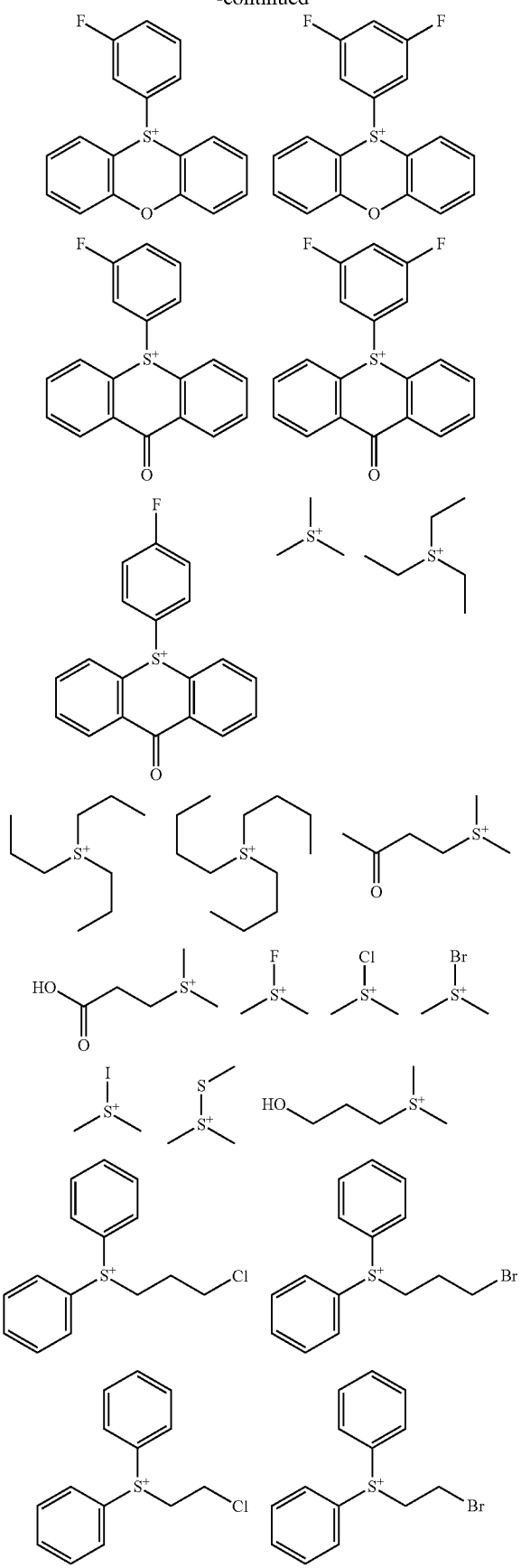
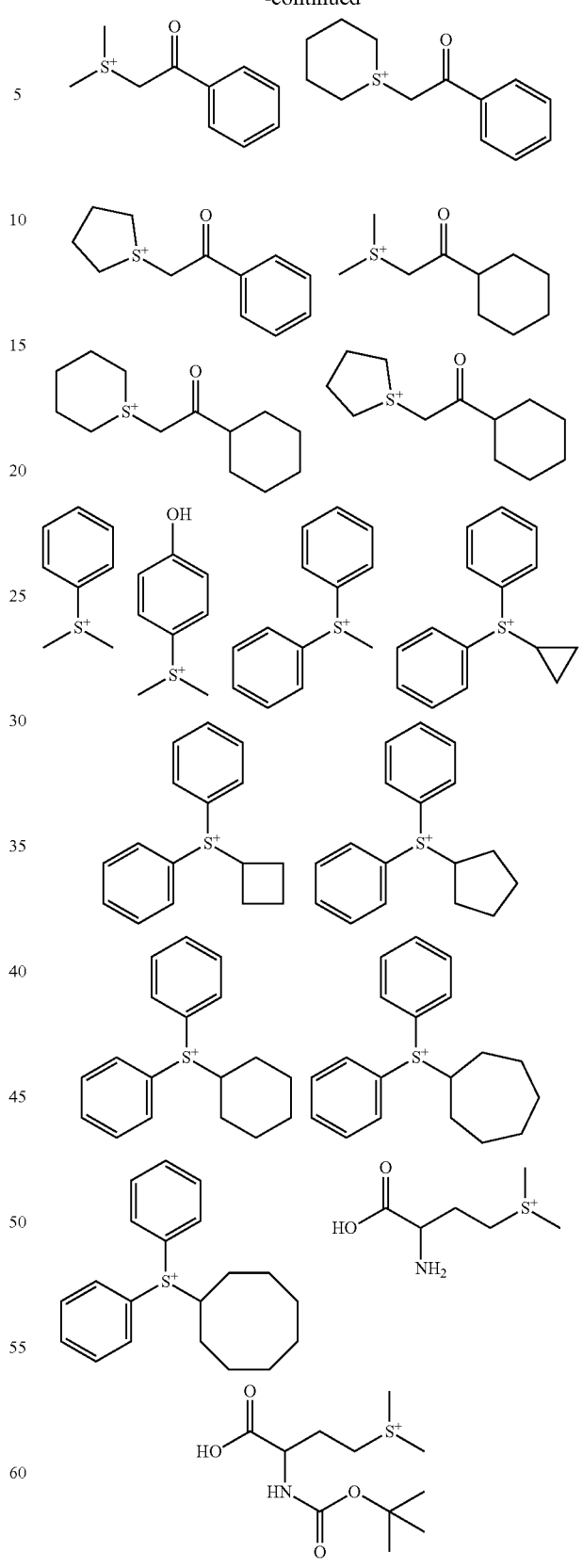
Examples of the cation in the iodonium salt having the formula (1-2) are shown below, but not limited thereto.

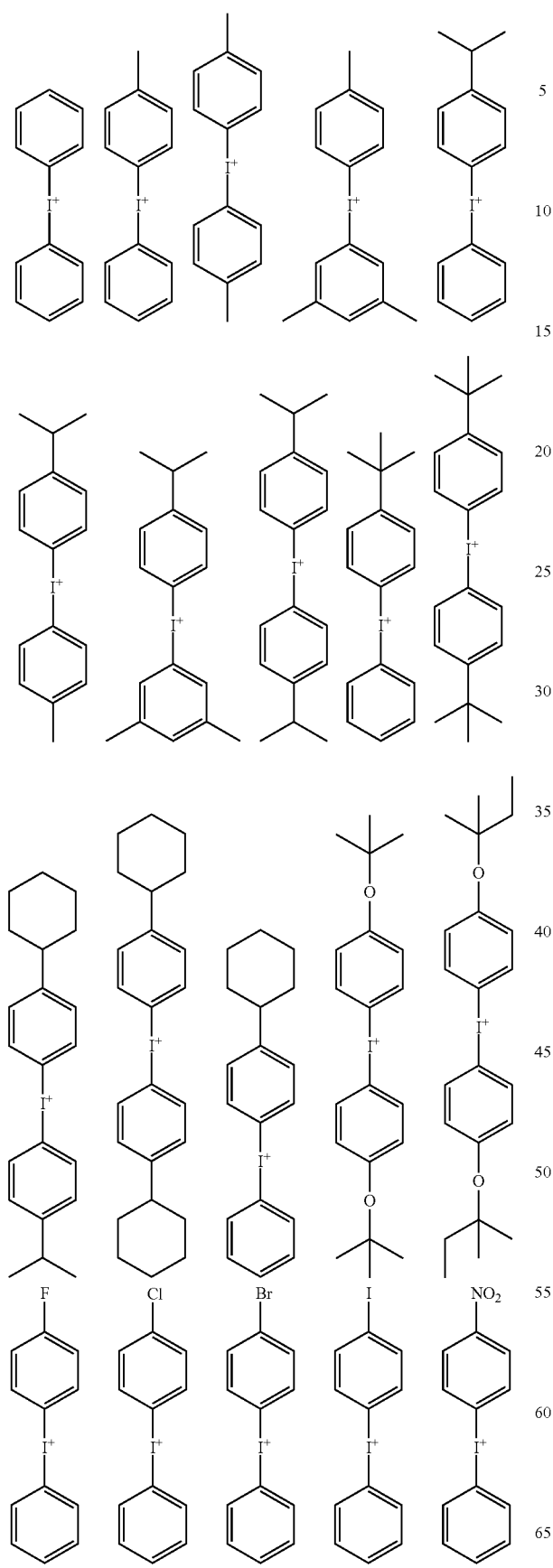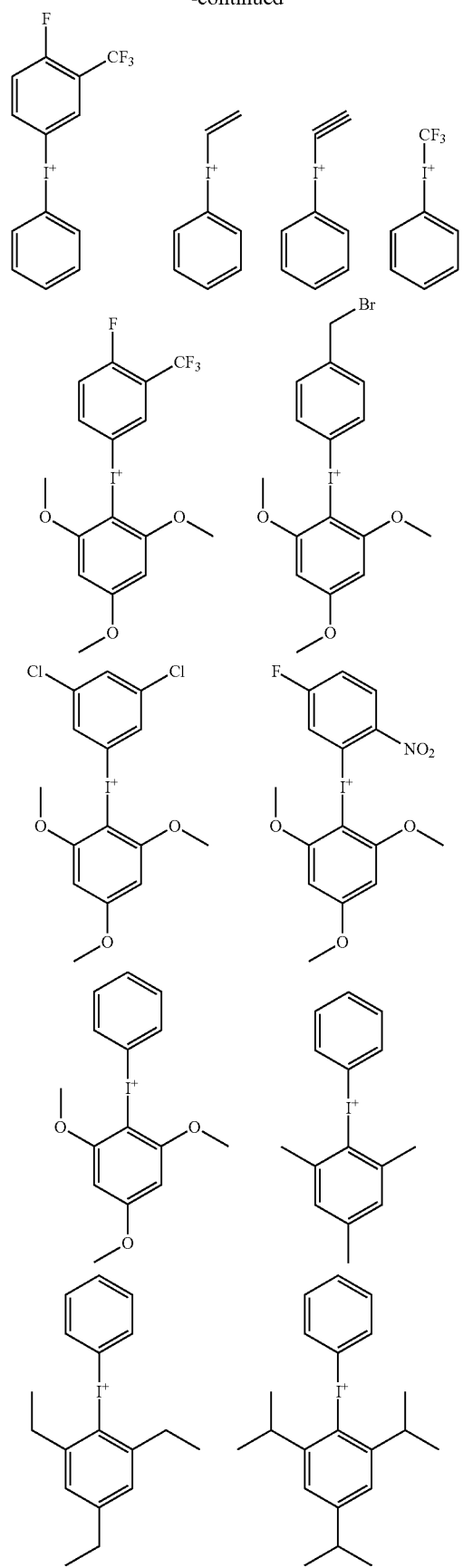

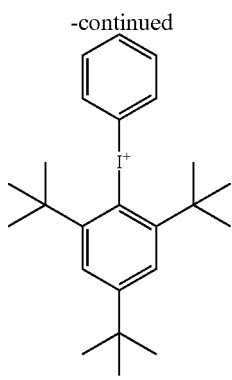

In the formulae (1-1) and (1-2), Xa⁻ is an anion of the following formula (1A), (1B), (1C) or (1D).

 (1A)

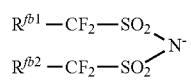 (1B)

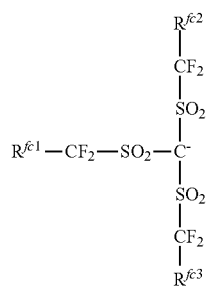 (1C)

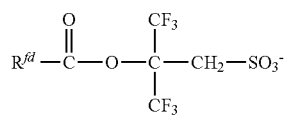 (1D)

In the formula (1A), $R^{fa}$ is fluorine or a $C_1$-$C_{40}$ hydrocarbyl group which may contain a heteroatom. The hydrocarbyl group may be saturated or unsaturated, and may be straight, branched, or cyclic. Examples thereof are as will be exemplified for the hydrocarbyl group of $R^{111}$ in the formula (1A').

Of the anions having the formula (1A), an anion having the formula (1A') is preferred.

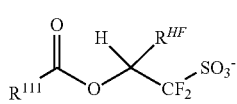 (1A')

In the formula (1A'), $R^{HF}$ is hydrogen or trifluoromethyl, preferably trifluoromethyl. $R^{111}$ is a $C_1$-$C_{38}$ hydrocarbyl group which may contain a heteroatom. As the heteroatom, oxygen, nitrogen, sulfur, and halogen atoms are preferred, with oxygen being most preferred. Of the hydrocarbyl groups represented by $R^{107}$, those groups of 6 to 30 carbon atoms are preferred from the aspect of achieving a high resolution in micropatterning.

The hydrocarbyl group of $R^{111}$ may be saturated or unsaturated, and straight, branched, or cyclic. Examples thereof include $C_1$-$C_{38}$ alkyl groups such as methyl, ethyl, propyl, isopropyl, butyl, isobutyl, sec-butyl, tert-butyl, pentyl, neopentyl, hexyl, heptyl, 2-ethylhexyl, nonyl, undecyl, tridecyl, pentadecyl, heptadecyl, and icosanyl; $C_3$-$C_{38}$ cyclic saturated hydrocarbyl groups such as cyclopentyl, cyclohexyl, 1-adamantyl, 2-adamantyl, 1-adamantylmethyl, norbornyl, norbornylmethyl, tricyclodecanyl, tetracyclododecanyl, tetracyclododecanylmethyl, and dicyclohexylmethyl; $C_2$-$C_{38}$ unsaturated aliphatic hydrocarbyl groups such as allyl and 3-cyclohexenyl; $C_6$-$C_{38}$ aryl groups such as phenyl, 1-naphthyl, and 2-naphthyl; $C_7$-$C_{38}$ aralkyl groups such as benzyl and diphenylmethyl, and groups obtained from combination thereof.

In these groups, some or all of the hydrogen atoms may be substituted by a group containing a heteroatom such as oxygen, sulfur, nitrogen, or halogen, or some carbon may be replaced by a group containing a heteroatom such as oxygen, sulfur, or nitrogen, so that the group may contain a hydroxyl group, a cyano group, a carbonyl group, an ether bond, an ester bond, a sulfonic acid ester bond, a carbonate group, a lactone ring, a sultone ring, a carboxylic anhydride, or a haloalkyl group. Examples of the heteroatom-containing hydrocarbyl group include groups such as tetrahydrofuryl, methoxymethyl, ethoxymethyl, methylthiomethyl, acetamidomethyl, trifluoroethyl, (2-methoxyethoxy)methyl, acetoxymethyl, 2-carboxy-1-cyclohexyl, 2-oxopropyl, 4-oxo-1-adamantyl, and 3-oxocyclohexyl.

With respect to the synthesis of the sulfonium salt having an anion of the formula (1A'), reference may be made to JP-A 2007-145797, JP-A 2008-106045, JP-A 2009-7327, and JP-A 2009-258695. Also useful are the sulfonium salts described in JP-A 2010-215608, JP-A 2012-41320, JP-A 2012-106986, and JP-A 2012-153644.

Examples of the anion having the formula (1A) are shown below, but not limited thereto. In the following formula, Ac is an acetyl group.

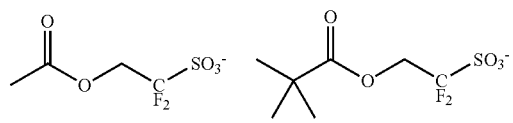

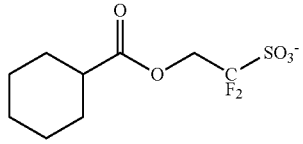

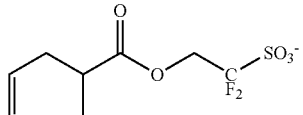

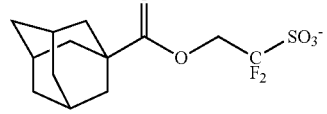

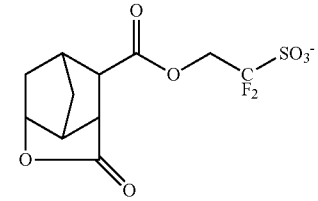

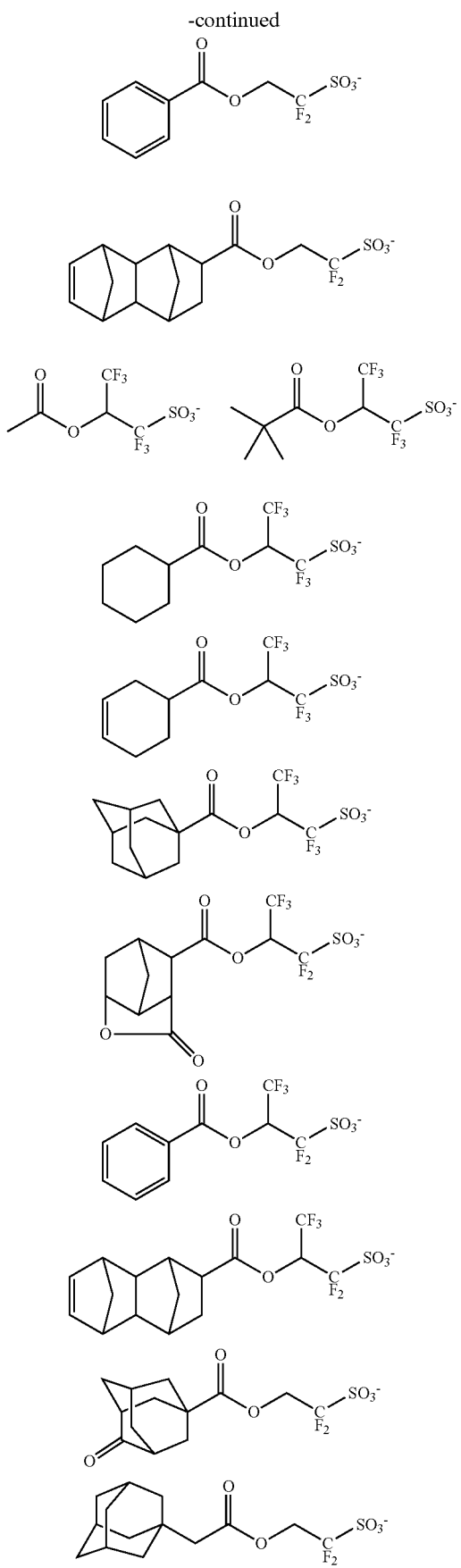
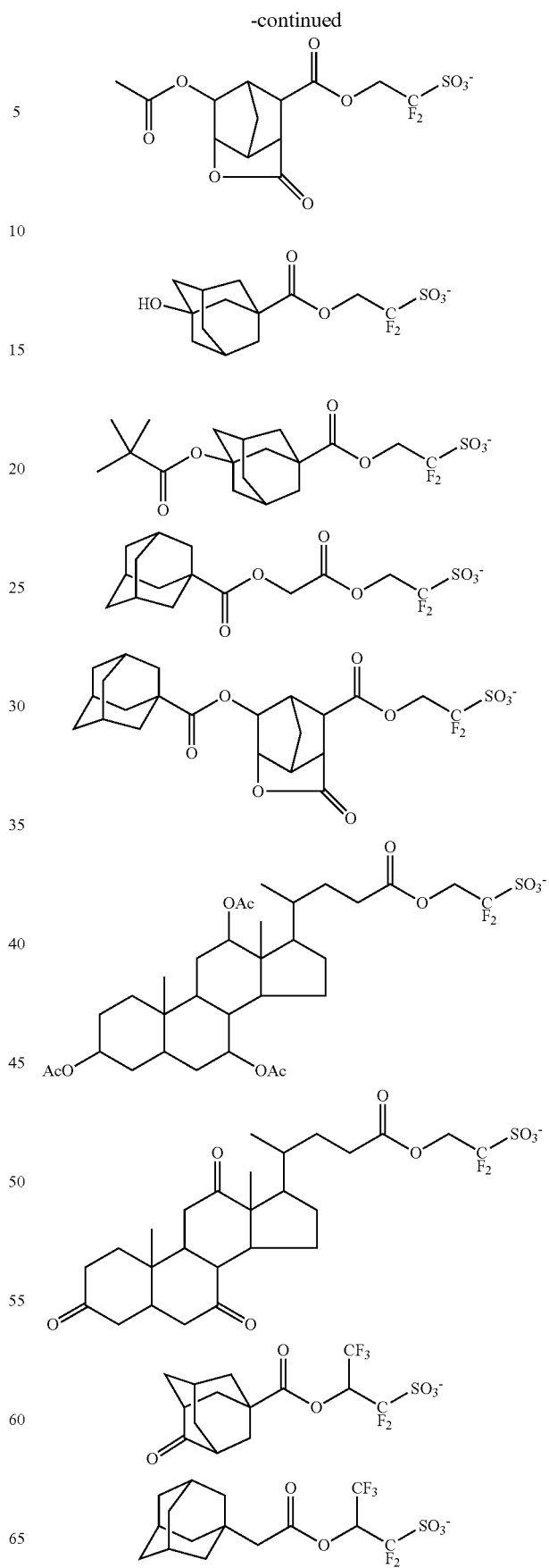

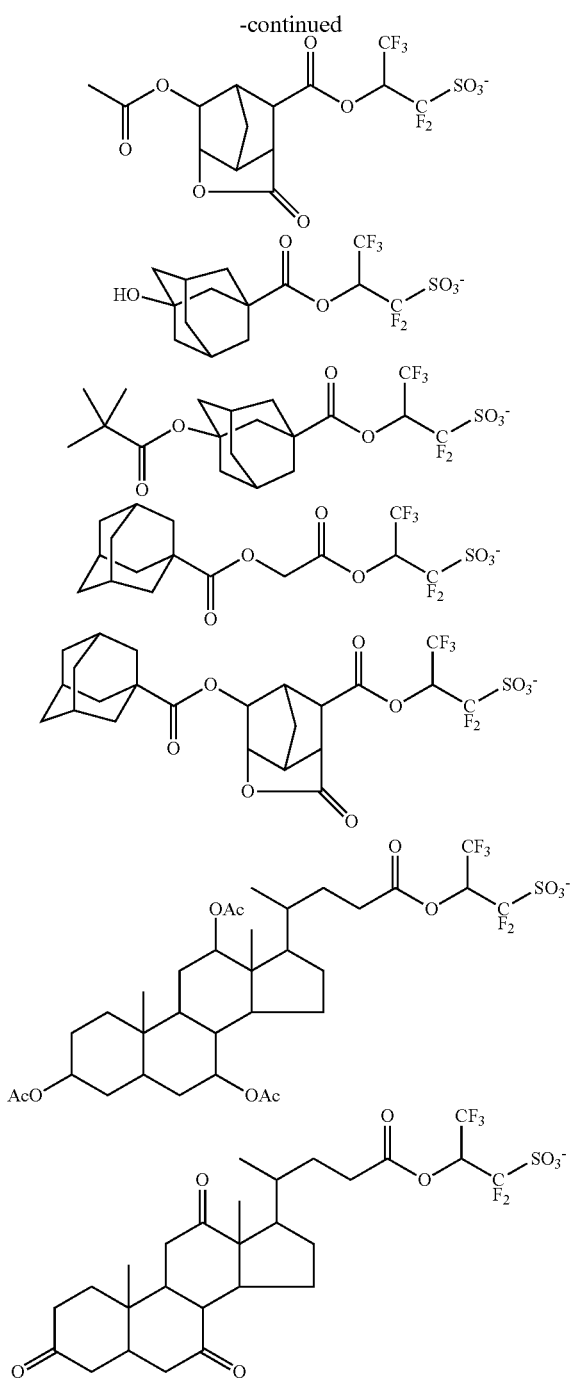

In the formula (1B), $R^{fb1}$ and $R^{fb2}$ are each independently fluorine or a $C_1$-$C_{40}$ hydrocarbyl group which may contain a heteroatom. The hydrocarbyl group may be saturated or unsaturated, and may be straight, branched, or cyclic. Examples thereof are as will be exemplified for the hydrocarbyl group of $R^{111}$ in the formula (1A'). Preferably $R^{fb1}$ and $R^{fb2}$ are each fluorine or a $C_1$-$C_4$ straight fluorinated alkyl group. Also, $R^{fb1}$ and $R^{fb2}$ may bond together to form a ring with the linkage: —$CF_2$—$SO_2$—$N^-$—$SO_2$—$CF_2$— to which they are attached. It is preferred that a combination of $R^{fb1}$ and $R^{fb2}$ be a fluorinated ethylene or fluorinated propylene group.

In the formula (1C), $R^{fc1}$, $R^{fc2}$, and $R^{fc3}$ are each independently fluorine or a $C_1$-$C_{40}$ hydrocarbyl group which may contain a heteroatom. The hydrocarbyl group may be saturated or unsaturated, and may be straight, branched, or cyclic. Examples thereof are as will be exemplified for the hydrocarbyl group of $R^{111}$ in the formula (1A'). Preferably $R^{fc1}$, $R^{fc2}$, and $R^{fc3}$ are each fluorine or a $C_1$-$C_4$ straight fluorinated alkyl group. Also, $R^{fc1}$ and $R^{fc2}$ may bond together to form a ring with the linkage: —$CF_2$—$SO_2$—$C^-$—$SO_2$—$CF_2$— to which they are attached. It is preferred that a combination of $R^{fc1}$ and $R^{fc2}$ be a fluorinated ethylene or fluorinated propylene group.

In the formula (1D), $R^{fd}$ is a $C_1$-$C_{40}$ hydrocarbyl group which may contain a heteroatom. The hydrocarbyl group may be saturated or unsaturated, and may be straight, branched, or cyclic. Examples thereof are as will be exemplified for the hydrocarbyl group of $R^{111}$ in the formula (1A').

With respect to the synthesis of the sulfonium salt having an anion of the formula (1D), reference may be made to JP-A 2010-215608 and JP-A 2014-133723.

Examples of the anion having the formula (1D) are shown below, but not limited thereto.

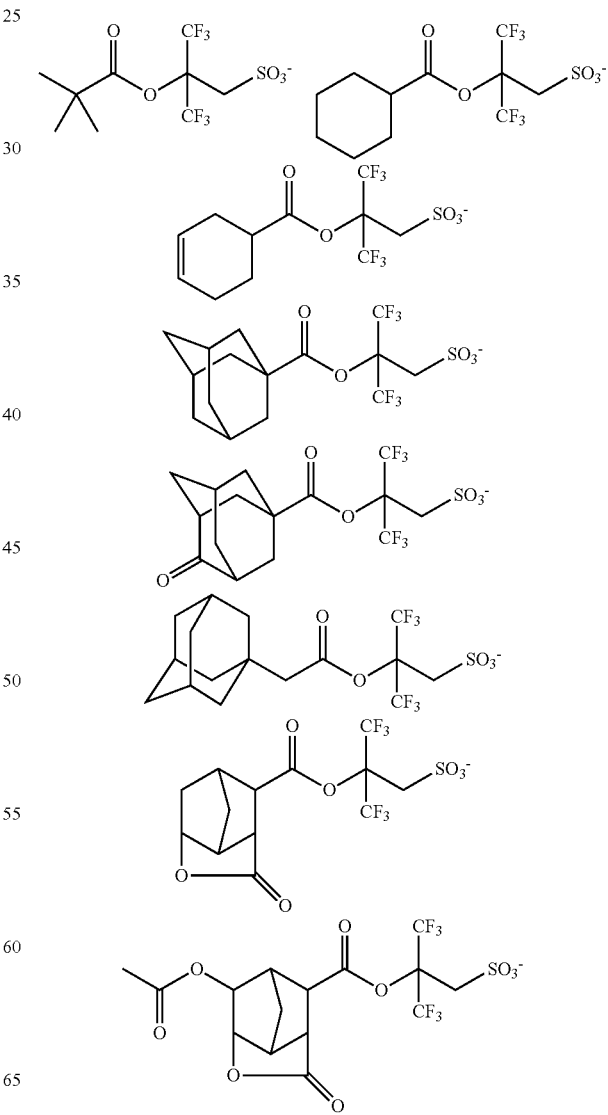

-continued

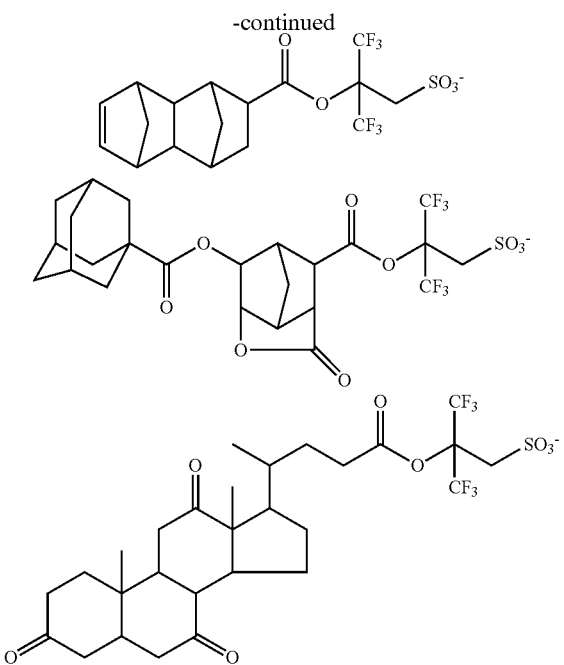

The PAG having the anion of the formula (1D) is free of fluorine at α-position of sulfo group, but has two trifluoromethyl groups at β-position, which ensures a sufficient acid strength to cleave acid labile groups in the base polymer. Thus the compound is an effective PAG.

Another preferred PAG is a compound having the formula (2).

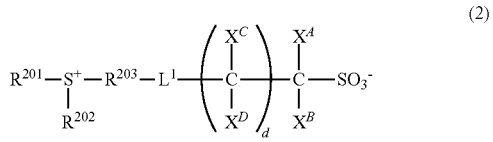

(2)

In the formula (2), $R^{201}$ and $R^{202}$ are each independently a halogen or a $C_1$-$C_{30}$ hydrocarbyl group which may contain a heteroatom. $R^{203}$ is a $C_1$-$C_{30}$ hydrocarbylene group which may contain a heteroatom. Any two of $R^{201}$, $R^{202}$, and $R^{203}$ may bond together to form a ring with the sulfur atom to which they are attached. Examples of the ring are as exemplified above as the ring that two $R^2$s, taken together, form when r=1 with the sulfur atom to which they are attached in the formula (A).

The hydrocarbyl groups of $R^{201}$ and $R^{202}$ may be saturated or unsaturated, and straight, branched, or cyclic. Examples thereof include $C_1$-$C_{30}$ alkyl groups such as methyl, ethyl, propyl, isopropyl, n-butyl, sec-butyl, tert-butyl, n-pentyl, tert-pentyl, n-hexyl, n-octyl, 2-ethylhexyl, n-nonyl, and n-decyl; $C_3$-$C_{30}$ cyclic saturated hydrocarbyl groups such as cyclopentyl, cyclohexyl, cyclopentylmethyl, cyclopentylethyl, cyclopentylbutyl, cyclohexylmethyl, cyclohexylethyl, cyclohexylbutyl, norbornyl, tricyclo[5.2.1.0$^{2,6}$]decanyl, and adamantyl; $C_6$-$C_{30}$ aryl groups such as phenyl, naphthyl, and anthracenyl; and groups obtained from combination thereof. In these groups, some or all of the hydrogen atoms may be substituted by a group containing a heteroatom such as oxygen, sulfur, nitrogen, or a halogen, or some carbon may be replaced by a group containing a heteroatom such as oxygen, sulfur, or nitrogen, so that the group may contain a hydroxyl, cyano, carbonyl, ether bond, ester bond, sulfonic acid ester bond, carbonate, lactone ring, sultone ring, carboxylic anhydride, or haloalkyl group.

The hydrocarbylene group of $R^{203}$ may be saturated or unsaturated, and straight, branched, or cyclic. Specific examples thereof include $C_1$-$C_{30}$ alkanediyl groups such as methanediyl, ethane-1,1-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, and heptadecane-1,17-diyl; $C_3$-$C_{30}$ cyclic saturated hydrocarbylene groups such as cyclopentanediyl, cyclohexanediyl, norbornanediyl, and adamantanediyl; arylene groups such as phenylene and naphthylene; and groups obtained from combination thereof. In these groups, some or all of the hydrogen atoms may be substituted by a group containing a heteroatom such as oxygen, sulfur, nitrogen, or a halogen, or some carbon may be replaced by a group containing a heteroatom such as oxygen, sulfur, or nitrogen, so that the group may contain a hydroxyl, cyano, carbonyl, ether bond, ester bond, sulfonic acid ester bond, carbonate, lactone ring, sultone ring, carboxylic anhydride, or haloalkyl group. Of the heteroatoms, oxygen is preferred.

In the formula (2), $L^1$ is a single bond, an ether bond, or a $C_1$-$C_{20}$ hydrocarbylene group which may contain a heteroatom. The hydrocarbylene group may be saturated or unsaturated, and straight, branched, or cyclic. Examples thereof are as exemplified above for $R^{203}$.

In the formula (2), $X^A$, $X^B$, $X^C$, and $X^D$ are each independently hydrogen, fluorine, or trifluoromethyl, with the proviso that at least one of $X^A$, $X^B$, $X^C$, or $X^D$ is fluorine or trifluoromethyl.

In the formula (2), d is an integer of 0 to 3.

Of the PAGs having the formula (2), those having the formula (2') are preferred.

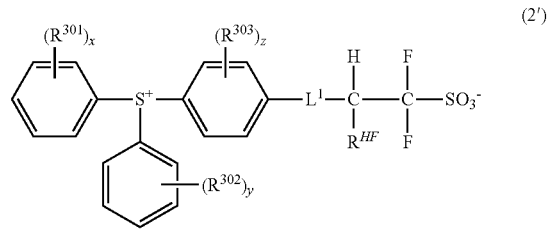

(2')

In the formula (2'), $L^1$ is as defined above. $R^{HF}$ is hydrogen or trifluoromethyl, preferably trifluoromethyl. $R^{301}$, $R^{302}$, and $R^{303}$ are each independently hydrogen or a $C_1$-$C_{20}$ hydrocarbyl group which may contain a heteroatom. The hydrocarbyl group may be saturated or unsaturated, and may be straight, branched, or cyclic. Examples thereof are as will be exemplified for the hydrocarbyl group of $R^{111}$ in the formula (1A'). The subscripts x and y are each independently an integer of 0 to 5, and z is an integer of 0 to 4.

Examples of the PAG having the formula (2) are as exemplified for the PAG having the formula (2) in JP-A 2017-026980.

Of the foregoing PAGs, those having an anion of the formula (1A') or (1D) are especially preferred because of reduced acid diffusion and high solubility in the solvent.

Also those having an anion of the formula (2') are especially preferred because of extremely reduced acid diffusion.

Also a sulfonium or iodonium salt having an iodized or brominated aromatic ring-containing anion may be used as the PAG. Suitable are sulfonium and iodonium salts having the formulae (3-1) and (3-2). Because iodine or bromine is highly absorptive to EUV, the addition of such an acid generator improves the sensitivity.

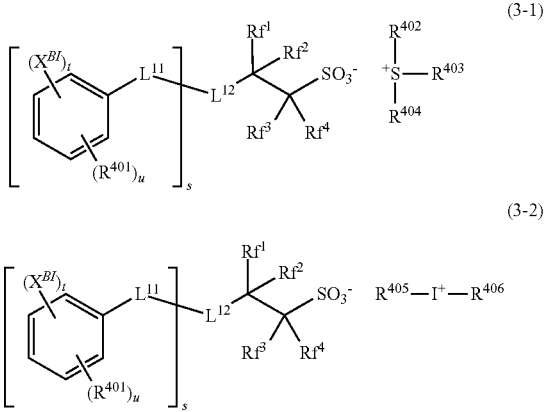

In the formulae (3-1) and (3-2), s is an integer of 1 to 3. t is an integer of 1 to 5, u is an integer of 0 to 3, and $1 \leq t+u \leq 5$. Preferably, t is an integer of 1 to 3, more preferably 2 or 3, and u is an integer of 0 to 2.

In the formulae (3-1) and (3-2), $X^{BI}$ is iodine or bromine. Groups $X^{BI}$ may be the same or different when s and/or t is 2 or more.

In the formulae (3-1) and (3-2), $L^{11}$ is a single bond, an ether bond, an ester bond, or a $C_1$-$C_6$ saturated hydrocarbylene group which may contain an ether bond or ester bond. The saturated hydrocarbylene group may be straight, branched, or cyclic.

In the formulae (3-1) and (3-2), $L^{12}$ is a single bond or a $C_1$-$C_{20}$ divalent linking group when s=1, or a $C_1$-$C_{20}$ (s+1)-valent linking group when s=2 or 3, the linking group optionally containing an oxygen, sulfur, or nitrogen atom.

In the formulae (3-1) and (3-2), $R^{401}$ is a hydroxyl group, a carboxyl group, fluorine, chlorine, or a $C_1$-$C_{20}$ hydrocarbyl, $C_1$-$C_{20}$ hydrocarbyloxy, $C_2$-$C_{20}$ hydrocarbylcarbonyl, $C_2$-$C_{20}$ hydrocarbyloxycarbonyl, $C_2$-$C_{20}$ hydrocarbylcarbonyloxy, or $C_1$-$C_{20}$ hydrocarbylsulfonyloxy group, which may contain fluorine, chlorine, bromine, hydroxyl, amino, or an ether bond, or —N($R^{401A}$)($R^{401B}$), —N($R^{401C}$)—C(=O)—$R^{401D}$, or —N($R^{401C}$)—C(=O)—O—$R^{401D}$. $R^{401A}$ and $R^{401B}$ are each independently hydrogen or a $C_1$-$C_6$ saturated hydrocarbyl group. $R^{401C}$ is hydrogen or a $C_1$-$C_6$ saturated hydrocarbyl group which may contain a halogen, hydroxyl, a $C_1$-$C_6$ alkoxy, $C_2$-$C_6$ saturated hydrocarbylcarbonyl, or $C_2$-$C_6$ saturated hydrocarbylcarbonyloxy group. $R^{401D}$ is a $C_1$-$C_{16}$ aliphatic hydrocarbyl, $C_6$-$C_{14}$ aryl, or $C_7$-$C_{15}$ aralkyl group which may contain a halogen, hydroxyl, a $C_1$-$C_6$ saturated hydrocarbyloxy, $C_2$-$C_6$ saturated hydrocarbylcarbonyl, or $C_2$-$C_6$ saturated hydrocarbylcarbonyloxy group. The aliphatic hydrocarbyl group may be saturated or unsaturated, and straight, branched, or cyclic. The saturated hydrocarbyl, saturated hydrocarbyloxy, saturated hydrocarbyloxycarbonyl, saturated hydrocarbylcarbonyl, and saturated hydrocarbylcarbonyloxy groups may be straight, branched, or cyclic. Groups $R^{401}$ may be the same or different when s and/or u is 2 or more.

Of these, $R^{401}$ is preferably hydroxyl, —N($R^{401C}$)—C(=O)—$R^{401D}$, —N($R^{401C}$)—C(=O)—O—$R^{401D}$, fluorine, chlorine, bromine, methyl, or methoxy.

In the formulae (3-1) and (3-2), $Rf^1$ to $Rf^4$ are each independently hydrogen, fluorine, or trifluoromethyl, at least one of $Rf^1$ to RV is fluorine or trifluoromethyl, or $Rf^1$ and $Rf^2$, taken together, may form a carbonyl group. It is particularly preferable that both $Rf^3$ and $Rf^4$ be fluorine.

In the formulae (3-1) and (3-2), $R^{402}$ to $R^{406}$ are each independently a halogen or a $C_1$-$C_{20}$ hydrocarbyl group which may contain a heteroatom. The hydrocarbyl group may be saturated or unsaturated, and may be straight, branched, or cyclic. Examples thereof are as will be exemplified for the hydrocarbyl group of $R^2$ in the formula (A). In these groups, some or all of the hydrogen atoms may be substituted by hydroxyl, carboxyl, halogen, cyano, nitro, mercapto, sultone, sulfone, or a sulfonium salt-containing group, and some carbon may be replaced by an ether bond, ester bond, carbonyl group, amide bond, carbonate group, or sulfonic acid ester bond. $R^{402}$ and $R^{403}$ may bond together to form a ring with the sulfur atom to which they are attached. Examples of the ring are as exemplified above as the ring that two $R^2$s, taken together, form when r=1 with the sulfur atom to which they are attached in the formula (A).

Examples of the cation in the sulfonium salt having the formula (3-1) include those exemplified above as the cation in the sulfonium salt having the formula (1-1). Examples of the cation in the iodonium salt having the formula (3-2) include those exemplified above as the cation in the iodonium salt having the formula (1-2).

Examples of the anion in the onium salts having the formulae (3-1) and (3-2) are shown below, but not limited thereto. Herein $X^{BI}$ is as defined above.

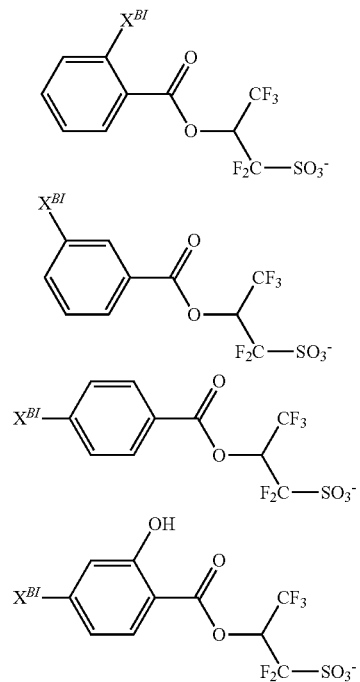

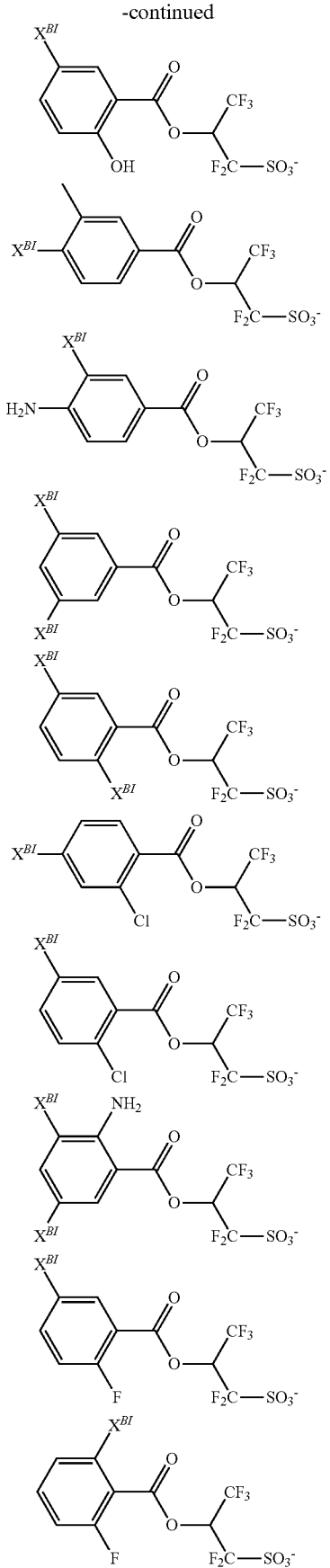
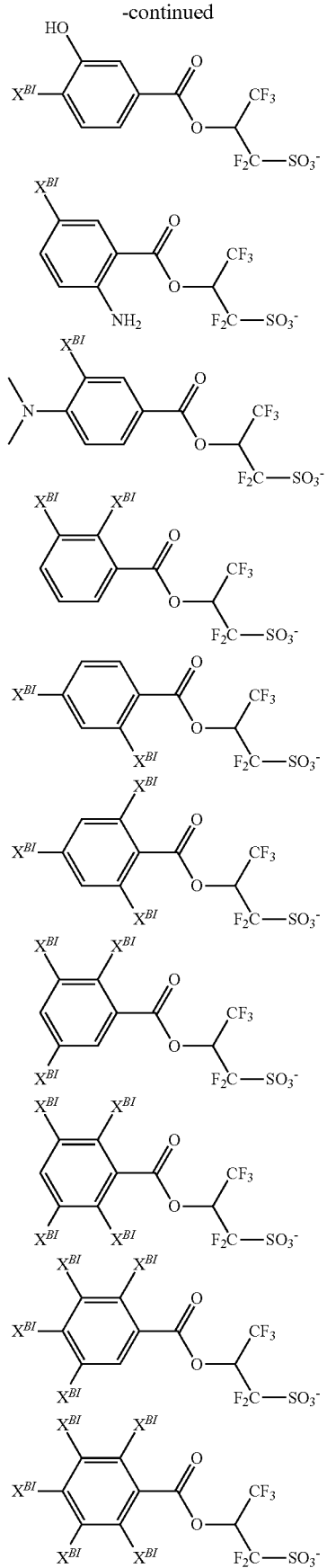

-continued
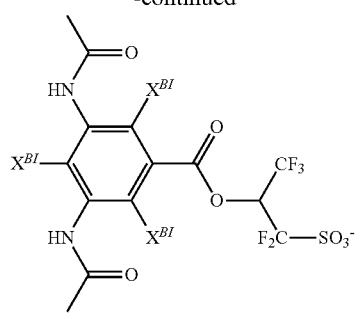
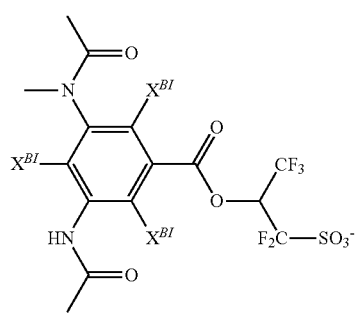
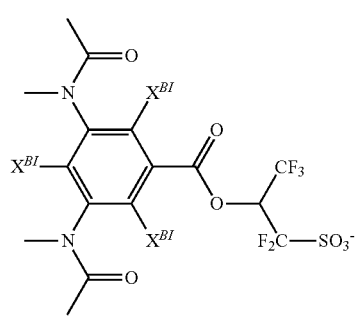
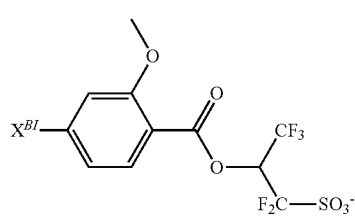
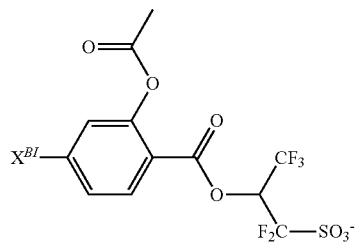
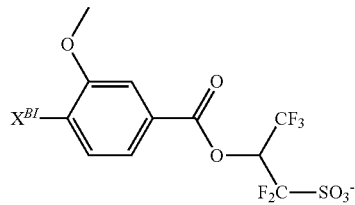
-continued
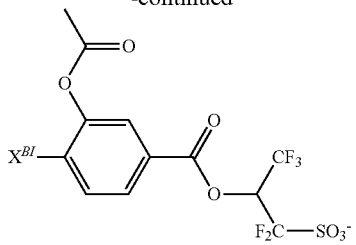
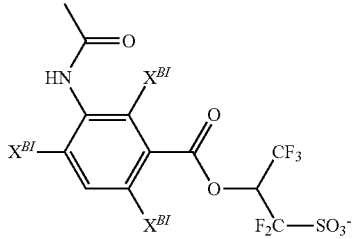
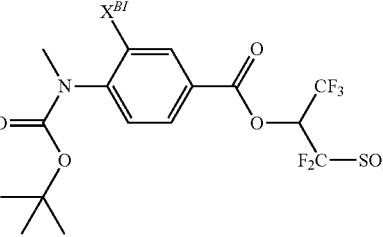
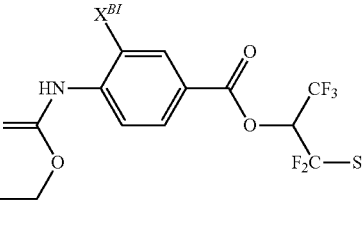
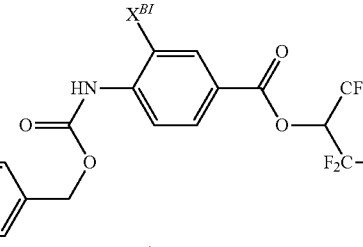
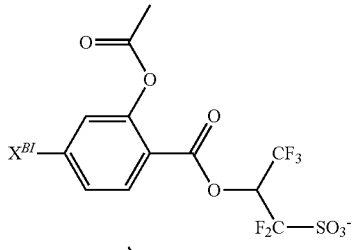
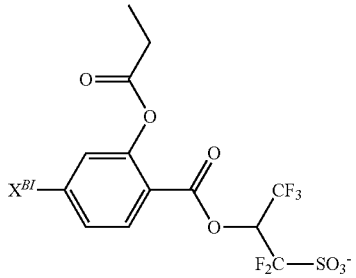

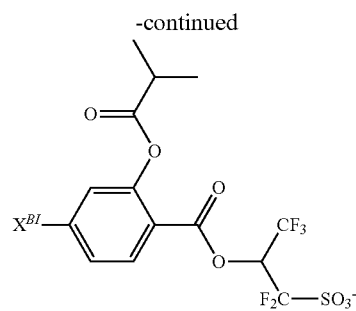
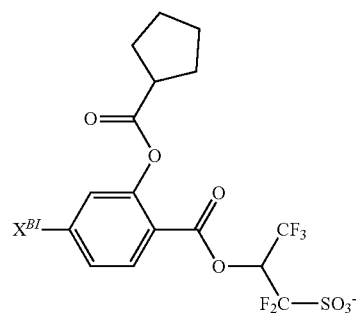
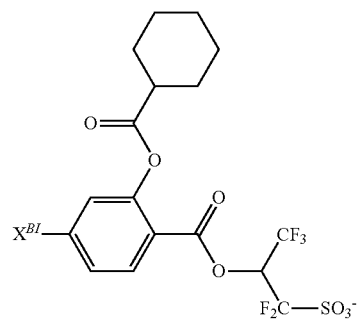
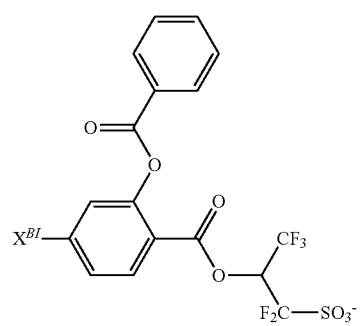
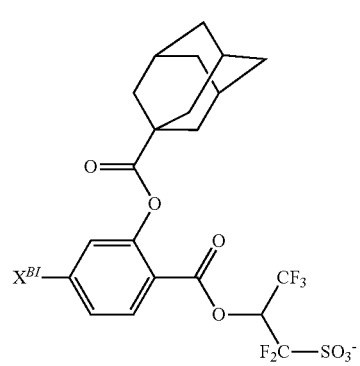
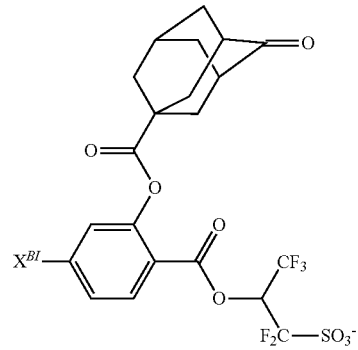
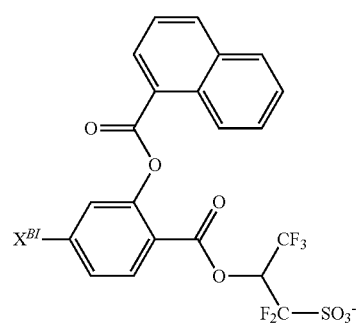
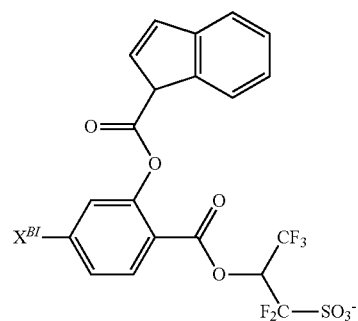
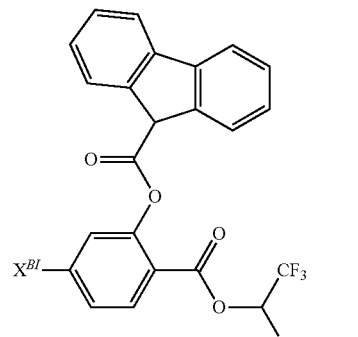
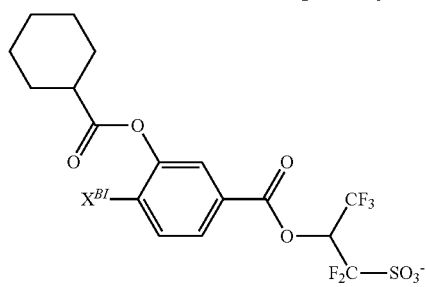

-continued
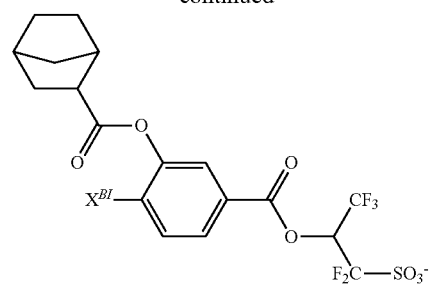
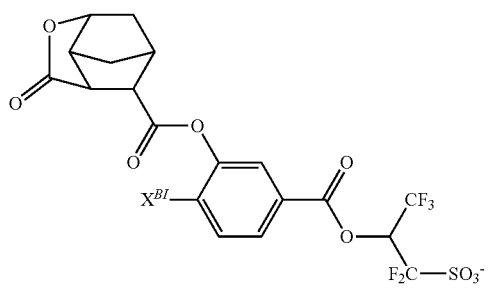
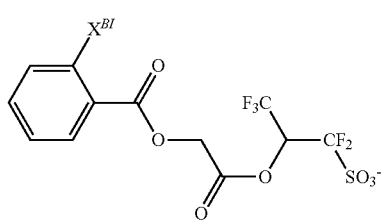
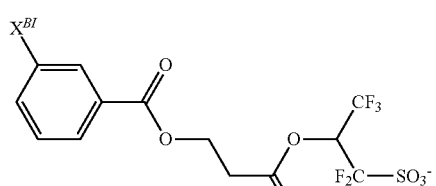
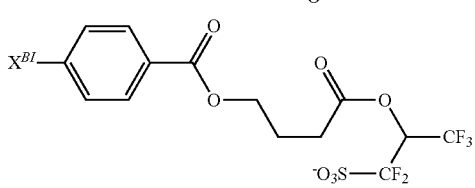
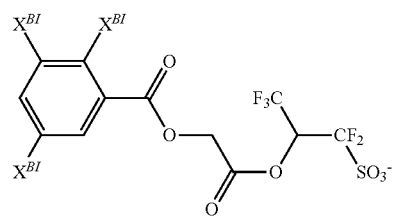
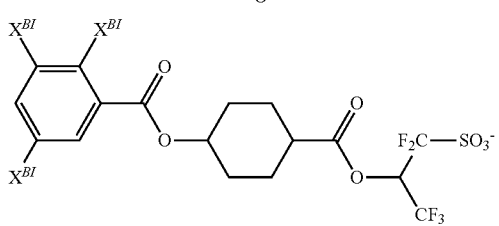
-continued
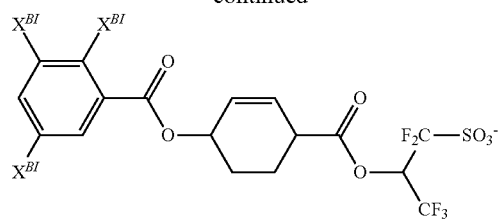
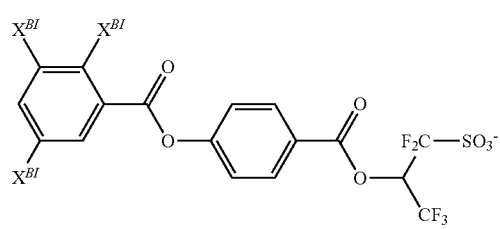
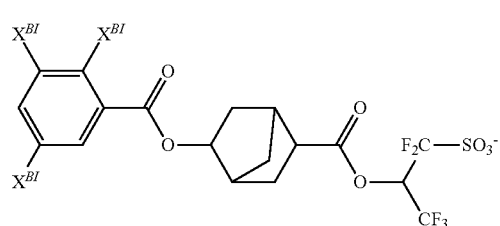
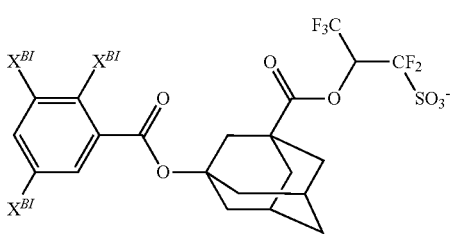
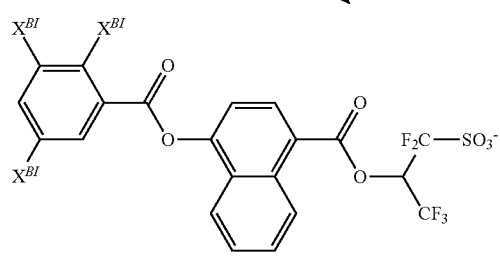
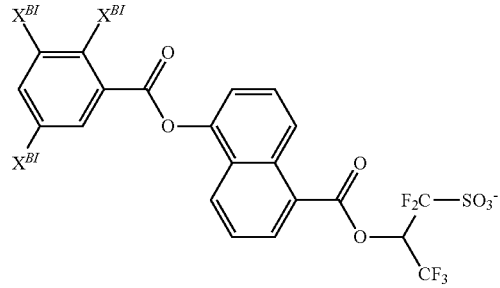
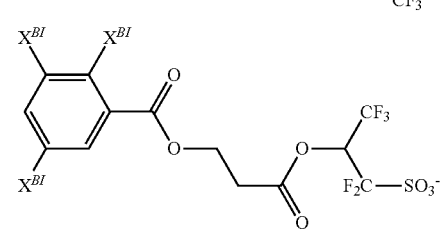

-continued
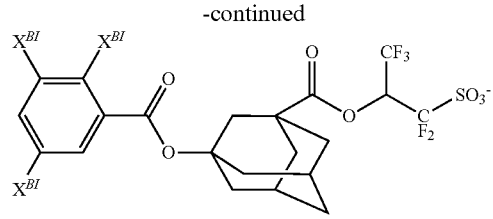
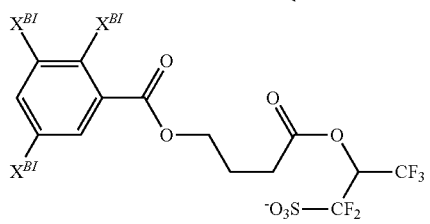
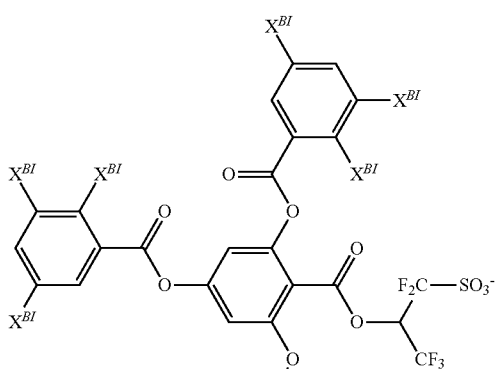
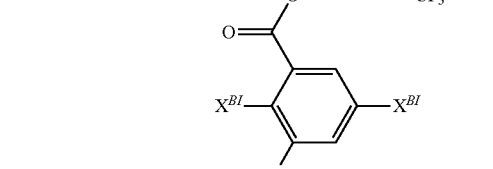
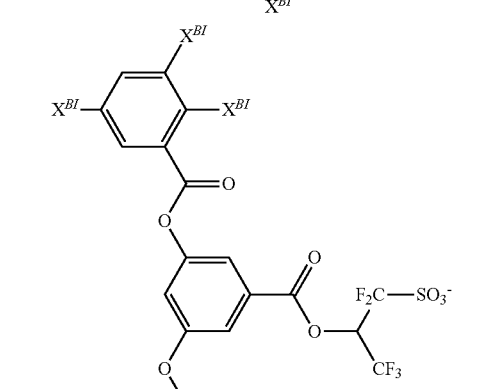
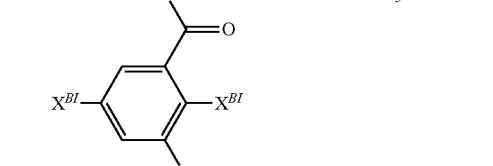
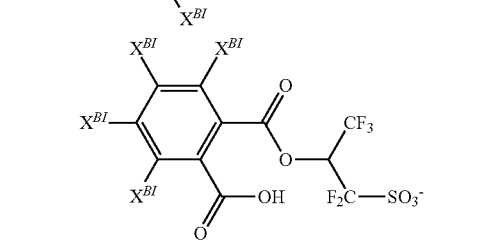
-continued
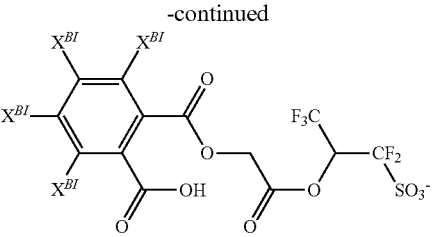
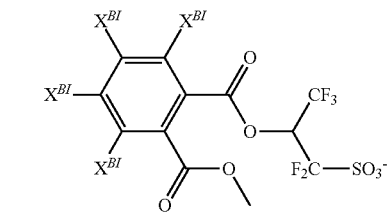
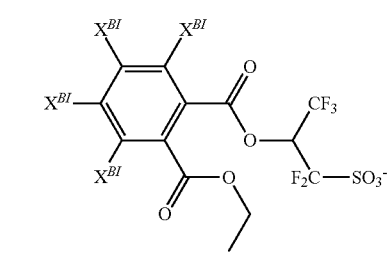
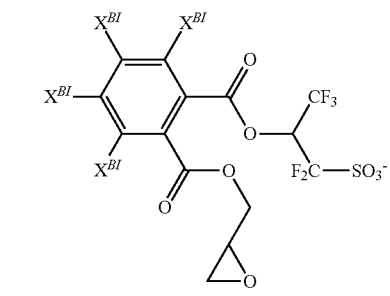
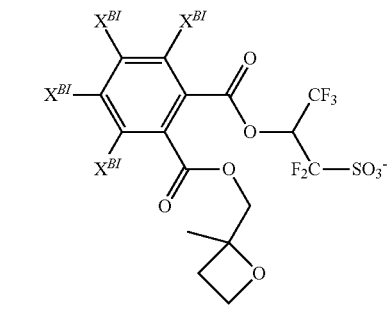
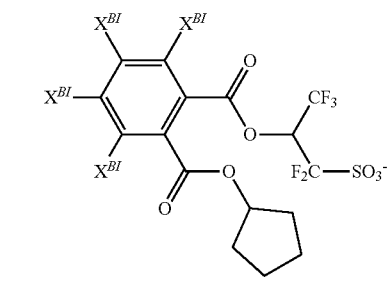

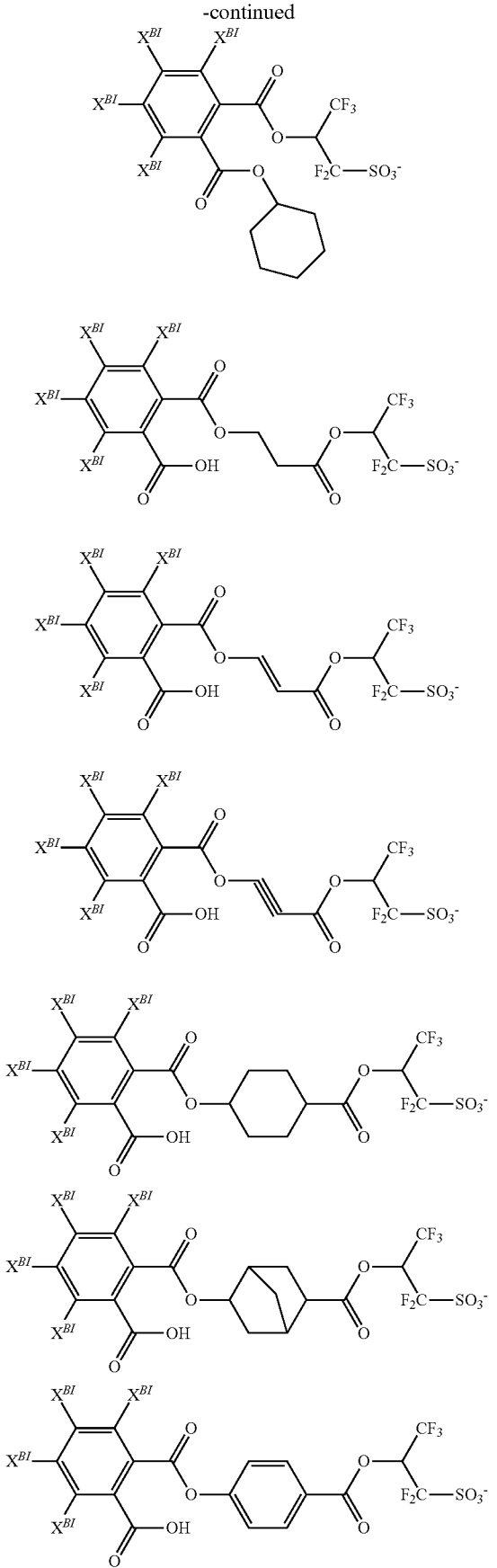
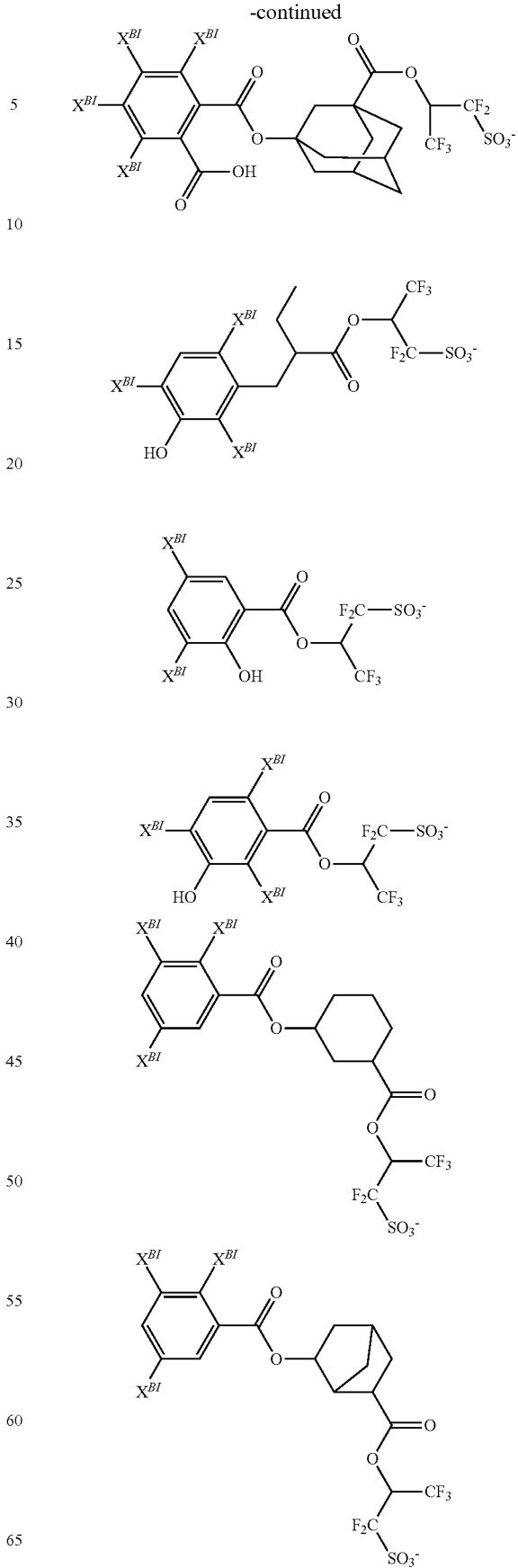

179
-continued
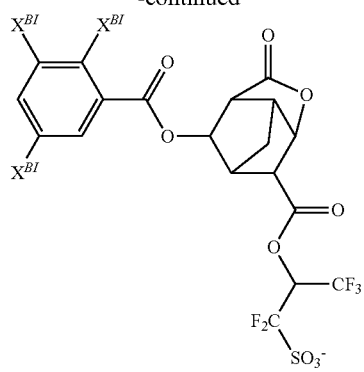
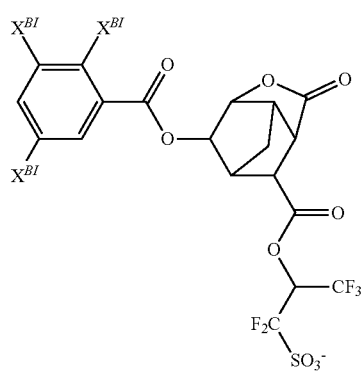
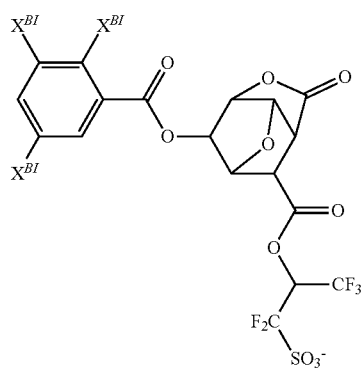
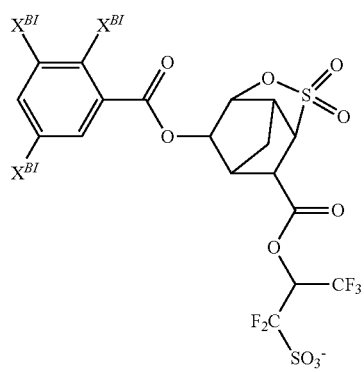
180
-continued
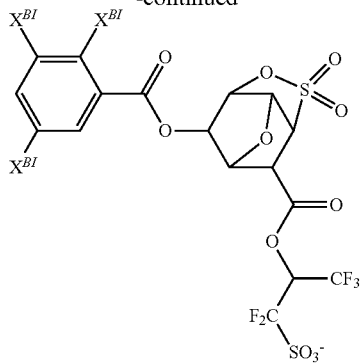
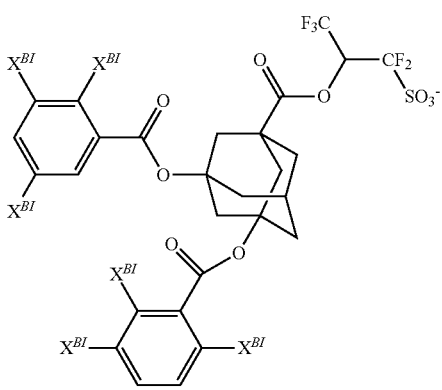
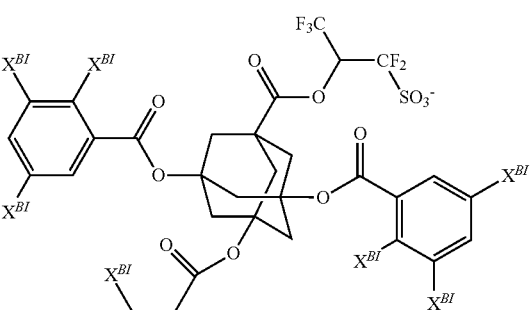
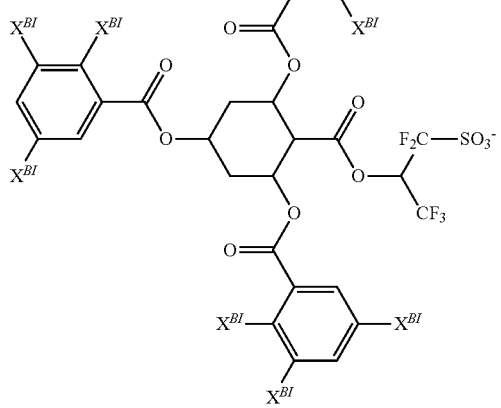

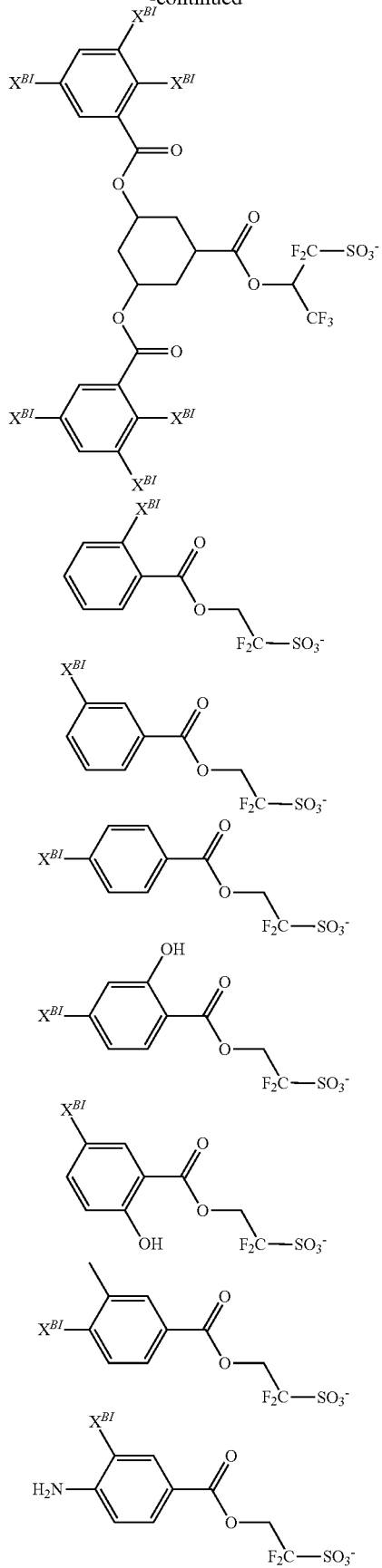
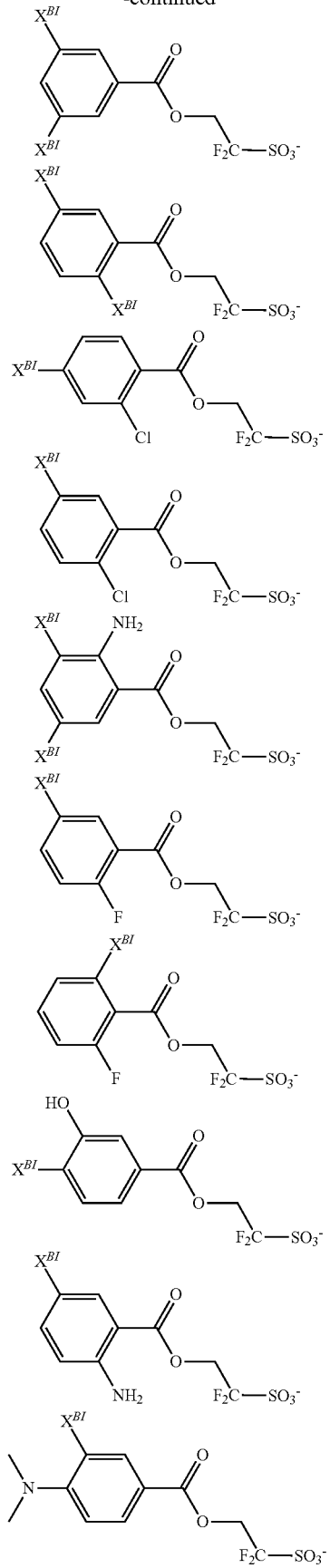

-continued
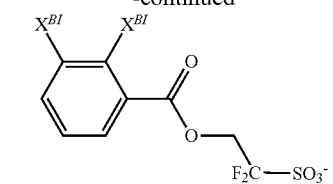
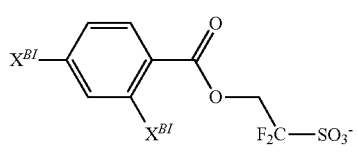
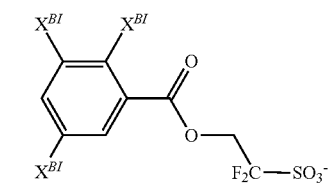
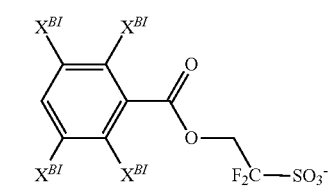
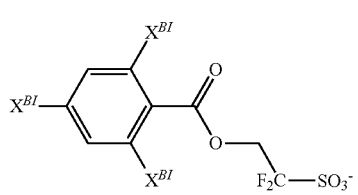
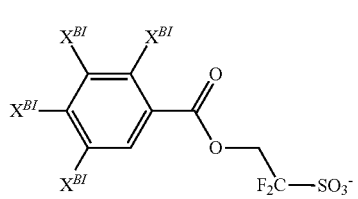
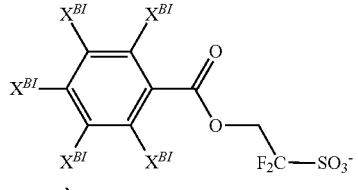
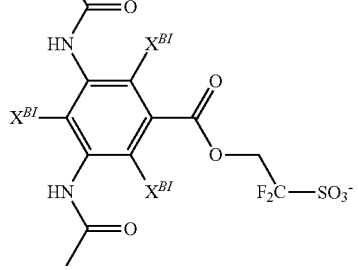
-continued
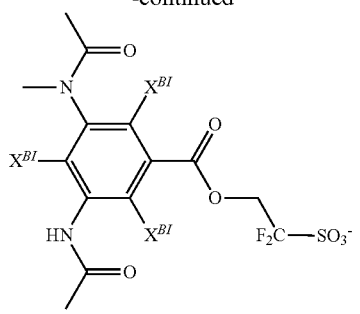
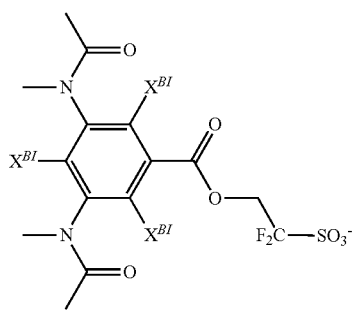
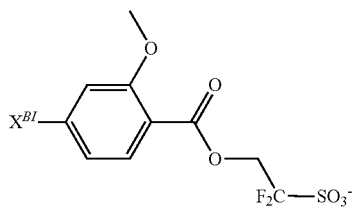
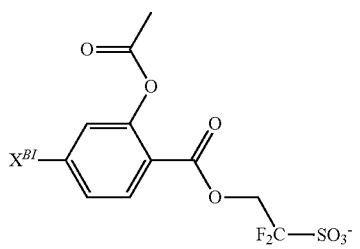
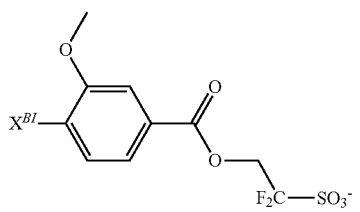
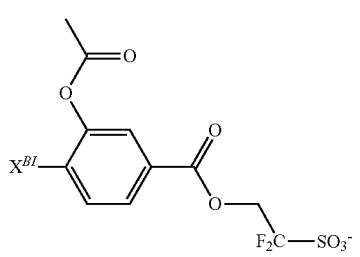

185
-continued
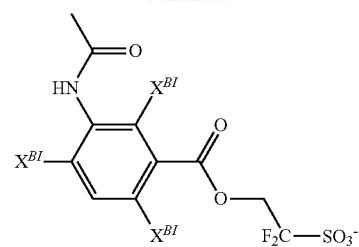
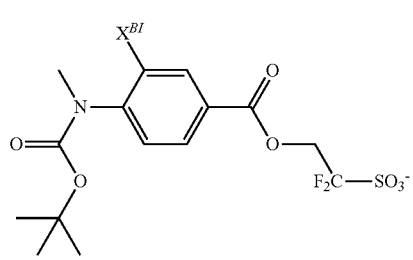
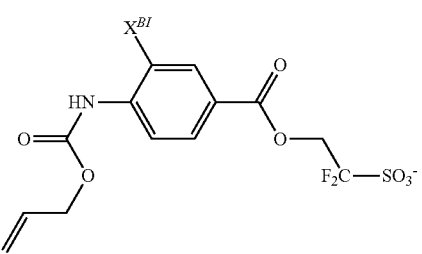
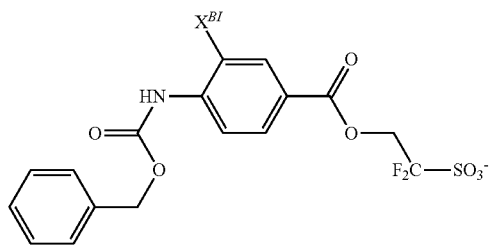
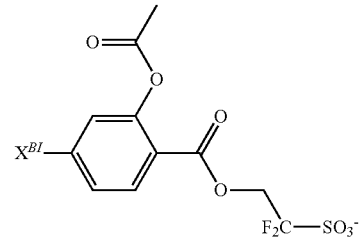
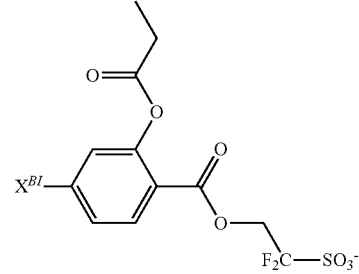
186
-continued
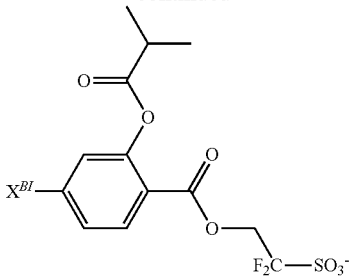
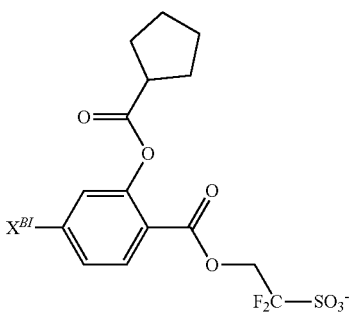
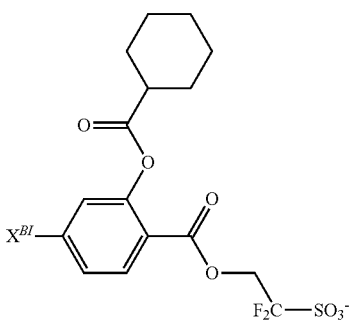
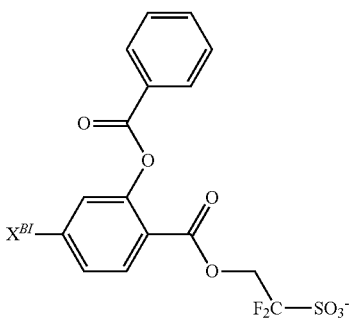
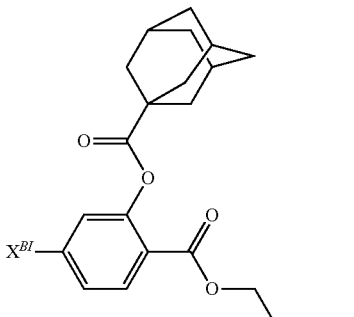

-continued
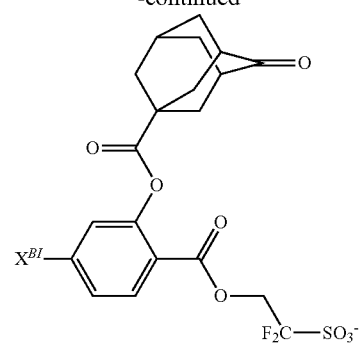
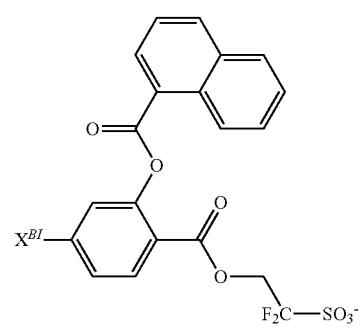
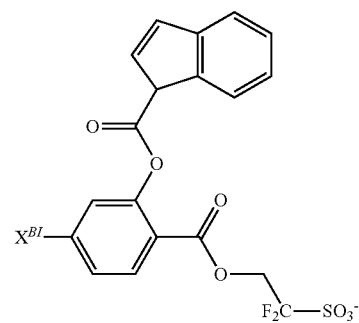
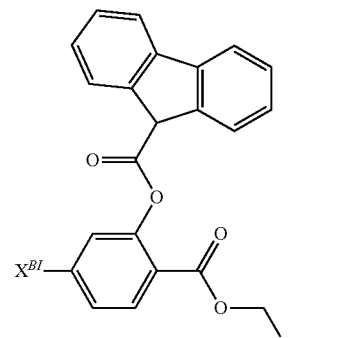
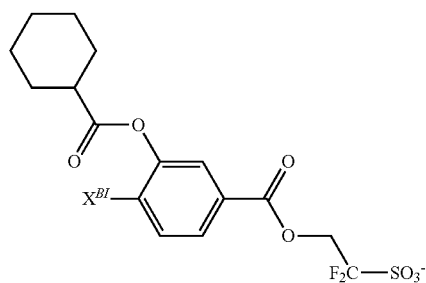
-continued
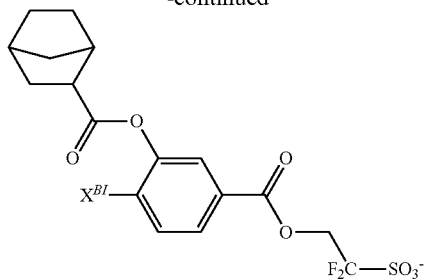
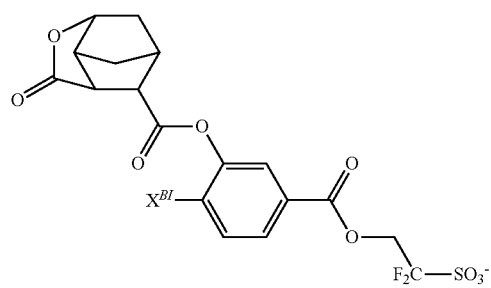
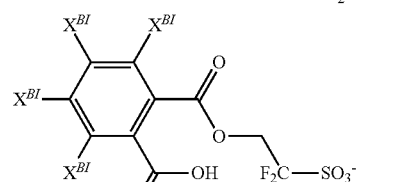
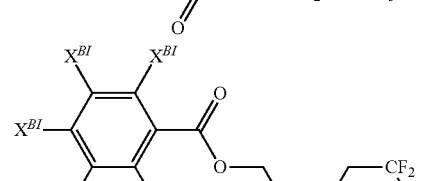
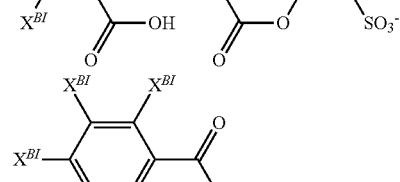
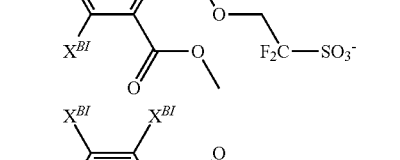
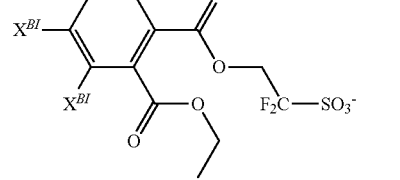
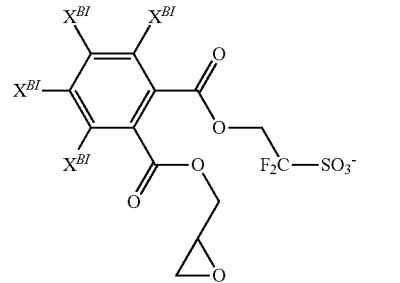

-continued
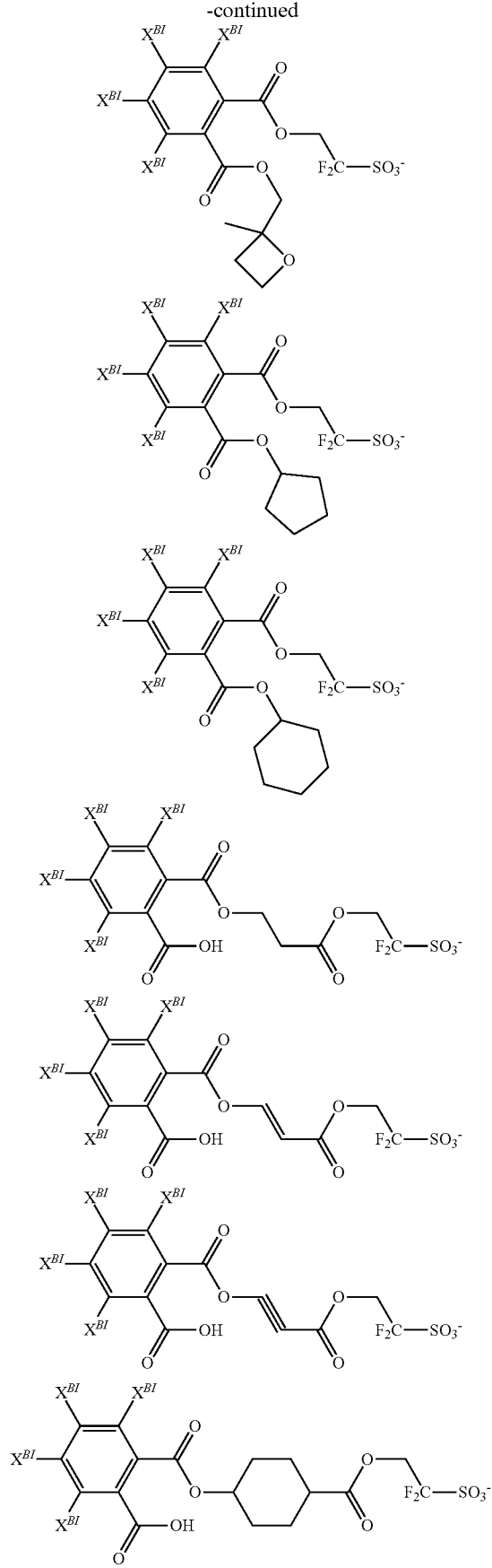
-continued
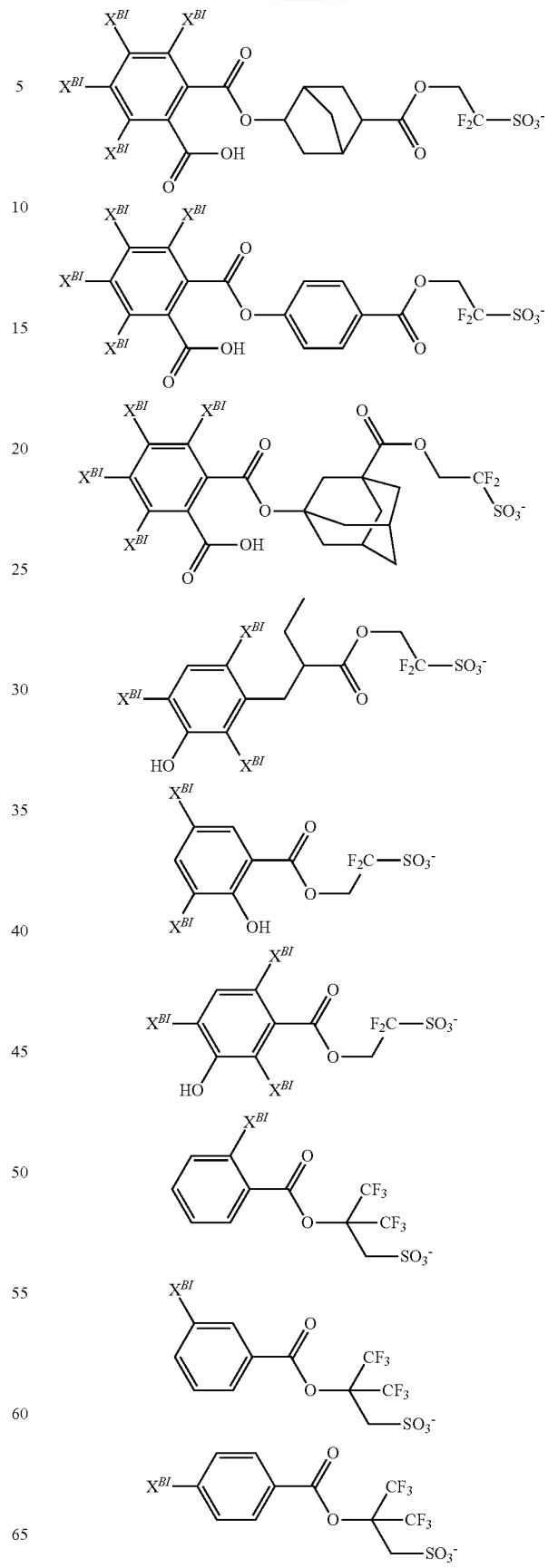

-continued
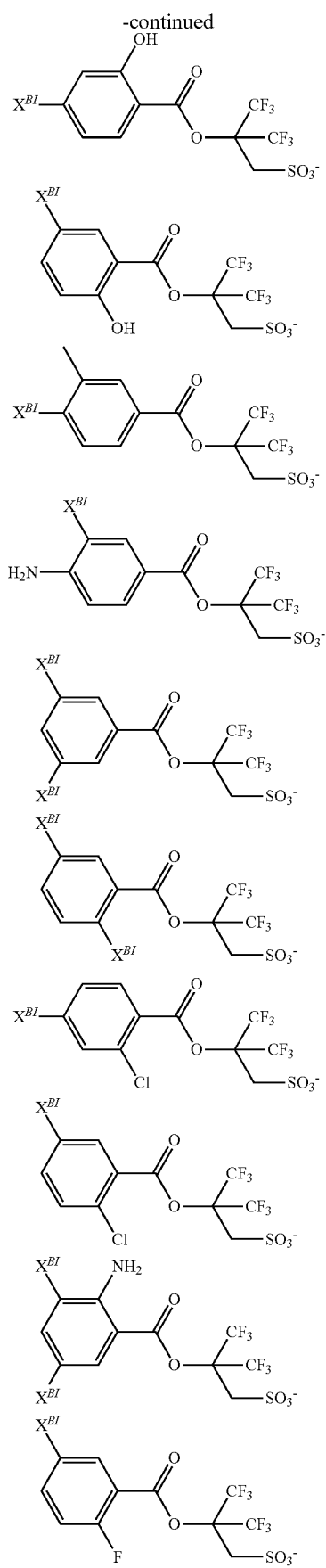
-continued
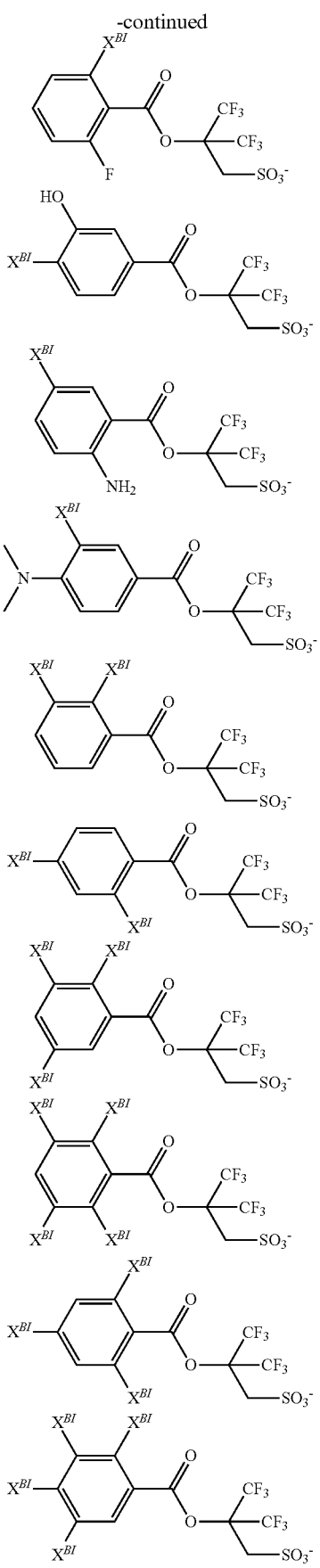

193
-continued
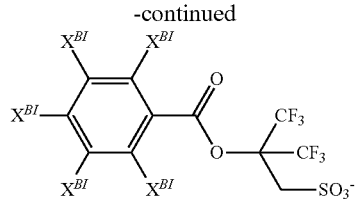
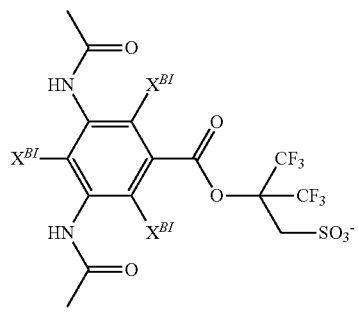
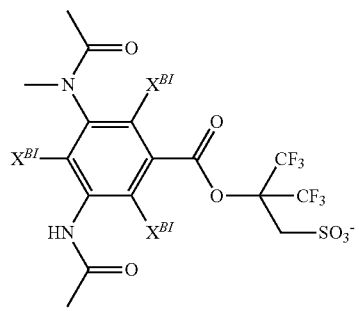
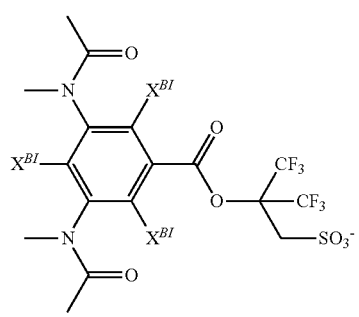
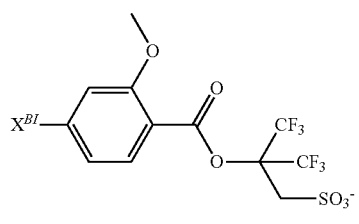
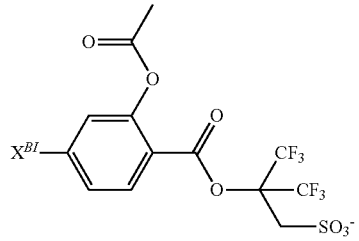
194
-continued
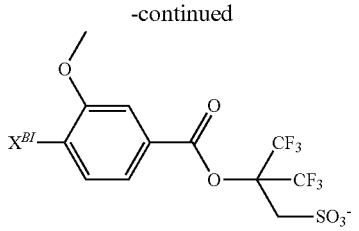
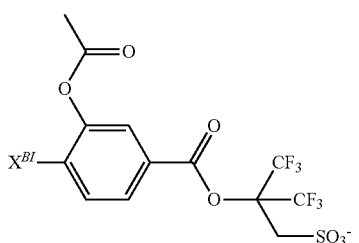
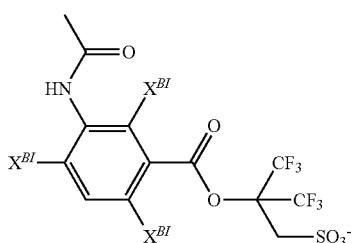
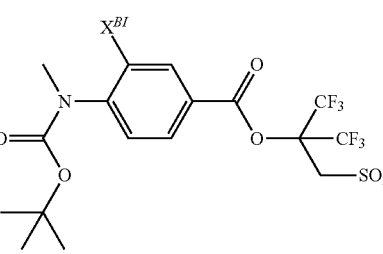
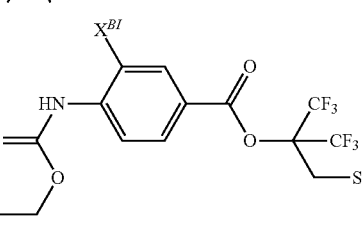
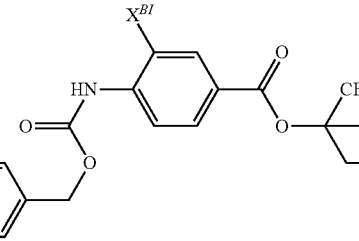
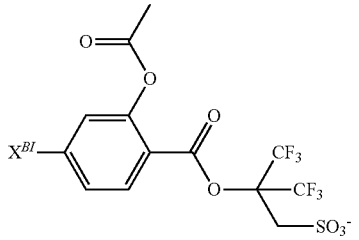

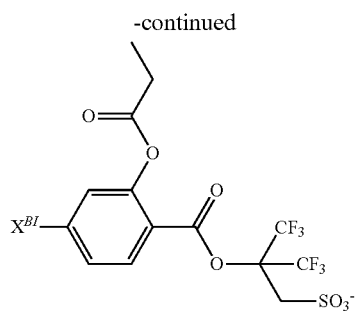
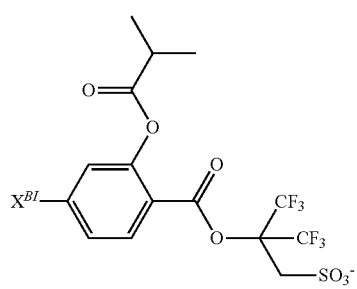
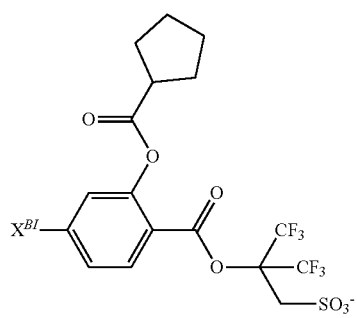
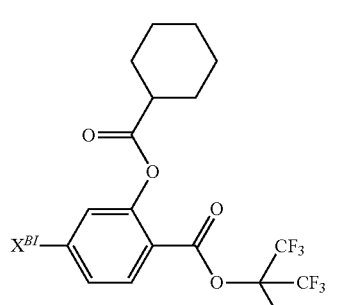
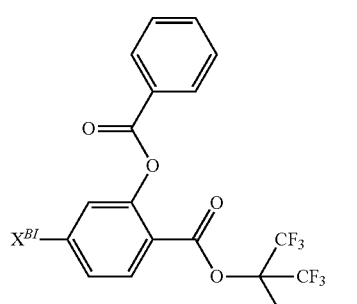
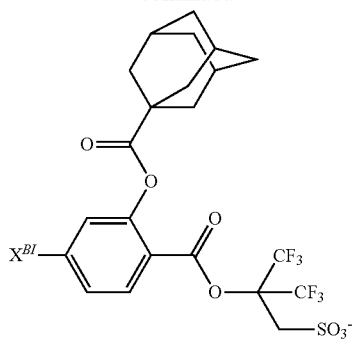
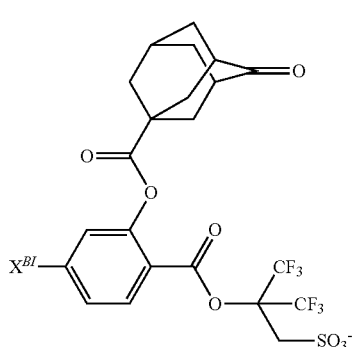
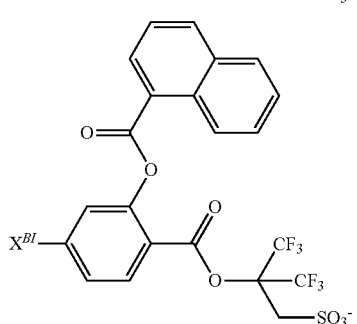
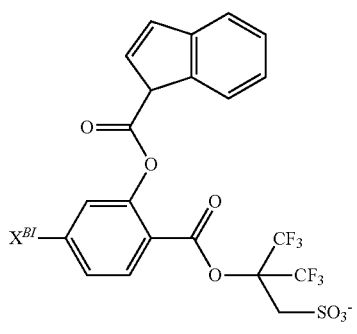
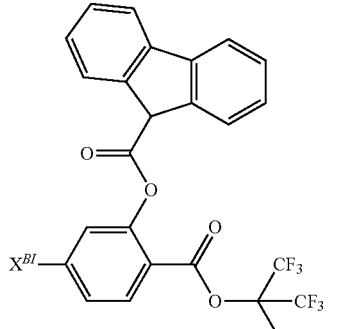

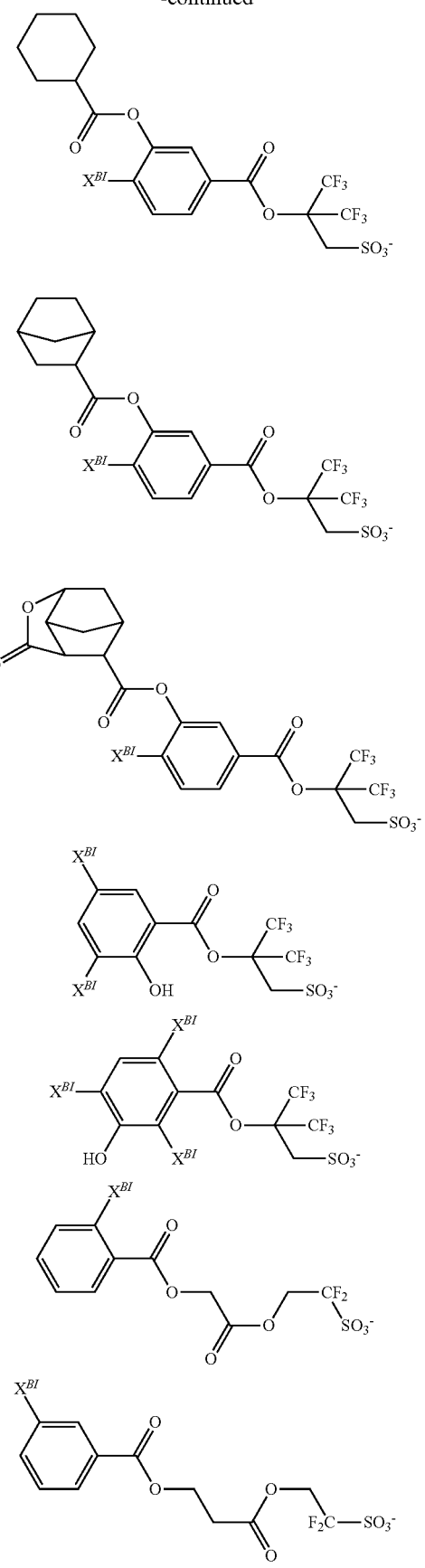
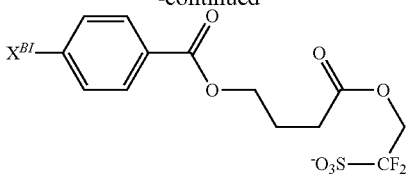
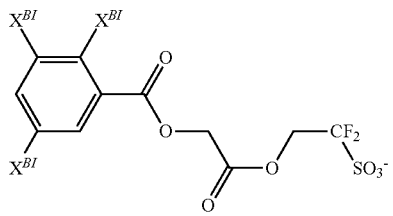
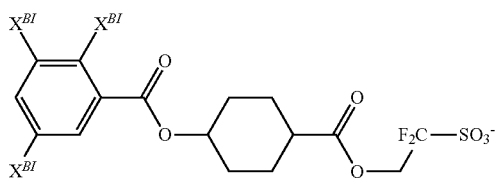
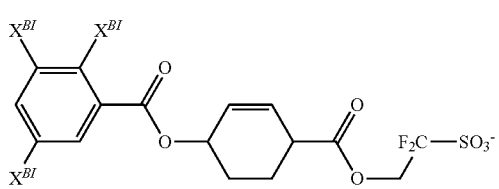
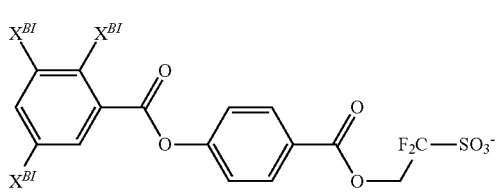
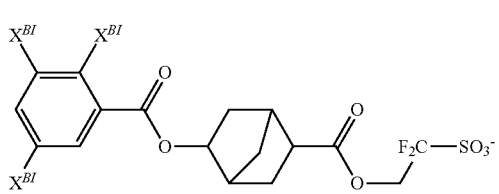
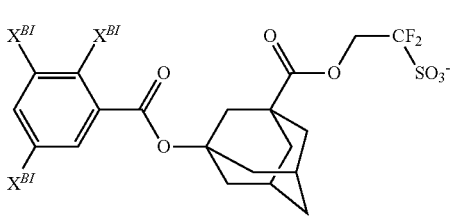
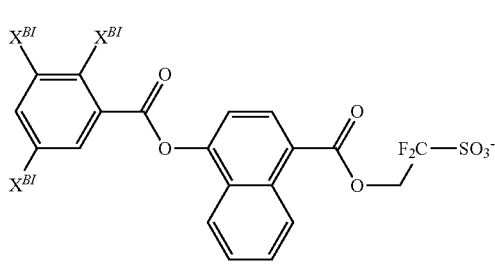

199
-continued
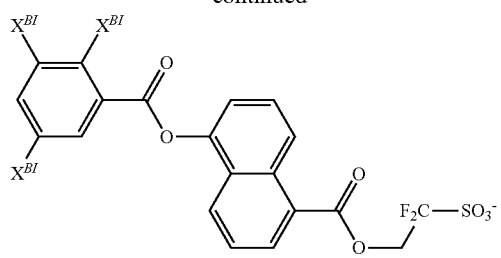
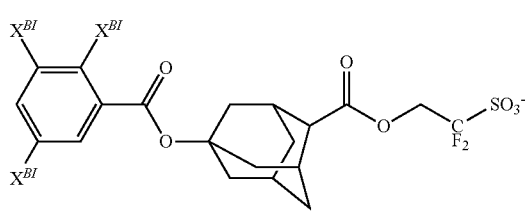
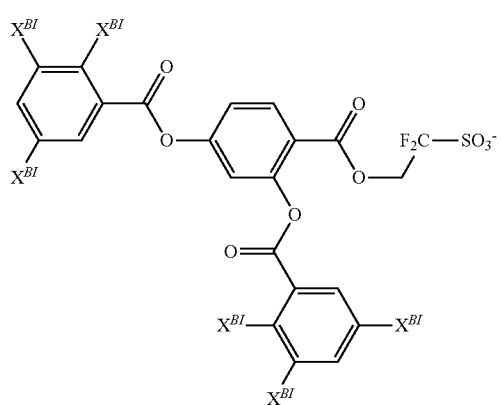
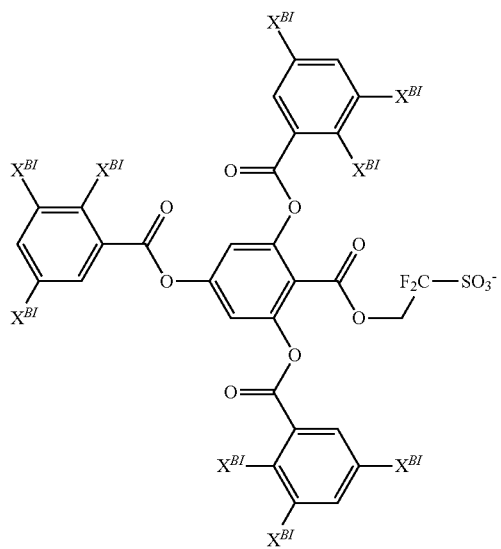
200
-continued
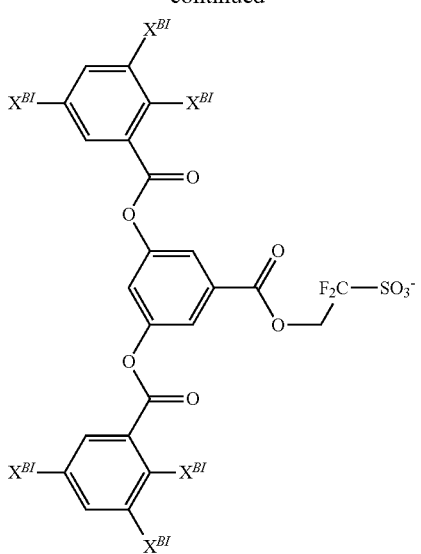
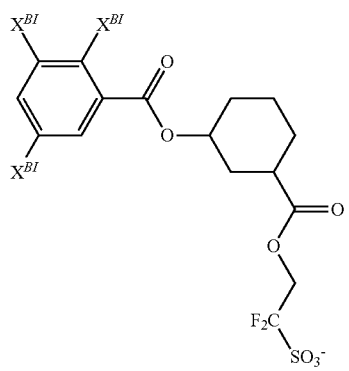
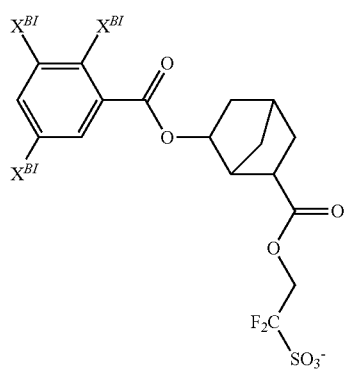
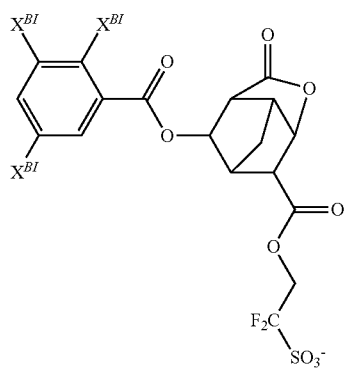

201
-continued
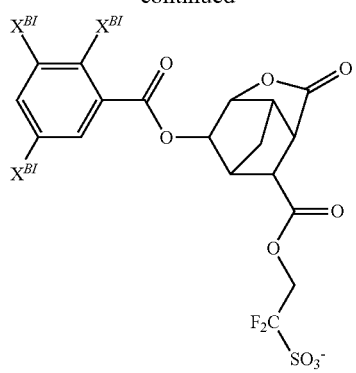
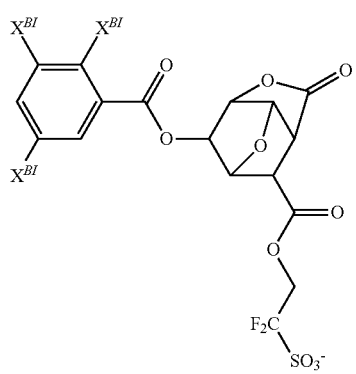
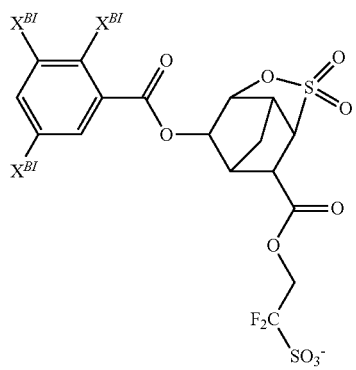
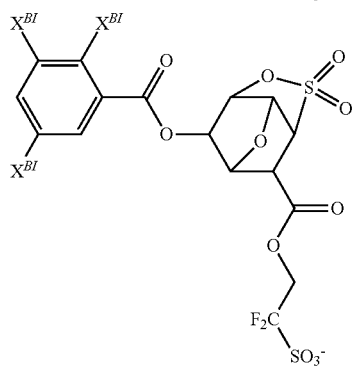
202
-continued
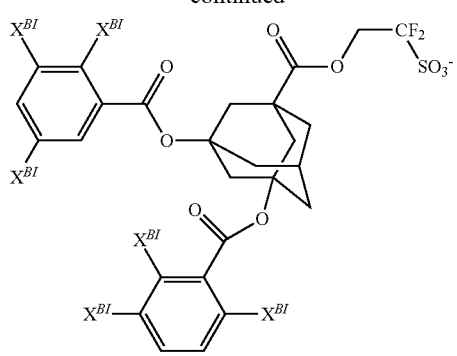
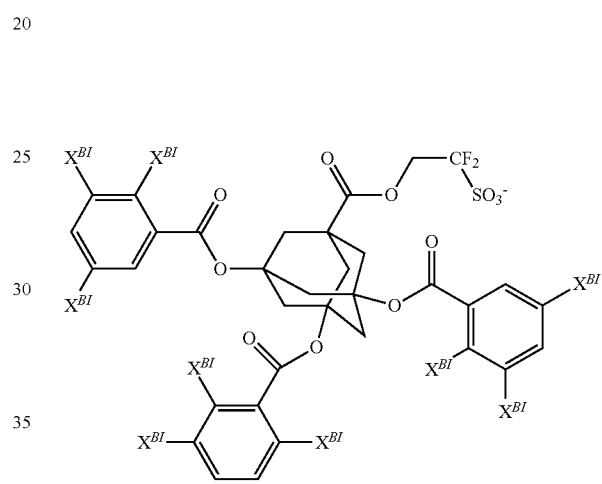

203
-continued
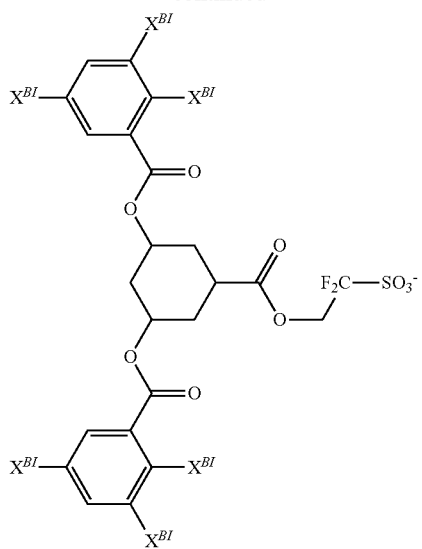
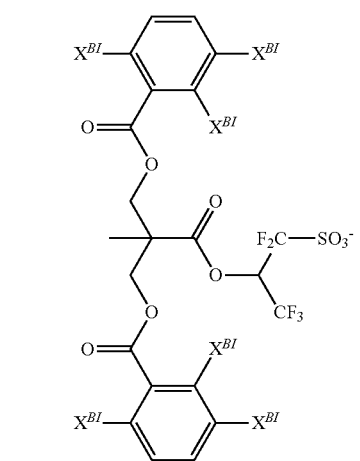
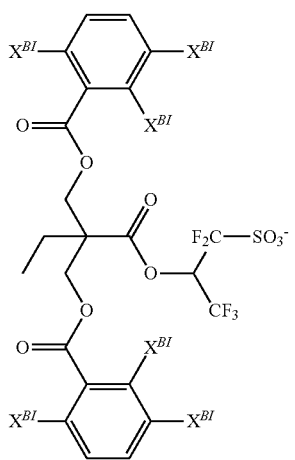
204
-continued
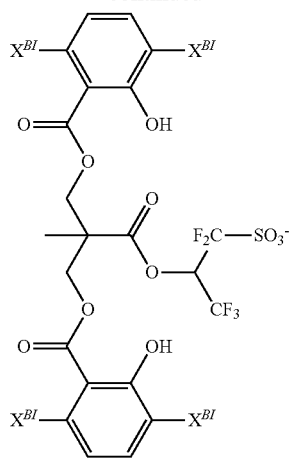
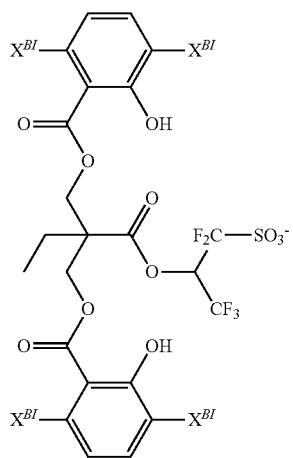
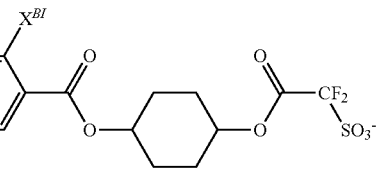
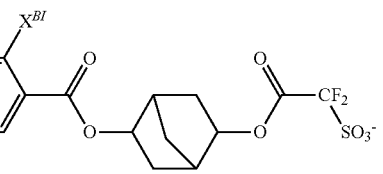
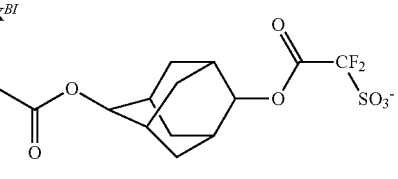
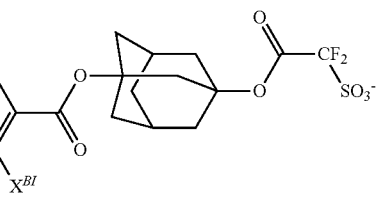

-continued
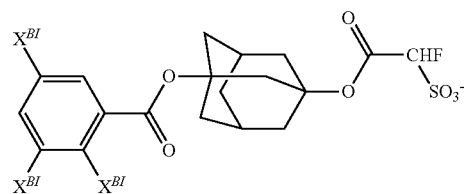
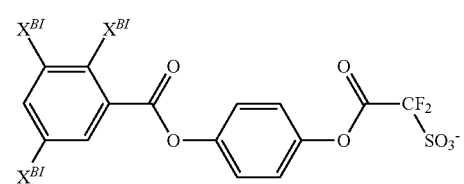
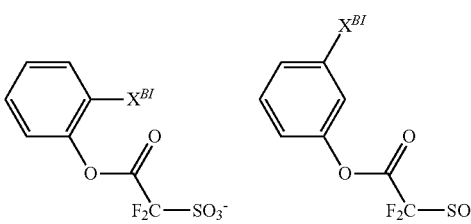
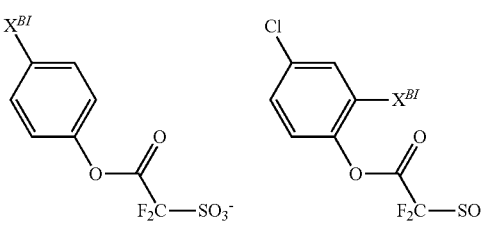
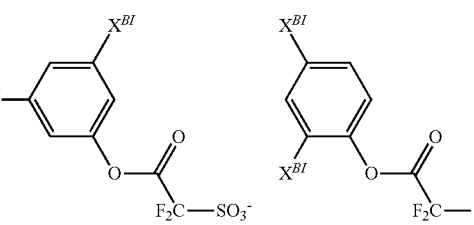
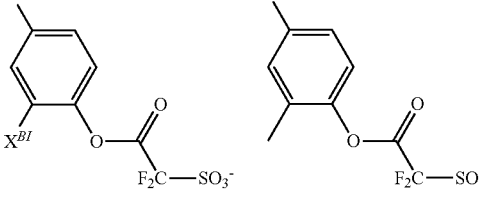
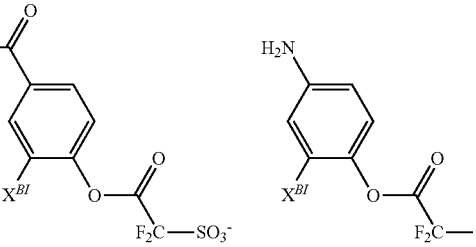
-continued
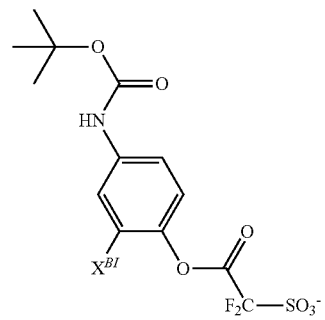
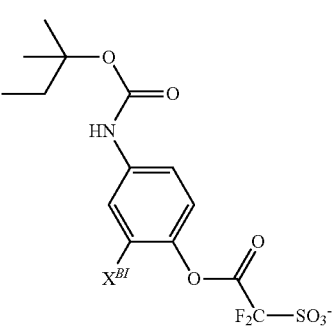
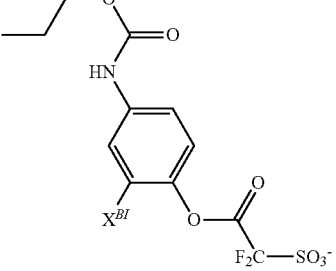
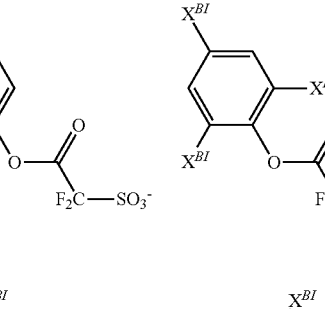
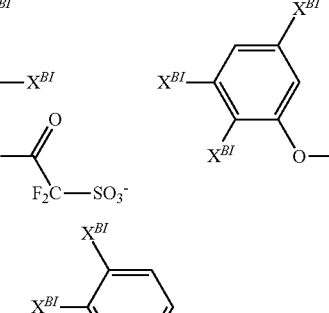
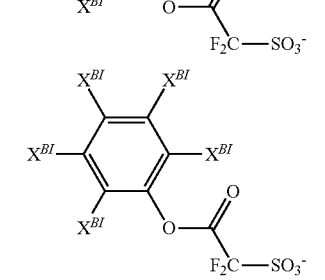

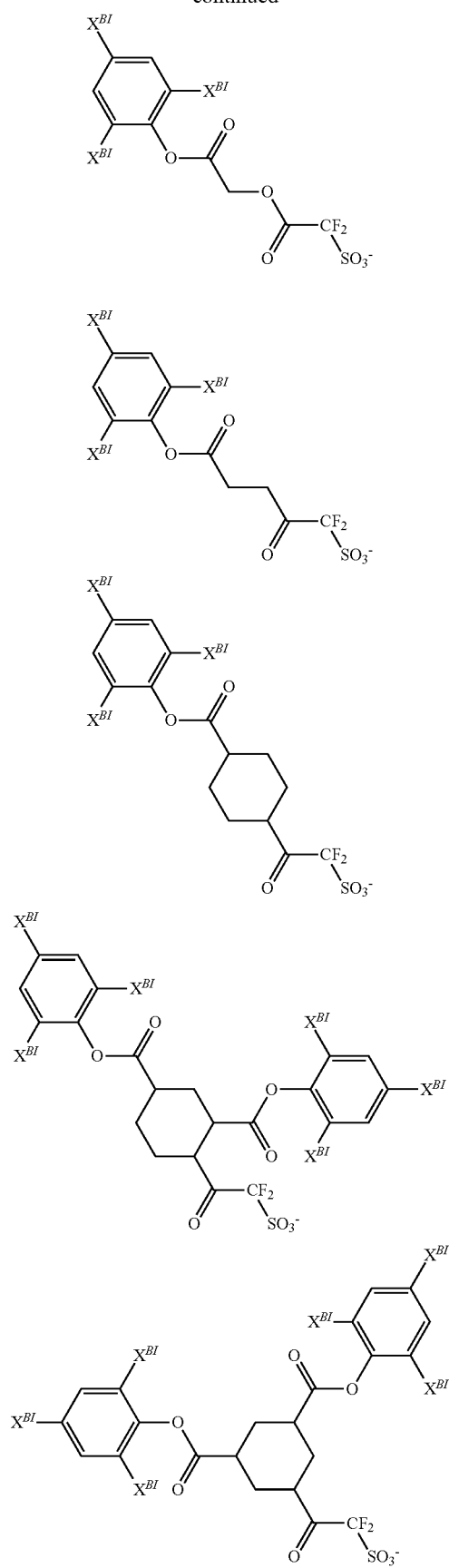
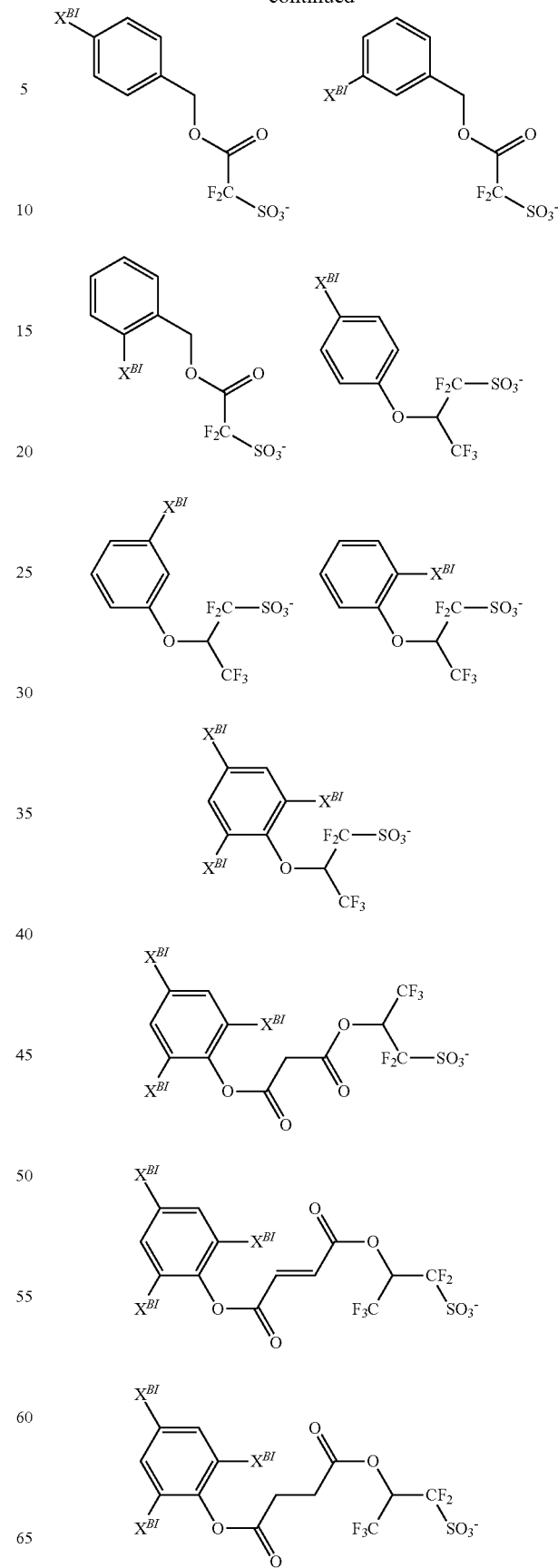

-continued
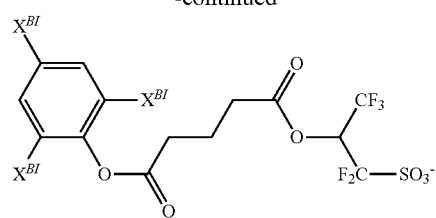
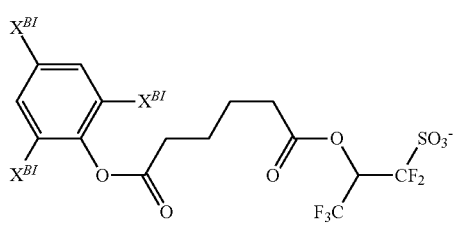
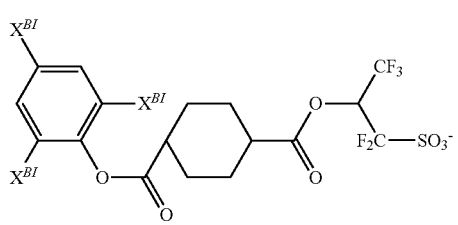
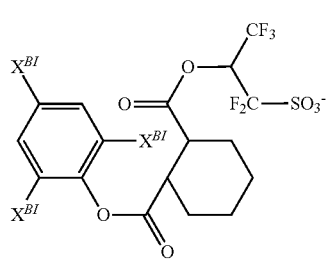
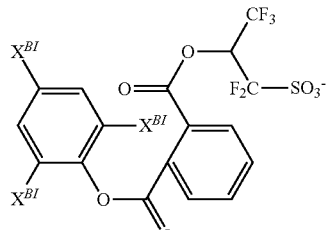
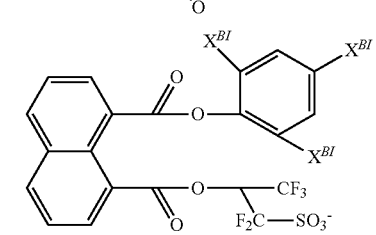
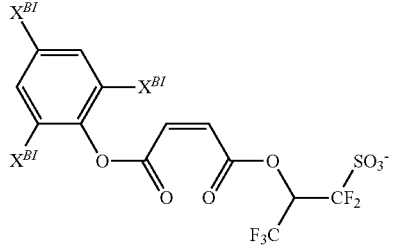
-continued
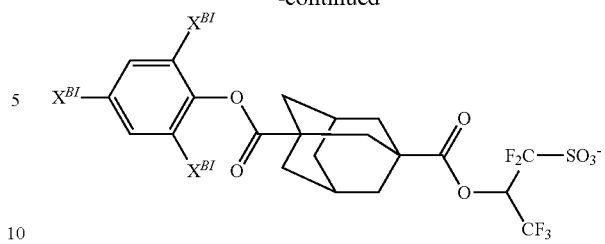
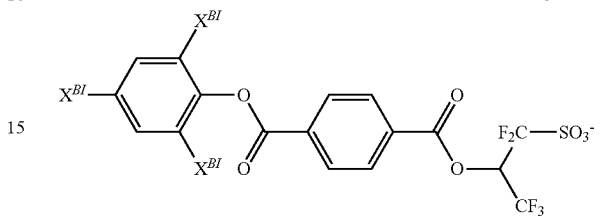
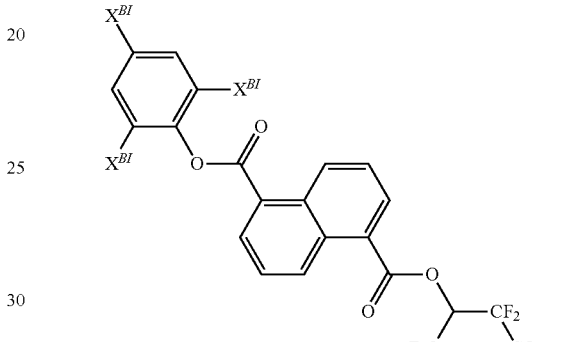
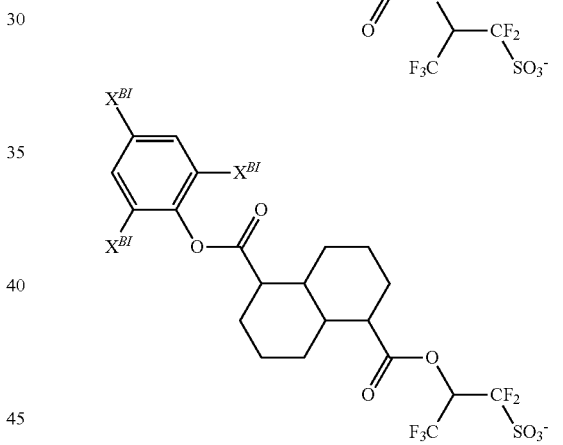
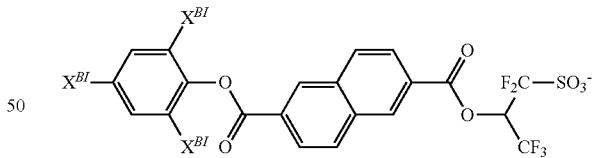
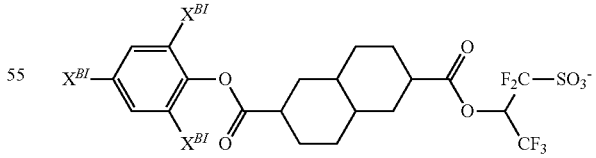
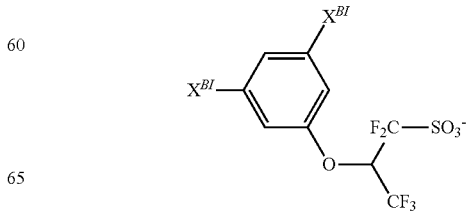

211
-continued
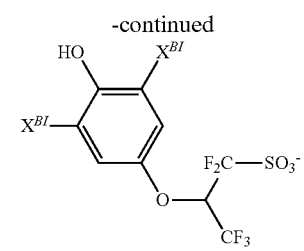
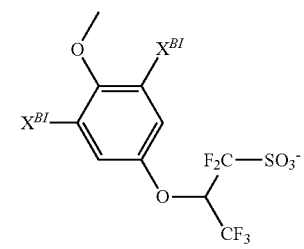
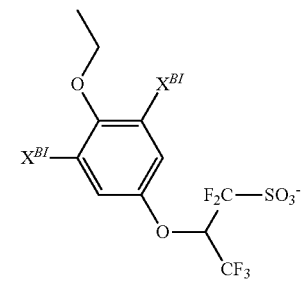
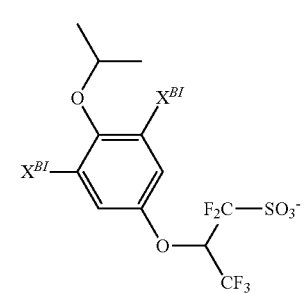
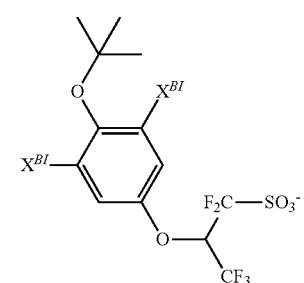
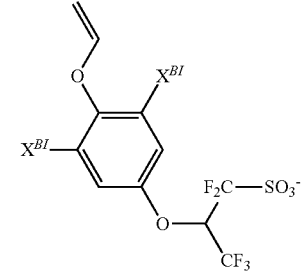
212
-continued
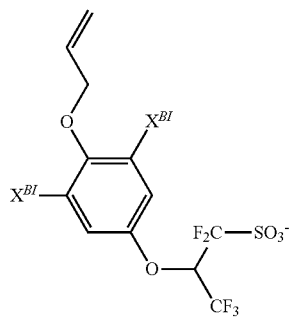
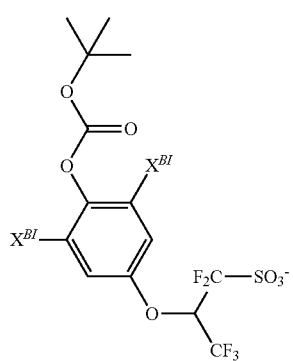
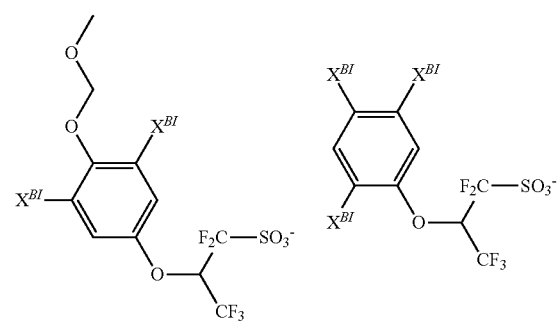
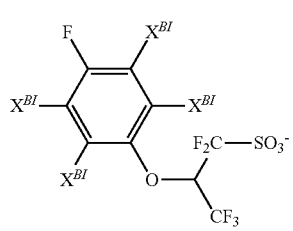
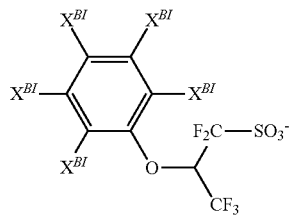
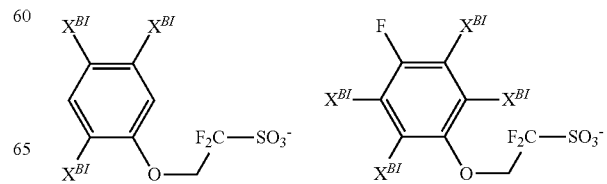

213
-continued
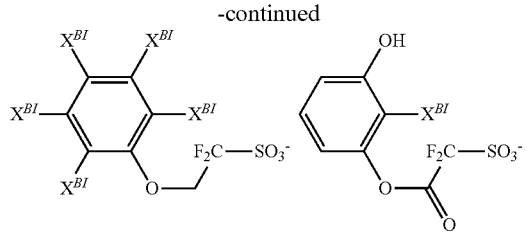
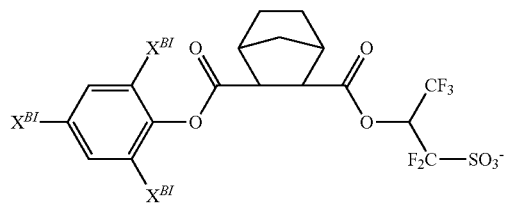
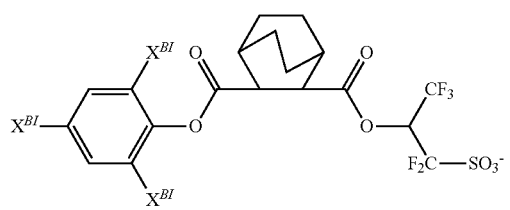
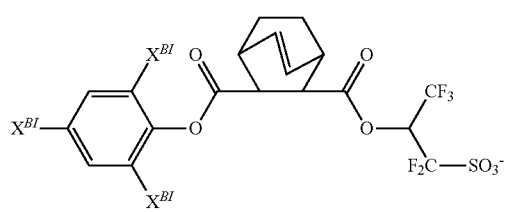
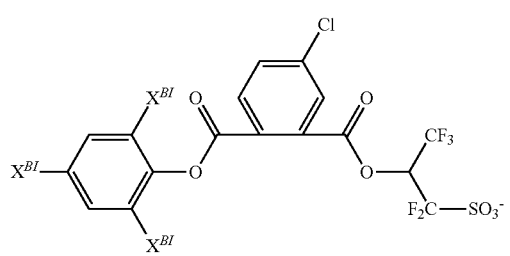
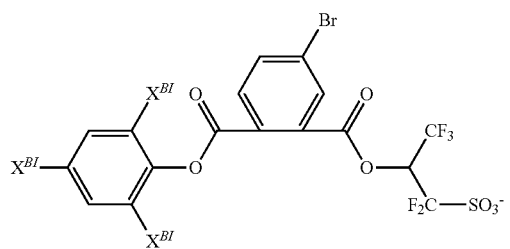
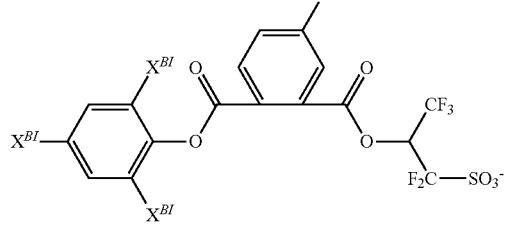
214
-continued
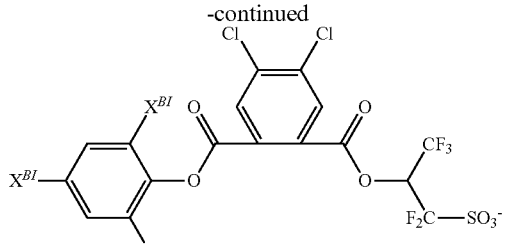
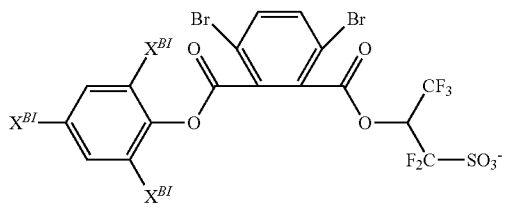
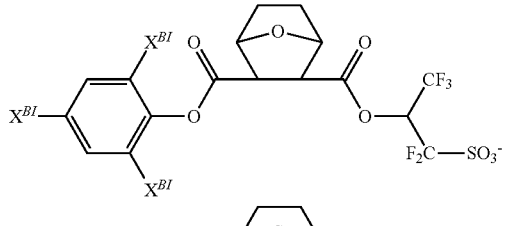
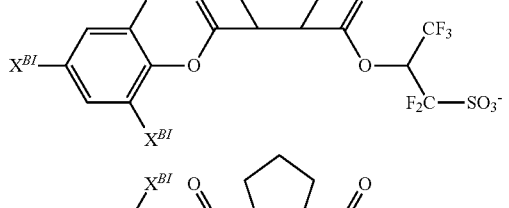
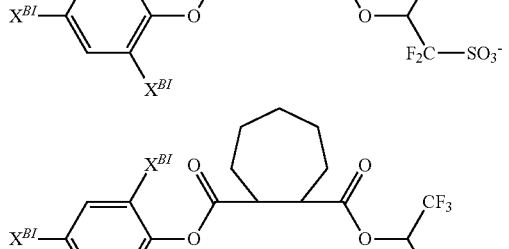
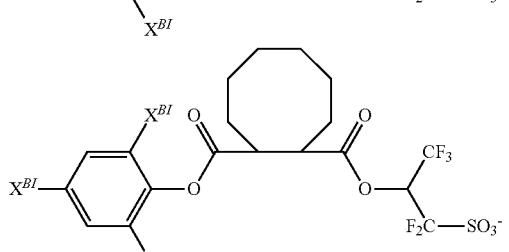
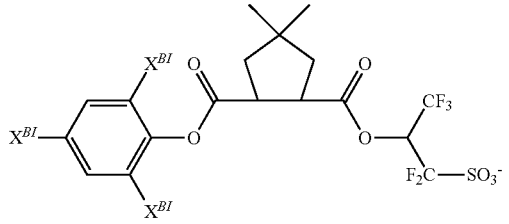

215
-continued
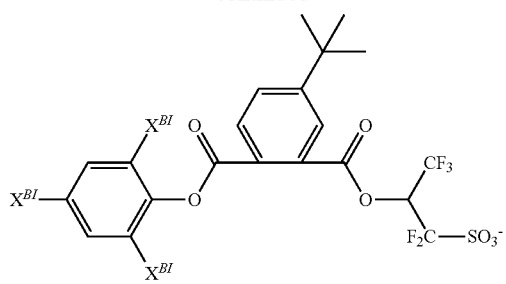
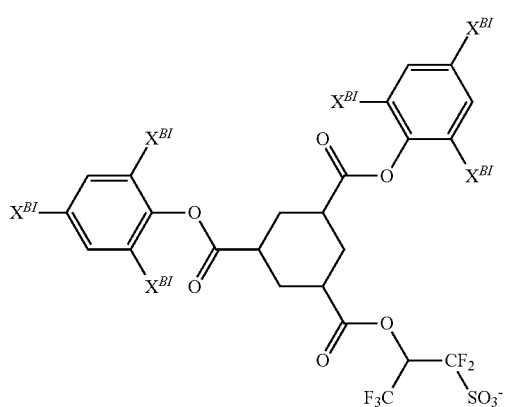
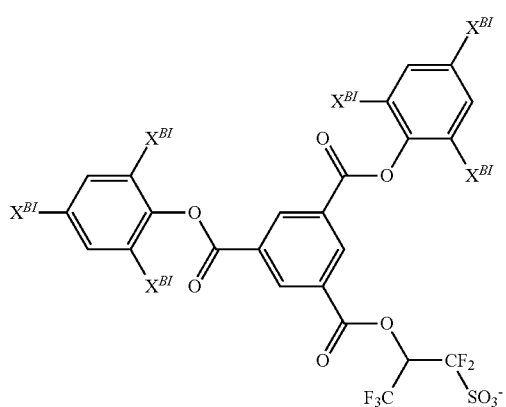
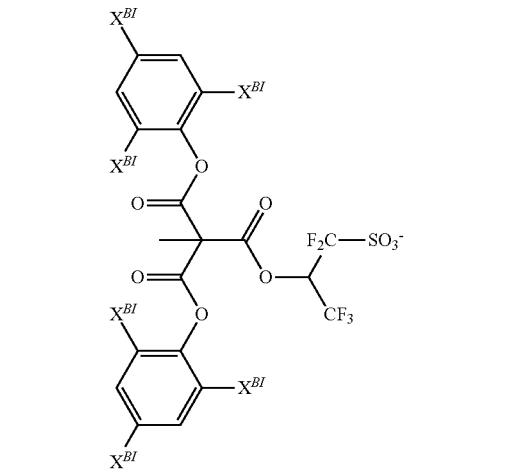
216
-continued
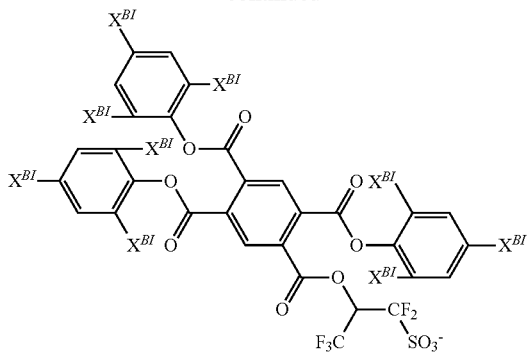
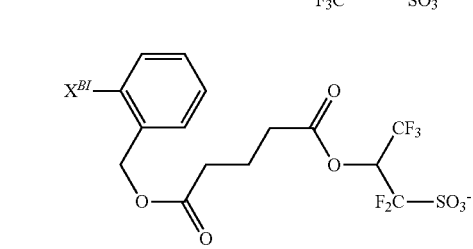
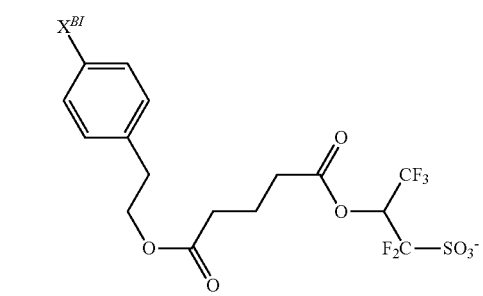
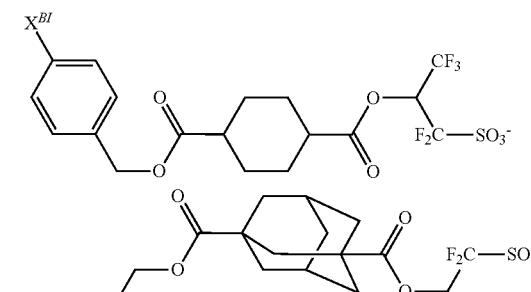
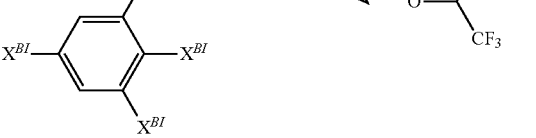
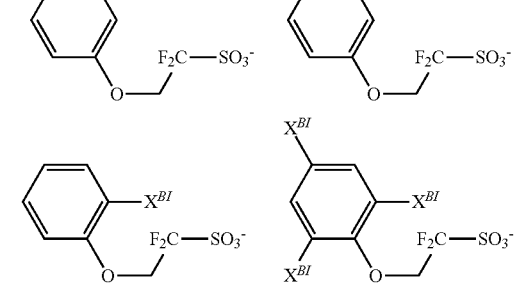

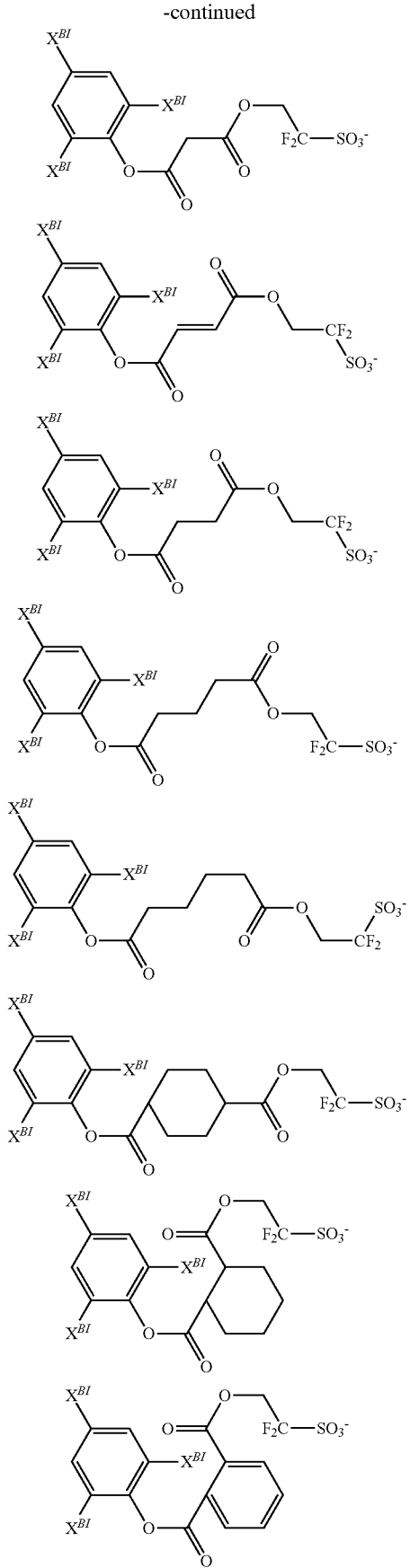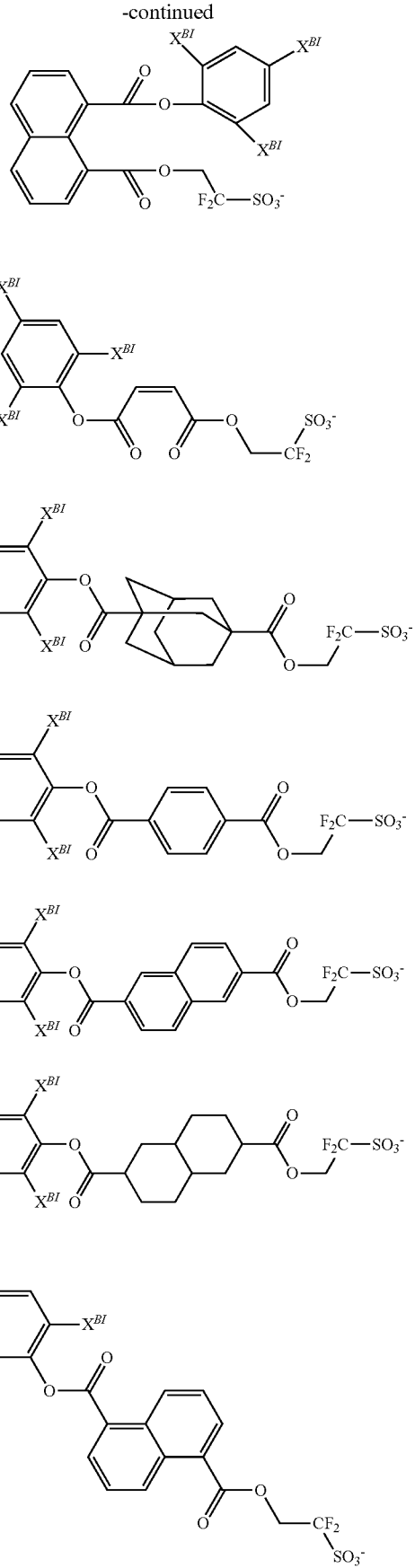

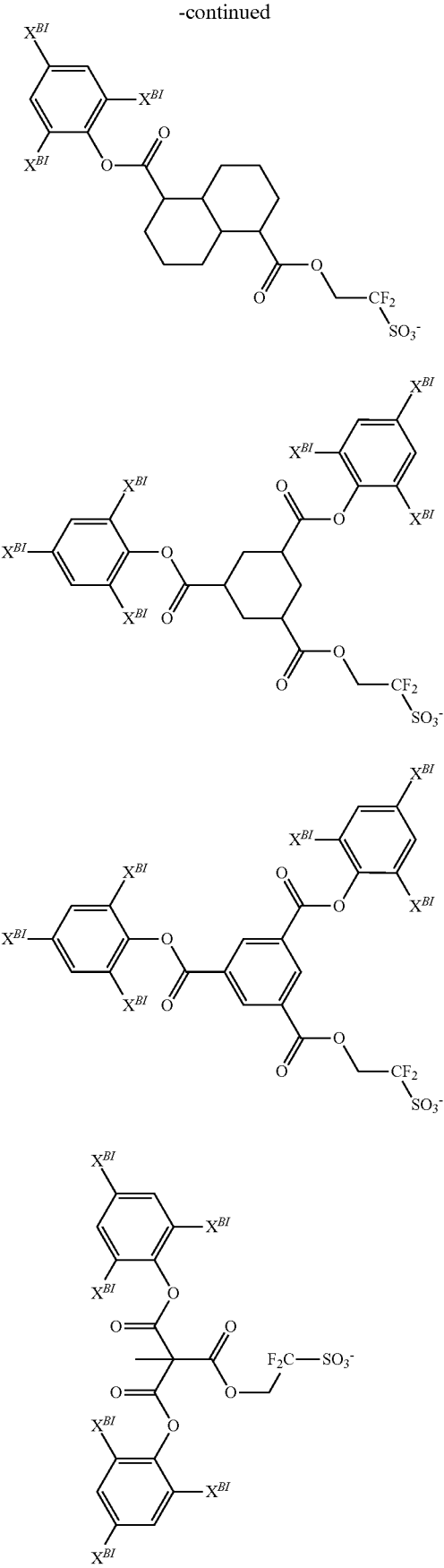
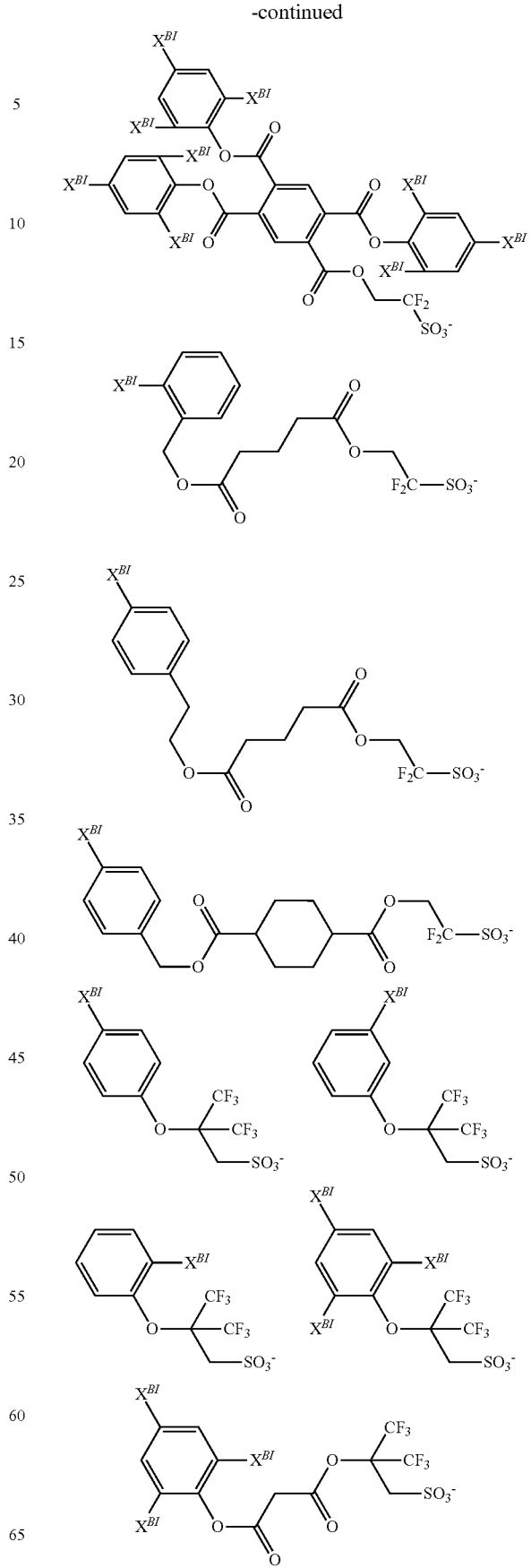

221
-continued
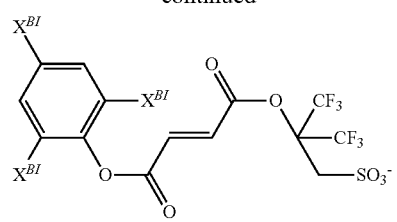
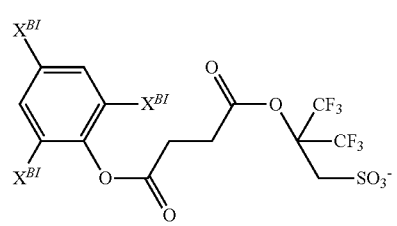
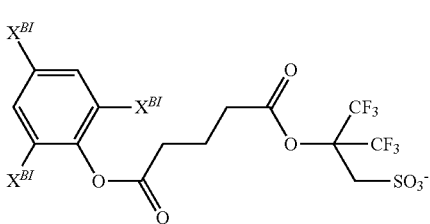
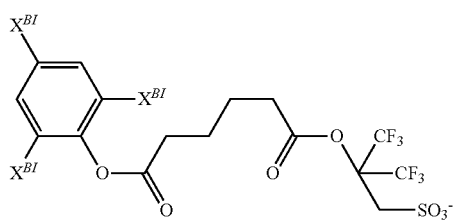
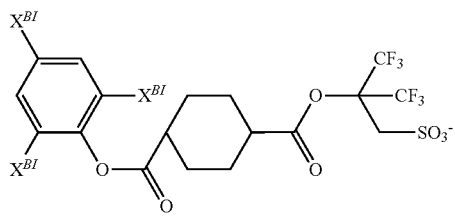
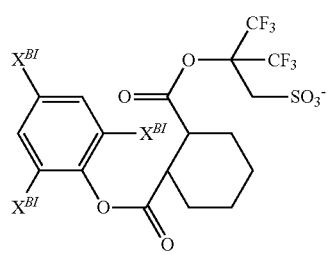
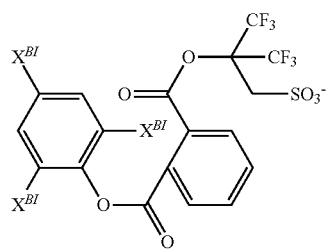
222
-continued
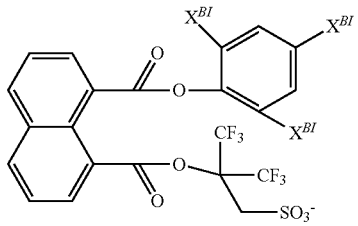
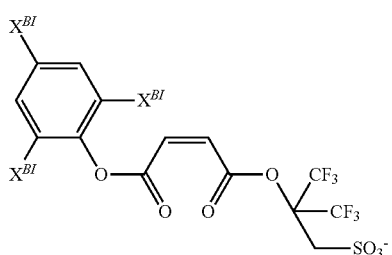
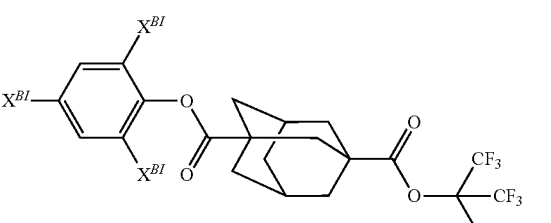
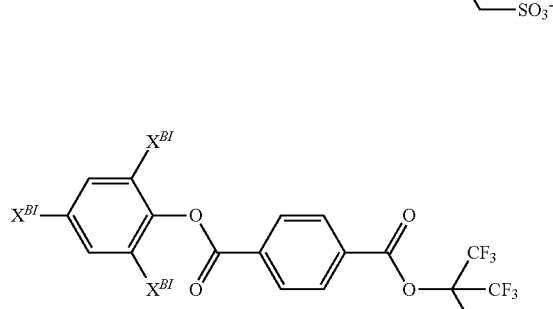
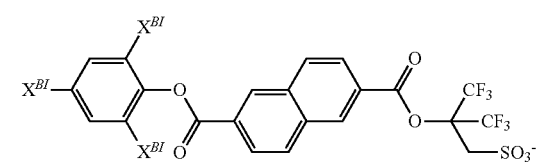
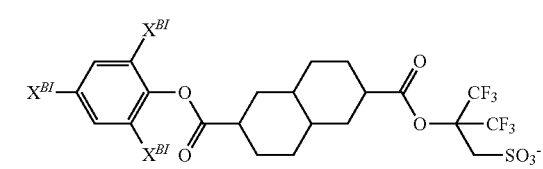

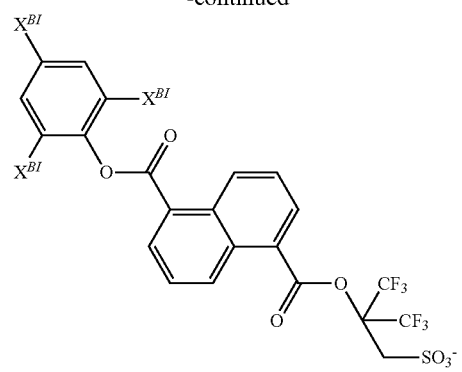
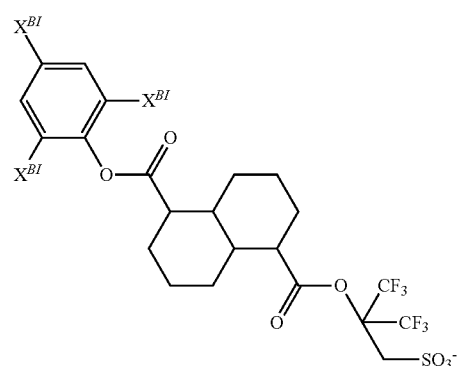
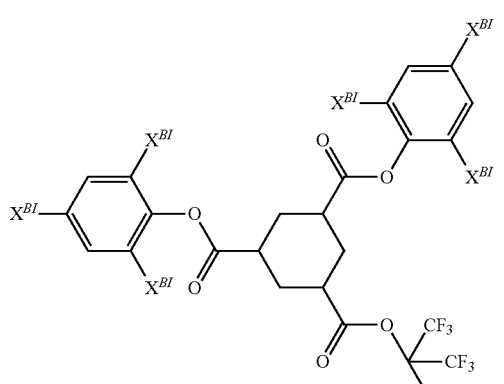
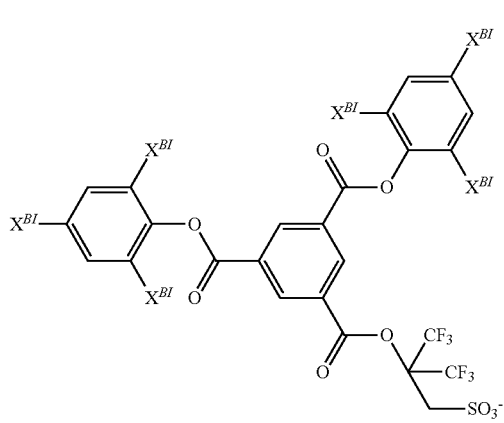
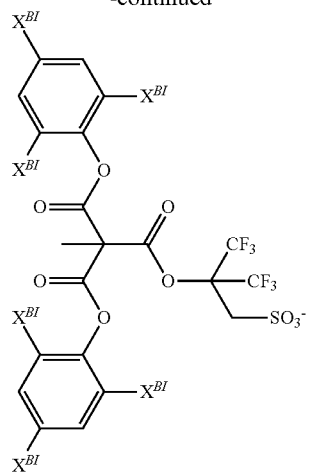
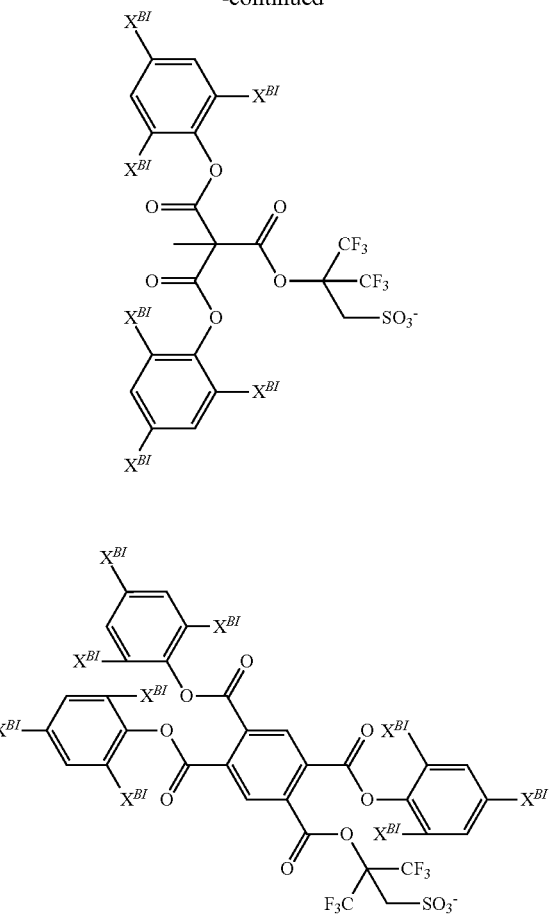
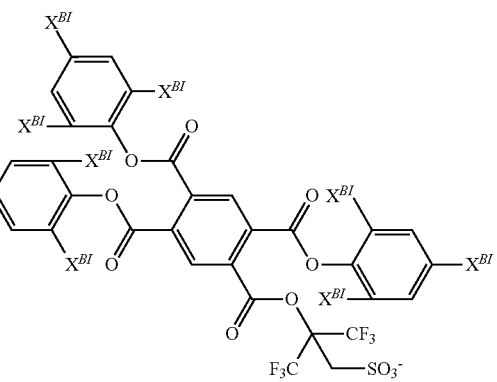
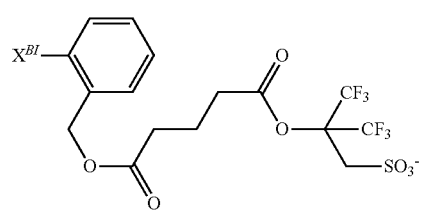
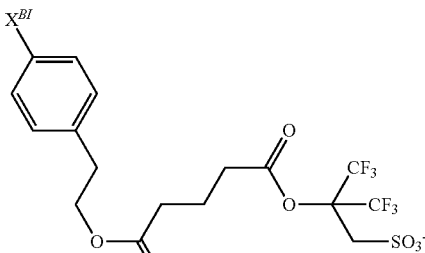
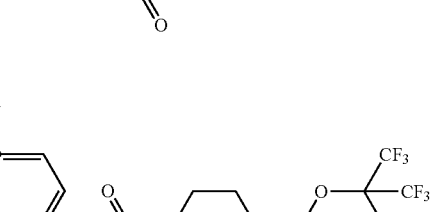

Another preferred PAG is a compound having the formula (4).

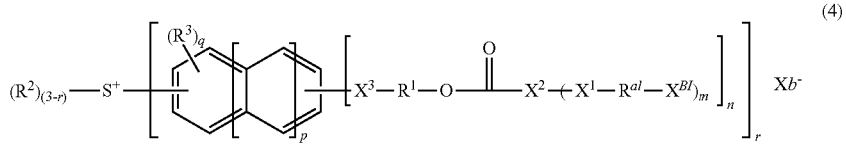

In the formula (4), $R^1$ to $R^3$, $R^{a1}$, $X^1$ to $X^3$, $X^{BI}$, m, n, p, q, and r are defined above. $Xb^-$ is an anion represented by any of the formulae (1A) to (1D) or an anion in the formulae (3-1) and (3-2). That is, the acid generator having the formula (4) is a compound obtained from combination of the anion represented by any of the formulae (1A) to (1D) or the anion in the formulae (3-1) and (3-2), with the cation in the formula (A). In particular in the case that $Xb^-$ is the anion in the formulae (3-1) and (3-2), further high sensitivity is expected because the increase in the number of iodine atoms in the acid generator leads to increase in the EUV absorption.

In the case that the resist composition comprises the acid generator of addition type, the acid generator is preferably added in an amount of 0.01 to 300 parts, and more preferably 0.1 to 100 parts by weight per 100 parts by weight of the base polymer.

Organic Solvent

The resist composition may comprise an organic solvent. The organic solvent is not particularly limited as long as each component described above and each component described below can be dissolved in the organic solvent. Examples of the organic solvent are described in JP-A 2008-111103, paragraphs [0144]-[0145], and include ketones such as cyclohexanone, cyclopentanone, methyl-2-n-pentyl ketone, and 2-heptanone, alcohols such as 3-methoxybutanol, 3-methyl-3-methoxybutanol, 1-methoxy-2-propanol, 1-ethoxy-2-propanol, and diacetone alcohol, ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether, esters such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate, and lactones such as γ-butyrolactone, which may be used alone or in admixture.

In the resist composition, the organic solvent is preferably added in an amount of 100 to 10,000 parts, more preferably 200 to 8,000 parts by weight per 100 parts by weight of the base polymer. The organic solvents may be used alone or in admixture.

Other Components

In the resist composition containing the foregoing components, other components such as a quencher other than the sulfonium salt having the formula (A) (hereinafter, also referred to as the other quencher), a surfactant, a dissolution inhibitor, and a crosslinker may be blended in any desired combination to formulate a positive or negative resist composition. This positive or negative resist composition has a very high sensitivity in that the dissolution rate in developer of the base polymer in exposed areas is accelerated by catalytic reaction. In this case, the resist film has a high dissolution contrast, resolution, exposure latitude, and process adaptability, and provides a good pattern profile after exposure, and minimal proximity bias because of restrained acid diffusion. By virtue of these advantages, the composition is fully useful in commercial application and suited as a pattern-forming material for the fabrication of VLSIs. Particularly when a chemically amplified positive resist composition capable of utilizing acid catalyzed reaction is formulated, the composition has a higher sensitivity and is further improved in the properties described above.

The other quencher is typically selected from conventional basic compounds. Examples of conventional basic compounds include primary, secondary, and tertiary aliphatic amines, mixed amines, aromatic amines, heterocyclic amines, nitrogen-containing compounds with a carboxyl group, nitrogen containing compounds with a sulfonyl group, nitrogen-containing compounds with a hydroxyl group, nitrogen-containing compounds with a hydroxyphenyl group, alcoholic nitrogen-containing compounds, amide derivatives, imide derivatives, and carbamate derivatives. Particularly preferable compounds among the conventional basic compounds are primary, secondary, and tertiary amine compounds, specifically amine compounds having a hydroxyl group, an ether bond, an ester bond, a lactone ring, a cyano group, or a sulfonic acid ester bond as described in JP-A 2008-111103, paragraphs [0146] to [0164], and compounds having a carbamate group as described in JP 3790649. Addition of such a basic compound may be effective for further suppressing the diffusion rate of acid in the resist film, correcting the pattern profile, or the like.

Onium salts such as sulfonium salts, iodonium salts, and ammonium salts of sulfonic acids which are not fluorinated at α-position as described in JP-A 2008-158339 and similar onium salts of carboxylic acids may also be used as the other quencher. While an α-fluorinated sulfonic acid, imide acid, and methide acid are necessary to deprotect the acid labile group of a carboxylic acid ester, an α-non-fluorinated sulfonic acid or a carboxylic acid is released by salt exchange with an α-non-fluorinated onium salt. An α-non-fluorinated sulfonic acid and a carboxylic acid function as a quencher because they do not induce deprotection reaction.

Also useful are quenchers of polymer type as described in JP-A 2008-239918. This quencher segregates at the resist film surface and thus enhances the rectangularity of resist pattern. When a protective film is applied as is often the case in the immersion lithography, the polymeric quencher is also effective for preventing a film thickness loss of resist pattern or rounding of pattern top.

In the case that the resist composition comprises the other quencher, the quencher is preferably added in an amount of 0 to 5 parts, and more preferably 0 to 4 parts by weight per 100 parts by weight of the base polymer. The other quenchers may be used alone or in admixture.

Examples of the surfactant include the surfactants described in JP-A 2008-111103, paragraphs [0165] to [0166]. Addition of a surfactant may improve or control the coating characteristics of the resist composition. In the case that the resist composition comprises the surfactant, the surfactant is preferably added in an amount of 0.0001 to 10 parts by weight per 100 parts by weight of the base polymer. The surfactant may be used alone or in admixture.

In the case of positive resist compositions, blending of a dissolution inhibitor may lead to an increased difference in dissolution rate between exposed and unexposed areas and a further improvement in resolution. The dissolution inhibitor which can be used herein is a compound having at least two phenolic hydroxyl groups on the molecule, in which an average of from 0 to 100 mol % of all the hydrogen atoms on the phenolic hydroxyl groups are replaced by acid labile groups or a compound having at least one carboxyl group on the molecule, in which an average of 50 to 100 mol % of all the hydrogen atoms on the carboxyl groups are replaced by acid labile groups, both the compounds preferably having a molecular weight of 100 to 1,000, and more preferably 150 to 800. Typical are bisphenol A, trisphenol, phenolphthalein, cresol novolac, naphthalenecarboxylic acid, adamantanecarboxylic acid, and cholic acid derivatives in which the hydrogen atom on the hydroxyl or carboxyl group is replaced by an acid labile group, as described in JP-A 2008-122932, paragraphs [0155] to [0178].

In the case that the resist composition is a positive resist composition containing the dissolution inhibitor, the dissolution inhibitor is preferably added in an amount of 0 to 50 parts, more preferably 5 to 40 parts by weight per 100 parts by weight of the base polymer. The dissolution inhibitors may be used alone or in admixture.

In the case of negative resist compositions, a negative pattern may be formed by adding a crosslinker to reduce the dissolution rate of exposed area. Examples of the crosslinker include epoxy compounds, melamine compounds, guanamine compounds, glycoluril compounds, and urea compounds having substituted thereon at least one group selected from among methylol, alkoxymethyl, and acyloxymethyl groups, isocyanate compounds, azide compounds, and compounds having a double bond such as an alkenyloxy group. These compounds may be used as an additive or introduced into a polymer side chain as a pendant. Hydroxy-containing compounds may also be used as the crosslinker.

Examples of the epoxy compound include tris(2,3-epoxypropyl) isocyanurate, trimethylolmethane triglycidyl ether, trimethylolpropane triglycidyl ether, and triethylolethane triglycidyl ether.

Examples of the melamine compound include hexamethylol melamine, hexamethoxymethyl melamine, hexamethylol melamine compounds having 1 to 6 methylol groups methoxymethylated and mixtures thereof, hexamethoxyethyl melamine, hexaacyloxymethyl melamine, hexamethylol melamine compounds having 1 to 6 methylol groups acyloxymethylated and mixtures thereof.

Examples of the guanamine compound include tetramethylol guanamine, tetramethoxymethyl guanamine, tetramethylol guanamine compounds having 1 to 4 methylol groups methoxymethylated and mixtures thereof, tetramethoxyethyl guanamine, tetraacyloxyguanamine, tetramethylol guanamine compounds having 1 to 4 methylol groups acyloxymethylated and mixtures thereof.

Examples of the glycoluril compound include tetramethylol glycoluril, tetramethoxyglycoluril, tetramethoxymethyl glycoluril, tetramethylol glycoluril compounds having 1 to 4 methylol groups methoxymethylated and mixtures thereof, tetramethylol glycoluril compounds having 1 to 4 methylol groups acyloxymethylated and mixtures thereof. Examples of the urea compound include tetramethylol urea, tetramethoxymethyl urea, tetramethylol urea compounds having 1 to 4 methylol groups methoxymethylated and mixtures thereof, and tetramethoxyethyl urea.

Examples of the isocyanate compound include tolylene diisocyanate, diphenylmethane diisocyanate, hexamethylene diisocyanate, and cyclohexane diisocyanate.

Examples of the azide compound include 1,1'-biphenyl-4,4'-bisazide, 4,4'-methylidenebisazide, and 4,4'-oxybisazide.

Examples of the alkenyloxy group-containing compound include ethylene glycol divinyl ether, triethylene glycol divinyl ether, 1,2-propanediol divinyl ether, 1,4-butanediol divinyl ether, tetramethylene glycol divinyl ether, neopentyl glycol divinyl ether, trimethylol propane trivinyl ether, hexanediol divinyl ether, 1,4-cyclohexanediol divinyl ether, pentaerythritol trivinyl ether, pentaerythritol tetravinyl ether, sorbitol tetravinyl ether, sorbitol pentavinyl ether, and trimethylol propane trivinyl ether.

In the case that the resist composition is a negative resist composition containing the crosslinker, the crosslinker is preferably added in an amount of 0.1 to 50 parts, more preferably 1 to 40 parts by weight per 100 parts by weight of the base polymer. The crosslinkers may be used alone or in admixture.

To the resist composition, a water repellency improver may also be added for improving the water repellency on surface of a resist film. The water repellency improver may be used in the topcoatless immersion lithography. Suitable water repellency improvers include polymers having a fluoroalkyl group and polymers having a specific structure with a 1,1,1,3,3,3-hexafluoro-2-propanol residue and are described in JP-A 2007-297590 and JP-A 2008-111103, for example. The water repellency improver should be soluble in alkaline developers and organic solvent developers. The water repellency improver of specific structure with a 1,1,1,3,3,3-hexafluoro-2-propanol residue is well soluble in the developer. A polymer having an amino group or amine salt copolymerized as recurring units may serve as the water repellency improver and is effective for preventing evaporation of acid during post exposure bake (PEB), thus preventing any hole pattern opening failure after development. In the case that the resist composition comprises the water repellency improver, the water repellency improver is preferably added in an amount of 0 to 20 parts, and more preferably 0.5 to 10 parts by weight per 100 parts by weight of the base polymer. The water repellency improvers may be used alone or in admixture.

Also, an acetylene alcohol may be blended in the resist composition. Examples of the acetylene alcohol include the acetylene alcohols described in JP-A 2008-122932, paragraphs [0179] to [0182]. In the case that the resist composition contains the acetylene alcohol, the acetylene alcohol is preferably added in an amount of 0 to 5 parts by weight per 100 parts by weight of the base polymer. The acetylene alcohols may be used alone or in admixture.

Pattern Forming Process

In a case where the resist composition is used in the fabrication of various integrated circuits, pattern formation using the resist composition may be performed by well-known lithography processes. The pattern forming process generally involves the steps of applying the resist composition onto a substrate to form a resist film thereon, exposing the resist film to high-energy radiation, and developing the exposed resist film in a developer.

For example, the resist composition is first applied onto a substrate on which an integrated circuit is to be formed (e.g., Si, $SiO_2$, SiN, SiON, TiN, WSi, BPSG, SOG, or organic antireflective coating) or a substrate on which a mask circuit is to be formed (e.g., Cr, CrO, CrON, MoSi$_2$, or SiO$_2$) by a suitable coating technique such as spin coating, roll coating, flow coating, dipping, spraying, or doctor coating. The coating is prebaked on a hotplate preferably at a temperature of 60 to 150° C. for 10 seconds to 30 minutes, more preferably at 80 to 120° C. for 30 seconds to 20 minutes. The resulting resist film is generally 0.01 to 2 µm thick.

Then the resist film is exposed to high-energy radiation. Examples of the high-energy radiation include ultraviolet (UV), deep-UV, EB, EUV of wavelength 3 to 15 nm, x-rays, soft x-rays, excimer laser radiation, γ-rays, and synchrotron radiation. When UV, deep-UV, EUV, x-ray, soft x-ray, excimer laser light, γ-ray or synchrotron radiation is used as the high-energy radiation, the resist film is exposed thereto directly or through a mask having a desired pattern in a dose of preferably about 1 to 200 mJ/cm$^2$, more preferably about 10 to 100 mJ/cm$^2$. On use of EB as the high-energy radiation, a pattern may be written directly or through a mask having a desired pattern, preferably in a dose of about 0.1 to 100 K/cm$^2$, more preferably about 0.5 to 50 µC/cm$^2$. The resist composition is suited for micropatterning using high-energy radiation such as KrF excimer laser radiation, ArF excimer laser radiation, EB, EUV, x-rays, soft x-rays, γ-rays, or synchrotron radiation, especially EB or EUV.

After the exposure, the resist film may be baked (PEB) on a hotplate or in an oven preferably at 60 to 150° C. for 10 seconds to 30 minutes, more preferably at 80 to 120° C. for 30 seconds to 20 minutes.

After the exposure or PEB, the resist film exposed is developed with a developer for 3 seconds to 3 minutes, preferably 5 seconds to 2 minutes by conventional techniques such as dip, puddle, and spray techniques, thereby forming a desired pattern. A typical developer is a 0.1 to 10 wt %, preferably 2 to 5 wt % aqueous alkaline solution of tetramethylammonium hydroxide (TMAH), tetraethylammonium hydroxide, tetrapropylammonium hydroxide, or tetrabutylammonium hydroxide. In the case of a positive resist composition, the resist film in the exposed area is dissolved in the developer whereas the resist film in the unexposed area is not dissolved. In this way, the desired positive pattern is formed on the substrate. Inversely in the case of a negative resist composition, the exposed area of resist film is insolubilized and the unexposed area is dissolved in the developer.

There may be performed negative development in which a negative pattern may be formed via organic solvent development using a positive resist composition comprising a base polymer having an acid labile group. Examples of the developer used at this time include 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate. The organic solvents may be used alone or in admixture.

At the end of development, the resist film is rinsed. As the rinsing liquid, a solvent which is miscible with the developer and does not dissolve the resist film is preferred. Suitable examples of the solvent include alcohols of 3 to 10 carbon atoms, ether compounds of 8 to 12 carbon atoms, alkanes, alkenes, and alkynes of 6 to 12 carbon atoms, and aromatic solvents.

Specific examples of the alcohols of 3 to 10 carbon atoms include n-propyl alcohol, isopropyl alcohol, 1-butyl alcohol, 2-butyl alcohol, isobutyl alcohol, tert-butyl alcohol, 1-pentanol, 2-pentanol, 3-pentanol, tert-pentyl alcohol, neopentyl alcohol, 2-methyl-1-butanol, 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol, cyclohexanol, and 1-octanol.

Examples of the ether compounds of 8 to 12 carbon atoms include di-n-butyl ether, diisobutyl ether, di-sec-butyl ether, di-n-pentyl ether, diisopentyl ether, di-sec-pentyl ether, di-tert-pentyl ether, and di-n-hexyl ether.

Examples of the alkanes of 6 to 12 carbon atoms include hexane, heptane, octane, nonane, decane, undecane, dodecane, methylcyclopentane, dimethylcyclopentane, cyclohexane, methylcyclohexane, dimethylcyclohexane, cycloheptane, cyclooctane, and cyclononane. Examples of the alkenes of 6 to 12 carbon atoms include hexene, heptene, octene, cyclohexene, methylcyclohexene, dimethylcyclohexene, cycloheptene, and cyclooctene. Examples of the alkynes of 6 to 12 carbon atoms include hexyne, heptyne, and octyne.

Examples of the aromatic solvents include toluene, xylene, ethylbenzene, isopropylbenzene, tert-butylbenzene, and mesitylene.

Rinsing is effective for minimizing the risks of resist pattern collapse and defect formation. However, rinsing is not essential. If rinsing is omitted, the amount of solvent used may be reduced.

A hole or trench pattern after development may be shrunk by the thermal flow, RELACS® or DSA process. A hole pattern is shrunk by coating a shrink agent thereto, the shrink agent may undergo crosslinking at the resist surface as a result of the acid catalyst diffusing from the resist film during bake, and the shrink agent may attach to the sidewall of the hole pattern. The bake is preferably at a temperature of 70 to 180° C., more preferably 80 to 170° C., preferably for a time of 10 to 300 seconds. The extra shrink agent is stripped and the hole pattern is shrunk.

EXAMPLES

Hereinafter, the invention is specifically described with reference to Synthesis Examples, Examples, and Comparative Examples, but the invention is not limited to the following Examples.

Quenchers Q-1 to Q-26 of the sulfonium salt used in the resist composition have the structure shown below. Quenchers Q-1 to Q-26 were synthesized by an esterification reaction between a sulfonium salt having a hydroxyl group and an iodized or brominated carboxylic acid.

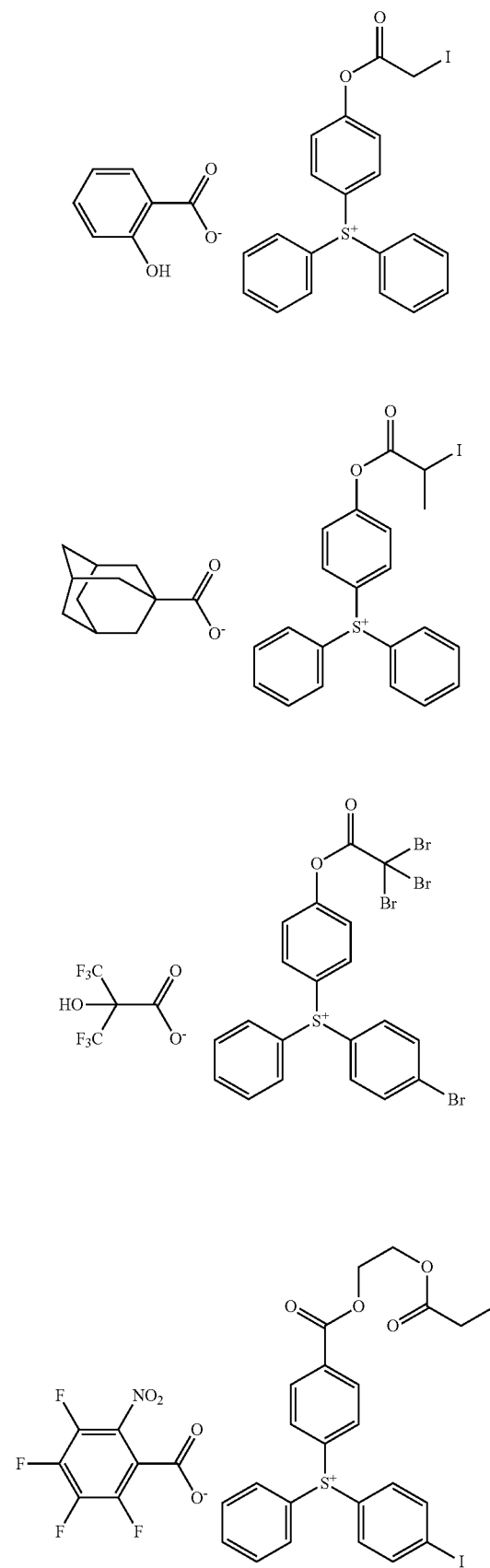
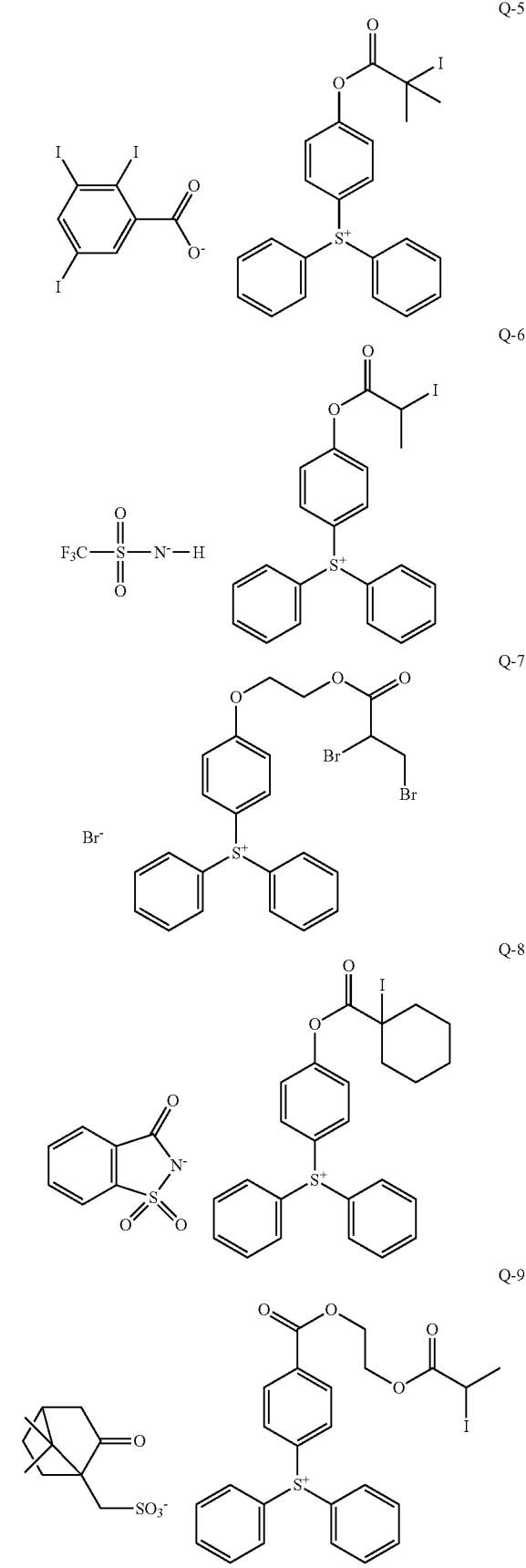

-continued
Q10
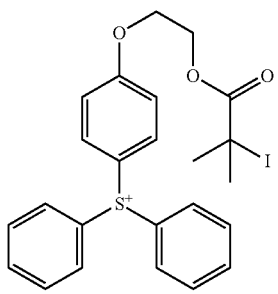
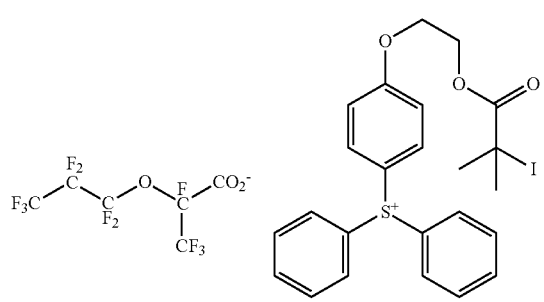
Q11
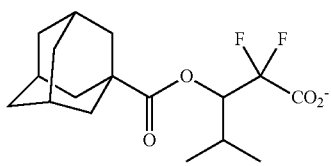
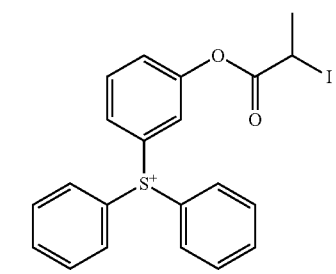
Q12
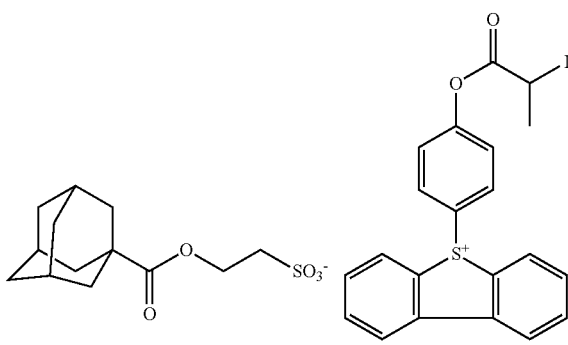
Q13
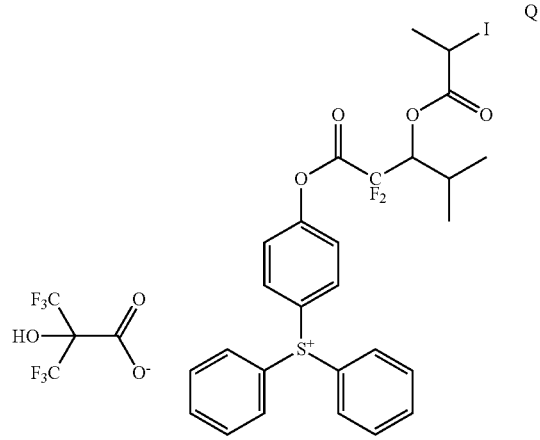
Q-14
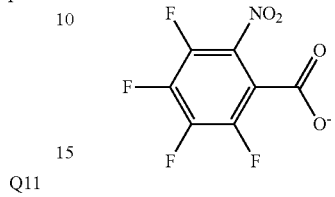
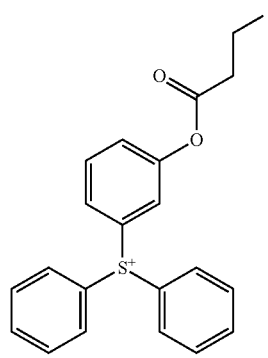
Q-15
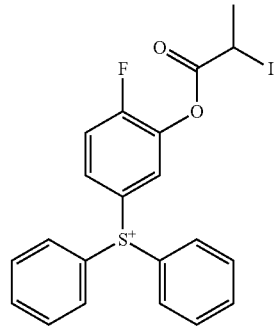
Q-16
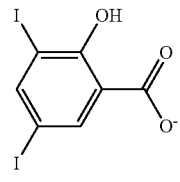
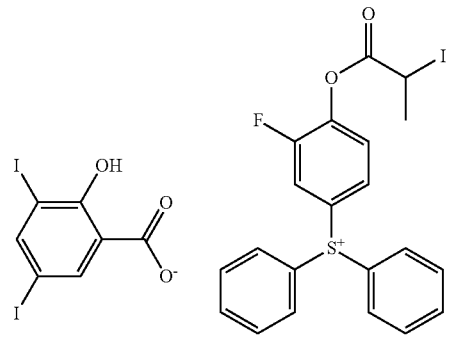
Q-17
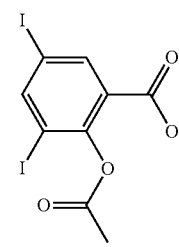
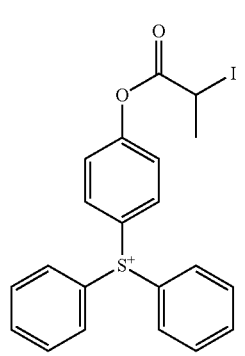

-continued
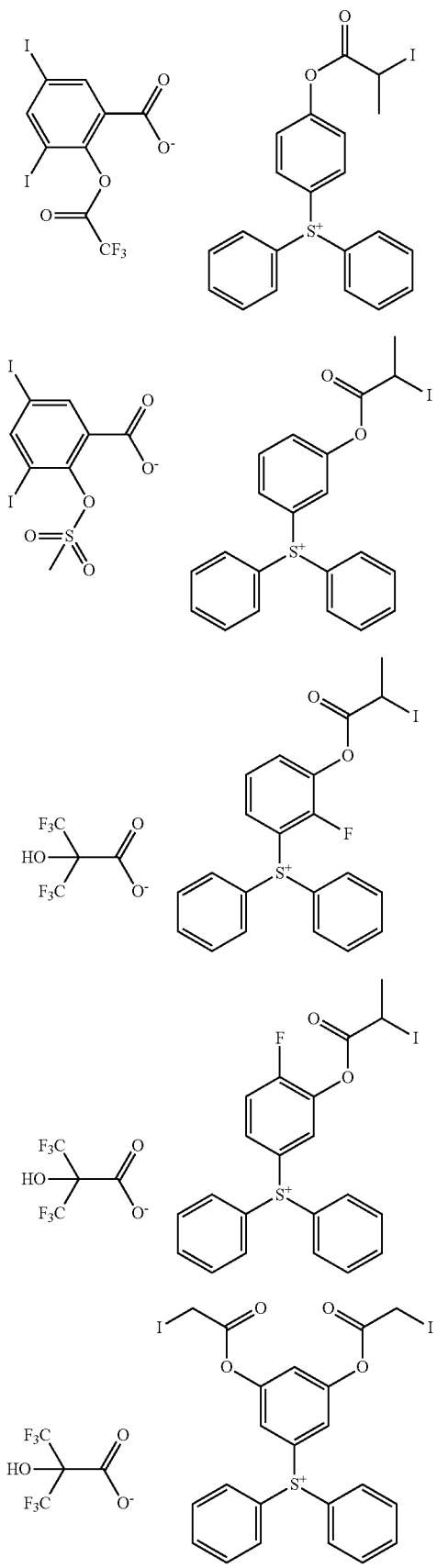
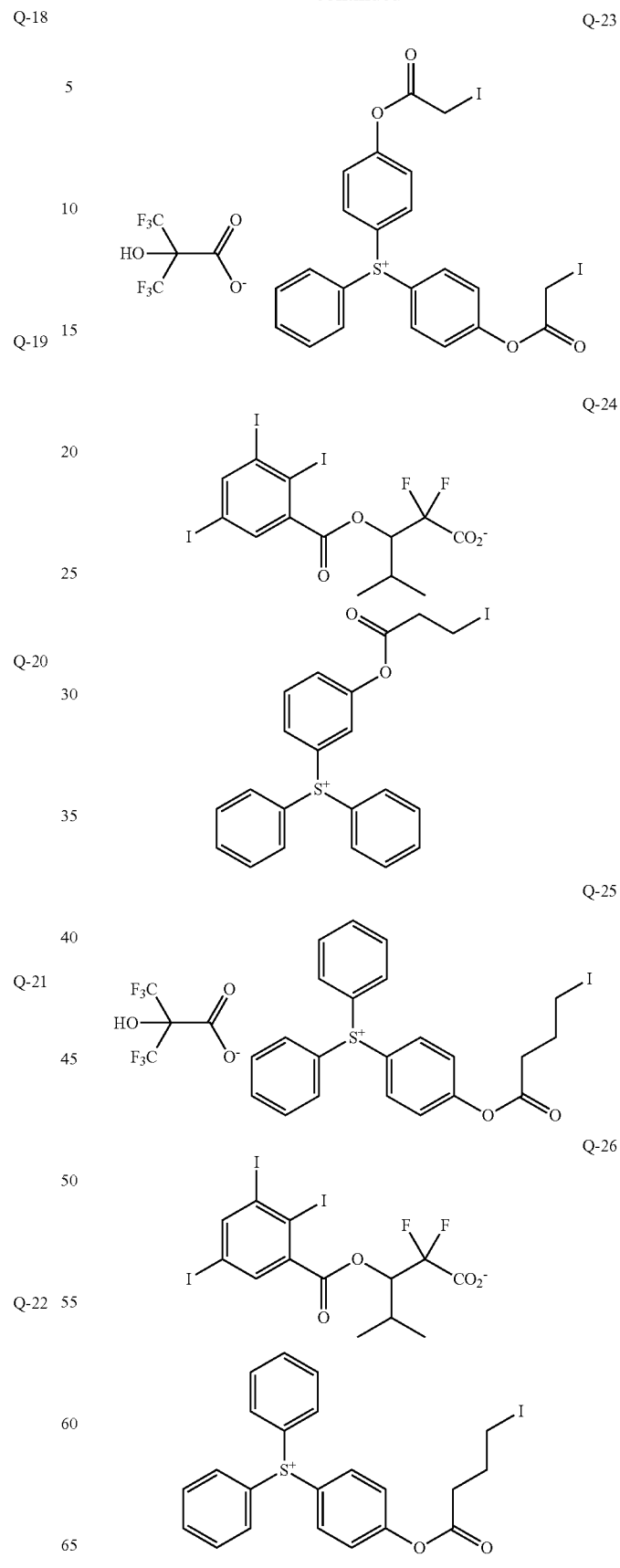

Synthesis Example

Synthesis of Base Polymer (Polymers 1 to 4)

Base polymers (Polymers 1 to 4) were prepared by combining suitable monomers, effecting copolymerization reaction thereof in THF, pouring the reaction solution into methanol for crystallization, repeatedly washing with hexane, isolation, and drying. The resulting base polymers were analyzed for composition by $^1$H-NMR spectroscopy, and for Mw and Mw/Mn by GPC versus polystyrene standards using THF solvent.

Polymer 1
Mw = 6,500
Mw/Mn = 1.66

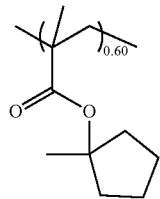 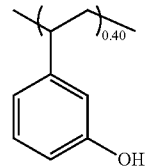

Polymer 2
Mw = 8,300
Mw/Mn = 1.69

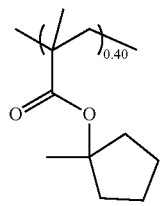 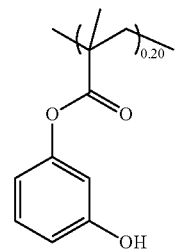

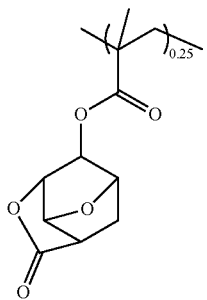 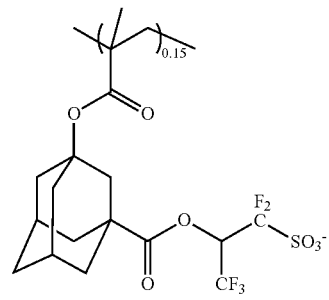

Polymer 3
Mw = 9,800
Mw/Mn = 1.66

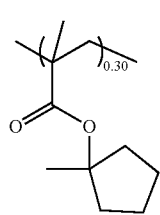 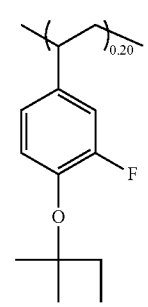

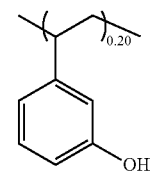 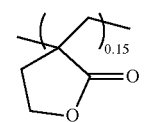

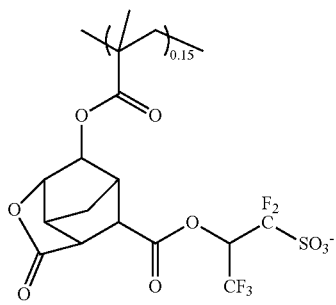
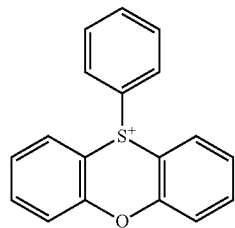 [SMILES: c1ccc([S+]2c3ccccc3Oc3ccccc32)cc1]

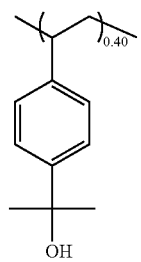
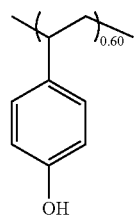

Polymer 4
Mw = 6,100
Mw/Mn = 1.54

Examples 1 to 29 and Comparative Examples 1 to 4

(1) Preparation of Resist Composition

Resist compositions were prepared by dissolving components in a solvent in accordance with the recipe shown in Tables 1 to 3, and filtering through a filter having a pore size of 0.2 μm. The solvent contained 100 ppm of surfactant PolyFox PF-636 (Omnova Solutions Inc.). The resist compositions of Examples 1 to 14 and 16 to 29 and Comparative Examples 1 to 3 are of positive tone, and the resist compositions of Example 15 and Comparative Example 4 are of negative tone.

The components in Tables 1 to 3 are as identified below.

Organic Solvent:
PGMEA (propylene glycol monomethyl ether acetate)
GBL (γ-butyrolactone)
CyH (cyclohexanone)
PGME (propylene glycol monomethyl ether)
DAA (diacetone alcohol)

Acid generators: PAG 1 to PAG 3

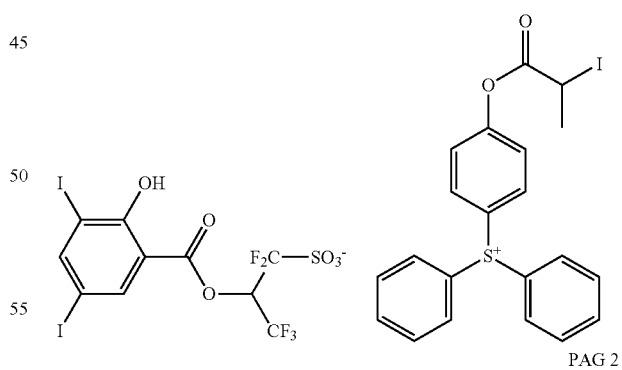
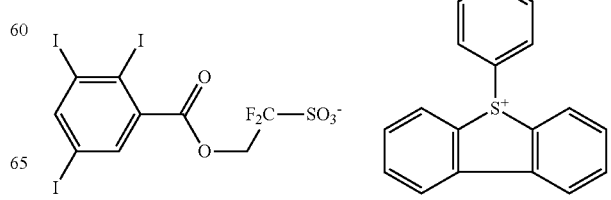

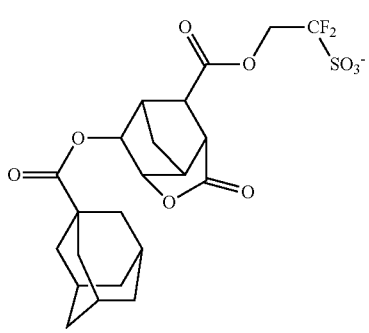

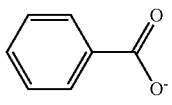
PAG 3

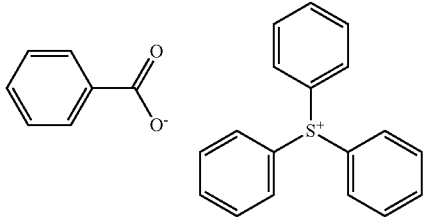
cQ-3

Comparative quencher: cQ-1 to cQ-3

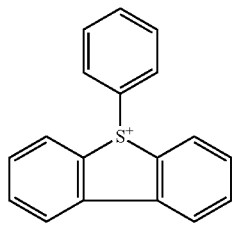
cQ-1

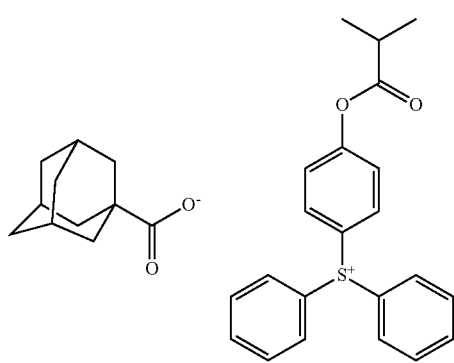
cQ-2

(2) EUV Lithography Test

Each of the resist compositions in Tables 1 to 3 was spin coated on a silicon substrate having a 20-nm coating of silicon-containing spin-on hard mask SHB-A940 (manufactured by Shin-Etsu Chemical Co., Ltd., silicon content 43 wt %) and prebaked on a hotplate at 105° C. for 60 seconds to form a resist film of 50 nm thick. Using an EUV scanner NXE3300 (manufactured by ASML, NA 0.33, σ 0.9/0.6, quadrupole illumination), the resist film was exposed to EUV through a mask bearing a hole pattern at a pitch 46 nm (on-wafer size) and +20% bias. The resist film was baked (PEB) on a hotplate at the temperature shown in Tables 1 to 3 for 60 seconds and developed in a 2.38 wt % TMAH aqueous solution for 30 seconds to form a pattern. In Examples 1 to 14 and 16 to 29 and Comparative Examples 1 to 3, a hole pattern having a size of 23 nm was obtained. In Example 15 and Comparative Example 4, a dot pattern having a size of 26 nm was obtained.

The exposure dose that provided a hole pattern having a size of 23 nm or a dot pattern having a size of 26 nm was measured and reported as the sensitivity. Using a critical dimension-scanning electron microscope manufactured by Hitachi High-Technologies Corporation (CG-5000), the sizes of 50 holes or 50 dots were measured, the standard deviation (σ) of the sizes was calculated, and three times of the standard deviation (3σ) was reported as the size variation (CDU).

The resist composition is shown in Tables 1 to 3 together with the sensitivity and CDU of EUV lithography.

TABLE 1

|  |  | Polymer (pbw) | Acid generator (pbw) | Quencher (pbw) | Organic solvent (pbw) | PEB (° C.) | Sensitivity (mJ/cm$^2$) | CDU (nm) |
|---|---|---|---|---|---|---|---|---|
| Example | 1 | Polymer 1 (100) | PAG 1 (26.7) | Q-1 (5.84) | PGMEA (400) CyH (2,000) PGME (100) | 95 | 24 | 3.7 |
|  | 2 | Polymer 1 (100) | PAG 2 (21.2) | Q-1 (5.84) | PGMEA (400) CyH (2,000) PGME (100) | 95 | 23 | 3.1 |
|  | 3 | Polymer 1 (100) | PAG 3 (15.3) | Q-1 (2.92) Q-2 (3.20) | PGMEA (2,000) DAA (500) | 95 | 29 | 3.0 |
|  | 4 | Polymer 2 (100) | — | Q-2 (6.40) | PGMEA (2,000) DAA (500) | 90 | 25 | 2.5 |

TABLE 1-continued

|  | Polymer (pbw) | Acid generator (pbw) | Quencher (pbw) | Organic solvent (pbw) | PEB (° C.) | Sensitivity (mJ/cm$^2$) | CDU (nm) |
|---|---|---|---|---|---|---|---|
| 5 | Polymer 2 (100) | — | Q-3 (8.43) | PGMEA (2,000) DAA (500) | 90 | 23 | 2.2 |
| 6 | Polymer 2 (100) | — | Q-4 (8.97) | PGMEA (2,000) DAA (500) | 90 | 23 | 2.5 |
| 7 | Polymer 2 (100) | — | Q-5 (11.01) | PGMEA (2,000) DAA (500) | 90 | 22 | 2.5 |
| 8 | Polymer 2 (100) | — | Q-6 (6.09) | PGMEA (2,000) DAA (500) | 90 | 25 | 2.7 |
| 9 | Polymer 2 (100) | — | Q-7 (6.17) | PGMEA (2,000) DAA (500) | 90 | 23 | 3.1 |
| 10 | Polymer 2 (100) | — | Q-8 (6.97) | PGMEA (2,000) DAA (500) | 90 | 26 | 2.7 |
| 11 | Polymer 2 (100) | — | Q-9 (7.64) | PGMEA (2,000) DAA (500) | 90 | 23 | 2.9 |
| 12 | Polymer 2 (100) | — | Q-10 (8.48) | PGMEA (2,000) DAA (500) | 90 | 24 | 2.7 |
| 13 | Polymer 2 (100) | — | Q-11 (7.90) | PGMEA (2,000) GBL (500) | 90 | 25 | 2.8 |
| 14 | Polymer 3 (100) | — | Q-12 (7.46) | PGMEA (2,000) GBL (500) | 90 | 22 | 3.0 |
| 15 | Polymer 4 (100) | PAG 3 (15.3) | Q-3 (8.43) | PGMEA (2,000) DAA (500) | 130 | 35 | 3.4 |

TABLE 2

|  |  | Polymer (pbw) | Acid generator (pbw) | Quencher (pbw) | Organic solvent (pbw) | PEB (° C.) | Sensitivity (mJ/cm$^2$) | CDU (nm) |
|---|---|---|---|---|---|---|---|---|
| Example | 16 | Polymer 2 (100) | — | Q-13 (8.22) | PGMEA (2,000) DAA (500) | 90 | 23 | 2.4 |
|  | 17 | Polymer 2 (100) | — | Q-14 (6.99) | PGMEA (2,000) DAA (500) | 90 | 20 | 2.6 |
|  | 18 | Polymer 2 (100) | — | Q-15 (9.78) | PGMEA (2,000) DAA (500) | 90 | 20 | 2.8 |
|  | 19 | Polymer 2 (100) | — | Q-16 (8.68) | PGMEA (2,000) DAA (500) | 90 | 22 | 2.8 |
|  | 20 | Polymer 2 (100) | — | Q-17 (8.92) | PGMEA (2,000) DAA (500) | 90 | 24 | 2.9 |
|  | 21 | Polymer 2 (100) | — | Q-18 (9.46) | PGMEA (2,000) DAA (500) | 90 | 23 | 2.6 |
|  | 22 | Polymer 2 (100) | — | Q-19 (9.27) | PGMEA (2,000) DAA (500) | 90 | 22 | 2.7 |
|  | 23 | Polymer 2 (100) | — | Q-20 (6.90) | PGMEA (2,000) DAA (500) | 90 | 22 | 2.6 |
|  | 24 | Polymer 2 (100) | — | Q-21 (6.90) | PGMEA (2,000) DAA (500) | 90 | 21 | 2.2 |
|  | 25 | Polymer 2 (100) | — | Q-22 (8.42) | PGMEA (2,000) DAA (500) | 90 | 20 | 2.2 |
|  | 26 | Polymer 2 (100) | — | Q-23 (8.42) | PGMEA (2,000) DAA (500) | 90 | 22 | 2.2 |
|  | 27 | Polymer 2 (100) | — | Q-24 (11.10) | PGMEA (2,000) DAA (500) | 90 | 23 | 2.3 |
|  | 28 | Polymer 2 (100) | — | Q-25 (6.86) | PGMEA (2,000) DAA (500) | 90 | 21 | 2.4 |
|  | 29 | Polymer 2 (100) | — | Q-26 (11.24) | PGMEA (2,000) DAA (500) | 90 | 22 | 2.4 |

TABLE 3

|  |  | Polymer (pbw) | Acid generator (pbw) | Quencher (pbw) | Organic solvent (pbw) | PEB (° C.) | Sensitivity (mJ/cm$^2$) | CDU (nm) |
|---|---|---|---|---|---|---|---|---|
| Comparative Example | 1 | Polymer 1 (100) | PAG 1 (26.7) | cQ-1 (5.28) | PGMEA (400) CyH (2,000) PGME (100) | 95 | 40 | 4.6 |
|  | 2 | Polymer 2 (100) | — | cQ-2 (4.72) | PGMEA (400) CyH (2,000) PGME (100) | 90 | 37 | 3.9 |

TABLE 3-continued

| | Polymer (pbw) | Acid generator (pbw) | Quencher (pbw) | Organic solvent (pbw) | PEB (°C.) | Sensitivity (mJ/cm$^2$) | CDU (nm) |
|---|---|---|---|---|---|---|---|
| 3 | Polymer 2 (100) | — | cQ-3 (3.84) | PGMEA (400) CyH (2,000) PGME (100) | 90 | 36 | 4.0 |
| 4 | Polymer 4 (100) | PAG 3 (15.3) | cQ-3 (3.84) | PGMEA (2,000) DAA (500) | 130 | 45 | 5.2 |

It is demonstrated in Tables 1 to 3 that the resist compositions comprising, as a quencher, the sulfonium salt having the formula (A) form patterns having high sensitivity and reduced values of CDU.

Japanese Patent Application No. 2020-031900 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A resist composition comprising a quencher containing a sulfonium salt having the formula (A):

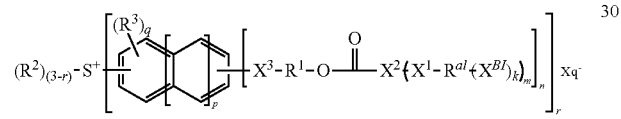

(A)

wherein k, m, and n are each independently an integer of 1 to 3, p is 0 or 1, q is an integer of 0 to 4, r is an integer of 1 to 3, $X^{BI}$ is iodine or bromine, $R^{a1}$ is a $C_1$-$C_{20}$ (k+1)-valent aliphatic hydrocarbon group which may contain at least one selected from an ether bond, a carbonyl group, an ester bond, an amide bond, a sultone ring, a lactam ring, a carbonate group, a halogen other than iodine, a $C_6$-$C_{12}$ aryl group, a hydroxyl group, or a carboxyl group, $X^1$ is a single bond, an ether bond, an ester bond, an amide bond, a carbonyl group, or a carbonate group, $X^2$ is a single bond or a $C_1$-$C_{20}$ (m+1)-valent hydrocarbon group which may contain at least one selected from an ether bond, a carbonyl group, an ester bond, an amide bond, a sultone ring, a lactam ring, a carbonate group, a halogen other than iodine, a hydroxyl group, or a carboxyl group, $X^3$ is a single bond, an ether bond, or an ester bond, $R^1$ is a single bond or a $C_1$-$C_{20}$ saturated hydrocarbylene group which may contain an ether bond, an ester bond, or a hydroxyl group, $R^2$ is a $C_1$-$C_{20}$ hydrocarbyl group which may contain a heteroatom, two $R^2$s may be the same or different, and may bond together to form a ring with a sulfur atom to which the two $R^2$s are attached when r=1, $R^3$ is a hydroxyl group, a carboxyl group, a nitro group, a cyano group, fluorine, chlorine, bromine, iodine, an amino group, or a $C_1$-$C_{20}$ saturated hydrocarbyl group, $C_1$-$C_{20}$ saturated hydrocarbyloxy group, $C_2$-$C_{20}$ saturated hydrocarbylcarbonyloxy group, $C_2$-$C_{20}$ saturated hydrocarbyloxycarbonyl group, or $C_1$-$C_4$ saturated hydrocarbylsulfonyloxy group which may contain fluorine, chlorine, bromine, iodine, a hydroxyl group, an amino group, or an ether bond, and Xq$^-$ is a halide ion, a sulfonic acid anion not having fluorine at an α-position, a carboxylic acid anion, or a sulfonamide anion.

2. The resist composition of claim 1, further comprising an organic solvent.

3. The resist composition of claim 1, further comprising an acid generator capable of generating fluorosulfonic acid, fluoroimidic acid, or fluoromethide acid.

4. The resist composition of claim 1, further comprising a base polymer.

5. The resist composition of claim 4, wherein the base polymer comprises recurring units having the formula (a1) or recurring units having the formula (a2):

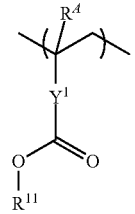

(a1)

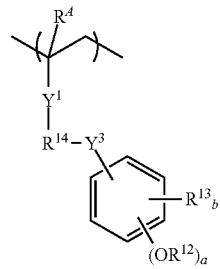

(a2)

wherein $R^A$ is each independently hydrogen or a methyl group, $Y^1$ is a single bond, a phenylene group, a naphthylene group, or a $C_1$-$C_{12}$ linking group containing at least one selected from an ester bond or a lactone ring, $Y^2$ is a single bond or an ester bond, $Y^3$ is a single bond, an ether bond, or an ester bond, $R^{11}$ and $R^{12}$ are each independently an acid labile group, $R^{13}$ is fluorine, a trifluoromethyl group, a cyano group, a $C_1$-$C_6$ saturated hydrocarbyl group, a $C_1$-$C_6$ saturated hydrocarbyloxy group, a $C_2$-$C_7$ saturated hydrocarbylcarbonyl group, a $C_2$-$C_7$ saturated hydrocarbylcarbonyloxy group, or a $C_2$-$C_7$ saturated hydrocarbyloxycarbonyl group, $R^{14}$ is a single bond or a $C_1$-$C_6$ alkanediyl group in which some carbon may be replaced by an ether bond or an ester bond, a is 1 or 2, b is an integer of 0 to 4, and 1≤a+b≤5.

6. The resist composition of claim 5 which is a chemically amplified positive resist composition.

7. The resist composition of claim 4, wherein the base polymer is free of an acid labile group.

8. The resist composition of claim 7 which is a chemically amplified negative resist composition.

9. The resist composition of claim 1, wherein the base polymer comprises recurring units having any one of the formulae (f1) to (f3):

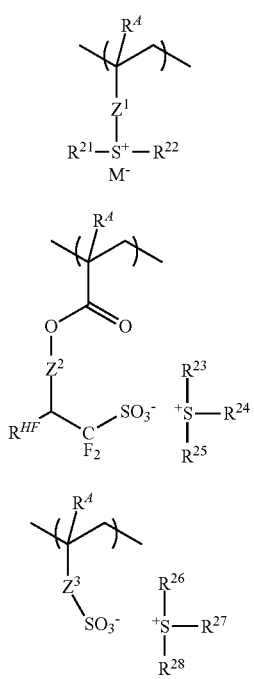

wherein $R^A$ is each independently hydrogen or a methyl group, $Z^1$ is a single bond, a $C_1$-$C_6$ aliphatic hydrocarbylene group, a phenylene group, a naphthylene group, a $C_7$-$C_{18}$ combination thereof, —O—$Z^{11}$—, —C(=O)—O—$Z^{11}$—, or —C(=O)—NH—$Z^{11}$—, $Z^{11}$ is a $C_1$-$C_6$ aliphatic hydrocarbylene group, a phenylene group, a naphthylene group, or a $C_7$-$C_{18}$ combination thereof, which may contain a carbonyl group, an ester bond, an ether bond, or a hydroxyl group, $Z^2$ is a single bond, —$Z^{21}$—C(=O)—O—, —$Z^{21}$—O—, or —$Z^{21}$—O—C(=O)—, $Z^{21}$ is a $C_1$-$C_{12}$ saturated hydrocarbylene group which may contain a carbonyl group, an ester bond, or an ether bond, $Z^3$ is a single bond, a methylene group, an ethylene group, a phenylene group, a fluorinated phenylene group, —O—$Z^{31}$—, —C(=O)—O—$Z^{31}$—, or —C(=O)—NH—$Z^{31}$—, $Z^{31}$ is a $C_1$-$C_6$ aliphatic hydrocarbylene group, a phenylene group, a fluorinated phenylene group, or a trifluoromethyl-substituted phenylene group which may contain a carbonyl group, an ester bond, an ether bond, or a hydroxyl group, $R^{21}$ to $R^{28}$ are each independently a halogen or a $C_1$-$C_{20}$ hydrocarbyl group which may contain a heteroatom, a pair of $R^{23}$ and $R^{24}$ or $R^{26}$ and $R^{27}$ may bond together to form a ring with a sulfur atom to which they are attached, $R^{HF}$ is hydrogen or a trifluoromethyl group, and M⁻ is a non-nucleophilic counter ion.

10. The resist composition of claim 1, further comprising a surfactant.

11. The resist composition of claim 1 wherein the halide ion is a chloride ion, a bromide ion, or an iodide ion, the sulfonic acid anion not having fluorine at the α-position is represented by the formula (B), the carboxylic acid anion is represented by the formula (C) or (D), and the sulfonamide anion is represented by the formula (E),

wherein $R^{q1}$ is hydrogen or a $C_1$-$C_{40}$ hydrocarbyl group which may contain a heteroatom, exclusive of the hydrocarbyl group in which the hydrogen bonded to the carbon atom at α-position of the sulfo group is substituted by fluorine or a fluoroalkyl group,

wherein $R^{q2}$ is a $C_1$-$C_{40}$ hydrocarbyl group which may contain a heteroatom,

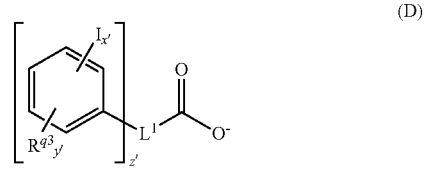

wherein $R^{q3}$ is hydroxyl, fluorine, chlorine, bromine, amino, nitro, cyano, or a $C_1$-$C_6$ saturated hydrocarbyl, $C_1$-$C_6$ saturated hydrocarbyloxy, $C_2$-$C_6$ saturated hydrocarbylcarbonyloxy, or $C_1$-$C_4$ saturated hydrocarbylsulfonyloxy group, in which some or all hydrogen may be substituted by a halogen, or —N($R^{q3A}$)—C(=O)—$R^{q3B}$, or —N($R^{q3A}$)—C(=O)—O—$R^{q3B}$, $R^{q3A}$ is hydrogen or a $C_1$-$C_6$ saturated hydrocarbyl group, $R^{q3B}$ is a $C_1$-$C_6$ saturated hydrocarbyl or $C_2$-$C_8$ unsaturated aliphatic hydrocarbyl group, x' is an integer of 1 to 5, y' is an integer of 0 to 3, z' is an integer of 1 to 3, and $L^1$ is a single bond, or a $C_1$-$C_{20}$ (z'+1)-valent linking group which may contain at least one group selected from an ether bond, a carbonyl group, an ester bond, an amide bond, a sultone ring, a lactam ring, a carbonate group, a halogen, a hydroxyl group, or a carboxyl group,

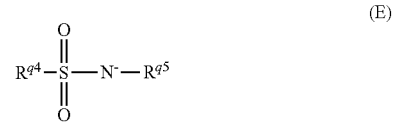

wherein $R^{q4}$ is fluorine, a $C_1$-$C_{10}$ hydrocarbyl group, or a $C_1$-$C_{10}$ fluorinated hydrocarbyl group, which may contain a hydroxyl group, an ether bond, or an ester bond, $R^{q5}$ is hydrogen or a $C_1$-$C_{10}$ hydrocarbyl group which may contain a hydroxyl group, an ether bond, or an ester bond, $R^{q4}$ and $R^{q5}$ may bond together to form a ring with the atom to which they are attached.

12. The resist composition of claim 1 wherein $Xq^-$ is a halide ion, a carboxylic acid anion, or a sulfonamide anion.

13. A pattern forming process comprising the steps of applying the resist composition of claim 1 to form a resist film on a substrate, exposing the resist film to high-energy radiation, and developing the exposed resist film in a developer.

14. The pattern forming process of claim 13, wherein the high-energy radiation is ArF excimer laser radiation of wavelength 193 nm or KrF excimer laser radiation of wavelength 248 nm.

15. The pattern forming process of claim 13, wherein the high-energy radiation is electron beam or extreme ultraviolet of wavelength 3 to 15 nm.

* * * * *